United States Patent
Kai et al.

(10) Patent No.: US 8,067,638 B2
(45) Date of Patent: Nov. 29, 2011

(54) AMIDE DERIVATIVE AND INSECTICIDE CONTAINING THE SAME

(75) Inventors: Akiyoshi Kai, Bunkyo-ku (JP); Takeo Wakita, Mobara (JP); Hiroyuki Katsuta, Chiba (JP); Kei Yoshida, Mobara (JP); Hidetaka Tsukada, Mobara (JP); Yusuke Takahashi, Mobara (JP); Nobuyuki Kawahara, Mobara (JP); Michikazu Nomura, Mobara (JP); Hidenori Daido, Mobara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 233 days.

(21) Appl. No.: 11/919,575

(22) PCT Filed: Jun. 20, 2006

(86) PCT No.: PCT/JP2006/312281
§ 371 (c)(1),
(2), (4) Date: Oct. 30, 2007

(87) PCT Pub. No.: WO2006/137376
PCT Pub. Date: Dec. 28, 2006

(65) Prior Publication Data
US 2009/0233962 A1    Sep. 17, 2009

(30) Foreign Application Priority Data
Jun. 21, 2005 (JP) .................. 2005-180660

(51) Int. Cl.
| C07C 233/64 | (2006.01) |
| C07D 213/00 | (2006.01) |
| C07D 207/00 | (2006.01) |
| C07D 231/00 | (2006.01) |
| C07D 261/00 | (2006.01) |
| C07D 277/00 | (2006.01) |
| C07D 275/00 | (2006.01) |
| C07D 241/00 | (2006.01) |
| C07D 315/00 | (2006.01) |
| C07D 307/00 | (2006.01) |

(52) U.S. Cl. ........ 564/155; 564/154; 549/425; 549/487; 548/200; 548/214; 548/248; 548/374.1; 548/537; 546/314; 546/315; 546/316; 544/406

(58) Field of Classification Search .................... None
See application file for complete search history.

(56) References Cited

U.S. PATENT DOCUMENTS

| 2,995,488 | A | 8/1961 | Jones et al. |
| 3,178,339 | A | 4/1965 | Frick et al. |
| 3,321,459 | A | 5/1967 | Voltz et al. |
| 4,567,136 | A | 1/1986 | Okaniwa et al. |
| 5,977,168 | A | 11/1999 | Konishi et al. |
| 6,166,054 | A | 12/2000 | Kuroda et al. |
| 6,548,514 | B1 | 4/2003 | Brown |
| 6,747,047 | B2 | 6/2004 | Lahm et al. |
| 6,995,178 | B2 | 2/2006 | Lahm et al. |
| 2002/0032238 | A1 | 3/2002 | Priepke et al. |
| 2003/0134859 | A1 | 7/2003 | Amemiya et al. |
| 2003/0229050 | A1 | 12/2003 | Lahm et al. |
| 2004/0142984 | A1 | 7/2004 | Lahm et al. |
| 2004/0235959 | A1 | 11/2004 | Lahm et al. |
| 2005/0176965 | A1 | 8/2005 | Chen et al. |
| 2006/0079561 | A1 | 4/2006 | Lahm et al. |
| 2007/0027154 | A1 | 2/2007 | Yoshida et al. |
| 2007/0275980 | A1 | 11/2007 | Yoshida et al. |
| 2009/0099204 | A1 | 4/2009 | Yoshida et al. |
| 2009/0162453 | A1 | 6/2009 | Kawahara et al. |
| 2009/0233962 | A1 | 9/2009 | Kai et al. |

FOREIGN PATENT DOCUMENTS
AU    2004268104 A1    3/2005
(Continued)

OTHER PUBLICATIONS

Database CAPLUS on STN, Acc. No. 1967:46001, Grammaticakis, Comptes Rendus des Seances de l'Academie des Sciences, Serie C: Sciences Chimiques (1966), 263(21), p. 1306-1309 (abstract).*

(Continued)

Primary Examiner — Brian J Davis
(74) Attorney, Agent, or Firm — Buchanan Ingersoll & Rooney PC

(57) ABSTRACT

The present invention is to provide a compound represented by the general formula (1) exhibiting a high insecticidal effect and an insecticide comprising the compound as an active ingredient. The compound represented by the general formula (1) and an insecticide comprising the compound as an active ingredient,

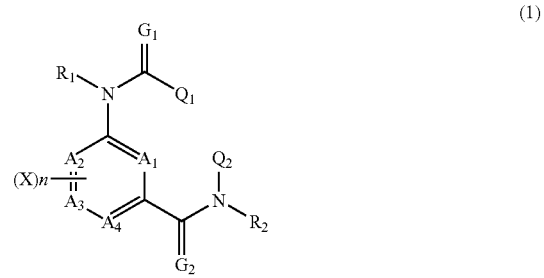

(1)

wherein, in the formula, $A_1$, $A_2$, $A_3$ and $A_4$ each represent a carbon atom or the like; $R_1$ and $R_2$ each represent a hydrogen atom or the like; $G_1$ and $G_2$ represent an oxygen atom or the like; Xs each represent a hydrogen atom, a halogen atom or the like; n represents an integer of 0 to 4; $Q_1$ represents a substituted phenyl group, a substituted heterocyclic group or the like; $Q_2$ represents a substituted phenyl group, a substituted heterocyclic group or the like.

9 Claims, No Drawings

FOREIGN PATENT DOCUMENTS

| | | |
|---|---|---|
| CA | 2554437 A1 | 8/2005 |
| CA | 2 589 773 A1 | 6/2006 |
| CA | 2 608 837 A1 | 12/2006 |
| CA | 2612507 A1 | 12/2006 |
| CA | 2616749 A1 | 2/2007 |
| CH | 373028 | 12/1963 |
| CH | 373029 | 12/1963 |
| CH | 419145 | 2/1967 |
| CN | 1152307 A | 6/1997 |
| DE | 35 23 705 A1 | 1/1987 |
| EP | 0 077 534 A2 | 4/1983 |
| EP | 0 148 725 A1 | 7/1985 |
| EP | 0 202 906 A1 | 11/1986 |
| GB | 954814 | 4/1964 |
| GB | 1047245 | 11/1966 |
| HU | 151362 | 5/1964 |
| JP | 57-094653 A | 6/1982 |
| JP | 58-170499 A | 10/1983 |
| JP | 58-175495 A | 10/1983 |
| JP | 59-016871 A | 1/1984 |
| JP | 6-220035 A | 8/1994 |
| JP | 11-349572 A | 12/1999 |
| JP | 2003-528070 A | 9/2003 |
| JP | 2005-504084 A | 2/2005 |
| JP | 2010-072101 A | 4/2010 |
| TW | 200518675 A | 6/2005 |
| TW | 200530156 A | 9/2005 |
| WO | WO 96/29871 A2 | 10/1996 |
| WO | WO 99/32433 A1 | 7/1999 |
| WO | WO 00/07980 A1 | 2/2000 |
| WO | WO 00/55120 A1 | 9/2000 |
| WO | WO 01/05769 A2 | 1/2001 |
| WO | WO 01/14339 A2 | 3/2001 |
| WO | WO 01/57024 A1 | 8/2001 |
| WO | WO 01/70671 A2 | 9/2001 |
| WO | WO 01/83427 A1 | 11/2001 |
| WO | WO 02/04403 A1 | 1/2002 |
| WO | WO 03/026415 A2 | 4/2003 |
| WO | WO 03/035602 A1 | 5/2003 |
| WO | WO 2004/035545 A2 | 4/2004 |
| WO | WO 2004/071440 A2 | 8/2004 |
| WO | WO 2004/098518 A2 | 11/2004 |
| WO | WO 2004/106324 A1 | 12/2004 |
| WO | WO 2005/021488 A1 | 3/2005 |
| WO | WO 2005/073165 A1 | 8/2005 |
| WO | WO 2006/131452 A1 | 12/2006 |
| WO | WO 2006/137376 A1 | 12/2006 |
| WO | WO 2006/067446 A1 | 5/2007 |
| WO | WO 2010/003023 A2 | 1/2010 |

OTHER PUBLICATIONS

Database CAPLUS on STN, Acc. No. 1997:558860, Parlow et al., Journal of Organic Chemistry (1997), 62(17), p. 5908-5919 (abstract).*

Database CAPLUS on STN, Acc. No. 1927:11951, Reverdin, Helvetica Chimica Acta (1927), 10, p. 3-4 (abstract).*

Database CAPLUS on STN, Acc. No. 2001:63978, Ricks et al., WO 2001005769 A2 (Jan. 25, 2001) (abstract).*

Official Action issued Jan. 26, 2010 in corresponding Taiwanese Patent Application No. 99011264.

Office Action issued Jun. 14, 2010 in corresponding Canadian Patent Application No. 2,612,976, Intellectual Property Office of Canada, CA.

Jun. 14, 2010 Canadian Official Action Citation D5: STN—Registry file and CAPLUS, 70 pages.

Jun. 14, 2010 Canadian Official Action Citation D6: STN—Registry file and CAPLUS, 18 pages.

Database CAPLUS on STN, Canadian Official Action Citation D5: Hynes, John, Jr., et al., "The discovery of (R)-2-(sec-butylamino)-N-(2-methyl-5-(methyl-carbamoyl)phenyl) thiazole-5-carboxamide (BMS-640994)—a potent and efficacious p38α MAP kinase inhibitor," *Bioorganic & Medicinal Chemistry Letters*, 2008, pp. 1762-1767, vol. 18, No. 6, Elsevier Ltd., USA.

Database CAPLUS on STN, Canadian Official Action Citation D5; Goto, Kazuki, et al., "Sequence-Specific Binding of m-Phenylene Ethynylene Foldamers to a Piperazinium Dihydrochloride Salt," *Organic Letters*, 2005, pp. 1683-1686, vol. 7, No. 9, American Chemical Society, USA.

Database CAPLUS on STN, Canadian Official Action Citation D5: Goto, Kazuki, et al., "Synthesis and folding properties of isomeric m-phenylene ethynylene oligomers containing short amide sequences," *Polymer Preprints* (Amercian Chemical Society, Division of Polymer Chemistry), 2003, pp. 594-595, vol. 44, No. 1, American Chemical Society, Division of Polymer Chemistry, USA.

Database CAPLUS on STN, Canadian Official Action Citation D5: Parlow, John, et al., "Utility of Complementary Molecular Reactivity and Molecular Recognition (CMR/R) Technology and Polymer-Supported Reagents in the Solution-Phase Synthesis of Heterocyclic Carboxamides," *Journal of Organic Chemistry*, 1997, pp. 5908-5919, vol. 62, No. 17, American Chemical Society, USA.

Database CAPLUS on STN, Canadian Official Action Citation D5: Kuroda, Noritaka, et al., "Further Development of a Robust Workup Process for Solution-Phase High-Throughput Library Synthesis to Address Environmental and Sample Tracking Issues," *Journal of Combinatorial Chemistry*, 2006, pp. 505-512, vol. 8, No. 4, American Chemical Society, USA.

Database CAPLUS on STN, Canadian Official Action Citation D5: Kojima, Takakazu, et al., "Solute-solvent interactions of oligo(m-benzamide)s in N,N-dimethylacetamide," *Journal of Polymer Science, Part B: Polymer Physics*, 1987, pp. 1481-1489, vol. 25, No. 7, J. Wiley & Sons, USA.

Database CAPLUS on STN, Canadian Official Action Citation D5: Miyamoto, Yoshinori, et al., "Synthesis and thermal stability of isomeric benzamide oligomers," *Kobunshi Ronbunshu (Japanese Journal of Polymer Science & Technology)*, 1982, pp. 41-47, vol. 39, No. 1, The Society of Polymer Science, Japan, JP.

Database CAPLUS on STN, Canadian Official Action Citation D5: Grammaticakis, Panos, "Preparation and ultraviolet absorption of some m-(amino- and m-(acylaminobenzoyl)aryl amines," *Comptes Rendus des Seances de l'Académie des Sciences, Serie C: Sciences Chimiques*, 1966, pp. 1306-1309, vol. 263, No. 21, Académie des Sciences, FR.

Database CAPLUS on STN, Canadian Official Action Citation D5: Adams, A., et al., "Search for trypanocides. III. Analogs of suranim," *Journal of the Chemical Society*, 1956, pp. 3739-3744, Chemical Society, UK.

Database CAPLUS on STN, Canadian Official Action Citation D5: Slifirski, St. Wen J., et al. "Arylamides,", *Bull. Trav. Inst. Pharm. Etat*, 1926, pp. 1-12, No. 4.

Database CAPLUS on STN, Canadian Official Action Citation D5: Reverdin, Frederic, "m-Nitro-p-phenetidine," *Helvetica Chimica Acta*, 1927, pp. 3-4, vol. 10, Verlag Helvetica Chimica Acta, Basel, CH.

Database CAPLUS on STN, Canadian Official Action Citation D6: Wang, Yonghui, et al., "Monoacylation of unprotected symmetrical diamines with resin-bound benzoic acids," *Tetrahedron Letters*, 2004, pp. 6645-6648, vol. 45, No. 35, Elsevier, USA.

Database CAPLUS on STN, Canadian Official Action Citation D6: Ogata, Masaru, et al., "Synthesis and antiviral activity of sulfonamidobenzophenone oximes and sulfonamidobenzamides," *Journal of Medicinal Chemistry*, 1986, pp. 417-423, vol. 29, No. 3, American Chemical Society, USA.

Database CAPLUS on STN, Canadian Official Action Citation D6: Chernova, N.I., et al., "Synthesis and optical properties of 5-substituted 2-(2-tosylaminophenyl)benzoxazoles," *Khimiya Geterotsiklicheskikh Soedinenii* (Chemistry of Heterocyclic Compounds), 1973, pp. 472-478, vol. 4, English translation published by Springer Science + Business Media, Inc., NY, USA.

Supplementary European Search Report issued Sep. 16, 2010, in corresponding European Patent Application No. 06 76 6942.4.

* cited by examiner

AMIDE DERIVATIVE AND INSECTICIDE CONTAINING THE SAME

TECHNICAL FIELD

The present invention relates to a new amide derivative and an insecticide containing the same.

BACKGROUND ART

In WO 2000/55120 and U.S. Pat. No. 6,548,514, a compound similar to the compound of the present invention for medicine use was described. But activity against insects was never described therein. Furthermore, it is obvious that such compounds are not included in the scope of the claims of the present invention.

In WO 2000/7980, a compound similar to the compound of the present invention for medicine use was described. But activity against insects was never described therein. Furthermore, it is obvious that such a compound is not included in the scope of the claims of the present invention.

In US Patent Laid-Open No. 2002-032238, a compound similar to the compound of the present invention for medicine use was described. But activity against insects was never described therein. Furthermore, it is obvious that such a compound is not included in the scope of the claims of the present invention.

DISCLOSURE OF THE INVENTION

The present invention provides a compound represented by the general formula (1) or (5), and an insecticide containing the same as an active ingredient.

In order to solve the above objects, the present inventors have repeatedly conducted an extensive study and as a result, have found a novel compound which is not described in any documents, and a new use of a compound of the present invention as an insecticide because the compound of the present invention has a remarkably excellent insecticidal effect.

That is, the present invention is specified by the following matters.

[1] A compound represented by the general formula (1),

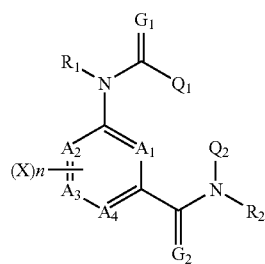

(1)

wherein, in the formula, $A_1$, $A_2$, $A_3$ and $A_4$ each represent a carbon atom, a nitrogen atom or an oxidized nitrogen atom;

$R_1$ and $R_2$ mutually independently represent a hydrogen atom, a C1-C4 alkyl group or a C1-C4 alkylcarbonyl group;

$G_1$ and $G_2$ mutually independently represent an oxygen atom or a sulfur atom;

Xs may be the same or different and represent a hydrogen atom, a halogen atom, a C1-C3 alkyl group or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group, a carbocyclic group (The carbocyclic group herein represents a naphthyl group, a tetrahydronaphthyl group, an indanyl group, a fluorenyl group, a 9-oxofluorenyl group, an adamantanyl group, an anthracenyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group (The carbocyclic group herein represents a naphthyl group, a tetrahydronaphthyl group, an indanyl group, a fluorenyl group, a 9-oxofluorenyl group, an adamantanyl group, an anthracenyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, an acridinyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, an acridinyl group or a dihydropyranyl group.); and $Q_2$ represents a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, a benzimidazolyl group or a dihydropyranyl group.), a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl, a pyridin-2-yl group, a pyridin-4-yl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, a benzimidazolyl group or a dihydropyranyl group.), a C1-C6 alkyl group, or a substituted C1-C6 alkyl group having one or more substituents which may be the same or different and are selected from a halogen atom, a C1-C4 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a group represented by general formula (2)

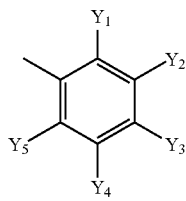

(2)

wherein, in the formula, $Y_1$, $Y_2$, $Y_3$, $Y_4$ and $Y_5$ may be the same or different and represent a hydrogen atom, a halogen atom, a C1-C6 alkyl group, a substituted C1-C6 alkyl group having one or more substituents which may be the same or different and are selected from a halogen atom, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a alkylsilyl group, a C1-C6 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C6 alkoxy group, a C1-C6 haloalkoxy group, a substituted C1-C6 haloalkoxy group having one or more substituents which may be the same or different and are selected from a hydrogen atom, a hydroxy group, a chlorine atom, a bromine atom, an iodine atom, a C1-C6 alkoxy group and a C1-C6 haloalkoxy group, a C1-C6 haloalkyl group which may be substituted with one or more hydroxyl groups, a C1-C6 haloalkyl group which may be substituted with one or more haloalkyl groups, a C1-C6 haloalkyl group which may be substituted with one or more alkoxy groups, a C1-C6 haloalkyl group which may be substituted with one or more haloalkoxy groups, a C1-C6 alkylthio group, a C1-C6 haloalkylthio group, a substituted C1-C6 haloalkylthio group having one or more substituents which may be the same or different and are selected from a hydrogen atom, a hydroxy group, a chlorine atom, a bromine atom, an iodine atom, a C1-C6 alkoxy group and a C1-C6 haloalkoxy group, a C1-C6 alkylsulfinyl group, a C1-C6 haloalkylsulfinyl group, a substituted C1-C6 haloalkylsulfinyl group having one or more substituents which may be the same or different and are selected from a hydrogen atom, a hydroxy group, a chlorine atom, a bromine atom, an iodine atom, a C1-C6 alkoxy group and a C1-C6 haloalkoxy group, a C1-C6 alkylsulfonyl group, a C1-C6 haloalkylsulfonyl group, a substituted C1-C6 haloalkylsulfonyl group having one or more substituents which may be the same or different and are selected from a hydrogen atom, a hydroxy group, a chlorine atom, a bromine atom, an iodine atom, a C1-C6 alkoxy group and a C1-C6 haloalkoxy group, a C1-C4 alkoxycarbonyl group, a C1-C4 haloalkoxycarbonyl group, a C1-C4 alkylcarbonylamino group, a C1-C4 haloalkylcarbonylamino group, a C1-C6 alkylsulfonyloxy group, a C1-C6 haloalkylsulfonyloxy group, a C1-C4 alkylcarbonyl group, a C1-C4 haloalkylcarbonyl group, a C1-C4 alkylcarbonyloxy group, a C1-C4 haloalkylcarbonyloxy group, a cyano group, a nitro group, a hydroxy group, a pentafluorosulfanyl group, a carboxyl group, a carbamoyl group, a C1-C3 alkylaminocarbonyl group, a phenylazo group, a pyridyloxy group, a substituted pyridyloxy group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), whereas $Y_1$ and $Y_5$ may be the same or different and when $Y_1$ and $Y_5$ represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group, $Y_3$ does not have a C2-C6 perfluoroalkyl group, a C1-C6 perfluoroalkylthio group, a C1-C6 perfluoroalkylsulfinyl group or a C1-C6 perfluoroalkylsulfonyl group.) or a group represented by general formula (3)

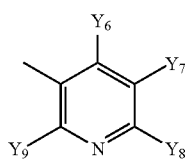

(3)

wherein, in the formula, $Y_6$, $Y_7$, $Y_8$ and $Y_9$ may be the same or different and represent a hydrogen atom, a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C4 alkoxy group, a C1-C4 haloalkoxy group, a C1-C6 haloalkyl group which may be substituted with one or more hydroxyl groups, a C1-C6 haloalkyl group which may be substituted with one or more alkoxy groups, a C1-C6 haloalkyl group which may be substituted with one or more haloalkoxy groups, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C1-C4 alkylcarbonyl group, a C1-C4 haloalkylcarbonyl group, a C1-C4 alkylcarbonyloxy group, a C1-C4 haloalkylcarbonyloxy group, a cyano group, a nitro group, a hydroxy group, a pentafluorosulfanyl group, a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), whereas $Y_6$ and $Y_9$ may be the same or different and when $Y_6$ and $Y_9$ represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group, $Y_8$ does not have a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group;

[2] the compound according to [1], wherein, in the general formula (1), $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (2),

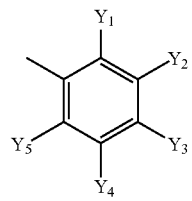

(2)

wherein, in the formula, $Y_1$ and $Y_5$ may be the same or different and represent a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a trifluoromethyl group, a C1-C6 perfluoroalkoxy group, a pentafluorosulfanyl group, a substituted C1-C6 haloalkoxy group having one or more substituents which may be the same or different and are selected from a hydrogen atom, a hydroxy group, a chlorine atom, a bromine atom, an iodine atom, a C1-C6 alkoxy group or a C1-C6 haloalkoxy group which may be the same or different, a substituted C1-C6 haloalkylthio group having at least one or more a hydrogen atom, a hydroxy group, a chlorine atom, a bromine atom, an iodine atom, a C1-C6 alkoxy group or a C1-C6 haloalkoxy group which may be the same or different, a substituted C1-C6 haloalkylsulfinyl group having one or more substituents which may be the same or different and are selected from a hydrogen atom, a hydroxy group, a chlorine atom, a bromine atom, an iodine atom, a C1-C6 alkoxy group or a C1-C6 haloalkoxy group, or a substituted C1-C6 haloalkylsulfonyl group having one or more substituents which may be the same or different and are selected from a hydrogen atom, a hydroxy group, a chlorine atom, bromine atom, iodine atom, C1-C6 alkoxy group or a C1-C6 haloalkoxy group;

[3] the compound according to [1], wherein, in the general formula (1), $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (2),

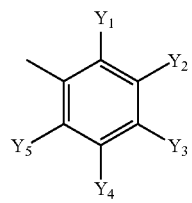

(2)

wherein, in the formula, $Y_1$ represents a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, or a C1-C4 alkyl group having one or more substituents which may be the same or different and are selected from halogen atom, C1-C3 alkoxy group, C1-C3 haloalkoxy group, C1-C3 alkylthio group, C1-C3 haloalkylthio group, C1-C3 alkylsulfinyl group, C1-C3 haloalkylsulfinyl group, C1-C3 alkylsulfonyl group, C1-C3 haloalkylsulfonyl group, C1-C4 alkylamino group, a di C1-C4 alkylamino group, cyano group, nitro group, hydroxy group, C1-C4 alkylcarbonyl group, C1-C4 haloalkylcarbonyl group, C1-C4 alkylcarbonyloxy group, C1-C4 haloalkylcarbonyloxy group, C1-C4 alkoxycarbonyl group, C1-C4 haloalkoxycarbonyl group, C1-C4 alkylcarbonylamino group, C1-C4 haloalkylcarbonylamino group, C1-C4 alkylsulfonyloxy group, C1-C4 haloalkylsulfonyloxy group, arylsulfonyloxy group, pentafluorosulfanyl group or alkylsilyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a C1-C4 haloalkoxy group, a C2-C6 perfluoroalkyl group, a C1-C6 perfluoroalkylthio group, a C1-C6 perfluoroalkylsulfinyl group, a C1-C6 perfluoroalkylsulfonyl group, a trifluoromethyl group, a C1-C6 perfluoroalkoxy group, a pentafluorosulfanyl group, a substituted C1-C6 haloalkoxy group having at least one or more substituents which may be the same or different and are selected from a hydrogen atom, a hydroxy group, a chlorine atom, a bromine atom, an iodine atoms, a C1-C6 alkoxy group or a C1-C6 haloalkoxy group, a substituted C1-C6 haloalkylthio group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group, a substituted C1-C6 haloalkylsulfinyl group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group, or a substituted C1-C6 haloalkylsulfonyl group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group;

[4] the compound according to [1], wherein, in the general formula (1), $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (2),

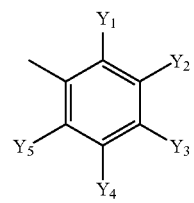

(2)

wherein, in the formula, $Y_1$ represents a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group or a C1-C6 haloalkylsulfonyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a halogen atom;

[5] The compound according to [1], wherein, in the general formula (1), $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (4),

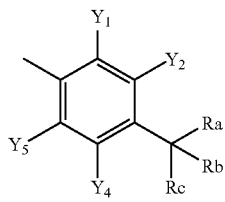

(4)

wherein, in the formula, $Y_1$ and $Y_5$ may be the same or different and represent a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group;

Ra represents a halogen atom or a hydroxy group; and

Rb and Rc may each independently represent a hydrogen atom, a hydroxy group, a halogen atom or a C1-C6 haloalkyl group, and at least either Rb or Rc has one or more hydrogen atoms, hydroxy groups, chlorine atoms, bromine atoms or iodine atoms included thereto.

[6] the compound according to any one of claims [1] to [5], wherein, in the general formula (1), at least one of $R_1$ and $R_2$ is a C1-C4 alkyl group;

[7] a compound represented by the general formula (5),

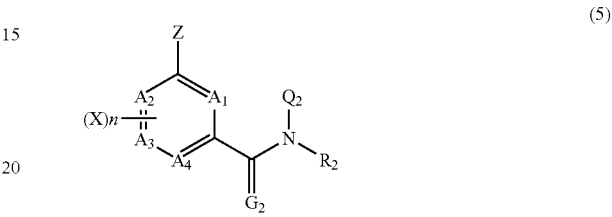

(5)

wherein, in the formula, $A_1$, $A_2$, $A_3$ and $A_4$ each represents a carbon atom, a nitrogen atom or an oxidized nitrogen atom;

Z represents —N($R_1$)SO$_2$Q$_1$ or —N($R_1$)Q$_1$;

$R_1$ and $R_2$ mutually independently represent a hydrogen atom, a C1-C4 alkyl group or a C1-C4 alkylcarbonyl group;

$G_2$ represents an oxygen atom or a sulfur atom;

Xs may be the same or different and represent a hydrogen atom, a halogen atom, a C1-C3 alkyl group or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, an amino group and a phenyl group, a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, an amino group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.); and $Q_2$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), a C1-C6 alkyl group, or a substituted C1-C6 alkyl group having one or more substituents which may be the same or different and are selected from a halogen atom, a C1-C4 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group; and

[8] an insecticide comprising the compound as described in any one of [1] to [7] and an active ingredient.

The compound of the present invention exhibits an excellent control effect as an insecticide in a small amount of chemicals, and also exhibits an excellent control effect when it is used in combination with other insecticides, miticides, nematicides, fungicides, herbicides, plant growth regulators, biological agrochemicals or the like.

BEST MODE FOR CARRYING OUT THE INVENTION

A compound of the present invention is represented by the general formula (1).

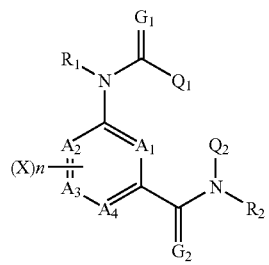

(1)

In the formula (1), $A_1$, $A_2$, $A_3$ and $A_4$ each represent a carbon atom, a nitrogen atom or an oxidized nitrogen atom;

$R_1$ and $R_2$ mutually independently represent a hydrogen atom, a C1-C4 alkyl group or a C1-C4 alkylcarbonyl group;

$G_1$ and $G_2$ mutually independently represent an oxygen atom or a sulfur atom;

Xs may be the same or different and represent a hydrogen atom, a halogen atom, a C1-C3 alkyl group or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group, a carbocyclic group (The carbocyclic group herein represents a naphthyl group, a tetrahydronaphthyl group, an indanyl group, a fluorenyl group, a 9-oxofluorenyl group, an adamantanyl group, an anthracenyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group (The carbocyclic group herein represents a naphthyl group, a tetrahydronaphthyl group, an indanyl group, a fluorenyl group, a 9-oxofluorenyl group, an adamantanyl group, an anthracenyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, an acridinyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, an amino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, a phenylalkynyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, an acridinyl group or a dihydropyranyl group.); and $Q_2$ represents a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, a benzimidazolyl group or a dihydropyranyl group.), a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl, a pyridin-2-yl group, a pyridin-4-yl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group, a benzimidazolyl group or a dihydropyranyl group.), a C1-C6 alkyl group, or a substituted C1-C6 alkyl group having one or more substituents which may be the same or different and are selected from a halogen atom, a C1-C4 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group,
a group represented by general formula (2)

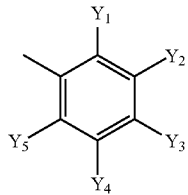
(2)

wherein, in the formula, $Y_1$, $Y_2$, $Y_3$, $Y_4$ and $Y_5$ may be the same or different and represent a hydrogen atom, a halogen atom, a C1-C6 alkyl group,
a substituted C1-C6 alkyl group having one or more substituents which may be the same or different and are selected from a halogen atom, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a alkylsilyl group,
a C1-C6 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C6 alkoxy group, a C1-C6 haloalkoxy group,
a substituted C1-C6 haloalkoxy group having one or more substituents which may be the same or different and are selected from a hydrogen atom, a hydroxy group, a chlorine atom, a bromine atom, an iodine atom, a C1-C6 alkoxy group and a C1-C6 haloalkoxy group,
a C1-C6 haloalkyl group which may be substituted with one or more hydroxyl groups,
a C1-C6 haloalkyl group which may be substituted with one or more haloalkyl groups,
a C1-C6 haloalkyl group which may be substituted with one or more alkoxy groups,
a C1-C6 haloalkyl group which may be substituted with one or more haloalkoxy groups,
a C1-C6 alkylthio group,
a C1-C6 haloalkylthio group,
a substituted C1-C6 haloalkylthio group having one or more substituents which may be the same or different and are selected from a hydrogen atom, a hydroxy group, a chlorine atom, a bromine atom, an iodine atom, a C1-C6 alkoxy group and a C1-C6 haloalkoxy group,
a C1-C6 alkylsulfinyl group,
a C1-C6 haloalkylsulfinyl group,
a substituted C1-C6 haloalkylsulfinyl group having one or more substituents which may be the same or different and are selected from a hydrogen atom, a hydroxy group, a chlorine atom, a bromine atom, an iodine atom, a C1-C6 alkoxy group and a C1-C6 haloalkoxy group,
a C1-C6 alkylsulfonyl group,
a C1-C6 haloalkylsulfonyl group,
a substituted C1-C6 haloalkylsulfonyl group having one or more substituents which may be the same or different and are selected from a hydrogen atom, a hydroxy group, a chlorine atom, a bromine atom, an iodine atom, a C1-C6 alkoxy group and a C1-C6 haloalkoxy group,
a C1-C4 alkoxycarbonyl group, a C1-C4 haloalkoxycarbonyl group, a C1-C4 alkylcarbonylamino group, a C1-C4 haloalkylcarbonylamino group,
a C1-C6 alkylsulfonyloxy group, a C1-C6 haloalkylsulfonyloxy group, a C1-C4 alkylcarbonyl group, a C1-C4 haloalkylcarbonyl group, a C1-C4 alkylcarbonyloxy group, a C1-C4 haloalkylcarbonyloxy group, a cyano group, a nitro group, a hydroxy group, a pentafluorosulfanyl group, a carboxyl group, a carbamoyl group, a C1-C3 alkylaminocarbonyl group, a phenylazo group, a pyridyloxy group,
a substituted pyridyloxy group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group,
a phenyl group,
a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group,
a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), whereas $Y_1$ and $Y_5$ may be the same or different and when $Y_1$ and $Y_5$ represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group, $Y_3$ does not have a C2-C6 perfluoroalkyl group, a C1-C6 perfluoroalkylthio group, a C1-C6 perfluoroalkylsulfinyl group or a C1-C6 perfluoroalkylsulfonyl group.) or a group represented by general formula (3)

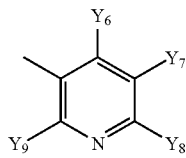

(3)

wherein, in the formula, $Y_6, Y_7, Y_8$ and $Y_9$ may be the same or different and represent a hydrogen atom, a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C4 alkoxy group, a C1-C4 haloalkoxy group, a C1-C6 haloalkyl group which may be substituted with one or more hydroxyl groups, a C1-C6 haloalkyl group which may be substituted with one or more alkoxy groups, a C1-C6 haloalkyl group which may be substituted with one or more haloalkoxy groups, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C1-C4 alkylcarbonyl group, a C1-C4 haloalkylcarbonyl group, a C1-C4 alkylcarbonyloxy group, a C1-C4 haloalkylcarbonyloxy group, a cyano group, a nitro group, a hydroxy group, a pentafluorosulfanyl group, a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), whereas $Y_6$ and $Y_9$ may be the same or different and when $Y_6$ and $Y_9$ represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group, $Y_8$ does not have a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group.

Furthermore, a compound of the present invention is represented by the general formula (5).

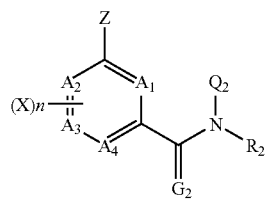

(5)

In the formula (5), $A_1$, $A_2$, $A_3$ and $A_4$ each represents a carbon atom, a nitrogen atom or an oxidized nitrogen atom;

Z represents —$N(R_1)SO_2Q_1$ or —$N(R_1)Q_1$;

$R_1$ and $R_2$ mutually independently represent a hydrogen atom, a C1-C4 alkyl group or a C1-C4 alkylcarbonyl group;

$G_1$ represents an oxygen atom or a sulfur atom;

Xs may be the same or different and represent a hydrogen atom, a halogen atom, a C1-C3 alkyl group or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, an amino group and a phenyl group, a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group, an amino group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.); and Q$_2$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a carbocyclic group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a substituted carbocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The carbocyclic group herein represents a naphthyl group, a tetrahydronaphthyl group, a C3-C8 cycloalkyl group, an indanyl group, a fluorenyl group, a 9-oxofluorenyl group, an adamantanyl group or a norbornyl group.), a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a benzothiazolyl group, a benzoxazolyl group, a benzofuranyl group, a benzothiophenyl group, a quinolyl group, an isoquinolyl group, an indolyl group, an isoindolyl group, an 1H-isoindolyl group, a 2,3-dihydro-benzo[1,4]dioxinyl group, a benzo[1,3]dioxolyl group, a tetrahydropyranyl group or a dihydropyranyl group.), a C1-C6 alkyl group, or a substituted C1-C6 alkyl group having one or more substituents which may be the same or different and are selected from a halogen atom, a C1-C4 haloalkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group.

Wordings used in general formulae such as the general formula (1) of the present invention and the like have the respective meanings as described hereinafter in terms of definitions.

The term "halogen atom" represents a fluorine atom, a chlorine atom, a bromine atom or an iodine atom.

In expression of "Ca-Cb (a and b represent an integer of not less than 1)," for example, "C1-C3" refers to 1 to 3 carbon atoms, "C2-C6" refers to 2 to 6 carbon atoms, and "C1-C4" refers to 1 to 4 carbon atoms.

"n-" refers to normal, "i-" refers to iso, "s-" refers to secondary and "t-" refers to tertiary.

The term "C1-C3 alkyl group" refers to a straight or branched alkyl group having 1 to 3 carbon atoms such as methyl, ethyl, n-propyl, i-propyl, cyclopropyl or the like, "C1-C4 alkyl group" refers to a straight or branched alkyl group having 1 to 4 carbon atoms such as n-butyl, s-butyl, i-butyl, t-butyl or the like in addition to "C1-C3 alkyl group," and "C1-C6 alkyl group" refers to a straight or branched alkyl group having 1 to 6 carbon atoms such as n-pentyl, 2-pentyl, 3-pentyl, neopentyl, n-hexyl, 2-hexyl, 4-methyl-2-pentyl, 3-methyl-n-pentyl or the like in addition to "C1-C4 alkyl group"

The term "C1-C3 haloalkyl group" refers to a straight or branched alkyl group having 1 to 3 carbon atoms which is substituted with one or more halogen atoms which may be the same or different, such as monofluoromethyl, difluoromethyl, trifluoromethyl, monochloromethyl, dichloromethyl, trichloromethyl, monobromomethyl, dibromomethyl, tribromomethyl, 1-fluoroethyl, 2-fluoroethyl, 2,2-difluoroethyl, 2,2,2-trifluoroethyl, 1-chloroethyl, 2-chloroethyl, 2,2-dichloroethyl, 2,2,2-trichloroethyl, 1-bromoethyl, 2-bromoethyl, 2,2-dibromoethyl, 2,2,2-tribromoethyl, 2-iodineethyl, pentafluoroethyl, 3-fluoro-n-propyl, 3-chloro-n-propyl, 3-bromo-n-propyl, 1,3-difluoro-2-propyl, 1,3-dichloro-2-propyl, 1,1,1-trifluoro-2-propyl, 1-chloro-3-fluoro-2-propyl, 1,1,1,3,3,3-hexafluoro-2-propyl, 1,1,1,3,3,3-hexafluoro-2-chloro-2-propyl, 2,2,3,3,3-pentafluoro-n-propyl, heptafluoro-i-propyl, heptafluoro-n-propyl, 1-bromo-1,1,2,3,3, 3-hexafluoro-2-propyl or the like, and "C1-C4 haloalkyl group" refers to a straight or branched alkyl group having 1 to 4 carbon atoms which is substituted with one or more halogen atoms which may be the same or different, such as 4-fluoro-n-butyl, nonafluoro-n-butyl, nonafluoro-2-butyl or the like in addition to "C1-C3 haloalkyl group", and "C1-C6 haloalkyl group" refers to a straight or branched alkyl group having 1 to 6 carbon atoms which is substituted with one or more halogen atoms which may be the same or different, such as 6,6,6-trifluoro-n-hexyl, nonafluoro-n-butyl, nonafluoro-2-butyl or the like in addition to "C1-C4 haloalkyl group".

The term "C2-C4 alkenyl group" refers to an alkenyl group of 2 to 4 carbon atoms having a double bond in the carbon chain such as vinyl, allyl, 2-butenyl, 3-butenyl or the like, and "C2-C4 haloalkenyl group" refers to a straight or branched alkenyl group of 2 to 4 carbon atoms having a double bond in the carbon chain which is substituted with one or more halogen atoms which may be the same or different, such as 3,3-difluoro-2-propenyl, 3,3-dichloro-2-propenyl, 3,3-dibromo-2-propenyl, 2,3-dibromo-2-propenyl, 4,4-difluoro-3-butenyl, 3,4,4-tribromo-3-butenyl or the like.

The term "C2-C4 alkynyl group" refers to a straight or branched alkynyl group of 2 to 4 carbon atoms having a triple bond in the carbon chain such as propargyl, 1-butyn-3-yl, 1-butyne-3-methyl-3-yl or the like, and "C2-C4 haloalkynyl group" refers to a straight or branched alkenyl group of 2 to 4 carbon atoms having a triple bond in the carbon chain which is substituted with one or more halogen atoms which may be the same or different.

The term "C3-C8 cycloalkyl group" refers to a cycloalkyl group of 3 to 8 carbon atoms having a ring structure, such as cyclopropyl, cyclobutyl, cyclopentyl, 2-methylcyclopentyl, 3-methylcyclopentyl, cyclohexyl, cycloheptyl or the like, and "C3-C8 halocycloalkyl group" refers to a cycloalkyl group of 3 to 8 carbon atoms having a ring structure which is substituted with one or more halogen atoms which may be the same or different, such as 2,2,3,3-tetrafluorocyclobutyl, 2-chlorocyclohexyl, 4-chlorocyclohexyl or the like.

The term "C1-C3 alkoxy group" refers to a straight or branched alkoxy group having 1 to 3 carbon atoms such as methoxy, ethoxy, n-propyloxy, isopropyloxy or the like, "C1-C4 alkoxy group" refers to a straight or branched alkoxy group having 1 to 4 carbon atoms such as 2-butyloxy or the like, in addition to "C1-C3 alkoxy group", "C1-C3 haloalkoxy group" refers to a straight or branched haloalkoxy group having 1 to 3 carbon atoms which is substituted with one or more halogen atoms which may be the same or different, such as trifluoromethoxy, 1,1,2-trifluoroethoxy, 1,1,1,3, 3,3-hexafluoro-2-propyloxy, 2,2,2-trifluoroethoxy, 2-chloroethoxy, 3-fluoro-n-propyloxy, 1,1,2,2-tetrafluoroethoxy, 1,1, 2,3,3,3-hexafluoropropyloxy, or the like, and "C1-C4 haloalkoxy group" refers to a straight or branched haloalkoxy group having 1 to 4 carbon atoms which is substituted with one or more halogen atoms which may be the same or different, such as 1,1,2,3,3,3-hexafluoro-n-propyloxy, 1,1,1,3,3,4, 4,4-octafluoro-2-butyloxy or the like, in addition to "C1-C3 haloalkoxy group."

The term "C1-C3 alkylthio group" refers to a straight or branched alkylthio group having 1 to 3 carbon atoms such as methylthio, ethylthio, n-propylthio, i-propylthio, cyclopropylthio or the like, "C1-C4 alkylthio group" refers to a straight or branched alkylthio group having 1 to 4 carbon atoms such as n-butylthio, i-butylthio, s-butylthio, t-butylthio, cyclopropylmethylthio or the like, in addition to "C1-C3 alkylthio group," "C1-C6 alkylthio group" refers to a straight or branched alkylthio group having 1 to 6 carbon atoms such as n-pentylthio, n-hexylthio or the like, in addition to "C1-C4 alkylthio group."

The term "C1-C3 haloalkylthio group" refers to a straight or branched alkylthio group having 1 to 3 carbon atoms which is substituted with one or more halogen atoms which may be the same or different, such as trifluoromethylthio, pentafluoroethylthio, 2-fluoroethylthio, 2,2,2-trifluoroethylthio, heptafluoro-n-propylthio, heptafluoro-i-propylthio, 1,1,2,2-tetrafluoroethylthio, 1,1,2,3,3,3-hexafluoropropylthio or the like, "C1-C4 haloalkylthio group" refers to a straight or branched alkylthio group having 1 to 4 carbon atoms which is substituted with one or more halogen atoms which may be the same or different, such as nonafluoro-n-butylthio, nonafluoro-s-butylthio, 4,4,4-trifluoro-n-butylthio or the like, in addition to "C1-C3 haloalkylthio group," and "C1-C6 haloalkylthio group" refers to a straight or branched alkylthio group having 1 to 6 carbon atoms which is substituted with one or more halogen atoms which may be the same or different, such as perfluoro-n-pentylthio, perfluoro-n-hexylthio or the like, in addition to "C1-C4 haloalkylthio group."

The term "C1-C3 alkylsulfinyl group" refers to a straight or branched alkylsulfinyl group having 1 to 3 carbon atoms, such as methylsulfinyl, ethylsulfinyl, n-propylsulfinyl, i-propylsulfinyl, cyclopropylsulfinyl or the like, and "C1-C6 alkylsulfinyl group" refers to a straight or branched alkylsulfinyl group having 1 to 6 carbon atoms, such as n-butylsulfinyl, t-butylsulfinyl, n-pentylsulfinyl, n-hexylsulfinyl or the like, in addition to "C1-C3 alkylsulfinyl group."

The term "C1-C3 haloalkylsulfinyl group" refers to a straight or branched alkylsulfinyl group having 1 to 3 carbon atoms which is substituted with one or more halogen atoms which may be the same or different, such as trifluoromethylsulfinyl, pentafluoroethylsulfinyl, 2,2,2-trifluoroethylsulfinyl, heptafluoro-n-propylsulfinyl, heptafluoro-i-propylsulfinyl, 1,1,2,2-tetrafluoroethylsulfinyl, 1,1,2,3,3,3-hexafluoropropylsulfinyl or the like, "C1-C6 haloalkylsulfinyl group" refers to a straight or branched alkylsulfinyl group having 1 to 6 carbon atoms which is substituted with one or more halogen atoms which may be the same or different, such as nonafluoro-n-butylsulfinyl, nonafluoro-s-butylsulfinyl, 4,4,4-trifluoro-n-butylsulfinyl, perfluoro-n-pentylsulfinyl, perfluoro-n-hexylsulfinyl or the like, in addition to "C1-C3 haloalkylsulfinyl group."

The term "C1-C3 alkylsulfonyl group" refers to a straight or branched alkylsulfonyl group having 1 to 3 carbon atoms, such as methylsulfonyl, ethylsulfonyl, n-propylsulfonyl, i-propylsulfonyl, cyclopropylsulfonyl or the like, "C1-C6 alkylsulfonyl group" refers to a straight or branched alkylsulfonyl group having 1 to 6 carbon atoms, such as n-butylsulfonyl, t-butylsulfonyl, n-pentylsulfonyl, n-hexylsulfonyl or the like, in addition to "C1-C3 alkylsulfonyl group."

The term "C1-C3 haloalkylsulfonyl group" refers to a straight or branched alkylsulfonyl group having 1 to 3 carbon atoms which is substituted with one or more halogen atoms which may be the same or different, such as trifluoromethylsulfonyl, pentafluoroethylsulfonyl, 2,2,2-trifluoroethylsulfonyl, heptafluoro-n-propylsulfonyl, heptafluoro-i-propylsulfonyl, 1,1,2,2-tetrafluoroetylsulfonyl, 1,1,2,3,3,3-hexafluoropropylsulfonyl or the like, "C1-C6 haloalkylsulfonyl group" refers to a straight or branched alkylsulfonyl group having 1 to 6 carbon atoms which is substituted with one or more halogen atoms which may be the same or different, such as nonafluoro-n-butylsulfonyl, nonafluoro-s-butylsulfonyl, 4,4,4-trifluoro-n-butylsulfonyl, perfluoro-n-pentylsulfonyl, perfluoro-n-hexylsulfonyl or the like, in addition to "C1-C3 haloalkylsulfonyl group."

The term "arylsulfonyloxy group" refers to an arylsulfonyloxy group of 6 to 14 carbon atoms having an aromatic ring, such as phenylsulfonyloxy, p-toluenesulfonyloxy, 1-naphthylsulfonyloxy, 2-naphthylsulfonyloxy, anthrylsulfonyloxy, phenanthrylsulfonyloxy, acenaphthylenylsulfonyloxy or the like.

The term "C1-C4 alkylamino group" refers to a straight, branched or cyclic alkylamino group having 1 to 4 carbon atoms, such as methylamino, ethylamino, n-propylamino, i-propylamino, n-butylamino, cyclopropylamino or the like, "a di C1-C4 alkylamino group" refers to a straight or branched amino group which is substituted with two alkyl groups having 1 to 4 carbon atoms which may be the same or different, such as dimethylamino, diethylamino, N-ethyl-N-methylamino or the like.

The term "C1-C4 perfluoroalkyl group" refers to a straight or branched alkyl group having 1 to 4 carbon atoms which is all substituted with fluorine atoms, such as trifluoromethyl, pentafluoroethyl, heptafluoro-n-propyl, heptafluoro-i-propyl, nonafluoro-n-butyl, nonafluoro-2-butyl, nonafluoro-i-butyl or the like, and "C2-C6 perfluoroalkyl group" refers to a straight or branched alkyl group having 2 to 6 carbon atoms which is all substituted with fluorine atoms, such as pentafluoroethyl, heptafluoro-n-propyl, heptafluoro-i-propyl, nonafluoro-n-butyl, nonafluoro-2-butyl, nonafluoro-i-butyl, undecafluoro-n-pentyl, tridecafluoro-n-hexyl or the like.

The term "C1-C6 perfluoroalkylthio group" refers to a straight or branched alkylthio group having 1 to 6 carbon atoms which is all substituted with fluorine atoms, such as trifluoromethylthio, pentafluoroethylthio, heptafluoro-n-propylthio, heptafluoro-i-propylthio, nonafluoro-n-butylthio, nonafluoro-2-butylthio, nonafluoro-i-butylthio, undecafluoro-n-pentylthio, tridecafluoro-n-hexylthio or the like.

The term "C1-C6 perfluoroalkylsulfinyl group" refers to a straight or branched alkylsulfinyl group having 1 to 6 carbon atoms which is all substituted with fluorine atoms, such as trifluoromethylsulfinyl, pentafluoroethylsulfinyl, heptafluoro-n-propylsulfinyl, heptafluoro-i-propylsulfinyl, nonafluoro-n-butylsulfinyl, nonafluoro-2-butylsulfinyl, nonafluoro-i-butylsulfinyl, undecafluoro-n-pentylsulfinyl, tridecafluoro-n-hexylsulfinyl or the like.

The term "C1-C6 perfluoroalkylsulfonyl group" refers to a straight or branched alkylsulfonyl group having 1 to 6 carbon atoms which is all substituted with fluorine atoms, such as trifluoromethylsulfonyl, pentafluoroethylsulfonyl, heptafluoro-n-propylsulfonyl, heptafluoro-i-propylsulfonyl, nonafluoro-n-butylsulfonyl, nonafluoro-2-butylsulfonyl, nonafluoro-1-butylsulfonyl, undecafluoro-n-pentylsulfonyl, tridecafluoro-n-hexylsulfonyl or the like.

The term "alkylsilyl group" refers to a straight or branched alkyl chain having silicon atom, such as methylsilyl group, trimethylsilyl group, etylsilyl group or the like.

The compound represented by the general formula (1) or (5) of the present invention contains one or more asymmetric carbon atoms or asymmetric centers in its structural formula in some cases and has two or more optical isomers in some cases. The present invention also includes all of the respective optical isomers and mixtures consisting of these isomers in any ratio. Furthermore, the compound represented by the general formula (1) or (5) of the present invention has two or more geometrical isomers derived from a carbon-carbon double bond in its structural formula in some cases. The present invention also includes all of the respective geometrical isomers and mixtures consisting of these isomers in any ratio.

Preferable examples of the substituents or atoms in the compounds represented by the general formula (1) and the like of the present invention are listed below.

$A_1$ is preferably a carbon atom, a nitrogen atom or an oxidized nitrogen atom and at the same time, $A_2$, $A_3$ and $A_4$ are all carbon atoms, and more preferably all of $A_1$, $A_2$, $A_3$ and $A_4$ are carbon atoms, in $A_1$, $A_2$, $A_3$, $A_4$.

$R_1$ is preferably a hydrogen atom or a C1-C4 alkyl group, and more preferably a hydrogen atom, a methyl group or an ethyl group.

$R_2$ is preferably a hydrogen atom or a C1-C4 alkyl group, and more preferably a hydrogen atom, a methyl group or an ethyl group.

$G_1$ and $G_2$ are all preferably oxygen atoms.

n is preferably 0, 1 or 2, and more preferably 0 or 1.

X is preferably a hydrogen atom or a halogen atom, and more preferably a hydrogen atom or a fluorine atom.

$Q_1$ is preferably a phenyl group, or a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group and an acetylamino group, a pyridyl group, or a substituted pyridyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino groups, a cyano group, a nitro group, a hydroxy group, a C1-C4 alkylcarbonyl group, a C1-C4 alkylcarbonyloxy group, a C1-C4 alkoxycarbonyl group and an acetylamino group.

$Q_1$ is more preferably a phenyl group, a substituted phenyl group having 1 to 3 substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group or a nitro group, a pyridyl group, or a pyridyl group having one or two substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group or a nitro group.

$Q_2$ is preferably a substituted phenyl group or a substituted pyridyl group represented by the general formula (2), (3) or (4).

When $Q_2$ is a substituted phenyl group represented by the general formula (2), (i)

$Y_1$ or $Y_5$, which may be the same or different, is preferably a fluorine atom, a chlorine atom, a bromine atom, an iodine atom, a methyl group, an ethyl group, a n-propyl group, a i-propyl group, a n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, a cyano group, $Y_2$ or $Y_4$ is preferably a hydrogen atom, $Y_3$ is preferably a trifluoromethyl group, a pentafluorosulfanyl group, a 1,1,2,3,3,3-hexafluoropropoxy group, a 2,2,2-trifluoro-1-trifluoromethylethoxy group, a 2-trifluoromethoxy-1,1,2-trifluoroethoxy group, a 1,1,2,2-tetrafluoroethoxy group, a 1,1,2,3,3,3-hexafluoropropylthio group, a 2,2,2-trifluoro-1-trifluoromethylethylthio group, a 2-trifluoromethoxy-1,1,2-trifluoroethylthio group, a 1,1,2,2-tetrafluoroethylthio group, a 1,1,2,3,3,3-hexafluoro propylsulfinyl group, a 2,2,2-trifluoro-1-trifluoromethylethylsulfinyl group, a 2-trifluoromethoxy-1,1,2-trifluoroethylsulfinyl group, a 1,1,2,2-tetrafluoroethylsulfinyl group, a 1,1,2,3,3,3-hexafluoro propylsulfonyl group, a 2,2,2-trifluoro-1-trifluoromethylethylsulfonyl group, a 2-trifluoromethoxy-1,1,2-trifluoroethylsulfonyl group, a 1,1,2,2-tetrafluoroethylsulfonyl group, or (ii)

$Y_1$ is preferably a hydroxymethyl group, a methoxymethyl group, a methylthiomethyl group, a methylsulfinylmethyl group, a methylsulfonylmethyl group, an acetyl group, a trifluoroacetyl group, an acetoxy group, an ethylcarbonyloxy group, trifluoroacetoxy group, a methoxycarbonyl group, an ethoxycarbonyl group, an acetylamino group, a trifluoroacetylamino group, a methylsulfonyloxy group, a trifluoromethylsulfonyloxy group, $Y_5$ is preferably a fluorine atom, a chlorine atom, a bromine atom, an iodine atom, a methyl group, an ethyl group, n-propyl group, i-propyl group, n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, a cyano group, $Y_2$ or $Y_4$ is preferably a hydrogen atom, $Y_3$ is preferably a pentafluoroethyl group, a heptafluoro-n-propyl group, a heptafluoro-i-propyl group, a nonafluoro-n-butyl group, a nonafluoro-2-butyl group, a nonafluoro-i-butyl group, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a trifluoromethylsulfonyl, a pentafluoroethylsulfonyl, a heptafluoro-n-propylsulfonyl, a heptafluoro-i-propylsulfonyl, a nonafluoro-n-butylsulfonyl, a nonafluoro-2-butylsulfonyl, a trifluoromethyl group, a 1,1,2,3,3,3-hexafluoropropoxy group, a 2,2,2-trifluoro-1-trifluoromethylethoxy group, a 2-trifluoromethoxy-1,1,2-trifluoroethoxy group, 1,1,2,2-tetrafluoroethoxy group, a 1,1,2,3,3,3-hexafluoropropylthio group, a 2,2,2-trifluoro-1-trifluoromethylethylthio group, a 2-trifluoromethoxy-1,1,2-trifluoroethylthio group, a 1,1,2,2-tetrafluoroethylthio group, a 1,1,2,3,3,3-hexafluoropropylsulfinyl group, a 2,2,2-trifluoro-1-trifluoromethylethylsulfinyl group, a 2-trifluoromethoxy-1,1,2-trifluoroethylsulfinyl group, a 1,1,2,2-tetrafluoroethylsulfinyl group, a 1,1,2,3,3,3-hexafluoropropylsulfonyl group, a 2,2,2-trifluoro-1-trifluoromethylethylsulfonyl group, a 2-trifluoromethoxy-1,1,2-trifluoroethylsulfonyl group, a 1,1,2,2-tetrafluoroethylsulfonyl group, or (iii)

$Y_1$ is preferably a trifluoromethoxy group, a pentafluoroethyl group, a trifluoromethylthio group, a pentafluoroethylthio group, a heptafluoropropylthio group, a heptafluoro-iso-propylthio group, a trifluoromethylsulfinyl group, a pentafluoroethylsulfinyl group, a heptafluoropropylsulfinyl group, a heptafluoro-iso-propylsulfinyl group, a trifluoromethylsulfonyl group, a pentafluoroethylsulfonyl group, a heptafluoropropylsulfonyl group, a heptafluoro-iso-propylsulfonyl group, $Y_5$ is preferably a fluorine atom, a chlorine atom, a bromine atom, an iodine atom, a methyl group, an ethyl group, a trifluoromethoxy group, a pentafluoroethyl group, a trifluoromethylthio group, a pentafluoroethylthio group, a heptafluoropropylthio group, a heptafluoro-iso-propylthio group, a trifluoromethylsulfinyl group, a pentafluoroethylsulfinyl group, a heptafluoropropylsulfinyl group, a heptafluoro-iso-propylsulfinyl group, a trifluoromethylsulfonyl group, a pentafluoroethylsulfonyl group, a heptafluoropropylsulfonyl group, a heptafluoro-iso-propylsulfonyl group, $Y_2$ or $Y_4$ is preferably a hydrogen atom, $Y_3$ is preferably a fluorine atom, a chlorine atom, a bromine atom, an iodine atom.

When $Q_2$ is a substituted phenyl group represented by the general formula (4), $Y_1$ or $Y_5$, which may be the same or different, is preferably a fluorine atom, a chlorine atom, a bromine atom, an iodine atom, a methyl group, an ethyl group, a n-propyl group, a i-propyl group, a n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, a cyano group, $Y_2$ or $Y_4$ is preferably a hydrogen atom, Ra is a bromodifluoro group and Rb is a fluorine atom and Rc is a trifluoromethyl group, or Ra is a chlorodifluoro group and Rb is a hydroxyl group and Rc is a chlorodifluoromethyl group.

The compounds of present invention represented the general formula (1) may contain the following compounds I to VIII. These compounds may is preferably used from the viewpoint of control effect on the insect pests.

(The Compound I)

The compound I represented by the general formula (1), wherein, in the formula, $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfonyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (2),

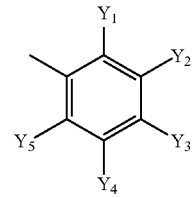

(2)

wherein, in the formula, $Y_1$ and $Y_5$ may be the same or different and represent a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a trifluoromethyl group, a C1-C6 perfluoroalkoxy group, a pentafluorosulfanyl group, a substituted C1-C6 haloalkoxy group having one or more substituents which may be the same or different and are selected from a hydrogen atom, a hydroxy group, a chlorine atom, a bromine atom, an iodine atom, a C1-C6 alkoxy group or a C1-C6 haloalkoxy group, a substituted C1-C6 haloalkylthio group having one or more substituents which may be the same or different and are selected from a hydrogen atom, a hydroxy group, a chlorine atom, a bromine atom, an iodine atom, a C1-C6 alkoxy group or a C1-C6 haloalkoxy group, a substituted C1-C6 haloalkylsulfinyl group having one or more substituents which may be the same or different and are selected from a hydrogen atom, a hydroxy group, a chlorine atom, a bromine atom, an iodine atom, a C1-C6 alkoxy group or a C1-C6 haloalkoxy group, or a substituted C1-C6 haloalkylsulfonyl group having one or more substituents which may be the same or different and are selected from a hydrogen atom, a hydroxy group, a chlorine atom, a bromine atom, an iodine atom, a C1-C6 alkoxy group or a C1-C6 haloalkoxy group.

(The Compound II)

The compound II represented by the general formula (1), wherein, in the formula, $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (2),

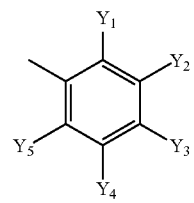

(2)

wherein, in the formula, $Y_1$ represents a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, or a C1-C4 alkyl group having one or more substituents which may be the same or different and are selected from halogen atom, C1-C3 alkoxy group, C1-C3 haloalkoxy group, C1-C3 alkylthio group, C1-C3 haloalkylthio group, C1-C3 alkylsulfinyl group, C1-C3 haloalkylsulfinyl group, C1-C3 alkylsulfonyl group, C1-C3 haloalkylsulfonyl group, C1-C4 alkylamino group, a di C1-C4 alkylamino group, cyano group, nitro group, hydroxy group, C1-C4 alkylcarbonyl group, C1-C4 haloalkylcarbonyl group, C1-C4 alkylcarbonyloxy group, C1-C4 haloalkylcarbonyloxy group, C1-C4 alkoxycarbonyl group, C1-C4 haloalkoxycarbonyl group, C1-C4 alkylcarbonylamino group, C1-C4 haloalkylcarbonylamino group, C1-C4 alkylsulfonyloxy group, C1-C4 haloalkylsulfonyloxy group, arylsulfonyloxy group, pentafluorosulfanyl group or alkylsilyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a C1-C4 haloalkoxy group, a C2-C6 perfluoroalkyl group, a C1-C6 perfluoroalkylthio group, a C1-C6 perfluoroalkylsulfinyl group, a C1-C6 perfluoroalkylsulfonyl group, a trifluoromethyl group, a C1-C6 perfluoroalkoxy group, a pentafluorosulfanyl group, a substituted C1-C6 haloalkoxy group having at least one or more substituents which may be the same or different and are selected from hydrogen atom, hydroxy group, chlorine atom, bromine atom, iodine atoms, C1-C6 alkoxy groups or C1-C6 haloalkoxy group, a substituted C1-C6 haloalkylthio group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group, a substituted C1-C6 haloalkylsulfinyl group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group, or a substituted C1-C6 haloalkylsulfonyl group having at least one or more substituents which may be the same or different and are selected from a hydrogen atom, a hydroxy group, a chlorine atom, a bromine atom, an iodine atom, a C1-C6 alkoxy group or a C1-C6 haloalkoxy group.

(The Compound III)

The compound III represented by the general formula (1), wherein, in the formula, $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3] dioxolyl group, a tetrahydropyranyl group or a dihydropyranyl group.); and $Q_2$ is represented by the general formula (2),

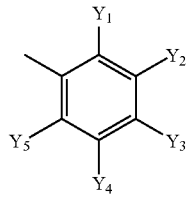

(2)

wherein, in the formula, $Y_1$ represents a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group or a C1-C6 haloalkylsulfonyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a halogen atom.

(The Compound IV)

The compound IV represented by the general formula (1), wherein, in the formula, $A_1$ represents a carbon atom, a nitrogen atom or an oxidized nitrogen atom;

$A_2$, $A_3$ and $A_4$ represent a carbon atom;

$R_1$ and $R_2$ mutually independently represent a hydrogen atom or a C1-C4 alkyl group;

$G_1$ and $G_2$ mutually independently represent an oxygen atom or a sulfur atom;

Xs may be the same or different and are a hydrogen atom, a halogen atom or a trifluoromethyl group;

n represents an integer of 0 to 4;

$Q_1$ represents a phenyl group, a substituted phenyl group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.), or a substituted heterocyclic group having one or more substituents which may be the same or different and are selected from a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group (The heterocyclic group herein represents a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group or a dihydropyranyl group.); and $Q_2$ is represented by the general formula (4),

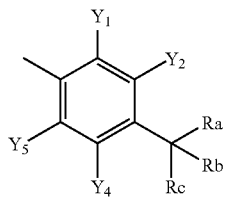

(4)

wherein, in the formula, $Y_1$ and $Y_5$ may be the same or different and represent a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group;

Ra represents a halogen atom or a hydroxy group; and

Rb and Rc may each independently represent a halogen atom or a C1-C6 haloalkyl group, and at least either Rb or Rc has one or more hydrogen atoms, hydroxy groups, chlorine atoms, bromine atoms or iodine atoms included thereto.

(The Compounds V to VIII)

The compounds V to VIII has a C1-C4 alkyl group at least one of $R_1$ and $R_2$ in each compounds I to IV represented by the general formula (1).

The compounds represented by the general formula (1) and (5) can be prepared according to methods of preparation methods 1 to 11 as described below. Typical preparation methods of the compound of the present invention are illustrated below. The compound of the present invention can be prepared according to the methods, but the preparation method paths are not restricted to the following preparation methods.

In the general formula represented by the following preparation methods, $Q_2$ represents the meanings as described in [1], the general formula (2) or the general formula (3),

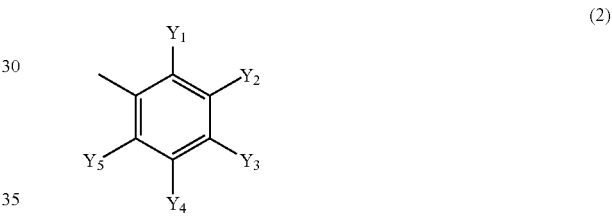

(2)

wherein, in the formula, $Y_1, Y_2, Y_3, Y_4$ and $Y_5$ represent the same as those in [1], or

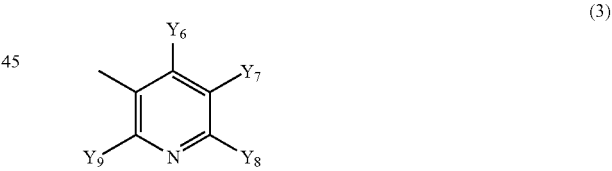

(3)

wherein, in the formula, $Y_6, Y_7, Y_8$ and $Y_9$ represent the same as those in [1].

Preparation Method 1

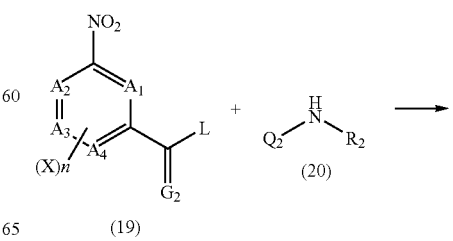

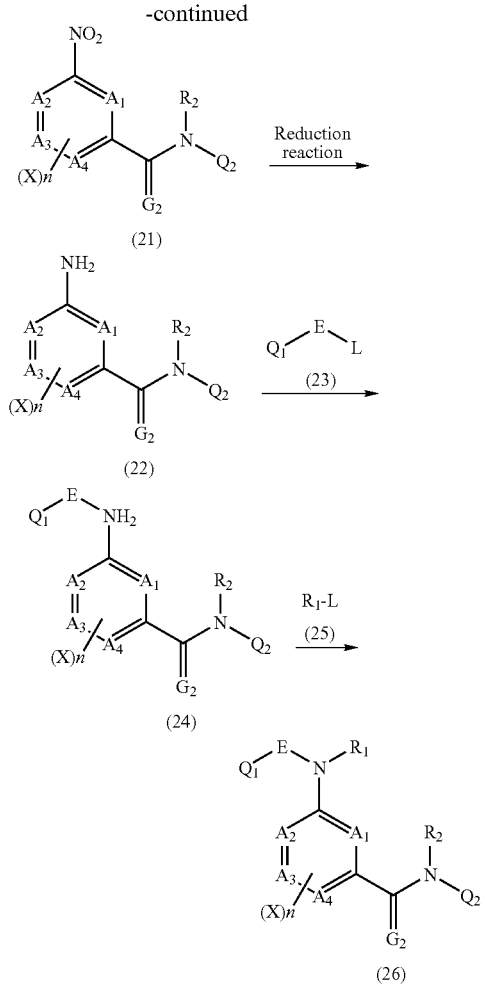

wherein, in the formula, E represents —C(=G₁)- or —SO₂—; A₁, A₂, A₃, A₄, G₁, G₂, R₁, R₂, X, n, Q₁ and Q₂ represent the same as those in [1]; and L represents a functional group having a leaving-group ability such as a halogen atom, a hydroxyl group or the like.

1-(i): General Formula (19)+General Formula (20)→General Formula (21)

By reacting an m-nitroaromatic carboxylic acid derivative having a leaving group represented by the general formula (19) with an aromatic amine derivative represented by the general formula (20) in a solvent or without a solvent, an aromatic carboxylic acid derivative having a nitro group represented by the general formula (21) can be prepared. In the process, a base can also be used.

Solvents may not remarkably hinder the progress of the reaction and examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitrites such as acetonitrile and the like; and inert solvents such as 1,3-dimethyl-2-imidazolidinone and the like. These solvents can be used singly or in combination of 2 or more kinds.

Furthermore, examples of the base include organic bases such as triethylamine, tri-n-butylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as di-potassium monohydrogen phosphate, tri-sodium phosphate and the like; alkali metal hydrides such as sodium hydride and the like; and alkali metal alcoholates such as sodium methoxide, sodium ethoxide and the like. These bases may be suitably selected in the range of 0.01 to 5 mole equivalents based on the compound represented by the general formula (19) and used accordingly.

The reaction temperature may be suitably selected in the range of −20° C. to the reflux temperature of a solvent in use, while the reaction time may be properly selected in the range of several minutes to 96 hours.

Of the compounds represented by the general formula (19), an aromatic carboxylic acid halide derivative can be easily prepared from an aromatic carboxylic acid according to a usual method using a halogenating agent. Examples of the halogenating agent include thionyl chloride, thionyl bromide, phosphorus oxychloride, oxalyl chloride, phosphorus trichloride and the like.

On the other hand, the compound represented by the general formula (21) can be prepared from the m-nitroaromatic carboxylic acid derivative and the compound represented by the general formula (20) without using a halogenating agent. As a method thereof, an additive such as 1-hydroxybenzotriazole and the like is suitably used according to a method, as described, for example, in Chem. Ber. P. 788 (1970) and a method employing a condensation agent using N,N'-dicyclohexylcarbodiimide can be exemplified. Other condensation agents to be used in this case include, for example, 1-ethyl-3-(3-dimethylaminopropyl)carbodiimide, 1,1'-carbonylbis-1H-imidazole and the like.

Furthermore, as other method for preparing the compound represented by the general formula (21), a mixed anhydride procedure using chloroformates can be cited. Also, the compound represented by the general formula (21) can be prepared according to a method as described in J. Am. Chem. Soc. P. 5012 (1967). Examples of chloroformates to be used in this case include isobutyl chloroformate, isopropyl chloroformate and the like. In addition to chloroformateS, diethylacetyl chloride, trimethylacetyl chloride and the like can be cited.

Both the method using a condensation agent and mixed anhydride procedure are not restricted to the solvent, reaction temperature and reaction time as described in the above documents, and an inert solvent which does not remarkably hinder the suitable progress of the reaction may be used. The reaction temperature and reaction time may be suitably selected as the reaction proceeds.

1-(ii): General Formula (21)→General Formula (22)

An aromatic carboxylic acid derivative having a nitro group represented by the general formula (21) can be made into an aromatic carboxylic acid amide derivative having an amino group represented by the general formula (22) by the reduction reaction. As the reduction reaction, a method employing the hydrogenation and a method employing a metallic compound (for example, tin(II)chloride (anhydride), iron powder, zinc powder and the like) can be cited.

The former method can be carried out in a proper solvent in the presence of a catalyst, in an atmospheric pressure or a increased pressure, in a hydrogen atmosphere. Such the catalyst includes, for example, palladium catalysts such as palladium carbon and the like, nickel catalysts such as Raney nickel and the like, cobalt catalysts, ruthenium catalysts, rhodium catalysts, platinum catalysts and the like. The solvent includes, for example, water; alcohols such as methanol, ethanol and the like; aromatic hydrocarbons such as benzene, toluene and the like; chained ethers or cyclic ethers such as ether, dioxane, tetrahydrofuran and the like; and esters such as ethyl acetate and the like. The pressure may be suitably selected in the range of 0.1 to 10 MPa, the reaction temperature may be suitably selected in the range of −20° C. to the reflux temperature of a solvent in use, and the reaction time may be properly selected in the range of several minutes to 96 hours. The compound of the general formula (22) can be more effectively prepared.

As the latter method, a method employing tin(II)chloride (anhydride) as a metallic compound according to the conditions as described in "Organic Syntheses" Coll. Vol. III P. 453 can be cited.

1-(iii): General Formula (22)+General Formula (23) →General Formula (24)

By reacting an aromatic carboxylic acid amide derivative having an amino group represented by the general formula (22) with a compound represented by the general formula (23) in a solvent, the compound represented by the general formula (24) of the present invention can be prepared. In this process, a base can also be used.

Solvents may not remarkably hinder the progress of the reaction and examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitriles such as acetonitrile and the like; and inert solvents such as 1,3-dimethyl-2-imidazolidinone and the like. These solvents can be used singly or in combination of 2 or more kinds.

Furthermore, examples of the base include organic bases such as triethylamine, tri-n-butylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as di-potassium monohydrogen phosphate, tri-sodium phosphate and the like; alkali metal hydrides such as sodium hydride and the like; and alkali metal alcoholates such as sodium methoxide, sodium ethoxide and the like. These bases may be suitably selected in the range of 0.01 to 5 mole equivalents based on the compound represented by the general formula (22) and used accordingly. The reaction temperature may be suitably selected in the range of −20° C. to the reflux temperature of a solvent in use, while the reaction time may be properly selected in the range of several minutes to 96 hours. Furthermore, a method employing a condensation agent as described in 1-(i) and a mixed anhydride procedure can also be used.

1-(iv): General Formula (24)+General Formula (25) →General Formula (26)

By reacting a compound represented by the general formula (24) with an alkyl compound having a leaving group represented by the general formula (25) in a solvent or without a solvent, a compound represented by the general formula (26) of the present invention can be prepared. Examples of the compound represented by the general formula (25) include alkyl halides such as methyl iodide, ethyl iodide, n-propyl bromide and the like; halogenated acyls such as acetyl chloride and the like. Furthermore, in this process, a suitable base or solvent can be used. As the base or solvent, the bases or solvents cited in 1-(i) can be used. The reaction temperature and reaction time cited in 1-(i) can be applied.

Furthermore, the compound represented by the general formula (26) can also be prepared by a method comprising reacting an alkylating agent such as dimethyl sulfate, diethyl sulfate or the like, instead of the compound represented by the general formula (25), with the compound represented by the general formula (24).

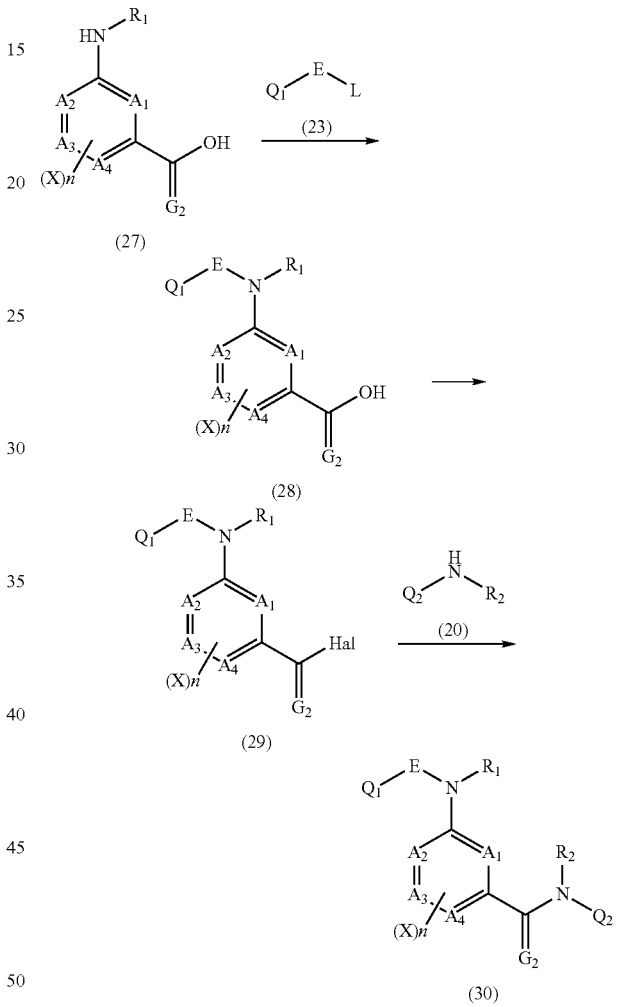

Preparation Method 2 wherein, in the formula, E represents —C(=G$_1$)- or —SO$_2$—; A$_1$, A$_2$, A$_3$, A$_4$, G$_1$, G$_2$, R$_1$, R$_2$, X, n, Q$_1$ and Q$_2$ represent the same as those in [1]; L represents a functional group having a leaving-group ability such as a halogen atom, a hydroxyl group or the like; and Hal represents a halogen atom.

2-(i): General Formula (27)+General Formula (23)→General Formula (28)

By reacting a carboxylic acids having an amino group represented by the general formula (27) as a starting material with a compound represented by the general formula (23) in accordance with the conditions described in 1-(i), carboxylic acids having an acylamino group represented by the general formula (28) can be prepared.

2-(ii): General Formula (28)→General Formula (29)

A compound represented by the general formula (29) can be prepared by a known usual method comprising reacting a compound represented by the general formula (28) with thionyl chloride, oxalyl chloride, phosgene, phosphorus oxychloride, phosphorus pentachloride, phosphorus trichloride, thionyl bromide, phosphorus tribromide, diethylaminosulfur trifluoride or the like.

2-(iii): General Formula (29)+General Formula (20) →General Formula (30)

By reacting a compound represented by the general formula (29) with a compound represented by the general formula (20) according to the conditions described in 1-(i), a compound represented by the general formula (30) can be prepared.

2-(iv): General Formula (28)+General Formula (20) →General Formula (30)

By reacting a compound represented by the general formula (28) with a compound represented by the general formula (20) according to the conditions using a condensation agent or a mixed anhydride procedure as described in 1-(i), a compound represented by the general formula (30) can be prepared.

formula (32) can be prepared. A solvent, reaction temperature and the like are not restricted to those described in the documents.

3-(ii): General Formula (32)+General Formula (23) →General Formula (33)

By reacting a compound represented by the general formula (32) with a compound represented by the general formula (23) according to the conditions as described in 1-(i), a compound represented by the general formula (33) can be prepared.

Preparation Method 4

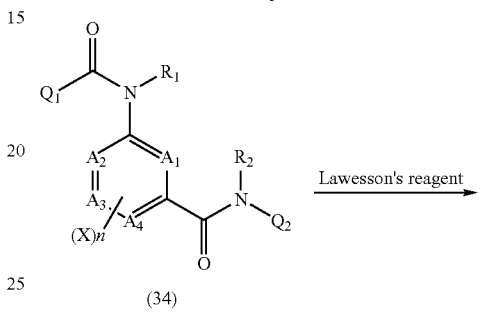

(34)

Preparation Method 3

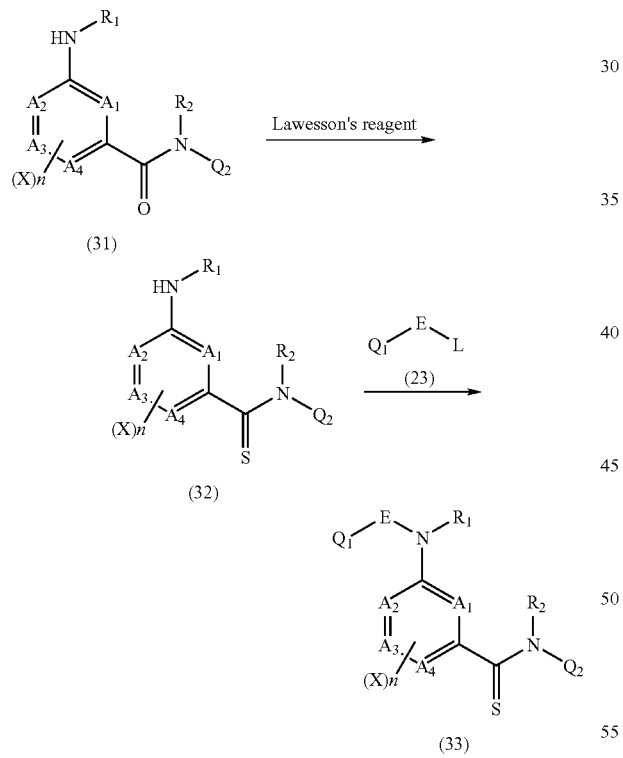

wherein, in the formula, E represents —C(=$G_1$)- or —$SO_2$—; $A_1$, $A_2$, $A_3$, $A_4$, $G_1$, $G_2$, $R_1$, $R_2$, X, n, $Q_1$ and $Q_2$ represent the same as those in [1]; and L represents a functional group having a leaving-group ability such as a halogen atom, a hydroxyl group or the like.

3-(i) General Formula (31)→General Formula (32)

By reacting a compound represented by the general formula (31) with a Lawesson's reagent according to the known conditions described in Synthesis p. 463 (1993), Synthesis p. 829 (1984) or the like, a compound represented by the general wherein, in the formula, $A_1$, $A_2$, $A_3$, $A_4$, $R_1$, $R_2$, X, n, $Q_1$ and $Q_2$ represent the same as those in [1].

Compounds represented by the general formulae (35) and (36) can be prepared from a compound represented by the general formula (34) according to the conditions as described in 3-(i). A solvent, reaction temperature and the like are not restricted to those described in the documents. These two compounds can be easily separated and purified by a known method of separation and purification technique such as silica gel column chromatography and the like.

Preparation Method 5

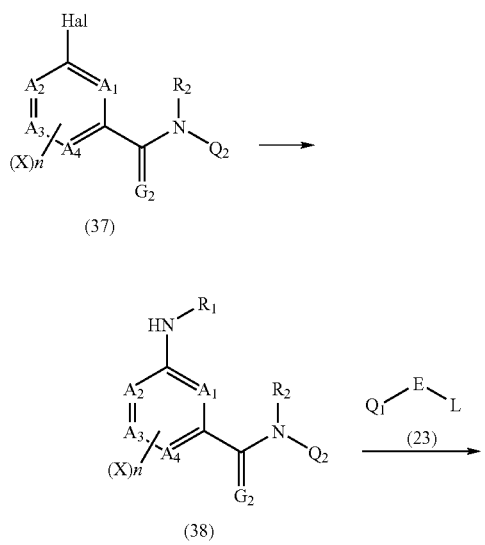

5-(1): General Formula (37)→General Formula (38)

A compound represented by the general formula (38) can be prepared by carrying out an amination reaction using ammonia according to the conditions described, for example, in J. Org. Chem. p. 280 (1958). The conditions such as a reaction solvent or the like are not restricted to those in the literature, and an inert solvent which does not remarkably hinder the proper progress of the reaction may be used. The reaction temperature and reaction time may be suitably selected as the reaction proceeds. Furthermore, examples of the amination agent include methylamine, ethylamine or the like, in addition to ammonia.

5-(ii): General Formula (38)+General Formula (23) →General Formula (39)

By reacting a compound represented by the general formula (38) with a compound represented by the general formula (23) according to the conditions described in 1-(i), a compound represented by the general formula (39) can be prepared.

Preparation Method 6

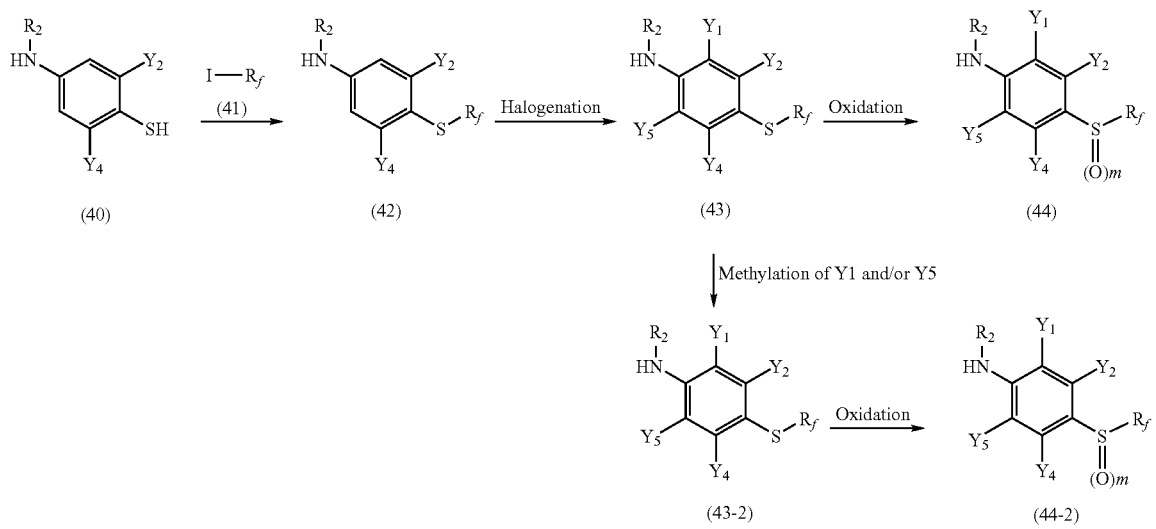

wherein, in the formula, $R_2$, $Y_2$ and $Y_4$ represents the same as those in [1]; $Y_1$ and $Y_5$ each represent a hydrogen atom, a methyl group, a chlorine atom, a bromine atom or an iodine atom; $R_f$ represents a C1-C6 perfluoroalkyl group; and m represents 1 or 2.

6-(i): General Formula (40)+General Formula (41)→General Formula (42)

By reacting aminothiophenols represented by the general formula (40) with haloalkyl iodide represented by the general formula (41) in accordance with a method described in J. Fluorine Chem. p. 207 (1994), a compound represented by the general formula (42) can be prepared.

Examples of the haloalkyl iodide represented by the general formula (41) include trifluoromethyl iodide, pentafluoroethyl iodide, heptafluoro-n-propyl iodide, heptafluoroisopropyl iodide, nonafluoro-n-butyl iodide, nonafluoroisobutyl iodide and the like. These may be suitably selected in the range of 1 to 10 mole equivalents, based on the compound represented by the general formula (40).

-continued

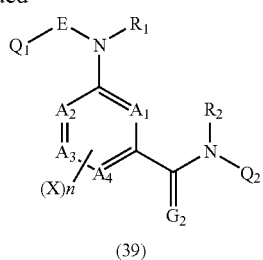

wherein, in the formula, $A_1$, $A_2$, $A_3$, $A_4$, $G_1$, $G_2$, $R_1$, $R_2$, X, n, $Q_1$ and $Q_2$ represent the same as those in [1]; and L represents a functional group having a leaving-group ability such as a halogen atom, a hydroxyl group or the like.

The solvent to be used in the process is not restricted to solvents described in the above documents and may not remarkably hinder the progress of the reaction. Examples thereof include water; aromatic hydrocarbons such as benzene, toluene, xylene and the like; halogenated hydrocarbons such as dichloromethane, chloroform, carbon tetrachloride and the like, chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitrites such as acetonitrile and the like; and inert solvents such as 1,3-dimethyl-2-imidazolidinone, hexamethylphosphoric triamide and the like. These solvents can be used singly or in combination of 2 or more kinds. Particularly preferable is a polar solvent. The reaction temperature may be suitably selected in the range of −20° C. to the reflux temperature of a solvent in use, while the reaction time may be properly selected in the range of several minutes to 96 hours.

6-(ii): General Formula (42)→General Formula (43)

A compound represented by the general formula (43) can be prepared by using a suitable halogenating agent. For example, a method as described in Synth. Commun. p. 1261 (1989) can be cited.

Examples of the halogenating agent include chlorine, bromine, iodine, N-chlorosuccinic acid imide, N-bromosuccinic acid imide, N-iodinesuccinic acid imide and the like. These may be suitably used in the range of 1 to 10 mole equivalents, based on a compound represented by the general formula (42).

In the process, a solvent can be used, but it is not restricted to solvents described in the above documents and may not remarkably hinder the progress of the reaction. Examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitrites such as acetonitrile and the like; and inert solvents such as 1,3-dimethyl-2-imidazolidinone, hexamethylphosphoric triamide and the like. These solvents can be used singly or in combination of 2 or more kinds. Particularly preferable is a polar solvent. The reaction temperature may be suitably selected in the range of −20° C. to the reflux temperature of a solvent in use, while the reaction time may be properly selected in the range of several minutes to 96 hours.

6-(iii): General Formula (43)→General Formula (44)

A compound represented by the general formula (44) can be prepared by using a suitable oxidizing agent. For example, a method described in Tetrahedron Lett. p. 4955 (1994) can be cited.

Examples of the oxidizing agent include organic peroxides such as m-chloroperbenzoic acid and the like, sodium metaperiodate, hydrogen peroxide, ozone, selenium dioxide, chromic acid, dinitrogen tetraoxide, acyl nitrate, iodine, bromine, N-bromosuccinic acid imide, iodosylbenzyl, t-butyl hypochlorite and the like.

The solvent to be used in the process is not restricted to solvents described in the above documents and may not remarkably hinder the progress of the reaction. These solvents can be used singly or in combination of 2 or more kinds. Particularly preferable is a polar solvent. The reaction temperature may be suitably selected in the range of −20° C. to the reflux temperature of a solvent in use, while the reaction time may be properly selected in the range of several minutes to 96 hours.

6-(iv): General Formula (43)→General Formula (43-2)

A compound represented by the general formula (43-2) (wherein, in the formula, any one of $Y_1$ and $Y_5$ must represent a methyl group) can be prepared from a compound represented by the general formula (43) by using a suitable methylating agent. In the process, for example, a method described in Tetrahedron Lett. p. 6237 (2000) can be cited.

6-(v): General Formula (43-2)→General Formula (44-2)

A compound represented by the general formula (44-2) (wherein, in the formula, any one of $Y_1$ and $Y_5$ must represent a methyl group) can be prepared according to a method described in preparation method 6-(iii).

Furthermore, the compound of the present invention can be prepared by suitably selecting a preparation method illustrated in the present invention using an aniline derivative represented by the general formulae (43), (44), (43-2), (44-2).

According to the same method, it is possible to prepare a compound represented general formula (1) of present invention, wherein, in the general formula (2), $Y_1, Y_2, Y_4$ and $Y_5$ are a C1-C6 perfluoroalkylthio group, a C1-C6 perfluoroalkylsulfinyl group or a C1-C6 perfluoroalkylsulfonyl group.

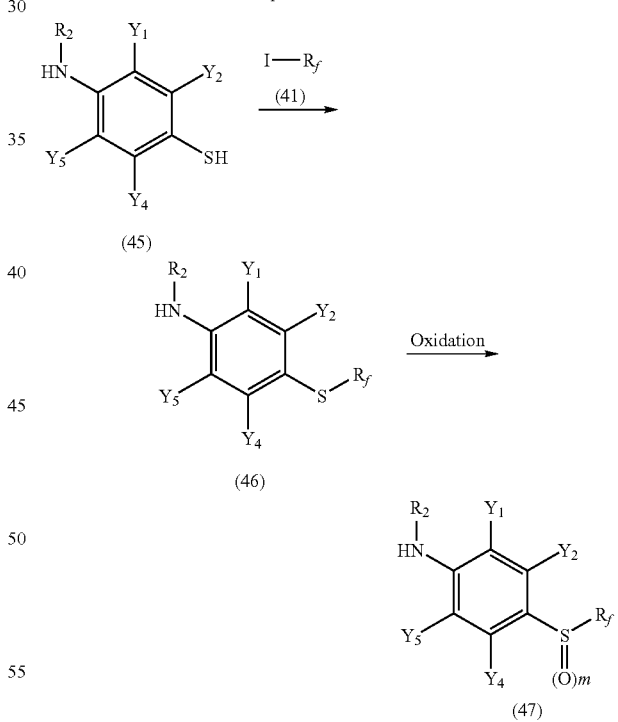

Preparation Method 7 wherein, in the formula, $R_2, Y_2$ and $Y_4$ represents the same as those in [1]; $Y_1$ and $Y_5$ each represent a hydrogen atom, a methyl group, a chlorine atom, a bromine atom or an iodine atom; $R_f$ represents a C1-C6 perfluoroalkyl group; and m represents 1 or 2.

An aniline derivative represented by the general formula (47) can be prepared using a compound represented by the general formula (45) as a starting raw material according to the preparation method 6. Furthermore, by suitably selecting a preparation method represented in the present invention, the compound of the present invention can be prepared.

According to the same method, it is possible to prepare a compound represented general formula (1) of present invention, wherein, in the general formula (2), $Y_1, Y_2, Y_4$ and $Y_5$ are a C1-C6 perfluoroalkylthio group, a C1-C6 perfluoroalkylsulfinyl group or a C1-C6 perfluoroalkylsulfonyl group.

Preparation Method 8

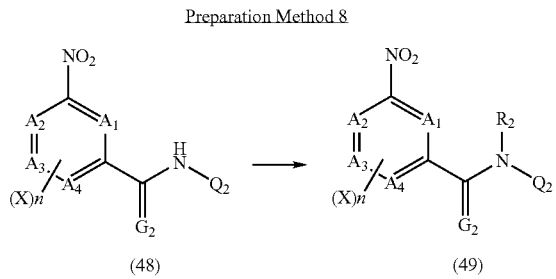

(48)        (49)

wherein, in the formula, $A_1, A_2, A_3, A_4, X, n, G_2, R_2,$ and $Q_2$ represent the same as those in [1].

By reacting a compound represented by the general formula (48) with a reactant using a base in a solvent, a compound represented by the general formula (49) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as methanol, ethanol and the like; and solvents such as 1,3-dimethyl-2-imidazolidinone, sulfolane, dimethylsulfoxide; water and the like. These solvents can be used singly or in combination of 2 or more kinds.

Examples of the base include organic bases such as triethylamine, tributylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as potassium mono-hydrogen phosphate, tri-sodium phosphate and the like; alkali metal hydrides such as sodium hydride and the like; alkali metal alkoxides such as sodium methoxide, sodium ethoxide and the like; organolithiums such as n-butyl lithium and the like; and Grignard reagents such as ethyl magnesium bromide and the like.

These bases may be suitably selected in the range of 0.01 to 5 mole equivalents based on the compound represented by the general formula (48) or may be used as a solvent.

Examples of the reactant include halogenated alkyls such as methyl iodide, ethyl bromide, trifluoromethyl iodide, 2,2,2-trifluoroethyl iodide and the like; halogenated allyls such as allyl iodide and the like; halogenated propargyls such as propargyl bromide and the like; halogenated acyls such as acetyl chloride and the like; acid anhydrides such as trifluoroacetic anhydride and the like; and alkyl sulfuric acids such as dimethyl sulfate, diethyl sulfate and the like.

These reactants may be suitably selected in the range of 1 to 5 mole equivalents, based on the compound represented by the general formula (48) or may be used as a solvent.

The reaction temperature may be suitably selected in the range of −80° C. to the reflux temperature of a solvent in use, while the reaction time may be properly selected in the range of several minutes to 96 hours.

Preparation Method 9

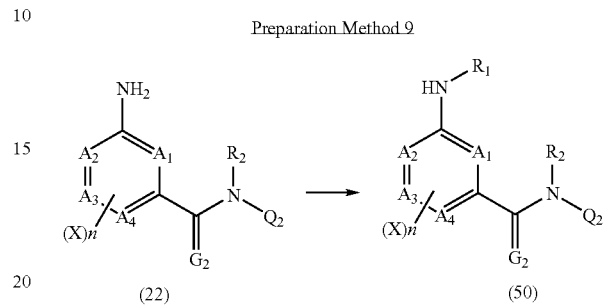

(22)        (50)

wherein, in the formula, $A_1, A_2, A_3, A_4, X, n, G_2, R_1, R_2$ and $Q_2$ represent the same as those in [1].

9-(i): General Formula (22)→General Formula (50)

By reacting a compound represented by the general formula (22) with aldehydes or ketones in a solvent, adding a catalyst and reacting the resultant in a hydrogen atmosphere, a compound represented by the general formula (50) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of 2 or more kinds.

Examples of the catalyst include palladium catalysts such as palladium carbon, palladium hydroxide carbon and the like, nickel catalysts such as Raney nickel and the like, cobalt catalysts, platinum catalysts ruthenium catalysts, rhodium catalysts and the like.

Examples of aldehydes include formaldehyde, acetoaldehyde, propionaldehyde, trifluoroacetoaldehyde, difluoroacetoaldehyde, fluoroacetoaldehyde, chloroacetoaldehyde, dichloroacetoaldehyde, trichloroacetoaldehyde, bromoacetoaldehyde and the like.

Examples of ketones include acetone, perfluoroacetone, methylethyl ketone and the like.

The reaction pressure may be suitably selected in the range of 1 to 100 atm.

The reaction temperature may be suitably selected in the range of −20° C. to the reflux temperature of a solvent in use, while the reaction time may be properly selected in the range of several minutes to 96 hours.

9-(ii): General Formula (22)→General Formula (50) (Alternative Method 1)

By reacting a compound represented by the general formula (22) with aldehydes or ketones in a solvent, and applying a reducing agent, a compound represented by the general formula (50) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of 2 or more kinds.

Examples of the reducing agent include borohydrides such as sodium borohydride, sodium cyanoborohydride, sodium triacetate borohydride and the like.

Examples of aldehydes include formaldehyde, acetoaldehyde, propionaldehyde, trifluoroacetoaldehyde, difluoroacetoaldehyde, fluoroacetoaldehyde, chloroacetoaldehyde, dichloroacetoaldehyde, trichloroacetoaldehyde, bromoacetoaldehyde and the like.

Examples of ketones include acetone, perfluoroacetone, methylethyl ketone and the like.

The reaction temperature may be suitably selected in the range of −20° C. to the reflux temperature of a solvent in use, while the reaction time may be properly selected in the range of several minutes to 96 hours.

9-(iii): General Formula (22)→General Formula (50) (Alternative Method 2)

By reacting a compound represented by the general formula (22) with a formylating agent in a solvent or without a solvent and applying an additive agent, it is possible to prepare a compound, wherein, in the general formula (50), $R_1$ is a methyl group.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of 2 or more kinds.

Examples of the formylating agent include anhydrous formic acids such as formaldehyde, formic acid, fluoroformic acid, formyl (2,2-dimethylpropionic acid) and the like; formic acid esters such as phenyl formate and the like; pentafluorobenzaldehyde, oxazole and the like.

Examples of the additive agent include inorganic acids such as sulfuric acid and the like; organic acids such as formic acid and the like; borohydrides such as sodium borohydride, sodium cyanoborohydride and the like; boronic acid, lithium aluminum hydride and the like.

The reaction temperature may be suitably selected in the range of −20° C. to the reflux temperature of a solvent in use, while the reaction time may be properly selected in the range of several minutes to 96 hours.

Preparation Method 10

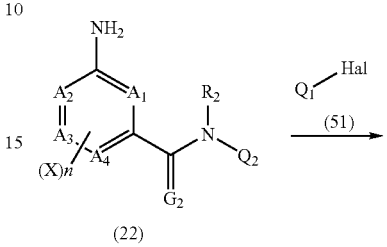

(22)

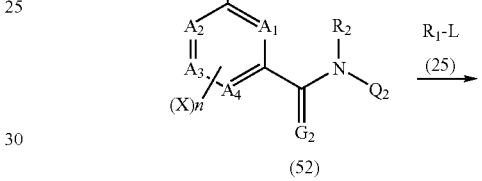

(52)

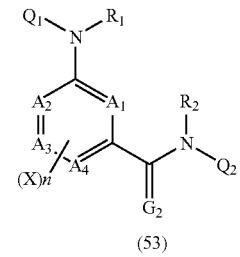

(53)

wherein, in the formula, $A_1, A_2, A_3, A_4, G_2, R_1, R_2, X, n, Q_1$ and $Q_2$ represent the same as those in [1]; and Hal represents a halogen atom.

10-(i): General Formula (22)+General Formula (51) →General Formula (52)

By reacting a compound represented by the general formula (22) with a compound represented by the general formula (51) according to known conditions as described in Tetrahedron Letters p. 3789 (1999) and the like, a compound represented by the general formula (52) can be prepared. Conditions such as a solvent, reaction temperature and the like are not restricted to those described in the documents.

10-(ii): General Formula (52)+General Formula (25) →General Formula (53)

By reacting a compound represented by the general formula (52) with a compound represented by the general formula (25) according to the conditions described in 1-(iv), a compound represented by the general formula (53) can be prepared.

Preparation Method 11

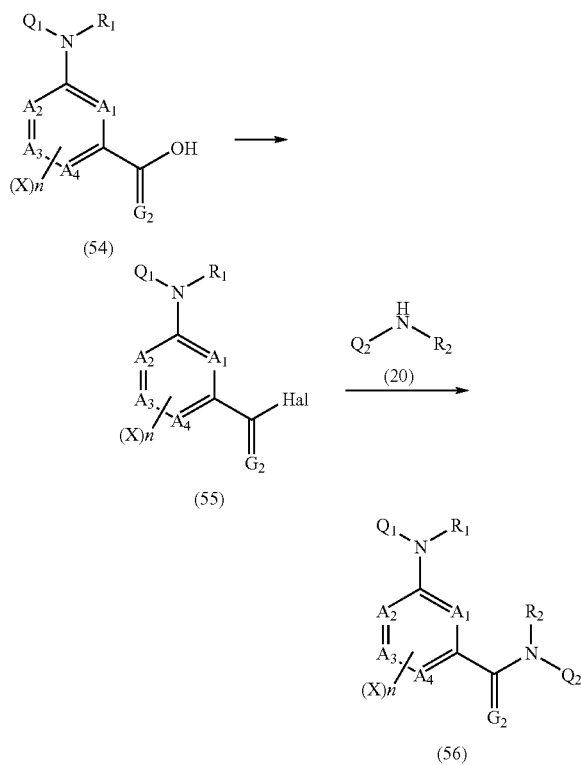

wherein, in the formula, $A_1, A_2, A_3, A_4, G_2, R_1, R_2, X, n, Q_1$ and $Q_2$ represent the same as those in [1]; and Hal represents a halogen atom.

11-(i): General Formula (54)→General Formula (55)

By reacting with a compound represented by the general formula (54) according to the conditions described in 2-(ii), a compound represented by the general formula (56) can be prepared.

11-(ii): General Formula (55)+General Formula (20) →General Formula (56)

By reacting a compound represented by the general formula (55) with a compound represented by the general formula (20) according to the conditions described in 1-(i), a compound represented by the general formula (55) can be prepared.

11-(iii): General Formula (54)+General Formula (20) →General Formula (56)

By reacting a compound represented by the general formula (54) with a compound represented by the general formula (20) according to the conditions using a condensation agent described in 1-(i) or the conditions using a mixed anhydride procedure, a compound represented by the general formula (56) can be prepared.

In all preparation methods as illustrated above, desired products may be isolated according to a usual method from the reaction system after completion of the reaction, and can be purified, if needed, by carrying out operations such as recrystallization, column chromatography, distillation and the like. Furthermore, desired products can also be supplied to the next reaction process without isolating them from the reaction system.

Typical compounds of the compound represented by the general formula (1) or (5) that is an active ingredient of an insecticide of the present invention are illustrated in Tables 1 to 4 below, but the present invention is not restricted thereto.

Incidentally, in the tables, "n-" refers to normal, "Me" refers to a methyl group, "Et" refers to an ethyl group, "n-Pr" refers to a normal propyl group, "i-Pr" refers to an isopropyl group, "n-Bu" refers to a normal butyl group, "i-Bu" refers to an isobutyl group, "s-Bu" refers to a secondary butyl group, "t-Bu" refers to a tertiary butyl group, "H" refers to a hydrogen atom, "O" refers to an oxygen atom, "S" refers to a sulfur atom, "C" refers to a carbon atom, "N" refers to a nitrogen atom, "F" refers to a fluorine atom, "Cl" refers to a chlorine atom, "Br" refers to a bromine atom, "I" refers to an iodine atom, "$CF_3$" refers to a trifluoromethyl group.

General Formula (A)

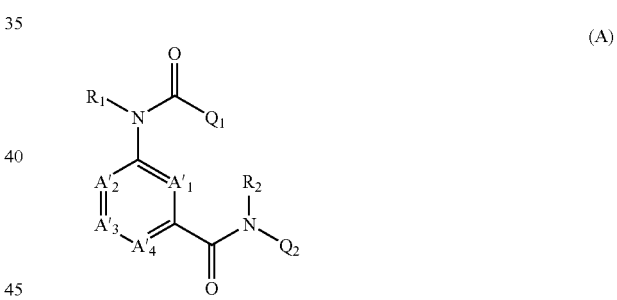

(A)

TABLE 1

| Compound No. | $Q_1$ | $A'_1$ | $A'_2$ | $A'_3$ | $A'_4$ | $R_1$ | $R_2$ | $Q_2$ |
|---|---|---|---|---|---|---|---|---|
| 1-1 | phenyl | CH | CH | CH | CH | H | H | 2,4-dibromo-6-trifluoromethylthiophenyl |
| 1-2 | 2-methylphenyl | CH | CH | CH | CH | H | H | 2,4-dibromo-6-trifluoromethylthiophenyl |
| 1-3 | 3-methylphenyl | CH | CH | CH | CH | H | H | 2,4-dibromo-6-trifluoromethylthiophenyl |
| 1-4 | 4-methylphenyl | CH | CH | CH | CH | H | H | 2,4-dibromo-6-trifluoromethylthiophenyl |
| 1-5 | 2-ethylphenyl | CH | CH | CH | CH | H | H | 2,4-dibromo-6-trifluoromethylthiophenyl |
| 1-6 | 3-ethylphenyl | CH | CH | CH | CH | H | H | 2,4-dibromo-6-trifluoromethylthiophenyl |
| 1-7 | 4-ethylphenyl | CH | CH | CH | CH | H | H | 2,4-dibromo-6-trifluoromethylthiophenyl |
| 1-8 | 2-fluorophenyl | CH | CH | CH | CH | H | H | 2,4-dibromo-6-trifluoromethylthiophenyl |
| 1-9 | 3-fluorophenyl | CH | CH | CH | CH | H | H | 2,4-dibromo-6-trifluoromethylthiophenyl |
| 1-10 | 4-fluorophenyl | CH | CH | CH | CH | H | H | 2,4-dibromo-6-trifluoromethylthiophenyl |
| 1-11 | 2-chlorophenyl | CH | CH | CH | CH | H | H | 2,4-dibromo-6-trifluoromethylthiophenyl |
| 1-12 | 3-chlorophenyl | CH | CH | CH | CH | H | H | 2,4-dibromo-6-trifluoromethylthiophenyl |
| 1-13 | 4-chlorophenyl | CH | CH | CH | CH | H | H | 2,4-dibromo-6-trifluoromethylthiophenyl |
| 1-14 | 2-bromophenyl | CH | CH | CH | CH | H | H | 2,4-dibromo-6-trifluoromethylthiophenyl |
| 1-15 | 3-bromophenyl | CH | CH | CH | CH | H | H | 2,4-dibromo-6-trifluoromethylthiophenyl |
| 1-16 | 4-bromophenyl | CH | CH | CH | CH | H | H | 2,4-dibromo-6-trifluoromethylthiophenyl |
| 1-17 | 2-iodophenyl | CH | CH | CH | CH | H | H | 2,4-dibromo-6-trifluoromethylthiophenyl |
| 1-18 | 3-iodophenyl | CH | CH | CH | CH | H | H | 2,4-dibromo-6-trifluoromethylthiophenyl |

TABLE 1-continued

| Compound No. | $Q_1$ | $A'_1$ | $A'_2$ | $A'_3$ | $A'_4$ | $R_1$ | $R_2$ | $Q_2$ |
|---|---|---|---|---|---|---|---|---|
| 1-19 | 4-iodophenyl | CH | CH | CH | CH | H | H | 2,4-dibromo-6-trifluoromethylthiophenyl |
| 1-20 | 3-cyanophenyl | CH | CH | CH | CH | H | H | 2,4-dibromo-6-trifluoromethylthiophenyl |
| 1-21 | 4-cyanophenyl | CH | CH | CH | CH | H | H | 2,4-dibromo-6-trifluoromethylthiophenyl |
| 1-22 | 2-nitrophenyl | CH | CH | CH | CH | H | H | 2,4-dibromo-6-trifluoromethylthiophenyl |
| 1-23 | 3-nitrophenyl | CH | CH | CH | CH | H | H | 2,4-dibromo-6-trifluoromethylthiophenyl |
| 1-24 | 4-nitrophenyl | CH | CH | CH | CH | H | H | 2,4-dibromo-6-trifluoromethylthiophenyl |
| 1-25 | 2-aminophenyl | CH | CH | CH | CH | H | H | 2,4-dibromo-6-trifluoromethylthiophenyl |
| 1-26 | 3-aminophenyl | CH | CH | CH | CH | H | H | 2,4-dibromo-6-trifluoromethylthiophenyl |
| 1-27 | 4-aminophenyl | CH | CH | CH | CH | H | H | 2,4-dibromo-6-trifluoromethylthiophenyl |
| 1-28 | 2-trifluoromethylphenyl | CH | CH | CH | CH | H | H | 2,4-dibromo-6-trifluoromethylthiophenyl |
| 1-29 | 3-trifluoromethylphenyl | CH | CH | CH | CH | H | H | 2,4-dibromo-6-trifluoromethylthiophenyl |
| 1-30 | 4-trifluoromethylphenyl | CH | CH | CH | CH | H | H | 2,4-dibromo-6-trifluoromethylthiophenyl |
| 1-31 | 2-hydroxyphenyl | CH | CH | CH | CH | H | H | 2,4-dibromo-6-trifluoromethylthiophenyl |
| 1-32 | 2-methoxyphenyl | CH | CH | CH | CH | H | H | 2,4-dibromo-6-trifluoromethylthiophenyl |
| 1-33 | 3-methoxyphenyl | CH | CH | CH | CH | H | H | 2,4-dibromo-6-trifluoromethylthiophenyl |
| 1-34 | 4-methoxyphenyl | CH | CH | CH | CH | H | H | 2,4-dibromo-6-trifluoromethylthiophenyl |
| 1-35 | 2-phenoxyphenyl | CH | CH | CH | CH | H | H | 2,4-dibromo-6-trifluoromethylthiophenyl |
| 1-36 | 4-(1,1-dimethylethyl)phenyl | CH | CH | CH | CH | H | H | 2,4-dibromo-6-trifluoromethylthiophenyl |
| 1-37 | 3-(dimethylamino)phenyl | CH | CH | CH | CH | H | H | 2,4-dibromo-6-trifluoromethylthiophenyl |
| 1-38 | 4-(dimethylamino)phenyl | CH | CH | CH | CH | H | H | 2,4-dibromo-6-trifluoromethylthiophenyl |
| 1-39 | 4-trifluoromethoxyphenyl | CH | CH | CH | CH | H | H | 2,4-dibromo-6-trifluoromethylthiophenyl |
| 1-40 | 2-(acetylamino)phenyl | CH | CH | CH | CH | H | H | 2,4-dibromo-6-trifluoromethylthiophenyl |
| 1-41 | 3-(acetylamino)phenyl | CH | CH | CH | CH | H | H | 2,4-dibromo-6-trifluoromethylthiophenyl |
| 1-42 | 4-(acetylamino)phenyl | CH | CH | CH | CH | H | H | 2,4-dibromo-6-trifluoromethylthiophenyl |
| 1-43 | 2-acetoxyphenyl | CH | CH | CH | CH | H | H | 2,4-dibromo-6-trifluoromethylthiophenyl |
| 1-44 | 2-(methoxycarbonyl)phenyl | CH | CH | CH | CH | H | H | 2,4-dibromo-6-trifluoromethylthiophenyl |
| 1-45 | 4-(methoxycarbonyl)phenyl | CH | CH | CH | CH | H | H | 2,4-dibromo-6-trifluoromethylthiophenyl |
| 1-46 | 2,3-dimethylphenyl | CH | CH | CH | CH | H | H | 2,4-dibromo-6-trifluoromethylthiophenyl |
| 1-47 | 2,4-dimethylphenyl | CH | CH | CH | CH | H | H | 2,4-dibromo-6-trifluoromethylthiophenyl |
| 1-48 | 2,6-dimethylphenyl | CH | CH | CH | CH | H | H | 2,4-dibromo-6-trifluoromethylthiophenyl |
| 1-49 | 2,3-difluorophenyl | CH | CH | CH | CH | H | H | 2,4-dibromo-6-trifluoromethylthiophenyl |
| 1-50 | 2,4-difluorophenyl | CH | CH | CH | CH | H | H | 2,4-dibromo-6-trifluoromethylthiophenyl |
| 1-51 | 2,5-difluorophenyl | CH | CH | CH | CH | H | H | 2,4-dibromo-6-trifluoromethylthiophenyl |
| 1-52 | 2,6-difluorophenyl | CH | CH | CH | CH | H | H | 2,4-dibromo-6-trifluoromethylthiophenyl |
| 1-53 | 3,4-difluorophenyl | CH | CH | CH | CH | H | H | 2,4-dibromo-6-trifluoromethylthiophenyl |
| 1-54 | 3,5-difluorophenyl | CH | CH | CH | CH | H | H | 2,4-dibromo-6-trifluoromethylthiophenyl |
| 1-55 | 2,3-dichlorophenyl | CH | CH | CH | CH | H | H | 2,4-dibromo-6-trifluoromethylthiophenyl |
| 1-56 | 2,4-dichlorophenyl | CH | CH | CH | CH | H | H | 2,4-dibromo-6-trifluoromethylthiophenyl |
| 1-57 | 2,5-dichlorophenyl | CH | CH | CH | CH | H | H | 2,4-dibromo-6-trifluoromethylthiophenyl |
| 1-58 | 2,6-dichlorophenyl | CH | CH | CH | CH | H | H | 2,4-dibromo-6-trifluoromethylthiophenyl |
| 1-59 | 3,4-dichlorophenyl | CH | CH | CH | CH | H | H | 2,4-dibromo-6-trifluoromethylthiophenyl |
| 1-60 | 2,4-dinitrophenyl | CH | CH | CH | CH | H | H | 2,4-dibromo-6-trifluoromethylthiophenyl |
| 1-61 | 3,4-dinitrophenyl | CH | CH | CH | CH | H | H | 2,4-dibromo-6-trifluoromethylthiophenyl |
| 1-62 | 2,6-dimethoxyphenyl | CH | CH | CH | CH | H | H | 2,4-dibromo-6-trifluoromethylthiophenyl |
| 1-63 | 3,5-dimethoxyphenyl | CH | CH | CH | CH | H | H | 2,4-dibromo-6-trifluoromethylthiophenyl |
| 1-64 | 3-methyl-4-nitrophenyl | CH | CH | CH | CH | H | H | 2,4-dibromo-6-trifluoromethylthiophenyl |
| 1-65 | 5-amino-2-fluorophenyl | CH | CH | CH | CH | H | H | 2,4-dibromo-6-trifluoromethylthiophenyl |
| 1-66 | 3-fluoro-2-methylphenyl | CH | CH | CH | CH | H | H | 2,4-dibromo-6-trifluoromethylthiophenyl |
| 1-67 | 2-fluoro-5-nitrophenyl | CH | CH | CH | CH | H | H | 2,4-dibromo-6-trifluoromethylthiophenyl |
| 1-68 | 4-fluoro-3-nitrophenyl | CH | CH | CH | CH | H | H | 2,4-dibromo-6-trifluoromethylthiophenyl |
| 1-69 | 5-fluoro-2-nitrophenyl | CH | CH | CH | CH | H | H | 2,4-dibromo-6-trifluoromethylthiophenyl |
| 1-70 | 2-fluoro-6-iodinephenyl | CH | CH | CH | CH | H | H | 2,4-dibromo-6-trifluoromethylthiophenyl |
| 1-71 | 2-fluoro-5-trifluoromethylphenyl | CH | CH | CH | CH | H | H | 2,4-dibromo-6-trifluoromethylthiophenyl |
| 1-72 | 2-chloro-4-nitrophenyl | CH | CH | CH | CH | H | H | 2,4-dibromo-6-trifluoromethylthiophenyl |
| 1-73 | 2-chloro-4-fluorophenyl | CH | CH | CH | CH | H | H | 2,4-dibromo-6-trifluoromethylthiophenyl |
| 1-74 | 2-chloro-6-fluorophenyl | CH | CH | CH | CH | H | H | 2,4-dibromo-6-trifluoromethylthiophenyl |
| 1-75 | 3-chloro-4-fluorophenyl | CH | CH | CH | CH | H | H | 2,4-dibromo-6-trifluoromethylthiophenyl |
| 1-76 | 4-chloro-2-fluorophenyl | CH | CH | CH | CH | H | H | 2,4-dibromo-6-trifluoromethylthiophenyl |
| 1-77 | 4-chloro-2-nitrophenyl | CH | CH | CH | CH | H | H | 2,4-dibromo-6-trifluoromethylthiophenyl |
| 1-78 | 3-methoxy-4-nitrophenyl | CH | CH | CH | CH | H | H | 2,4-dibromo-6-trifluoromethylthiophenyl |
| 1-79 | 2-methoxy-4-nitrophenyl | CH | CH | CH | CH | H | H | 2,4-dibromo-6-trifluoromethylthiophenyl |
| 1-80 | 2,3,4-trifluorophenyl | CH | CH | CH | CH | H | H | 2,4-dibromo-6-trifluoromethylthiophenyl |
| 1-81 | 2,4,6-trimethylphenyl | CH | CH | CH | CH | H | H | 2,4-dibromo-6-trifluoromethylthiophenyl |
| 1-82 | 2,3,6-trifluorophenyl | CH | CH | CH | CH | H | H | 2,4-dibromo-6-trifluoromethylthiophenyl |
| 1-83 | 2,4,5-trimethoxyphenyl | CH | CH | CH | CH | H | H | 2,4-dibromo-6-trifluoromethylthiophenyl |
| 1-84 | 3,4,5-trimethoxyphenyl | CH | CH | CH | CH | H | H | 2,4-dibromo-6-trifluoromethylthiophenyl |
| 1-85 | 2,3,4,5,6-pentafluorophenyl | CH | CH | CH | CH | H | H | 2,4-dibromo-6-trifluoromethylthiophenyl |
| 1-86 | 2-biphenyl | CH | CH | CH | CH | H | H | 2,4-dibromo-6-trifluoromethylthiophenyl |
| 1-87 | 3-biphenyl | CH | CH | CH | CH | H | H | 2,4-dibromo-6-trifluoromethylthiophenyl |
| 1-88 | 1-naphthyl | CH | CH | CH | CH | H | H | 2,4-dibromo-6-trifluoromethylthiophenyl |
| 1-89 | 2-naphthyl | CH | CH | CH | CH | H | H | 2,4-dibromo-6-trifluoromethylthiophenyl |
| 1-90 | pyridin-2-yl | CH | CH | CH | CH | H | H | 2,4-dibromo-6-trifluoromethylthiophenyl |
| 1-91 | pyridin-3-yl | CH | CH | CH | CH | H | H | 2,4-dibromo-6-trifluoromethylthiophenyl |
| 1-92 | pyridin-4-yl | CH | CH | CH | CH | H | H | 2,4-dibromo-6-trifluoromethylthiophenyl |
| 1-93 | 2-methylpyridin-5-yl | CH | CH | CH | CH | H | H | 2,4-dibromo-6-trifluoromethylthiophenyl |

TABLE 1-continued

| Compound No. | Q1 | A'1 | A'2 | A'3 | A'4 | R1 | R2 | Q2 |
|---|---|---|---|---|---|---|---|---|
| 1-94 | 3-methylpyridin-2-yl | CH | CH | CH | CH | H | H | 2,4-dibromo-6-trifluoromethylthiophenyl |
| 1-95 | 2-fluoropyridin-3-yl | CH | CH | CH | CH | H | H | 2,4-dibromo-6-trifluoromethylthiophenyl |
| 1-96 | 2-chloropyridin-3-yl | CH | CH | CH | CH | H | H | 2,4-dibromo-6-trifluoromethylthiophenyl |
| 1-97 | 2-chloropyridin-4-yl | CH | CH | CH | CH | H | H | 2,4-dibromo-6-trifluoromethylthiophenyl |
| 1-98 | 2-chloropyridin-6-yl | CH | CH | CH | CH | H | H | 2,4-dibromo-6-trifluoromethylthiophenyl |
| 1-99 | 2-chloropyridin-5-yl | CH | CH | CH | CH | H | H | 2,4-dibromo-6-trifluoromethylthiophenyl |
| 1-100 | 5-chloropyridin-2-yl | CH | CH | CH | CH | H | H | 2,4-dibromo-6-trifluoromethylthiophenyl |
| 1-101 | 4-trifluoromethylpyridin-3-yl | CH | CH | CH | CH | H | H | 2,4-dibromo-6-trifluoromethylthiophenyl |
| 1-102 | 3-hydroxypyridin-2-yl | CH | CH | CH | CH | H | H | 2,4-dibromo-6-trifluoromethylthiophenyl |
| 1-103 | 2-phenoxypyridin-3-yl | CH | CH | CH | CH | H | H | 2,4-dibromo-6-trifluoromethylthiophenyl |
| 1-104 | 2-methylthiopyridin-3-yl | CH | CH | CH | CH | H | H | 2,4-dibromo-6-trifluoromethylthiophenyl |
| 1-105 | 2,6-dimethoxypyridin-3-yl | CH | CH | CH | CH | H | H | 2,4-dibromo-6-trifluoromethylthiophenyl |
| 1-106 | 2,3-dichloropyridin-5-yl | CH | CH | CH | CH | H | H | 2,4-dibromo-6-trifluoromethylthiophenyl |
| 1-107 | 2,5-dichloropyridin-3-yl | CH | CH | CH | CH | H | H | 2,4-dibromo-6-trifluoromethylthiophenyl |
| 1-108 | 2,6-dichloropyridin-3-yl | CH | CH | CH | CH | H | H | 2,4-dibromo-6-trifluoromethylthiophenyl |
| 1-109 | 3,5-dichloropyridin-4-yl | CH | CH | CH | CH | H | H | 2,4-dibromo-6-trifluoromethylthiophenyl |
| 1-110 | pyridin-N-oxid-2-yl | CH | CH | CH | CH | H | H | 2,4-dibromo-6-trifluoromethylthiophenyl |
| 1-111 | N-methylpyrrol-2-yl | CH | CH | CH | CH | H | H | 2,4-dibromo-6-trifluoromethylthiophenyl |
| 1-112 | pyrazin-2-yl | CH | CH | CH | CH | H | H | 2,4-dibromo-6-trifluoromethylthiophenyl |
| 1-113 | 2-methylpyrazin-5-yl | CH | CH | CH | CH | H | H | 2,4-dibromo-6-trifluoromethylthiophenyl |
| 1-114 | 4-trifluoromethylpyrimidin-5-yl | CH | CH | CH | CH | H | H | 2,4-dibromo-6-trifluoromethylthiophenyl |
| 1-115 | furan-2-yl | CH | CH | CH | CH | H | H | 2,4-dibromo-6-trifluoromethylthiophenyl |
| 1-116 | furan-3-yl | CH | CH | CH | CH | H | H | 2,4-dibromo-6-trifluoromethylthiophenyl |
| 1-117 | 2-tetrahydrofuranyl | CH | CH | CH | CH | H | H | 2,4-dibromo-6-trifluoromethylthiophenyl |
| 1-118 | 3-tetrahydrofuranyl | CH | CH | CH | CH | H | H | 2,4-dibromo-6-trifluoromethylthiophenyl |
| 1-119 | benzofuran-2-yl | CH | CH | CH | CH | H | H | 2,4-dibromo-6-trifluoromethylthiophenyl |
| 1-120 | tetrahydropyran-2-yl | CH | CH | CH | CH | H | H | 2,4-dibromo-6-trifluoromethylthiophenyl |
| 1-121 | 2-methyl-5,6-dihydro-4H-pyran-3-yl | CH | CH | CH | CH | H | H | 2,4-dibromo-6-trifluoromethylthiophenyl |
| 1-122 | thiophen-2-yl | CH | CH | CH | CH | H | H | 2,4-dibromo-6-trifluoromethylthiophenyl |
| 1-123 | thiophen-3-yl | CH | CH | CH | CH | H | H | 2,4-dibromo-6-trifluoromethylthiophenyl |
| 1-124 | 3-methylthiophen-2-yl | CH | CH | CH | CH | H | H | 2,4-dibromo-6-trifluoromethylthiophenyl |
| 1-125 | 2-nitrothiophen-4-yl | CH | CH | CH | CH | H | H | 2,4-dibromo-6-trifluoromethylthiophenyl |
| 1-126 | 2-methylthiophen-5-yl | CH | CH | CH | CH | H | H | 2,4-dibromo-6-trifluoromethylthiophenyl |
| 1-127 | 3-chlorothiophen-2-yl | CH | CH | CH | CH | H | H | 2,4-dibromo-6-trifluoromethylthiophenyl |
| 1-128 | 2-chlorothiophen-5-yl | CH | CH | CH | CH | H | H | 2,4-dibromo-6-trifluoromethylthiophenyl |
| 1-129 | 3-bromothiophen-2-yl | CH | CH | CH | CH | H | H | 2,4-dibromo-6-trifluoromethylthiophenyl |
| 1-130 | 2-bromothiophen-5-yl | CH | CH | CH | CH | H | H | 2,4-dibromo-6-trifluoromethylthiophenyl |
| 1-131 | 3-iodinethiophen-2-yl | CH | CH | CH | CH | H | H | 2,4-dibromo-6-trifluoromethylthiophenyl |
| 1-132 | 3-phenylthiophen-2-yl | CH | CH | CH | CH | H | H | 2,4-dibromo-6-trifluoromethylthiophenyl |
| 1-133 | 2,4-dimethylthiophen-5-yl | CH | CH | CH | CH | H | H | 2,4-dibromo-6-trifluoromethylthiophenyl |
| 1-134 | benzothiophen-2-yl | CH | CH | CH | CH | H | H | 2,4-dibromo-6-trifluoromethylthiophenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-135 | 4-nitro-1H-pyrrol-2-yl | CH | CH | CH | CH | H | H | 2,4-dibromo-6-trifluoromethylthiophenyl |
| 1-136 | 3-ethyl-3H-pyrazol-4-yl | CH | CH | CH | CH | H | H | 2,4-dibromo-6-trifluoromethylthiophenyl |
| 1-137 | 1-methyl-3-nitro-1H-pyrazol-4-yl | CH | CH | CH | CH | H | H | 2,4-dibromo-6-trifluoromethylthiophenyl |
| 1-138 | 3-chloro-1-methyl-1H-pyrazol-4-yl | CH | CH | CH | CH | H | H | 2,4-dibromo-6-trifluoromethylthiophenyl |
| 1-139 | 3-bromo-1-methyl-1H-pyrazol-4-yl | CH | CH | CH | CH | H | H | 2,4-dibromo-6-trifluoromethylthiophenyl |
| 1-140 | 1-methyl-3-trifluoromethyl-1H-pyrazol-4-yl | CH | CH | CH | CH | H | H | 2,4-dibromo-6-trifluoromethylthiophenyl |
| 1-141 | 1-methyl-5-trifluoromethyl-1H-pyrazol-4-yl | CH | CH | CH | CH | H | H | 2,4-dibromo-6-trifluoromethylthiophenyl |
| 1-142 | isoxazol-5-yl | CH | CH | CH | CH | H | H | 2,4-dibromo-6-trifluoromethylthiophenyl |
| 1-143 | 4-trifluoromethylthiazol-5-yl | CH | CH | CH | CH | H | H | 2,4-dibromo-6-trifluoromethylthiophenyl |
| 1-144 | 2,4-dimethylthiazol-5-yl | CH | CH | CH | CH | H | H | 2,4-dibromo-6-trifluoromethylthiophenyl |
| 1-145 | 2-ethyl-4-methylthiazol-5-yl | CH | CH | CH | CH | H | H | 2,4-dibromo-6-trifluoromethylthiophenyl |
| 1-146 | 2-chloro-4-methylthiazol-5-yl | CH | CH | CH | CH | H | H | 2,4-dibromo-6-trifluoromethylthiophenyl |
| 1-147 | 3-methyl-isothiazol-5-yl | CH | CH | CH | CH | H | H | 2,4-dibromo-6-trifluoromethylthiophenyl |
| 1-148 | 3,4-dichloro-isothiazol-5-yl | CH | CH | CH | CH | H | H | 2,4-dibromo-6-trifluoromethylthiophenyl |
| 1-149 | 3-chlorobenzothiazol-2-yl | CH | CH | CH | CH | H | H | 2,4-dibromo-6-trifluoromethylthiophenyl |
| 1-150 | 2,2-difluoro-benzo[1.3]dioxol-5-yl | CH | CH | CH | CH | H | H | 2,4-dibromo-6-trifluoromethylthiophenyl |
| 1-151 | 2,2-difluoro-benzo[1.3]dioxol-4-yl | CH | CH | CH | CH | H | H | 2,4-dibromo-6-trifluoromethylthiophenyl |
| 1-152 | phenyl | CF | CH | CH | CH | H | H | 2,4-dibromo-6-trifluoromethylthiophenyl |
| 1-153 | 2-fluorophenyl | CF | CH | CH | CH | H | H | 2,4-dibromo-6-trifluoromethylthiophenyl |
| 1-154 | 4-fluorophenyl | CF | CH | CH | CH | H | H | 2,4-dibromo-6-trifluoromethylthiophenyl |
| 1-155 | 4-chlorophenyl | CF | CH | CH | CH | H | H | 2,4-dibromo-6-trifluoromethylthiophenyl |
| 1-156 | 2-chloropyridin-3-yl | CF | CH | CH | CH | H | H | 2,4-dibromo-6-trifluoromethylthiophenyl |
| 1-157 | 4-nitrophenyl | CF | CH | CH | CH | H | H | 2,4-dibromo-6-trifluoromethylthiophenyl |
| 1-158 | 4-cyanophenyl | CF | CH | CH | CH | H | H | 2,4-dibromo-6-trifluoromethylthiophenyl |
| 1-159 | phenyl | CH | CH | CH | CH | Me | H | 2,4-dibromo-6-trifluoromethylthiophenyl |
| 1-160 | 2-fluorophenyl | CH | CH | CH | CH | Me | H | 2,4-dibromo-6-trifluoromethylthiophenyl |
| 1-161 | 4-fluorophenyl | CH | CH | CH | CH | Me | H | 2,4-dibromo-6-trifluoromethylthiophenyl |
| 1-162 | 4-chlorophenyl | CH | CH | CH | CH | Me | H | 2,4-dibromo-6-trifluoromethylthiophenyl |
| 1-163 | 2-chloropyridin-3-yl | CH | CH | CH | CH | Me | H | 2,4-dibromo-6-trifluoromethylthiophenyl |
| 1-164 | 4-nitrophenyl | CH | CH | CH | CH | Me | H | 2,4-dibromo-6-trifluoromethylthiophenyl |
| 1-165 | 4-cyanophenyl | CH | CH | CH | CH | Me | H | 2,4-dibromo-6-trifluoromethylthiophenyl |
| 1-166 | phenyl | CH | CH | CH | CH | H | Me | 2,4-dibromo-6-trifluoromethylthiophenyl |
| 1-167 | 2-fluorophenyl | CH | CH | CH | CH | H | Me | 2,4-dibromo-6-trifluoromethylthiophenyl |
| 1-168 | 4-fluorophenyl | CH | CH | CH | CH | H | Me | 2,4-dibromo-6-trifluoromethylthiophenyl |
| 1-169 | 4-chlorophenyl | CH | CH | CH | CH | H | Me | 2,4-dibromo-6-trifluoromethylthiophenyl |
| 1-170 | 2-chloropyridin-3-yl | CH | CH | CH | CH | H | Me | 2,4-dibromo-6-trifluoromethylthiophenyl |
| 1-171 | 4-nitrophenyl | CH | CH | CH | CH | H | Me | 2,4-dibromo-6-trifluoromethylthiophenyl |
| 1-172 | 4-cyanophenyl | CH | CH | CH | CH | H | Me | 2,4-dibromo-6-trifluoromethylthiophenyl |
| 1-173 | phenyl | CH | CH | CH | CH | Me | Me | 2,4-dibromo-6-trifluoromethylthiophenyl |
| 1-174 | 2-fluorophenyl | CH | CH | CH | CH | Me | Me | 2,4-dibromo-6-trifluoromethylthiophenyl |
| 1-175 | 4-fluorophenyl | CH | CH | CH | CH | Me | Me | 2,4-dibromo-6-trifluoromethylthiophenyl |
| 1-176 | 4-chlorophenyl | CH | CH | CH | CH | Me | Me | 2,4-dibromo-6-trifluoromethylthiophenyl |
| 1-177 | 2-chloropyridin-3-yl | CH | CH | CH | CH | Me | Me | 2,4-dibromo-6-trifluoromethylthiophenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-178 | 4-nitrophenyl | CH | CH | CH | CH | Me | Me | 2,4-dibromo-6-trifluoromethylthiophenyl |
| 1-179 | 4-cyanophenyl | CH | CH | CH | CH | Me | Me | 2,4-dibromo-6-trifluoromethylthiophenyl |
| 1-180 | phenyl | CF | CH | CH | CH | H | H | 2,4-dibromo-6-trifluoromethylsulfinylphenyl |
| 1-181 | 2-fluorophenyl | CF | CH | CH | CH | H | H | 2,4-dibromo-6-trifluoromethylsulfinylphenyl |
| 1-182 | 4-fluorophenyl | CF | CH | CH | CH | H | H | 2,4-dibromo-6-trifluoromethylsulfinylphenyl |
| 1-183 | 4-chlorophenyl | CF | CH | CH | CH | H | H | 2,4-dibromo-6-trifluoromethylsulfinylphenyl |
| 1-184 | 2-chloropyridin-3-yl | CF | CH | CH | CH | H | H | 2,4-dibromo-6-trifluoromethylsulfinylphenyl |
| 1-185 | 4-nitrophenyl | CF | CH | CH | CH | H | H | 2,4-dibromo-6-trifluoromethylsulfinylphenyl |
| 1-186 | 4-cyanophenyl | CF | CH | CH | CH | H | H | 2,4-dibromo-6-trifluoromethylsulfinylphenyl |
| 1-187 | phenyl | CH | CH | CH | CH | Me | H | 2,4-dibromo-6-trifluoromethylsulfinylphenyl |
| 1-188 | 2-fluorophenyl | CH | CH | CH | CH | Me | H | 2,4-dibromo-6-trifluoromethylsulfinylphenyl |
| 1-189 | 4-fluorophenyl | CH | CH | CH | CH | Me | H | 2,4-dibromo-6-trifluoromethylsulfinylphenyl |
| 1-190 | 4-chlorophenyl | CH | CH | CH | CH | Me | H | 2,4-dibromo-6-trifluoromethylsulfinylphenyl |
| 1-191 | 2-chloropyridin-3-yl | CH | CH | CH | CH | Me | H | 2,4-dibromo-6-trifluoromethylsulfinylphenyl |
| 1-192 | 4-nitrophenyl | CH | CH | CH | CH | Me | H | 2,4-dibromo-6-trifluoromethylsulfinylphenyl |
| 1-193 | 4-cyanophenyl | CH | CH | CH | CH | Me | H | 2,4-dibromo-6-trifluoromethylsulfinylphenyl |
| 1-194 | phenyl | CH | CH | CH | CH | H | Me | 2,4-dibromo-6-trifluoromethylsulfinylphenyl |
| 1-195 | 2-fluorophenyl | CH | CH | CH | CH | H | Me | 2,4-dibromo-6-trifluoromethylsulfinylphenyl |
| 1-196 | 4-fluorophenyl | CH | CH | CH | CH | H | Me | 2,4-dibromo-6-trifluoromethylsulfinylphenyl |
| 1-197 | 4-chlorophenyl | CH | CH | CH | CH | H | Me | 2,4-dibromo-6-trifluoromethylsulfinylphenyl |
| 1-198 | 2-chloropyridin-3-yl | CH | CH | CH | CH | H | Me | 2,4-dibromo-6-trifluoromethylsulfinylphenyl |
| 1-199 | 4-nitrophenyl | CH | CH | CH | CH | H | Me | 2,4-dibromo-6-trifluoromethylsulfinylphenyl |
| 1-200 | 4-cyanophenyl | CH | CH | CH | CH | H | Me | 2,4-dibromo-6-trifluoromethylsulfinylphenyl |
| 1-201 | phenyl | CH | CH | CH | CH | Me | Me | 2,4-dibromo-6-trifluoromethylsulfinylphenyl |
| 1-202 | 2-fluorophenyl | CH | CH | CH | CH | Me | Me | 2,4-dibromo-6-trifluoromethylsulfinylphenyl |
| 1-203 | 4-fluorophenyl | CH | CH | CH | CH | Me | Me | 2,4-dibromo-6-trifluoromethylsulfinylphenyl |
| 1-204 | 4-chlorophenyl | CH | CH | CH | CH | Me | Me | 2,4-dibromo-6-trifluoromethylsulfinylphenyl |
| 1-205 | 2-chloropyridin-3-yl | CH | CH | CH | CH | Me | Me | 2,4-dibromo-6-trifluoromethylsulfinylphenyl |
| 1-206 | 4-nitrophenyl | CH | CH | CH | CH | Me | Me | 2,4-dibromo-6-trifluoromethylsulfinylphenyl |
| 1-207 | 4-cyanophenyl | CH | CH | CH | CH | Me | Me | 2,4-dibromo-6-trifluoromethylsulfinylphenyl |
| 1-208 | phenyl | CF | CH | CH | CH | H | H | 2,4-dibromo-6-trifluoromethylsulfonylphenyl |
| 1-209 | 2-fluorophenyl | CF | CH | CH | CH | H | H | 2,4-dibromo-6-trifluoromethylsulfonylphenyl |
| 1-210 | 4-fluorophenyl | CF | CH | CH | CH | H | H | 2,4-dibromo-6-trifluoromethylsulfonylphenyl |
| 1-211 | 4-chlorophenyl | CF | CH | CH | CH | H | H | 2,4-dibromo-6-trifluoromethylsulfonylphenyl |
| 1-212 | 2-chloropyridin-3-yl | CF | CH | CH | CH | H | H | 2,4-dibromo-6-trifluoromethylsulfonylphenyl |
| 1-213 | 4-nitrophenyl | CF | CH | CH | CH | H | H | 2,4-dibromo-6-trifluoromethylsulfonylphenyl |
| 1-214 | 4-cyanophenyl | CF | CH | CH | CH | H | H | 2,4-dibromo-6-trifluoromethylsulfonylphenyl |
| 1-215 | phenyl | CH | CH | CH | CH | Me | H | 2,4-dibromo-6-trifluoromethylsulfonylphenyl |
| 1-216 | 2-fluorophenyl | CH | CH | CH | CH | Me | H | 2,4-dibromo-6-trifluoromethylsulfonylphenyl |
| 1-217 | 4-fluorophenyl | CH | CH | CH | CH | Me | H | 2,4-dibromo-6-trifluoromethylsulfonylphenyl |
| 1-218 | 4-chlorophenyl | CH | CH | CH | CH | Me | H | 2,4-dibromo-6-trifluoromethylsulfonylphenyl |
| 1-219 | 2-chloropyridin-3-yl | CH | CH | CH | CH | Me | H | 2,4-dibromo-6-trifluoromethylsulfonylphenyl |
| 1-220 | 4-nitrophenyl | CH | CH | CH | CH | Me | H | 2,4-dibromo-6-trifluoromethylsulfonylphenyl |
| 1-221 | 4-cyanophenyl | CH | CH | CH | CH | Me | H | 2,4-dibromo-6-trifluoromethylsulfonylphenyl |
| 1-222 | phenyl | CH | CH | CH | CH | H | Me | 2,4-dibromo-6-trifluoromethylsulfonylphenyl |
| 1-223 | 2-fluorophenyl | CH | CH | CH | CH | H | Me | 2,4-dibromo-6-trifluoromethylsulfonylphenyl |
| 1-224 | 4-fluorophenyl | CH | CH | CH | CH | H | Me | 2,4-dibromo-6-trifluoromethylsulfonylphenyl |
| 1-225 | 4-chlorophenyl | CH | CH | CH | CH | H | Me | 2,4-dibromo-6-trifluoromethylsulfonylphenyl |
| 1-226 | 2-chloropyridin-3-yl | CH | CH | CH | CH | H | Me | 2,4-dibromo-6-trifluoromethylsulfonylphenyl |
| 1-227 | 4-nitrophenyl | CH | CH | CH | CH | H | Me | 2,4-dibromo-6-trifluoromethylsulfonylphenyl |
| 1-228 | 4-cyanophenyl | CH | CH | CH | CH | H | Me | 2,4-dibromo-6-trifluoromethylsulfonylphenyl |
| 1-229 | phenyl | CH | CH | CH | CH | Me | Me | 2,4-dibromo-6-trifluoromethylsulfonylphenyl |
| 1-230 | 2-fluorophenyl | CH | CH | CH | CH | Me | Me | 2,4-dibromo-6-trifluoromethylsulfonylphenyl |
| 1-231 | 4-fluorophenyl | CH | CH | CH | CH | Me | Me | 2,4-dibromo-6-trifluoromethylsulfonylphenyl |
| 1-232 | 4-chlorophenyl | CH | CH | CH | CH | Me | Me | 2,4-dibromo-6-trifluoromethylsulfonylphenyl |
| 1-233 | 2-chloropyridin-3-yl | CH | CH | CH | CH | Me | Me | 2,4-dibromo-6-trifluoromethylsulfonylphenyl |
| 1-234 | 4-nitrophenyl | CH | CH | CH | CH | Me | Me | 2,4-dibromo-6-trifluoromethylsulfonylphenyl |
| 1-235 | 4-cyanophenyl | CH | CH | CH | CH | Me | Me | 2,4-dibromo-6-trifluoromethylsulfonylphenyl |
| 1-236 | phenyl | CF | CH | CH | CH | H | H | 2,4-dibromo-6-trifluoromethylsulfinylphenyl |
| 1-237 | 2-fluorophenyl | CF | CH | CH | CH | H | H | 2,4-dibromo-6-trifluoromethylsulfinylphenyl |
| 1-238 | 4-fluorophenyl | CF | CH | CH | CH | H | H | 2,4-dibromo-6-trifluoromethylsulfinylphenyl |
| 1-239 | 4-chlorophenyl | CF | CH | CH | CH | H | H | 2,4-dibromo-6-trifluoromethylsulfinylphenyl |
| 1-240 | 2-chloropyridin-3-yl | CF | CH | CH | CH | H | H | 2,4-dibromo-6-trifluoromethylsulfinylphenyl |
| 1-241 | 4-nitrophenyl | CF | CH | CH | CH | H | H | 2,4-dibromo-6-trifluoromethylsulfinylphenyl |
| 1-242 | 4-cyanophenyl | CF | CH | CH | CH | H | H | 2,4-dibromo-6-trifluoromethylsulfinylphenyl |
| 1-243 | phenyl | CH | CH | CH | CH | Me | H | 2,4-dibromo-6-trifluoromethylsulfinylphenyl |
| 1-244 | 2-fluorophenyl | CH | CH | CH | CH | Me | H | 2,4-dibromo-6-trifluoromethylsulfinylphenyl |
| 1-245 | 4-fluorophenyl | CH | CH | CH | CH | Me | H | 2,4-dibromo-6-trifluoromethylsulfinylphenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-246 | 4-chlorophenyl | CH | CH | CH | CH | Me | H | 2,4-dibromo-6-trifluoromethylsulfinylphenyl |
| 1-247 | 2-chloropyridin-3-yl | CH | CH | CH | CH | Me | H | 2,4-dibromo-6-trifluoromethylsulfinylphenyl |
| 1-248 | 4-nitrophenyl | CH | CH | CH | CH | Me | H | 2,4-dibromo-6-trifluoromethylsulfinylphenyl |
| 1-249 | 4-cyanophenyl | CH | CH | CH | CH | Me | H | 2,4-dibromo-6-trifluoromethylsulfinylphenyl |
| 1-250 | phenyl | CH | CH | CH | CH | H | Me | 2,4-dibromo-6-trifluoromethylsulfinylphenyl |
| 1-251 | 2-fluorophenyl | CH | CH | CH | CH | H | Me | 2,4-dibromo-6-trifluoromethylsulfinylphenyl |
| 1-252 | 4-fluorophenyl | CH | CH | CH | CH | H | Me | 2,4-dibromo-6-trifluoromethylsulfinylphenyl |
| 1-253 | 4-chlorophenyl | CH | CH | CH | CH | H | Me | 2,4-dibromo-6-trifluoromethylsulfinylphenyl |
| 1-254 | 2-chloropyridin-3-yl | CH | CH | CH | CH | H | Me | 2,4-dibromo-6-trifluoromethylsulfinylphenyl |
| 1-255 | 4-nitrophenyl | CH | CH | CH | CH | H | Me | 2,4-dibromo-6-trifluoromethylsulfinylphenyl |
| 1-256 | 4-cyanophenyl | CH | CH | CH | CH | H | Me | 2,4-dibromo-6-trifluoromethylsulfinylphenyl |
| 1-257 | phenyl | CH | CH | CH | CH | Me | Me | 2,4-dibromo-6-trifluoromethylsulfinylphenyl |
| 1-258 | 2-fluorophenyl | CH | CH | CH | CH | Me | Me | 2,4-dibromo-6-trifluoromethylsulfinylphenyl |
| 1-259 | 4-fluorophenyl | CH | CH | CH | CH | Me | Me | 2,4-dibromo-6-trifluoromethylsulfinylphenyl |
| 1-260 | 4-chlorophenyl | CH | CH | CH | CH | Me | Me | 2,4-dibromo-6-trifluoromethylsulfinylphenyl |
| 1-261 | 2-chloropyridin-3-yl | CH | CH | CH | CH | Me | Me | 2,4-dibromo-6-trifluoromethylsulfinylphenyl |
| 1-262 | 4-nitrophenyl | CH | CH | CH | CH | Me | Me | 2,4-dibromo-6-trifluoromethylsulfinylphenyl |
| 1-263 | 4-cyanophenyl | CH | CH | CH | CH | Me | Me | 2,4-dibromo-6-trifluoromethylsulfinylphenyl |
| 1-264 | phenyl | CH | CH | CH | CH | H | H | 4-bromo-2-chloro-6-trifluoromethylthiophenyl |
| 1-265 | phenyl | CH | CH | CH | CH | H | H | 2-bromo-4-chloro-6-trifluoromethylthiophenyl |
| 1-266 | phenyl | CH | CH | CH | CH | H | H | 2-chloro-4-(4-cyanophenyl)-6-trifluoromethylthiophenyl |
| 1-267 | phenyl | CH | CH | CH | CH | H | H | 2-chloro-4-(2-trifluoromethylphenyl)-6-trifluoromethylthiophenyl |
| 1-268 | phenyl | CH | CH | CH | CH | H | H | 2,6-dimethyl-4-(2-bromo-1,2,2-trifluoro-1-trifluoromethylethyl)phenyl |
| 1-269 | 2-fluorophenyl | CH | CH | CH | CH | H | H | 2,6-dimethyl-4-(2-bromo-1,2,2-trifluoro-1-trifluoromethylethyl)phenyl |
| 1-270 | 4-fluorophenyl | CH | CH | CH | CH | H | H | 2,6-dimethyl-4-(2-bromo-1,2,2-trifluoro-1-trifluoromethylethyl)phenyl |
| 1-271 | 4-chlorophenyl | CH | CH | CH | CH | H | H | 2,6-dimethyl-4-(2-bromo-1,2,2-trifluoro-1-trifluoromethylethyl)phenyl |
| 1-272 | 2-chloropyridin-3-yl | CH | CH | CH | CH | H | H | 2,6-dimethyl-4-(2-bromo-1,2,2-trifluoro-1-trifluoromethylethyl)phenyl |
| 1-273 | 4-nitrophenyl | CH | CH | CH | CH | H | H | 2,6-dimethyl-4-(2-bromo-1,2,2-trifluoro-1-trifluoromethylethyl)phenyl |
| 1-274 | 4-cyanophenyl | CH | CH | CH | CH | H | H | 2,6-dimethyl-4-(2-bromo-1,2,2-trifluoro-1-trifluoromethylethyl)phenyl |
| 1-275 | phenyl | CF | CH | CH | CH | H | H | 2,6-dimethyl-4-(2-bromo-1,2,2-trifluoro-1-trifluoromethylethyl)phenyl |
| 1-276 | 2-fluorophenyl | CF | CH | CH | CH | H | H | 2,6-dimethyl-4-(2-bromo-1,2,2-trifluoro-1-trifluoromethylethyl)phenyl |
| 1-277 | 4-fluorophenyl | CF | CH | CH | CH | H | H | 2,6-dimethyl-4-(2-bromo-1,2,2-trifluoro-1-trifluoromethylethyl)phenyl |
| 1-278 | 4-chlorophenyl | CF | CH | CH | CH | H | H | 2,6-dimethyl-4-(2-bromo-1,2,2-trifluoro-1-trifluoromethylethyl)phenyl |
| 1-279 | 2-chloropyridin-3-yl | CF | CH | CH | CH | H | H | 2,6-dimethyl-4-(2-bromo-1,2,2-trifluoro-1-trifluoromethylethyl)phenyl |
| 1-280 | 4-nitrophenyl | CF | CH | CH | CH | H | H | 2,6-dimethyl-4-(2-bromo-1,2,2-trifluoro-1-trifluoromethylethyl)phenyl |
| 1-281 | 4-cyanophenyl | CF | CH | CH | CH | H | H | 2,6-dimethyl-4-(2-bromo-1,2,2-trifluoro-1-trifluoromethylethyl)phenyl |
| 1-282 | phenyl | CH | CH | CH | CH | Me | H | 2,6-dimethyl-4-(2-bromo-1,2,2-trifluoro-1-trifluoromethylethyl)phenyl |
| 1-283 | 2-fluorophenyl | CH | CH | CH | CH | Me | H | 2,6-dimethyl-4-(2-bromo-1,2,2-trifluoro-1-trifluoromethylethyl)phenyl |
| 1-284 | 4-fluorophenyl | CH | CH | CH | CH | Me | H | 2,6-dimethyl-4-(2-bromo-1,2,2-trifluoro-1-trifluoromethylethyl)phenyl |
| 1-285 | 4-chlorophenyl | CH | CH | CH | CH | Me | H | 2,6-dimethyl-4-(2-bromo-1,2,2-trifluoro-1-trifluoromethylethyl)phenyl |
| 1-286 | 2-chloropyridin-3-yl | CH | CH | CH | CH | Me | H | 2,6-dimethyl-4-(2-bromo-1,2,2-trifluoro-1-trifluoromethylethyl)phenyl |
| 1-287 | 4-nitrophenyl | CH | CH | CH | CH | Me | H | 2,6-dimethyl-4-(2-bromo-1,2,2-trifluoro-1-trifluoromethylethyl)phenyl |
| 1-288 | 4-cyanophenyl | CH | CH | CH | CH | Me | H | 2,6-dimethyl-4-(2-bromo-1,2,2-trifluoro-1-trifluoromethylethyl)phenyl |
| 1-289 | phenyl | CH | CH | CH | CH | H | Me | 2,6-dimethyl-4-(2-bromo-1,2,2-trifluoro-1-trifluoromethylethyl)phenyl |
| 1-290 | 2-fluorophenyl | CH | CH | CH | CH | H | Me | 2,6-dimethyl-4-(2-bromo-1,2,2-trifluoro-1-trifluoromethylethyl)phenyl |
| 1-291 | 4-fluorophenyl | CH | CH | CH | CH | H | Me | 2,6-dimethyl-4-(2-bromo-1,2,2-trifluoro-1-trifluoromethylethyl)phenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-292 | 4-chlorophenyl | CH | CH | CH | CH | H | Me | 2,6-dimethyl-4-(2-bromo-1,2,2-trifluoro-1-trifluoromethylethyl)phenyl |
| 1-293 | 2-chloropyridin-3-yl | CH | CH | CH | CH | H | Me | 2,6-dimethyl-4-(2-bromo-1,2,2-trifluoro-1-trifluoromethylethyl)phenyl |
| 1-294 | 4-nitrophenyl | CH | CH | CH | CH | H | Me | 2,6-dimethyl-4-(2-bromo-1,2,2-trifluoro-1-trifluoromethylethyl)phenyl |
| 1-295 | 4-cyanophenyl | CH | CH | CH | CH | H | Me | 2,6-dimethyl-4-(2-bromo-1,2,2-trifluoro-1-trifluoromethylethyl)phenyl |
| 1-296 | phenyl | CH | CH | CH | CH | Me | Me | 2,6-dimethyl-4-(2-bromo-1,2,2-trifluoro-1-trifluoromethylethyl)phenyl |
| 1-297 | 2-fluorophenyl | CH | CH | CH | CH | Me | Me | 2,6-dimethyl-4-(2-bromo-1,2,2-trifluoro-1-trifluoromethylethyl)phenyl |
| 1-298 | 4-fluorophenyl | CH | CH | CH | CH | Me | Me | 2,6-dimethyl-4-(2-bromo-1,2,2-trifluoro-1-trifluoromethylethyl)phenyl |
| 1-299 | 4-chlorophenyl | CH | CH | CH | CH | Me | Me | 2,6-dimethyl-4-(2-bromo-1,2,2-trifluoro-1-trifluoromethylethyl)phenyl |
| 1-300 | 4-chloropyridin-3-yl | CH | CH | CH | CH | Me | Me | 2,6-dimethyl-4-(2-bromo-1,2,2-trifluoro-1-trifluoromethylethyl)phenyl |
| 1-301 | 4-nitrophenyl | CH | CH | CH | CH | Me | Me | 2,6-dimethyl-4-(2-bromo-1,2,2-trifluoro-1-trifluoromethylethyl)phenyl |
| 1-302 | 4-cyanophenyl | CH | CH | CH | CH | Me | Me | 2,6-dimethyl-4-(2-bromo-1,2,2-trifluoro-1-trifluoromethylethyl)phenyl |
| 1-303 | phenyl | CH | CH | CH | CH | H | H | 6-bromo-8-heptafluoroisopropylquinolin-5-yl |
| 1-304 | 2-fluorophenyl | CH | CH | CH | CH | H | H | 6-bromo-8-heptafluoroisopropylquinolin-5-yl |
| 1-305 | 4-nitrophenyl | CH | CH | CH | CH | H | H | 6-bromo-8-heptafluoroisopropylquinolin-5-yl |
| 1-306 | phenyl | CH | CH | CH | CH | H | H | 2,6-dimethyl-4-(2-bromo-1,2,2-trifluoro-1-trifluoromethylethyl)phenyl |
| 1-307 | phenyl | CH | CH | CH | CH | H | H | 2,6-dichloro-4-(2,2,2-trifluoro-1-trifluoromethylethoxy)phenyl |
| 1-308 | 2-fluorophenyl | CH | CH | CH | CH | H | H | 2,6-dichloro-4-(2,2,2-trifluoro-1-trifluoromethylethoxy)phenyl |
| 1-309 | phenyl | CH | CH | CH | CH | H | H | 5,7-dibromo-2,2,3,3-tetrafluoro-1,4-benzodioxan-5-yl |
| 1-310 | 2-fluorophenyl | CH | CH | CH | CH | H | H | 5,7-dibromo-2,2,3,3-tetrafluoro-1,4-benzodioxan-5-yl |
| 1-311 | 4-fluorophenyl | CH | CH | CH | CH | H | H | 5,7-dibromo-2,2,3,3-tetrafluoro-1,4-benzodioxan-5-yl |
| 1-312 | 4-nitrophenyl | CH | CH | CH | CH | H | H | 5,7-dibromo-2,2,3,3-tetrafluoro-1,4-benzodioxan-5-yl |
| 1-313 | phenyl | CH | CH | CH | CH | H | H | 5,7-dibromo-2,2,-difluoro-1,3-benzodioxolol-4-yl |
| 1-314 | 2-fluorophenyl | CH | CH | CH | CH | H | H | 2,6-dichloro-4-trifluoromethylphenyl |
| 1-315 | 2,6-difluorophenyl | CH | CH | CH | CH | H | H | 2,6-dichloro-4-trifluoromethylphenyl |
| 1-316 | phenyl | CH | CH | CH | CH | H | H | 2,4-dibromo-6-trifluoromethylphenyl |
| 1-317 | 4-fluoro-3-nitrophenyl | CH | CH | CH | CH | H | H | 2,4-dibromo-6-trifluoromethylphenyl |
| 1-318 | 5-fluoro-2-nitrophenyl | CH | CH | CH | CH | H | H | 2,4-dibromo-6-trifluoromethylphenyl |
| 1-319 | 2-fluoro-6-iodophenyl | CH | CH | CH | CH | H | H | 2,4-dibromo-6-trifluoromethylphenyl |
| 1-320 | 4-nitrophenyl | CH | CH | CH | CH | H | H | 2,4-dibromo-6-trifluoromethylphenyl |
| 1-321 | 4-phenylazophenyl | CH | CH | CH | CH | H | H | 2,4-dibromo-6-trifluoromethylphenyl |
| 1-322 | 2-(4-trifluoromethylphenyl)phenyl | CH | CH | CH | CH | H | H | 2,4-dibromo-6-trifluoromethylphenyl |
| 1-323 | 4-methoxycarbonylphenyl | CH | CH | CH | CH | H | H | 2,4-dibromo-6-trifluoromethylphenyl |
| 1-324 | 2,6-dimethoxyphenyl | CH | CH | CH | CH | H | H | 2,4-dibromo-6-trifluoromethylphenyl |
| 1-325 | pyrrol-2-yl | CH | CH | CH | CH | H | H | 2,4-dibromo-6-trifluoromethylphenyl |
| 1-326 | 5-(phenylethynyl)furan-2-yl | CH | CH | CH | CH | H | H | 2,4-dibromo-6-trifluoromethylphenyl |
| 1-327 | 5-(phenylethynyl)pyridin-3-yl | CH | CH | CH | CH | H | H | 2,4-dibromo-6-trifluoromethylphenyl |
| 1-328 | 4-pyridine | CH | CH | CH | CH | H | H | 2,4-dibromo-6-trifluoromethylphenyl |
| 1-329 | 2,4-dichloro-3-pyridine | CH | CH | CH | CH | H | H | 2,4-dibromo-6-trifluoromethylphenyl |
| 1-330 | 3-thienyl | CH | CH | CH | CH | H | H | 2,4-dibromo-6-trifluoromethylphenyl |
| 1-331 | 2-methoxyphenyl | CH | CH | CH | CH | H | H | 2,4-dibromo-6-trifluoromethylphenyl |
| 1-332 | 2-phenoxyphenyl | CH | CH | CH | CH | H | H | 2,4-dibromo-6-trifluoromethylphenyl |
| 1-333 | 2-quinolyl | CH | CH | CH | CH | H | H | 2,4-dibromo-6-trifluoromethylphenyl |
| 1-334 | 4-quinolyl | CH | CH | CH | CH | H | H | 2,4-dibromo-6-trifluoromethylphenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-335 | 2-phenylquinolin-4-yl | CH | CH | CH | CH | H | H | 2,4-dibromo-6-trifluoromethylphenyl |
| 1-336 | 1-naphthyl | CH | CH | CH | CH | H | H | 2,4-dibromo-6-trifluoromethylphenyl |
| 1-337 | anthracen-9-yl | CH | CH | CH | CH | H | H | 2,4-dibromo-6-trifluoromethylphenyl |
| 1-338 | acridin-9-yl | CH | CH | CH | CH | H | H | 2,4-dibromo-6-trifluoromethylphenyl |
| 1-339 | phenyl | CH | CH | CH | CH | H | H | 2-bromo-4,6-bis(trifluoromethyl)phenyl |
| 1-340 | phenyl | CH | CH | CH | CH | H | H | 2,4-bis(trifluoromethyl)phenyl |
| 1-341 | 2-cyanophenyl | CH | CH | CH | CH | H | H | 2,4-bis(trifluoromethyl)phenyl |
| 1-342 | 3,5-difluorophenyl | CH | CH | CH | CH | H | H | 2,4-bis(trifluoromethyl)phenyl |
| 1-343 | 2,6-difluorophenyl | CH | CH | CH | CH | H | H | 2,4-bis(trifluoromethyl)phenyl |
| 1-344 | 2,3,4-trifluorophenyl | CH | CH | CH | CH | H | H | 2,4-bis(trifluoromethyl)phenyl |
| 1-345 | 4-chlorophenyl | CH | CH | CH | CH | H | H | 2,4-bis(trifluoromethyl)phenyl |
| 1-346 | 2,4-dichlorophenyl | CH | CH | CH | CH | H | H | 2,4-bis(trifluoromethyl)phenyl |
| 1-347 | 4,5-difluoro-2-nitrophenyl | CH | CH | CH | CH | H | H | 2,4-bis(trifluoromethyl)phenyl |
| 1-348 | 3-fluoro-2-methylphenyl | CH | CH | CH | CH | H | H | 2,4-bis(trifluoromethyl)phenyl |
| 1-349 | 4-methylphenyl | CH | CH | CH | CH | H | H | 2,4-bis(trifluoromethyl)phenyl |
| 1-350 | 4-ethylphenyl | CH | CH | CH | CH | H | H | 2,4-bis(trifluoromethyl)phenyl |
| 1-351 | 3-methoxyphenyl | CH | CH | CH | CH | H | H | 2,4-bis(trifluoromethyl)phenyl |
| 1-352 | 4-methoxyphenyl | CH | CH | CH | CH | H | H | 2,4-bis(trifluoromethyl)phenyl |
| 1-353 | 3,4,5-trimethoxyphenyl | CH | CH | CH | CH | H | H | 2,4-bis(trifluoromethyl)phenyl |
| 1-354 | 1-naphthyl | CH | CH | CH | CH | H | H | 2,4-bis(trifluoromethyl)phenyl |
| 1-355 | 2-naphthyl | CH | CH | CH | CH | H | H | 2,4-bis(trifluoromethyl)phenyl |
| 1-356 | 5-chloro-2-thienyl | CH | CH | CH | CH | H | H | 2,4-bis(trifluoromethyl)phenyl |
| 1-357 | 2-chloro-3-pyridyl | CH | CH | CH | CH | H | H | 2,4-bis(trifluoromethyl)phenyl |
| 1-358 | 6-methyl-2-pyridyl | CH | CH | CH | CH | H | H | 2,4-bis(trifluoromethyl)phenyl |
| 1-359 | 5-chloro-2-pyridyl | CH | CH | CH | CH | H | H | 2,4-bis(trifluoromethyl)phenyl |
| 1-360 | 6-hydroxy-2-pyridyl | CH | CH | CH | CH | H | H | 2,4-bis(trifluoromethyl)phenyl |
| 1-361 | 5-methyl-pyrazin-2-yl | CH | CH | CH | CH | H | H | 2,4-bis(trifluoromethyl)phenyl |
| 1-362 | pyrazin-2-yl | CH | CH | CH | CH | H | H | 2,4-bis(trifluoromethyl)phenyl |
| 1-363 | 5-methyl-2-thienyl | CH | CH | CH | CH | H | H | 2,4-bis(trifluoromethyl)phenyl |
| 1-364 | 3-methyl-2-thienyl | CH | CH | CH | CH | H | H | 2,4-bis(trifluoromethyl)phenyl |
| 1-365 | phenyl | CH | CH | CH | CH | H | H | 2,5-bis(trifluoromethyl)phenyl |
| 1-366 | phenyl | CH | CH | CH | CH | H | H | 2-chloro-4,6-bis(trifluoromethyl)phenyl |
| 1-367 | 2,6-difluorophenyl | CH | CH | CH | CH | H | H | 2-chloro-4,6-bis(trifluoromethyl)phenyl |
| 1-368 | 4-nitrophenyl | CH | CH | CH | CH | H | H | 2-chloro-4,6-bis(trifluoromethyl)phenyl |
| 1-369 | phenyl | CH | CH | CH | CH | H | H | 2-bromo-6-methyl-4-(trifluoromethanesulfonyloxy)phenyl |
| 1-370 | 2-fluorophenyl | CH | CH | CH | CH | H | H | 2-bromo-6-methyl-4-(trifluoromethanesulfonyloxy)phenyl |
| 1-371 | phenyl | CH | CH | CH | CH | H | H | 2-chloro-6-methyl-4-(trifluoromethanesulfonyloxy)phenyl |
| 1-372 | phenyl | CH | CH | CH | CH | H | H | 2-methyl-4-(trifluoromethanesulfonyloxy)phenyl |
| 1-373 | phenyl | CH | CH | CH | CH | H | H | 4-(heptafluoroisopropyl)-2-methylnaphthyl |
| 1-374 | 2-fluorophenyl | CH | CH | CH | CH | H | H | 4-(heptafluoroisopropyl)-2-methylnaphthyl |
| 1-375 | phenyl | CH | CH | CH | CH | H | H | 7-heptafluoroisopropylindan-4-yl |
| 1-376 | phenyl | CH | CH | CH | CH | H | H | 2,6-dichloro-4-pentafluorosulfanylphenyl |
| 1-377 | phenyl | CH | CH | CH | CH | H | H | 4-(3,4-dfluorophenyl)-2,6-dimethylphenyl |
| 1-378 | phenyl | CH | CH | CH | CH | H | H | 4-(4-fluoro-3-methylphenyl)-2,6-dimethylphenyl |
| 1-379 | phenyl | CH | CH | CH | CH | H | H | 4-(furan-3-yl)-2,6-dimethylphenyl |
| 1-380 | 2-chlorophenyl | CH | CH | CH | CH | H | H | 2,6-dimethyl-4-(thiophen-2-yl)phenyl |
| 1-381 | 2-chlorophenyl | CH | CH | CH | CH | H | H | 2,6-dimethyl-4-(thiophen-3-yl)phenyl |
| 1-382 | phenyl | CH | CH | CH | CH | H | H | 2,6-dibromo-4-cyclohexylphenyl |
| 1-383 | phenyl | CH | CH | CH | CH | H | H | 3-cyclohexylphenyl |
| 1-384 | phenyl | CH | CH | CH | CH | H | H | 2,6-dimethyl-4-(pentafluoropropionyl)phenyl |
| 1-385 | phenyl | CH | CH | CH | CH | H | H | 4-(heptafluorobutyryl)-2,6-dimethylphenyl |
| 1-386 | phenyl | CH | CH | CH | CH | H | H | 2,6-dimethyl-4-(2,2,2-trifluoro-1-trifluoromethylethyl)phenyl |
| 1-387 | phenyl | CH | CH | CH | CH | H | H | 2-bromo-6-(2,2,2-trifluoro-1-trifluoromethylethoxy)pyridin-3-yl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-388 | phenyl | CH | CH | CH | CH | H | H | 2,2,3,3,4,4,4-pentafluorobutyl |
| 1-389 | phenyl | CH | CH | CH | CH | H | H | 2,2,3,3,3-pentafluoropropyl |
| 1-390 | phenyl | CH | CH | CH | CH | H | H | 2,4,6-tribromo-3-heptafluoropropylthiophenyl |
| 1-391 | 2-chloropyridin-3-yl | CH | CH | CH | CH | H | H | 2,4,6-tribromo-3-heptafluoropropylthiophenyl |
| 1-392 | 2-fluorophenyl | CH | CH | CH | CH | H | H | 2,4,6-tribromo-3-heptafluoropropylthiophenyl |
| 1-393 | 2-fluorophenyl | CH | CH | CH | CH | H | H | 4-trifluoromethylthiophenyl |
| 1-394 | 2-fluorophenyl | CH | CH | CH | CH | H | H | 4-trifluoromethylsulfonylphenyl |
| 1-395 | phenyl | CH | CH | CH | CH | H | H | 4-heptafluoropropylthiophenyl |
| 1-396 | phenyl | CH | CH | CH | CH | H | H | 4-heptafluoroisopropylthiophenyl |
| 1-397 | phenyl | CH | CH | CH | CH | H | H | 4-heptafluoropropylthio-2-methylphenyl |
| 1-398 | 4-hydroxyphenyl | CH | CH | CH | CH | Me | Me | 4-heptafluoropropylsulfonylphenyl |
| 1-399 | 2-fluorophenyl | CH | CH | CH | CH | H | H | 4-heptafluoropropylthio-2-methylphenyl |
| 1-400 | phenyl | CH | CH | CH | CH | H | H | 4-methyl-6-(2,2,2-trifluoro-1-trifluoromethyl-ethoxy)pyridin-3-yl |
| 1-401 | 2-fluorophenyl | CH | CH | CH | CH | H | H | 4-methyl-6-(2,2,2-trifluoro-1-trifluoromethyl-ethoxy)pyridin-3-yl |
| 1-402 | 2-fluorophenyl | CH | CH | CH | CH | H | H | 2-bromo-6-(2,2,2-trifluoro-1-trifluoromethyl-ethoxy)pyridin-3-yl |
| 1-403 | phenyl | CH | CH | CH | CH | H | H | 4-{2,2,2-trifluoro-1-(trifluoromethyl)-exhoxy}pyridin-3-yl |
| 1-404 | 2-fluorophenyl | CH | CH | CH | CH | H | H | 4-{2,2,2-trifluoro-1-(trifluoromethyl)-ethoxy}pyridin-3-yl |
| 1-405 | phenyl | CH | CH | CH | CH | H | H | 2,4-dibromo-6-trifluoromethoxyphenyl |
| 1-406 | 2-fluorophenyl | CH | CH | CH | CH | H | H | 2,4-dibromo-6-trifluoromethoxyphenyl |
| 1-407 | 4-nitrophenyl | CH | CH | CH | CH | H | H | 2,4-dibromo-6-trifluoromethoxyphenyl |
| 1-408 | phenyl | CH | CH | CH | CH | H | H | 4-bromo-6-trifluoromethoxyphenyl |
| 1-409 | 2,4-difluorophenyl | CH | CH | CH | CH | H | H | 2,4-dibromo-6-trifluoromethylphenyl |
| 1-410 | phenyl | CH | CH | CH | CH | H | H | 2,4-dibromo-6-(heptafluoropropylthio)phenyl |
| 1-411 | 2-fluorophenyl | CH | CH | CH | CH | H | H | 2,4-dibromo-6-(heptafluoropropylthio)phenyl |
| 1-412 | 4-nitrophenyl | CH | CH | CH | CH | H | H | 2,4-dibromo-6-(heptafluoropropylthio)phenyl |
| 1-413 | phenyl | CH | CH | CH | CH | H | H | 2,4-dibromo-6-(nonafluorobutylthio)phenyl |
| 1-414 | 2-fluorophenyl | CH | CH | CH | CH | H | H | 2-bromo-4-chloro-6-trifluoromethylphenyl |
| 1-415 | phenyl | CH | CH | CH | CH | H | H | 2-bromo-4-chloro-6-trifluoromethylphenyl |
| 1-416 | 2-fluorophenyl | CH | CH | CH | CH | H | H | 2-bromo-6-chloro-4-trifluoromethylphenyl |
| 1-417 | phenyl | CH | CH | CH | CH | H | H | 4-bromo-2-chloro-6-trifluoromethylphenyl |
| 1-418 | 2,6-difluorophenyl | CH | CH | CH | CH | H | H | 4-bromo-2-chloro-6-trifluoromethylphenyl |
| 1-419 | phenyl | CH | CH | CH | CH | H | H | 2-bromo-4-fluoro-6-trifluoromethylphenyl |
| 1-420 | phenyl | CH | CH | CH | CH | H | H | 4-fluoro-6-trifluoromethylphenyl |
| 1-421 | 2-iodophenyl | CH | CH | CH | CH | H | H | 4-heptafluoroisopropyl-2-methylphenyl |
| 1-422 | phenyl | CH | CH | CH | CH | H | H | 2-sec-butyl-4-heptafluoroisopropylphenyl |
| 1-423 | phenyl | CH | CH | CH | CH | H | H | 2-chloro-4-heptafluoroisopropylphenyl |
| 1-424 | 2-fluorophenyl | CH | CH | CH | CH | H | H | 4-heptafluoroisopropylphenyl |
| 1-425 | phenyl | CH | CH | CH | CH | H | H | 2-methanesulfonyl-4-heptafluoroisopropylphenyl |
| 1-426 | 4-nitrophenyl | CH | CH | CH | CH | H | H | 2-methanesulfonyl-4-heptafluoroisopropylphenyl |
| 1-427 | phenyl | CH | CH | CH | CH | H | H | 2,6-dibromo-4-trifluoromethylphenyl |
| 1-428 | 2-fluorophenyl | CH | CH | CH | CH | H | H | 2,6-dibromo-4-trifluoromethylphenyl |
| 1-429 | 2,6-difluorophenyl | CH | CH | CH | CH | H | H | 2,6-dibromo-4-trifluoromethylphenyl |
| 1-430 | phenyl | CH | CH | CH | CH | H | H | 2,6-dichloro-4-(2,2,3,3,3,-pentafluoropropoxy)phenyl |
| 1-431 | 2-fluorophenyl | CH | CH | CH | CH | H | H | 2,6-dichloro-4-(2,2,3,3,3,-pentafluoropropoxy)phenyl |
| 1-432 | phenyl | CH | CH | CH | CH | H | H | 2-methyl-4-(2,2,2-trifluoroethoxy)phenyl |
| 1-433 | 2-chloropyridin-3-yl | CH | CH | CH | CH | H | H | 2,6-dichloro-4-(2,2,3,3,3,-pentafluoropropoxy)phenyl |
| 1-434 | phenyl | CH | CH | CH | CH | H | H | 2,6-dimethyl-4-(2-chloro-2,2-difluoro-1-(chlorodifluoromethyl)-1-hydroxyethyl)phenyl |
| 1-435 | phenyl | CH | CH | CH | CH | H | H | 2,6-dimethyl-4-(2,2,2-trifluoro-1-trifluoromethyl-1-methoxy)phenyl |
| 1-436 | 2-fluorophenyl | CH | CH | CH | CH | H | H | 2,6-dimethyl-4-(2,2,2-trifluoro-1-trifluoromethyl-1-methoxy)phenyl |
| 1-437 | phenyl | CH | CH | CH | CH | H | H | 2,6-dichloro-4-trifluoromethoxyphenyl |
| 1-438 | phenyl | CH | CH | CH | CH | H | H | 2-methyl-4-(trifluoromethoxy)phenyl |
| 1-439 | phenyl | CH | CH | CH | CH | H | H | 5-nitropyridin-2-yl |
| 1-440 | phenyl | CH | CH | CH | CH | H | H | 5-chloropyridin-2-yl |
| 1-441 | phenyl | CH | CH | CH | CH | H | H | 4-methyl-6-(heptafluoroisopropyl)pyridin-3-yl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-442 | phenyl | CH | CH | CH | CH | H | H | 3-chloro-5-trifluoromethylpyridin-2-yl |
| 1-443 | phenyl | CH | CH | CH | CH | H | H | 5-heptafluoroisopropyl-2-methoxycarbonyl-4-methylthiophen-3-yl |
| 1-444 | 2-fluorophenyl | CH | CH | CH | CH | H | H | 5-heptafluoroisopropyl-2-methoxycarbonyl-4-methylthiophen-3-yl |
| 1-445 | phenyl | CH | CH | CH | CH | H | H | 2-bromo-6-chloro-4-methylpyridin-3-yl |
| 1-446 | phenyl | CH | CH | CH | CH | H | H | 2,6-dimethyl-4-trifluoromethylphenyl |
| 1-447 | 2-fluorophenyl | CH | CH | CH | CH | H | H | 2,6-dimethyl-4-trifluoromethylphenyl |
| 1-448 | phenyl | CH | CH | CH | CH | H | H | 4-trifluoromethylbenzyl |
| 1-449 | phenyl | CH | CH | CH | CH | H | H | 3-trifluoromethylbenzyl |
| 1-450 | phenyl | CH | CH | CH | CH | H | H | 2-trifluoromethylbenzyl |
| 1-451 | phenyl | CH | CH | CH | CH | H | H | 4-nitrobenzyl |
| 1-452 | phenyl | CH | CH | CH | CH | H | H | 3,5-bis(trifluoromethyl)benzyl |
| 1-453 | phenyl | CH | CH | CH | CH | H | H | 4-chloro-2,6-dimethylphenyl |
| 1-454 | phenyl | CH | CH | CH | CH | H | H | 4-bromo-2,6-dimethylphenyl |
| 1-455 | phenyl | CH | CH | CH | CH | H | H | 4-iodine-2,6-dimethylphenyl |
| 1-456 | 2,6-difluorophenyl | CH | CH | CH | CH | H | H | 4-iodine-2,6-dimethylphenyl |
| 1-457 | phenyl | CH | CH | CH | CH | H | H | 4-chloro-2-trifluoromethylphenyl |
| 1-458 | phenyl | CH | CH | CH | CH | H | H | 2-chloro-6-trifluoromethylphenyl |
| 1-459 | phenyl | CH | CH | CH | CH | H | H | 4-iodine-2-trifluoromethylphenyl |
| 1-460 | phenyl | CH | CH | CH | CH | H | H | 2-chloro-4-iodine-6-methylphenyl |
| 1-461 | phenyl | CH | CH | CH | CH | H | H | 2,6-dimethylphenyl |
| 1-462 | phenyl | CH | CH | CH | CH | H | H | 4-bromo-2-methyl-5-trifluoromethyl-2H-pyrazol-3-yl |
| 1-463 | phenyl | CH | CH | CH | CH | H | H | 2,3,5,6-tetrafluoro-4-trifluoromethylphenyl |
| 1-464 | phenyl | CH | CH | CH | CH | H | H | 2,3,4,5,6-pentafluorophenyl |
| 1-465 | 2-fluorophenyl | CH | CH | CH | CH | H | H | 2,3,4-trifluorophenyl |
| 1-466 | 2-fluorophenyl | CH | CH | CH | CH | H | H | 4-trifluoromethylphenyl |
| 1-467 | 2-fluorophenyl | CH | CH | CH | CH | H | H | 2-bromo-4-trifluoromethylphenyl |
| 1-468 | phenyl | CH | CH | CH | CH | H | H | 2-bromo-6-chloro-4-trifluoromethylphenyl |
| 1-469 | 2-fluorophenyl | CH | CH | CH | CH | H | H | 2-trifluoromethylphenyl |
| 1-470 | phenyl | CH | CH | CH | CH | H | H | 2,4-dichloro-6-trifluoromethylphenyl |
| 1-471 | phenyl | CH | CH | CH | CH | H | H | 2-bromo-4-isopropyl-6-trifluoromethylphenyl |
| 1-472 | 2-fluorophenyl | CH | CH | CH | CH | H | H | 2-bromo-4-isopropyl-6-trifluoromethylphenyl |
| 1-473 | phenyl | CH | CH | CH | CH | H | H | 4-(heptafluoroisopropylcarbonyl)phenyl |
| 1-474 | phenyl | CH | CH | CH | CH | H | H | 2-methyl-4-nitrophenyl |
| 1-475 | phenyl | CH | CH | CH | CH | H | H | 2,4-dichlorophenyl |
| 1-476 | phenyl | CH | CH | CH | CH | H | H | 3-iodine-5-nitrophenyl |
| 1-477 | phenyl | CH | CH | CH | CH | H | H | 2,6-dimethyl-4-nitrophenyl |
| 1-478 | phenyl | CH | CH | CH | CH | H | H | 5-nitro-2-pyrimidinyl |
| 1-479 | phenyl | CH | CH | CH | CH | H | H | 3-bromo-5-nitro-2-pyridine |
| 1-480 | phenyl | CH | CH | CH | CH | H | H | 4-tert-butylcarbonyloxy-2-methylphenyl |
| 1-481 | phenyl | CH | CH | CH | CH | H | H | 4-benzoyloxy-2-methylphenyl |
| 1-482 | phenyl | CH | CH | CH | CH | H | H | 4-benzoyloxy-6-chloro-2-methylphenyl |
| 1-483 | phenyl | CH | CH | CH | CH | H | H | 6-chloro-4-hydroxy-2-methylphenyl |
| 1-484 | phenyl | CH | CH | CH | CH | H | H | 2-bromo-4-hydroxy-6-methylphenyl |
| 1-485 | phenyl | CH | CH | CH | CH | H | H | 2-bromo-6-methyl-4-(p-toluenesulfonyloxy)phenyl |
| 1-486 | phenyl | CH | CH | CH | CH | Me | H | 2,6-dibromo-4-(pyrrolidine-1-carbonyl)phenyl |
| 1-487 | phenyl | CH | CH | CH | CH | Me | H | 2,6-dibromo-4-ethoxycarbonylphenyl |
| 1-488 | phenyl | CH | CH | CH | CH | H | H | 2,6-dichloro-4-(2,5-dioxo-3,3,4,4-tetrafluoropyrrolidin-1-yl)phenyl |
| 1-489 | phenyl | CH | CH | CH | CH | H | H | 2,6-dichloro-4-(2,5-dioxopyrrolidin-1-yl)phenyl |
| 1-490 | phenyl | CH | CH | CH | CH | H | H | 2,6-dichloro-4-(1,3-dioxoisoindolin-2-yl)phenyl |
| 1-491 | phenyl | CH | CH | CH | CH | H | H | benzothiazol-2-yl |
| 1-492 | phenyl | CH | CH | CH | CH | H | H | benzothiazol-6-yl |
| 1-493 | phenyl | CH | CH | CH | CH | H | H | 6-chlorobenzothiazol-2-yl |
| 1-494 | phenyl | CH | CH | CH | CH | H | H | 5,6-dimethylbenzothiazol-2-yl |
| 1-495 | phenyl | CH | CH | CH | CH | H | H | 6-methoxybenzothiazol-2-yl |
| 1-496 | phenyl | CH | CH | CH | CH | H | H | 5-chlorobenzoxazol-2-yl |

TABLE 1-continued

| Compound No. | $Q_1$ | $A'_1$ | $A'_2$ | $A'_3$ | $A'_4$ | $R_1$ | $R_2$ | $Q_2$ |
|---|---|---|---|---|---|---|---|---|
| 1-497 | phenyl | CH | CH | CH | CH | H | H | 4,6-dibromo-3H-benzo[d]imidazol-5-yl |
| 1-498 | 2-chloropyridin-3-yl | CH | CH | CH | CH | H | H | 4,6-dibromo-3H-benzo[d]imidazol-5-yl |
| 1-499 | phenyl | CH | CH | CH | CH | H | H | quinolin-8-yl |
| 1-500 | phenyl | CH | CH | CH | CH | H | H | quinolin-3-yl |
| 1-501 | phenyl | CH | CH | CH | CH | H | H | isoquinolin-1-yl |
| 1-502 | phenyl | CH | CH | CH | CH | H | H | 4-phenylazophenyl |
| 1-503 | phenyl | CH | CH | CH | CH | H | H | 4-phenylthiazol-2-yl |
| 1-504 | phenyl | CH | CH | CH | CH | H | H | 3-methylisothiazol-5-yl |
| 1-505 | phenyl | CH | CH | CH | CH | H | H | 5-phenyl-2H-pyrazol-3-yl |
| 1-506 | phenyl | CH | CH | CH | CH | H | H | fluoren-2-yl |
| 1-507 | phenyl | CH | CH | CH | CH | H | H | 9-oxofluoren-2-yl |
| 1-508 | phenyl | CH | CH | CH | CH | H | H | adamantan-1-yl |
| 1-509 | phenyl | CH | CH | CH | CH | H | H | adamantan-2-yl |
| 1-510 | phenyl | CH | CH | CH | CH | H | H | 3H-isoindol-1-yl |
| 1-511 | phenyl | CH | CH | CH | CH | H | H | 2,6-dimethylpyrimidin-4-yl |
| 1-512 | phenyl | CH | CH | CH | CH | H | H | 3,4-dicyanophenyl |
| 1-513 | phenyl | CH | CH | CH | CH | H | H | 5-methylthio-1H-[1,2,4]triazol-3-yl |
| 1-514 | phenyl | CH | CH | CH | CH | H | H | 5-bromothiazol-2-yl |
| 1-515 | phenyl | CH | CH | CH | CH | H | H | 4-methylthiazol-2-yl |
| 1-516 | phenyl | CH | CH | CH | CH | H | H | 2-norbornyl |
| 1-517 | phenyl | CH | CH | CH | CH | H | H | 4-methyl-6-(heptafluoroisopropyl)-benzothiazol-2-yl |
| 1-518 | 2-fluorophenyl | CH | CH | CH | CH | H | H | 4,6-dimethyl-2-(heptafluoroisopropyl)pyrimidin-5-yl |
| 1-519 | 2-chloropyridin-3-yl | CH | CH | CH | CH | Me | H | 4,6-dimethoxy-2-(heptafluoroisopropyl)pyrimidin-5-yl |
| 1-520 | phenyl | CH | CH | CH | CH | Me | H | 4,6-dimethoxy-2-(heptafluoroisopropyl)pyrimidin-5-yl |
| 1-521 | phenyl | CH | CH | CH | CH | H | H | 3,5-dichloro-2,6-difluoropyridin-4-yl |
| 1-522 | 2-fluorophenyl | CH | CH | CH | CH | H | H | 3,5-dichloro-2,6-difluoropyridin-4-yl |
| 1-523 | phenyl | CH | CH | CH | CH | Me | H | 2-carboxy-6-nitrophenyl |
| 1-524 | phenyl | CH | CH | CH | CH | Me | H | 2-(methylaminocarbonyl)-6-nitrophenyl |
| 1-525 | phenyl | CH | CH | CH | CH | Me | H | 2-(isopropylaminocarbonyl)-6-nitrophenyl |
| 1-526 | phenyl | CH | CH | CH | CH | H | H | 2-carboxy-6-nitrophenyl |
| 1-527 | phenyl | CH | CH | CH | CH | Me | H | 2-carboxy-6-chlorophenyl |
| 1-528 | phenyl | CH | CH | CH | CH | Me | H | 2,4-dibromo-6-carboxyphenyl |
| 1-529 | phenyl | CH | CH | CH | CH | Me | H | 2-carboxy-4,6-dichlorophenyl |
| 1-530 | phenyl | CH | CH | CH | CH | Me | H | 2,6-dichloro-4-methylsulfonyl |
| 1-531 | 2-hydroxyphenyl | CH | CH | CH | CH | Me | Me | 2,6-dibromo-4-methoxysulfonylphenyl |
| 1-532 | 3-hydroxyphenyl | CH | CH | CH | CH | Me | Me | 2,6-dibromo-4-methoxysulfonylphenyl |
| 1-533 | 4-hydroxyphenyl | CH | CH | CH | CH | Me | Me | 2,6-dibromo-4-methoxysulfonylphenyl |
| 1-534 | 2-fluorophenyl | CH | CH | CH | CH | H | H | 4-propylthiophenyl |
| 1-535 | 2-fluorophenyl | CH | CH | CH | CH | H | H | 4-propylsulfinylphenyl |
| 1-536 | 2-fluorophenyl | CH | CH | CH | CH | H | H | 2,6-dibromo-4-propylthiophenyl |
| 1-537 | 2-fluorophenyl | CH | CH | CH | CH | H | H | 2,6-dibromo-4-propylsulfonylphenyl |
| 1-538 | 2-fluorophenyl | CH | CH | CH | CH | H | H | 2,6-dibromo-4-propylsulfinylphenyl |
| 1-539 | 2-fluorophenyl | CH | CH | CH | CH | H | H | 2,6-dibromo-4-phenylthiophenyl |
| 1-540 | phenyl | CH | CH | CH | CH | H | H | 2,6-dibromo-4-phenylthiophenyl |
| 1-541 | phenyl | CH | CH | CH | CH | H | H | 2,6-dibromo-4-(4-trifluoromethylphenylmethylthio)phenyl |
| 1-542 | 2-fluorophenyl | CH | CH | CH | CH | H | H | 2,6-dibromo-4-(4-trifluoromethylphenylmethylthio)phenyl |
| 1-543 | 2-chloropyridin-3-yl | CH | CH | CH | CH | H | H | 2,6-dibromo-4-(4-trifluoromethylphenylmethylthio)phenyl |
| 1-544 | 4-nitrophenyl | CH | CH | CH | CH | H | H | 2,6-dibromo-4-(4-trifluoromethylphenylmethylthio)phenyl |
| 1-545 | 4-fluorophenyl | CH | CH | CH | CH | H | H | 2,6-dibromo-4-(4-trifluoromethylphenylmethylthio)phenyl |
| 1-546 | phenyl | CH | CH | CH | CH | H | H | 2,6-dibromo-4-(2,2,2-trifluoroethylthio)phenyl |
| 1-547 | 2-fluorophenyl | CH | CH | CH | CH | H | H | 2,6-dibromo-4-(2,2,2-trifluoroethylthio)phenyl |
| 1-548 | 2-chloropyridin-3-yl | CH | CH | CH | CH | H | H | 2,6-dibromo-4-(2,2,2-trifluoroethylthio)phenyl |
| 1-549 | 4-nitrophenyl | CH | CH | CH | CH | H | H | 2,6-dibromo-4-(2,2,2-trifluoroethylthio)phenyl |
| 1-550 | phenyl | CH | CH | CH | CH | H | H | 2,6-dichloro-4-nitrophenyl |
| 1-551 | phenyl | CH | CH | CH | CH | Me | H | 2,6-dichloro-4-cyanophenyl |
| 1-552 | phenyl | CH | CH | CH | CH | H | H | 4-amino-2,6-dichlorophenyl |
| 1-553 | phenyl | CH | CH | CH | CH | H | H | 4-cyano-1-methyl-3-(4-trifluoromethylphenyl)-1H-pyrazol-5-yl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-554 | phenyl | CH | CH | CH | CH | H | H | 4-acetamino-2,6-dichlorophenyl |
| 1-555 | phenyl | CH | CH | CH | CH | H | H | 4-benzoylamino-2,6-dichlorophenyl |
| 1-556 | phenyl | CH | CH | CH | CH | Me | H | 2,6-dibromo-4-methylcarbamoylphenyl |
| 1-557 | phenyl | CH | CH | CH | CH | H | H | 1-(3-chloro-5-trifluoromethylpyridin-2-yl)-4-cyano-1H-imidazol-5-yl |
| 1-558 | 2-chloropyridin-3-yl | CH | CH | CH | CH | H | H | 4-cyano-1-methyl-1H-pyrazol-5-yl |
| 1-559 | 2-fluorophenyl | CH | CH | CH | CH | H | H | 4-cyano-1-methyl-1H-pyrazol-5-yl |
| 1-560 | phenyl | CH | CH | CH | CH | H | H | 4-cyano-1-t-butyl-1H-pyrazol-5-yl |
| 1-561 | phenyl | CH | CH | CH | CH | H | H | 4-methyl-6-(heptafluoroisopropyl)benzo[d]thiazol-2-yl |
| 1-562 | phenyl | CH | CH | CH | CH | H | H | 4-methyl-6-(4-trifluoromethylphenyl)-1H-pyrazol-5-yl |
| 1-563 | phenyl | CH | CH | CH | CH | Me | H | 2,6-dibromo-4-(1H-1,2,4-triazol-1-yl)phenyl |
| 1-564 | phenyl | CH | CH | CH | CH | Me | H | 2,6-dibromo-4-(oxazol-4-yl)phenyl |
| 1-565 | phenyl | CH | CH | CH | CH | H | H | 2,6-dibromo-4-(1,2,3-thiadiazol-4-yl)phenyl |
| 1-566 | phenyl | CH | CH | CH | CH | H | H | 4-heptafluoroisopropyl-2-hydroxy-6-methylphenyl |
| 1-567 | phenyl | CH | CH | CH | CH | Me | H | 4-heptafluoroisopropyl-2-hydroxy-6-methylphenyl |
| 1-568 | phenyl | CH | CH | CH | CH | Me | H | 4-heptafluoroisopropyl-2-methanesulfonyloxy-6-methylphenyl |
| 1-569 | phenyl | CH | CH | CH | CH | Me | H | 4-heptafluoroisopropyl-2-trifluoromethanesulfonyloxy-6-methylphenyl |
| 1-570 | phenyl | CH | CH | CH | CH | Me | H | 2-acetoxy-4-heptafluoroisopropyl-6-methylphenyl |
| 1-571 | phenyl | CH | CH | CH | CH | H | H | 4-heptafluoroisopropyl-2-hydroxymethyl-6-methylphenyl |
| 1-572 | phenyl | CH | CH | CH | CH | H | H | 4-heptafluoroisopropyl-2-methoxymethyl-6-methylphenyl |
| 1-573 | phenyl | CH | CH | CH | CH | H | H | 2-methylthiomethyl-4-heptafluoroisopropyl-6-trifluoromethylphenyl |
| 1-574 | phenyl | CH | CH | CH | CH | H | H | 2-bromo-6-chloro-4-(3,5-dichloro-pyridin-2-yloxy)phenyl |
| 1-575 | phenyl | CH | CH | CH | CH | Me | H | 2-bromo-4-(3-chloro-5-trifluoromethylpyridin-2-yloxy)-6-methylphenyl |
| 1-576 | phenyl | CH | CH | CH | CH | H | H | 2-bromo-4-(3-chloro-5-trifluoromethylpyridin-2-yloxy)-6-methylphenyl |
| 1-577 | 2-fluorophenyl | CH | CH | CH | CH | H | H | 2-bromo-4-(3-chloro-5-trifluoromethylpyridin-2-yloxy)-6-methylphenyl |
| 1-578 | 2,6-difluorophenyl | CH | CH | CH | CH | H | H | 2-bromo-4-(3-chloro-5-trifluoromethylpyridin-2-yloxy)-6-methylphenyl |
| 1-579 | 2-cloropyridin-3-yl | CH | CH | CH | CH | H | H | 2-bromo-4-(3-chloro-5-trifluoromethylpyridin-2-yloxy)-6-methylphenyl |
| 1-580 | phenyl | CH | CH | CH | CH | Me | H | 2-chloro-4-(3,5-dichloropyridin-2-yloxy)phenyl |
| 1-581 | phenyl | CH | CH | CH | CH | H | H | 2-chloro-4-(4-fluorophenyl)-6-trifluoromethylthiophenyl |
| 1-582 | 2-cloropyridin-3-yl | phenyl | CH | CH | CH | CH | H | 2-chloro-4-(4-fluorophenyl)-6-trifluoromethylthiophenyl |
| 1-583 | phenyl | CH | CH | CH | CH | H | H | 4-(2,4-bis(trifluoromethyl)phenyl)-2-chloro-6-trifluoromethylthiophenyl |
| 1-584 | phenyl | CH | CH | CH | CH | Me | H | 4-(3,5-bis(trifluoromethyl)-1H-pyrazol-1-yl)-2,6-dibromophenyl |
| 1-585 | 2-fluorophenyl | CH | CH | CH | CH | Me | H | 4-(3,5-bis(trifluoromethyl)-1H-pyrazol-1-yl)-2,6-dibromophenyl |
| 1-586 | 2-cloropyridin-3-yl | CH | CH | CH | CH | Me | H | 4-(3,5-bis(trifluoromethyl)-1H-pyrazol-1-yl)-2,6-dibromophenyl |

TABLE 1-continued

| Compound No. | Q₁ | A'₁ | A'₂ | A'₃ | A'₄ | R₁ | R₂ | Q₂ |
|---|---|---|---|---|---|---|---|---|
| 1-587 | phenyl | CH | CH | CH | CH | H | H | 4-(3,5-bis(trifluoromethyl)-1H-pyrazol-1-yl)-2,6-dibromophenyl |
| 1-588 | 2-fluorophenyl | CH | CH | CH | CH | H | H | 4-(3,5-bis(trifluoromethyl)-1H-pyrazol-1-yl)-2,6-dibromophenyl |
| 1-589 | 2-cloropyridin-3-yl | CH | CH | CH | CH | H | H | 4-(3,5-bis(trifluoromethyl)-1H-pyrazol-1-yl)-2,6-dibromophenyl |
| 1-590 | 4-fluorophenyl | CH | CH | CH | CH | H | H | 4-(3,5-bis(trifluoromethyl)-1H-pyrazol-1-yl)-2,6-dibromophenyl |
| 1-591 | phenyl | CH | CH | CH | CH | Me | H | 4-(3,5-bis(trifluoromethyl)-1H-pyrazol-1-yl)-2,6-dichlorophenyl |
| 1-592 | phenyl | CH | CH | CH | CH | H | H | 4-(3,5-bis(trifluoromethyl)-1H-pyrazol-1-ylmethyl)-2-bromo-6-methylphenyl |
| 1-593 | 2-fluorophenyl | CH | CH | CH | CH | H | H | 4-(3,5-bis(trifluoromethyl)-1H-pyrazol-1-ylmethyl)-2-bromo-6-methylphenyl |
| 1-594 | 2-cloropyridin-3-yl | CH | CH | CH | CH | H | H | 4-(3,5-bis(trifluoromethyl)-1H-pyrazol-1-ylmethyl)-2-bromo-6-methylphenyl |
| 1-595 | phenyl | CH | CH | CH | CH | Me | H | 4-(3,5-bis(trifluoromethyl)-1H-pyrazole-1-ylmethyl)-2-bromo-6-methylphenyl |
| 1-596 | phenyl | CH | CH | CH | CH | H | H | 5-bromo-7-(heptafluoroisopropyl)-2,3-dihydro-1H-inden-4-yl |
| 1-597 | 2-fluorophenyl | CH | CH | CH | CH | H | H | 5-bromo-7-(heptafluoroisopropyl)-2,3-dihydro-1H-inden-4-yl |
| 1-598 | phenyl | CH | CH | CH | CH | H | H | 5-chloro-7-(heptafluoroisopropyl)-2,3-dihydro-1H-inden-4-yl |
| 1-599 | 2-fluorophenyl | CH | CH | CH | CH | H | H | 5-chloro-7-(heptafluoroisopropyl)-2,3-dihydro-1H-inden-4-yl |
| 1-600 | 2-fluorophenyl | CCl | CH | CH | CH | Me | H | 4-methyl-6-{2,2,2-trifluoro-1-(trifluoromethyl)ethoxy}pyridin-3-yl |
| 1-601 | phenyl | CF | CH | CH | CF | H | H | 4-heptafluoroisopropyl-2-methylphenyl |
| 1-602 | phenyl | CCl | CH | CH | CH | H | H | 2,4-bis(trifluoromethyl)phenyl |
| 1-603 | 2-fluorophenyl | CH | CH | CH | CH | H | Me | 4-heptafluoroisopropyl-2-methanesulfonylphenyl |
| 1-604 | phenyl | CH | CH | CH | CH | H | n-Bu | 2-tert-butyl-4-heptafluoroisopropylphenyl |
| 1-605 | phenyl | CH | CH | CH | CH | H | H | 2-chloro-6-trifluoromethylthiophenyl |

TABLE 2

| Compound No. | Q₁ | A'₁ | A'₂ | A'₃ | A'₄ | R₁ | R₂ | Q₂ |
|---|---|---|---|---|---|---|---|---|
| 2-1 | phenyl | CH | CH | CH | CH | H | H | 2,6-dibromo-4-{1,1,2,3,3,3-hexafluoropropoxy)phenyl |
| 2-2 | 2-methylphenyl | CH | CH | CH | CH | H | H | 2,6-dibromo-4-{1,1,2,3,3,3-hexafluoropropoxy)phenyl |
| 2-3 | 3-methylphenyl | CH | CH | CH | CH | H | H | 2,6-dibromo-4-{1,1,2,3,3,3-hexafluoropropoxy)phenyl |
| 2-4 | 4-methylphenyl | CH | CH | CH | CH | H | H | 2,6-dibromo-4-{1,1,2,3,3,3-hexafluoropropoxy)phenyl |
| 2-5 | 2-ethylphenyl | CH | CH | CH | CH | H | H | 2,6-dibromo-4-{1,1,2,3,3,3-hexafluoropropoxy)phenyl |
| 2-6 | 3-ethylphenyl | CH | CH | CH | CH | H | H | 2,6-dibromo-4-{1,1,2,3,3,3-hexafluoropropoxy)phenyl |
| 2-7 | 4-ethylphenyl | CH | CH | CH | CH | H | H | 2,6-dibromo-4-{1,1,2,3,3,3-hexafluoropropoxy)phenyl |
| 2-8 | 2-fluorophenyl | CH | CH | CH | CH | H | H | 2,6-dibromo-4-{1,1,2,3,3,3-hexafluoropropoxy)phenyl |
| 2-9 | 3-fluorophenyl | CH | CH | CH | CH | H | H | 2,6-dibromo-4-{1,1,2,3,3,3-hexafluoropropoxy)phenyl |
| 2-10 | 4-fluorophenyl | CH | CH | CH | CH | H | H | 2,6-dibromo-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-11 | 2-chlorophenyl | CH | CH | CH | CH | H | H | 2,6-dibromo-4-{1,1,2,3,3,3-hexafluoropropoxy)phenyl |
| 2-12 | 3-chlorophenyl | CH | CH | CH | CH | H | H | 2,6-dibromo-4-{1,1,2,3,3,3-hexafluoropropoxy)phenyl |
| 2-13 | 4-chlorophenyl | CH | CH | CH | CH | H | H | 2,6-dibromo-4-{1,1,2,3,3,3-hexafluoropropoxy)phenyl |
| 2-14 | 2-bromophenyl | CH | CH | CH | CH | H | H | 2,6-dibromo-4-{1,1,2,3,3,3-hexafluoropropoxy)phenyl |
| 2-15 | 3-bromophenyl | CH | CH | CH | CH | H | H | 2,6-dibromo-4-{1,1,2,3,3,3-hexafluoropropoxy)phenyl |
| 2-16 | 4-bromophenyl | CH | CH | CH | CH | H | H | 2,6-dibromo-4-{1,1,2,3,3,3-hexafluoropropoxy)phenyl |
| 2-17 | 2-iodophenyl | CH | CH | CH | CH | H | H | 2,6-dibromo-4-{1,1,2,3,3,3-hexafluoropropoxy)phenyl |
| 2-18 | 3-iodophenyl | CH | CH | CH | CH | H | H | 2,6-dibromo-4-{1,1,2,3,3,3-hexafluoropropoxy)phenyl |
| 2-19 | 4-iodophenyl | CH | CH | CH | CH | H | H | 2,6-dibromo-4-{1,1,2,3,3,3-hexafluoropropoxy)phenyl |
| 2-20 | 3-cyanophenyl | CH | CH | CH | CH | H | H | 2,6-dibromo-4-{1,1,2,3,3,3-hexafluoropropoxy)phenyl |
| 2-21 | 4-cyanophenyl | CH | CH | CH | CH | H | H | 2,6-dibromo-4-{1,1,2,3,3,3-hexafluoropropoxy)phenyl |
| 2-22 | 2-nitrophenyl | CH | CH | CH | CH | H | H | 2,6-dibromo-4-{1,1,2,3,3,3-hexafluoropropoxy)phenyl |
| 2-23 | 3-nitrophenyl | CH | CH | CH | CH | H | H | 2,6-dibromo-4-{1,1,2,3,3,3-hexafluoropropoxy)phenyl |
| 2-24 | 4-nitrophenyl | CH | CH | CH | CH | H | H | 2,6-dibromo-4-{1,1,2,3,3,3-hexafluoropropoxy)phenyl |
| 2-25 | 2-aminophenyl | CH | CH | CH | CH | H | H | 2,6-dibromo-4-{1,1,2,3,3,3-hexafluoropropoxy)phenyl |
| 2-26 | 3-aminophenyl | CH | CH | CH | CH | H | H | 2,6-dibromo-4-{1,1,2,3,3,3-hexafluoropropoxy)phenyl |
| 2-27 | 4-aminophenyl | CH | CH | CH | CH | H | H | 2,6-dibromo-4-{1,1,2,3,3,3-hexafluoropropoxy)phenyl |
| 2-28 | 2-trifluoromethylphenyl | CH | CH | CH | CH | H | H | 2,6-dibromo-4-{1,1,2,3,3,3-hexafluoropropoxy)phenyl |
| 2-29 | 3-trifluoromethylphenyl | CH | CH | CH | CH | H | H | 2,6-dibromo-4-{1,1,2,3,3,3-hexafluoropropoxy)phenyl |
| 2-30 | 4-trifluoromethylphenyl | CH | CH | CH | CH | H | H | 2,6-dibromo-4-{1,1,2,3,3,3-hexafluoropropoxy)phenyl |
| 2-31 | 2-hydroxyphenyl | CH | CH | CH | CH | H | H | 2,6-dibromo-4-{1,1,2,3,3,3-hexafluoropropoxy)phenyl |
| 2-32 | 2-methoxyphenyl | CH | CH | CH | CH | H | H | 2,6-dibromo-4-{1,1,2,3,3,3-hexafluoropropoxy)phenyl |
| 2-33 | 3-methoxyphenyl | CH | CH | CH | CH | H | H | 2,6-dibromo-4-{1,1,2,3,3,3-hexafluoropropoxy)phenyl |
| 2-34 | 4-methoxyphenyl | CH | CH | CH | CH | H | H | 2,6-dibromo-4-{1,1,2,3,3,3-hexafluoropropoxy)phenyl |
| 2-35 | 2-phenoxyphenyl | CH | CH | CH | CH | H | H | 2,6-dibromo-4-{1,1,2,3,3,3-hexafluoropropoxy)phenyl |
| 2-36 | 4-(1,1-dimethylethyl)phenyl | CH | CH | CH | CH | H | H | 2,6-dibromo-4-{1,1,2,3,3,3-hexafluoropropoxy)phenyl |
| 2-37 | 3-(dimethylamino)phenyl | CH | CH | CH | CH | H | H | 2,6-dibromo-4-{1,1,2,3,3,3-hexafluoropropoxy)phenyl |
| 2-38 | 4-(dimethylamino)phenyl | CH | CH | CH | CH | H | H | 2,6-dibromo-4-{1,1,2,3,3,3-hexafluoropropoxy)phenyl |
| 2-39 | 4-trifluoromethoxyphenyl | CH | CH | CH | CH | H | H | 2,6-dibromo-4-{1,1,2,3,3,3-hexafluoropropoxy)phenyl |
| 2-40 | 2-(acetylamino)phenyl | CH | CH | CH | CH | H | H | 2,6-dibromo-4-{1,1,2,3,3,3-hexafluoropropoxy)phenyl |
| 2-41 | 3-(acetylamino)phenyl | CH | CH | CH | CH | H | H | 2,6-dibromo-4-{1,1,2,3,3,3-hexafluoropropoxy)phenyl |
| 2-42 | 4-(acetylamino)phenyl | CH | CH | CH | CH | H | H | 2,6-dibromo-4-{1,1,2,3,3,3-hexafluoropropoxy)phenyl |
| 2-43 | 2-acetoxyphenyl | CH | CH | CH | CH | H | H | 2,6-dibromo-4-{1,1,2,3,3,3-hexafluoropropoxy)phenyl |
| 2-44 | 2-(methoxycarbonyl)phenyl | CH | CH | CH | CH | H | H | 2,6-dibromo-4-{1,1,2,3,3,3-hexafluoropropoxy)phenyl |
| 2-45 | 4-(methoxycarbonyl)phenyl | CH | CH | CH | CH | H | H | 2,6-dibromo-4-{1,1,2,3,3,3-hexafluoropropoxy)phenyl |
| 2-46 | 2,3-dimethylphenyl | CH | CH | CH | CH | H | H | 2,6-dibromo-4-{1,1,2,3,3,3-hexafluoropropoxy)phenyl |
| 2-47 | 2,4-dimethylphenyl | CH | CH | CH | CH | H | H | 2,6-dibromo-4-{1,1,2,3,3,3-hexafluoropropoxy)phenyl |
| 2-48 | 2,6-dimethylphenyl | CH | CH | CH | CH | H | H | 2,6-dibromo-4-{1,1,2,3,3,3-hexafluoropropoxy)phenyl |
| 2-49 | 2,3-difluorophenyl | CH | CH | CH | CH | H | H | 2,6-dibromo-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-50 | 2,4-difluorophenyl | CH | CH | CH | CH | H | H | 2,6-dibromo-4-{1,1,2,3,3,3-hexafluoropropoxy)phenyl |
| 2-51 | 2,5-difluorophenyl | CH | CH | CH | CH | H | H | 2,6-dibromo-4-{1,1,2,3,3,3-hexafluoropropoxy)phenyl |
| 2-52 | 2,6-difluorophenyl | CH | CH | CH | CH | H | H | 2,6-dibromo-4-{1,1,2,3,3,3-hexafluoropropoxy)phenyl |
| 2-53 | 3,4-difluorophenyl | CH | CH | CH | CH | H | H | 2,6-dibromo-4-{1,1,2,3,3,3-hexafluoropropoxy)phenyl |
| 2-54 | 3,5-difluorophenyl | CH | CH | CH | CH | H | H | 2,6-dibromo-4-{1,1,2,3,3,3-hexafluoropropoxy)phenyl |
| 2-55 | 2,3-dichlorophenyl | CH | CH | CH | CH | H | H | 2,6-dibromo-4-{1,1,2,3,3,3-hexafluoropropoxy)phenyl |
| 2-56 | 2,4-dichlorophenyl | CH | CH | CH | CH | H | H | 2,6-dibromo-4-{1,1,2,3,3,3-hexafluoropropoxy)phenyl |
| 2-57 | 2,5-dichlorophenyl | CH | CH | CH | CH | H | H | 2,6-dibromo-4-{1,1,2,3,3,3-hexafluoropropoxy)phenyl |
| 2-58 | 2,6-dichlorophenyl | CH | CH | CH | CH | H | H | 2,6-dibromo-4-{1,1,2,3,3,3-hexafluoropropoxy)phenyl |
| 2-59 | 3,4-dichlorophenyl | CH | CH | CH | CH | H | H | 2,6-dibromo-4-{1,1,2,3,3,3-hexafluoropropoxy)phenyl |
| 2-60 | 2,4-dinitrophenyl | CH | CH | CH | CH | H | H | 2,6-dibromo-4-{1,1,2,3,3,3-hexafluoropropoxy)phenyl |
| 2-61 | 3,4-dinitrophenyl | CH | CH | CH | CH | H | H | 2,6-dibromo-4-{1,1,2,3,3,3-hexafluoropropoxy)phenyl |
| 2-62 | 2,6-dimethoxyphenyl | CH | CH | CH | CH | H | H | 2,6-dibromo-4-{1,1,2,3,3,3-hexafluoropropoxy)phenyl |
| 2-63 | 3,5-dimethoxyphenyl | CH | CH | CH | CH | H | H | 2,6-dibromo-4-{1,1,2,3,3,3-hexafluoropropoxy)phenyl |
| 2-64 | 3-methyl-4-nitrophenyl | CH | CH | CH | CH | H | H | 2,6-dibromo-4-{1,1,2,3,3,3-hexafluoropropoxy)phenyl |
| 2-65 | 5-amino-2-fluorophenyl | CH | CH | CH | CH | H | H | 2,6-dibromo-4-{1,1,2,3,3,3-hexafluoropropoxy)phenyl |
| 2-66 | 3-fluoro-2-methylphenyl | CH | CH | CH | CH | H | H | 2,6-dibromo-4-{1,1,2,3,3,3-hexafluoropropoxy)phenyl |
| 2-67 | 2-fluoro-5-nitrophenyl | CH | CH | CH | CH | H | H | 2,6-dibromo-4-{1,1,2,3,3,3-hexafluoropropoxy)phenyl |
| 2-68 | 4-fluoro-3-nitrophenyl | CH | CH | CH | CH | H | H | 2,6-dibromo-4-{1,1,2,3,3,3-hexafluoropropoxy)phenyl |
| 2-69 | 5-fluoro-2-nitrophenyl | CH | CH | CH | CH | H | H | 2,6-dibromo-4-{1,1,2,3,3,3-hexafluoropropoxy)phenyl |
| 2-70 | 2-fluoro-6-iodinephenyl | CH | CH | CH | CH | H | H | 2,6-dibromo-4-{1,1,2,3,3,3-hexafluoropropoxy)phenyl |
| 2-71 | 2-fluoro-5-trifluoromethylphenyl | CH | CH | CH | CH | H | H | 2,6-dibromo-4-{1,1,2,3,3,3-hexafluoropropoxy)phenyl |
| 2-72 | 2-chloro-4-nitrophenyl | CH | CH | CH | CH | H | H | 2,6-dibromo-4-{1,1,2,3,3,3-hexafluoropropoxy)phenyl |
| 2-73 | 2-chloro-4-fluorophenyl | CH | CH | CH | CH | H | H | 2,6-dibromo-4-{1,1,2,3,3,3-hexafluoropropoxy)phenyl |
| 2-74 | 2-chloro-6-fluorophenyl | CH | CH | CH | CH | H | H | 2,6-dibromo-4-{1,1,2,3,3,3-hexafluoropropoxy)phenyl |
| 2-75 | 3-chloro-4-fluorophenyl | CH | CH | CH | CH | H | H | 2,6-dibromo-4-{1,1,2,3,3,3-hexafluoropropoxy)phenyl |
| 2-76 | 4-chloro-2-fluorophenyl | CH | CH | CH | CH | H | H | 2,6-dibromo-4-{1,1,2,3,3,3-hexafluoropropoxy)phenyl |
| 2-77 | 4-chloro-2-nitrophenyl | CH | CH | CH | CH | H | H | 2,6-dibromo-4-{1,1,2,3,3,3-hexafluoropropoxy)phenyl |
| 2-78 | 3-methoxy-4-nitrophenyl | CH | CH | CH | CH | H | H | 2,6-dibromo-4-{1,1,2,3,3,3-hexafluoropropoxy)phenyl |
| 2-79 | 2-methoxy-4-nitrophenyl | CH | CH | CH | CH | H | H | 2,6-dibromo-4-{1,1,2,3,3,3-hexafluoropropoxy)phenyl |
| 2-80 | 2,3,4-trifluorophenyl | CH | CH | CH | CH | H | H | 2,6-dibromo-4-{1,1,2,3,3,3-hexafluoropropoxy)phenyl |
| 2-81 | 2,4,6-trimethylphenyl | CH | CH | CH | CH | H | H | 2,6-dibromo-4-{1,1,2,3,3,3-hexafluoropropoxy)phenyl |
| 2-82 | 2,3,6-trifluorophenyl | CH | CH | CH | CH | H | H | 2,6-dibromo-4-{1,1,2,3,3,3-hexafluoropropoxy)phenyl |
| 2-83 | 2,4,5-trimethoxyphenyl | CH | CH | CH | CH | H | H | 2,6-dibromo-4-{1,1,2,3,3,3-hexafluoropropoxy)phenyl |
| 2-84 | 3,4,5-trimethoxyphenyl | CH | CH | CH | CH | H | H | 2,6-dibromo-4-{1,1,2,3,3,3-hexafluoropropoxy)phenyl |
| 2-85 | 2,3,4,5,6-pentafluorophenyl | CH | CH | CH | CH | H | H | 2,6-dibromo-4-{1,1,2,3,3,3-hexafluoropropoxy)phenyl |
| 2-86 | 2-biphenyl | CH | CH | CH | CH | H | H | 2,6-dibromo-4-{1,1,2,3,3,3-hexafluoropropoxy)phenyl |
| 2-87 | 3-biphenyl | CH | CH | CH | CH | H | H | 2,6-dibromo-4-{1,1,2,3,3,3-hexafluoropropoxy)phenyl |
| 2-88 | 1-naphthyl | CH | CH | CH | CH | H | H | 2,6-dibromo-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-89 | 2-naphthyl | CH | CH | CH | CH | H | H | 2,6-dibromo-4-{1,1,2,3,3,3-hexafluoropropoxy)phenyl |
| 2-90 | pyridin-2-yl | CH | CH | CH | CH | H | H | 2,6-dibromo-4-{1,1,2,3,3,3-hexafluoropropoxy)phenyl |
| 2-91 | pyridin-3-yl | CH | CH | CH | CH | H | H | 2,6-dibromo-4-{1,1,2,3,3,3-hexafluoropropoxy)phenyl |
| 2-92 | pyridin-4-yl | CH | CH | CH | CH | H | H | 2,6-dibromo-4-{1,1,2,3,3,3-hexafluoropropoxy)phenyl |
| 2-93 | 2-methylpyridin-5-yl | CH | CH | CH | CH | H | H | 2,6-dibromo-4-{1,1,2,3,3,3-hexafluoropropoxy)phenyl |
| 2-94 | 3-methylpyridin-2-yl | CH | CH | CH | CH | H | H | 2,6-dibromo-4-{1,1,2,3,3,3-hexafluoropropoxy)phenyl |
| 2-95 | 2-fluoropyridin-3-yl | CH | CH | CH | CH | H | H | 2,6-dibromo-4-{1,1,2,3,3,3-hexafluoropropoxy)phenyl |
| 2-96 | 2-chloropyridin-3-yl | CH | CH | CH | CH | H | H | 2,6-dibromo-4-{1,1,2,3,3,3-hexafluoropropoxy)phenyl |
| 2-97 | 2-chloropyridin-4-yl | CH | CH | CH | CH | H | H | 2,6-dibromo-4-{1,1,2,3,3,3-hexafluoropropoxy)phenyl |
| 2-98 | 2-chloropyridin-6-yl | CH | CH | CH | CH | H | H | 2,6-dibromo-4-{1,1,2,3,3,3-hexafluoropropoxy)phenyl |
| 2-99 | 2-chloropyridin-5-yl | CH | CH | CH | CH | H | H | 2,6-dibromo-4-{1,1,2,3,3,3-hexafluoropropoxy)phenyl |
| 2-100 | 5-chloropyridin-2-yl | CH | CH | CH | CH | H | H | 2,6-dibromo-4-{1,1,2,3,3,3-hexafluoropropoxy)phenyl |
| 2-101 | 4-trifluoromethylpyridin-3-yl | CH | CH | CH | CH | H | H | 2,6-dibromo-4-{1,1,2,3,3,3-hexafluoropropoxy)phenyl |
| 2-102 | 3-hydroxypyridin-2-yl | CH | CH | CH | CH | H | H | 2,6-dibromo-4-{1,1,2,3,3,3-hexafluoropropoxy)phenyl |
| 2-103 | 2-phenoxypyridin-3-yl | CH | CH | CH | CH | H | H | 2,6-dibromo-4-{1,1,2,3,3,3-hexafluoropropoxy)phenyl |
| 2-104 | 2-methylthiopyridin-3-yl | CH | CH | CH | CH | H | H | 2,6-dibromo-4-{1,1,2,3,3,3-hexafluoropropoxy)phenyl |
| 2-105 | 2,6-dimethoxypyridin-3-yl | CH | CH | CH | CH | H | H | 2,6-dibromo-4-{1,1,2,3,3,3-hexafluoropropoxy)phenyl |
| 2-106 | 2,3-dichloropyridin-5-yl | CH | CH | CH | CH | H | H | 2,6-dibromo-4-{1,1,2,3,3,3-hexafluoropropoxy)phenyl |
| 2-107 | 2,5-dichloropyridin-3-yl | CH | CH | CH | CH | H | H | 2,6-dibromo-4-{1,1,2,3,3,3-hexafluoropropoxy)phenyl |
| 2-108 | 2,6-dichloropyridin-3-yl | CH | CH | CH | CH | H | H | 2,6-dibromo-4-{1,1,2,3,3,3-hexafluoropropoxy)phenyl |
| 2-109 | 3,5-dichloropyridin-4-yl | CH | CH | CH | CH | H | H | 2,6-dibromo-4-{1,1,2,3,3,3-hexafluoropropoxy)phenyl |
| 2-110 | pyridin-N-oxid-2-yl | CH | CH | CH | CH | H | H | 2,6-dibromo-4-{1,1,2,3,3,3-hexafluoropropoxy)phenyl |
| 2-111 | N-methylpyrrol-2-yl | CH | CH | CH | CH | H | H | 2,6-dibromo-4-{1,1,2,3,3,3-hexafluoropropoxy)phenyl |
| 2-112 | pyrazin-2-yl | CH | CH | CH | CH | H | H | 2,6-dibromo-4-{1,1,2,3,3,3-hexafluoropropoxy)phenyl |
| 2-113 | 2-methylpyrazin-5-yl | CH | CH | CH | CH | H | H | 2,6-dibromo-4-{1,1,2,3,3,3-hexafluoropropoxy)phenyl |
| 2-114 | 4-trifluoromethylpyrimidin-5-yl | CH | CH | CH | CH | H | H | 2,6-dibromo-4-{1,1,2,3,3,3-hexafluoropropoxy)phenyl |
| 2-115 | furan-2-yl | CH | CH | CH | CH | H | H | 2,6-dibromo-4-{1,1,2,3,3,3-hexafluoropropoxy)phenyl |
| 2-116 | furan-3-yl | CH | CH | CH | CH | H | H | 2,6-dibromo-4-{1,1,2,3,3,3-hexafluoropropoxy)phenyl |
| 2-117 | 2-tetrahydrofuranyl | CH | CH | CH | CH | H | H | 2,6-dibromo-4-{1,1,2,3,3,3-hexafluoropropoxy)phenyl |
| 2-118 | 3-tetrahydrofuranyl | CH | CH | CH | CH | H | H | 2,6-dibromo-4-{1,1,2,3,3,3-hexafluoropropoxy)phenyl |
| 2-119 | benzofuran-2-yl | CH | CH | CH | CH | H | H | 2,6-dibromo-4-{1,1,2,3,3,3-hexafluoropropoxy)phenyl |
| 2-120 | tetrahydropyran-2-yl | CH | CH | CH | CH | H | H | 2,6-dibromo-4-{1,1,2,3,3,3-hexafluoropropoxy)phenyl |
| 2-121 | 2-methyl-5,6-dihydro-4H-pyran-3-yl | CH | CH | CH | CH | H | H | 2,6-dibromo-4-{1,1,2,3,3,3-hexafluoropropoxy)phenyl |
| 2-122 | thiophen-2-yl | CH | CH | CH | CH | H | H | 2,6-dibromo-4-{1,1,2,3,3,3-hexafluoropropoxy)phenyl |
| 2-123 | thiophen-3-yl | CH | CH | CH | CH | H | H | 2,6-dibromo-4-{1,1,2,3,3,3-hexafluoropropoxy)phenyl |
| 2-124 | 3-methylthiophen-2-yl | CH | CH | CH | CH | H | H | 2,6-dibromo-4-{1,1,2,3,3,3-hexafluoropropoxy)phenyl |
| 2-125 | 2-nitrothiophen-4-yl | CH | CH | CH | CH | H | H | 2,6-dibromo-4-{1,1,2,3,3,3-hexafluoropropoxy)phenyl |
| 2-126 | 2-methylthiophen-5-yl | CH | CH | CH | CH | H | H | 2,6-dibromo-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-127 | 3-chlorothiophen-2-yl | CH | CH | CH | CH | H | H | 2,6-dibromo-4-{1,1,2,3,3,3-hexafluoropropoxy)phenyl |
| 2-128 | 2-chlorothiophen-5-yl | CH | CH | CH | CH | H | H | 2,6-dibromo-4-{1,1,2,3,3,3-hexafluoropropoxy)phenyl |
| 2-129 | 3-bromothiophen-2-yl | CH | CH | CH | CH | H | H | 2,6-dibromo-4-{1,1,2,3,3,3-hexafluoropropoxy)phenyl |
| 2-130 | 2-bromothiophen-5-yl | CH | CH | CH | CH | H | H | 2,6-dibromo-4-{1,1,2,3,3,3-hexafluoropropoxy)phenyl |
| 2-131 | 3-iodinethiophen-2-yl | CH | CH | CH | CH | H | H | 2,6-dibromo-4-{1,1,2,3,3,3-hexafluoropropoxy)phenyl |
| 2-132 | 3-phenylthiophen-2-yl | CH | CH | CH | CH | H | H | 2,6-dibromo-4-{1,1,2,3,3,3-hexafluoropropoxy)phenyl |
| 2-133 | 2,4-dimethylthiophen-5-yl | CH | CH | CH | CH | H | H | 2,6-dibromo-4-{1,1,2,3,3,3-hexafluoropropoxy)phenyl |
| 2-134 | benzothiophen-2-yl | CH | CH | CH | CH | H | H | 2,6-dibromo-4-{1,1,2,3,3,3-hexafluoropropoxy)phenyl |
| 2-135 | 4-nitro-1H-pyrrol-2-yl | CH | CH | CH | CH | H | H | 2,6-dibromo-4-{1,1,2,3,3,3-hexafluoropropoxy)phenyl |
| 2-136 | 3-ethyl-3H-pyrazol-4-yl | CH | CH | CH | CH | H | H | 2,6-dibromo-4-{1,1,2,3,3,3-hexafluoropropoxy)phenyl |
| 2-137 | 1-methyl-3-nitro-1H-pyrazol-4-yl | CH | CH | CH | CH | H | H | 2,6-dibromo-4-{1,1,2,3,3,3-hexafluoropropoxy)phenyl |
| 2-138 | 3-chloro-1-methyl-1H-pyrazol-4-yl | CH | CH | CH | CH | H | H | 2,6-dibromo-4-{1,1,2,3,3,3-hexafluoropropoxy)phenyl |
| 2-139 | 3-bromo-1-methyl-1H-pyrazol-4-yl | CH | CH | CH | CH | H | H | 2,6-dibromo-4-{1,1,2,3,3,3-hexafluoropropoxy)phenyl |
| 2-140 | 1-methyl-3-trifluoromethyl-1H-pyrazol-4-yl | CH | CH | CH | CH | H | H | 2,6-dibromo-4-{1,1,2,3,3,3-hexafluoropropoxy)phenyl |
| 2-141 | 1-methyl-5-trifluoromethyl-1H-pyrazol-4-yl | CH | CH | CH | CH | H | H | 2,6-dibromo-4-{1,1,2,3,3,3-hexafluoropropoxy)phenyl |
| 2-142 | isoxazol-5-yl | CH | CH | CH | CH | H | H | 2,6-dibromo-4-{1,1,2,3,3,3-hexafluoropropoxy)phenyl |
| 2-143 | 4-trifluoromethylthiazol-5-yl | CH | CH | CH | CH | H | H | 2,6-dibromo-4-{1,1,2,3,3,3-hexafluoropropoxy)phenyl |
| 2-144 | 2,4-dimethylthiazol-5-yl | CH | CH | CH | CH | H | H | 2,6-dibromo-4-{1,1,2,3,3,3-hexafluoropropoxy)phenyl |
| 2-145 | 2-ethyl-4-methylthiazol-5-yl | CH | CH | CH | CH | H | H | 2,6-dibromo-4-{1,1,2,3,3,3-hexafluoropropoxy)phenyl |
| 2-146 | 2-chloro-4-methylthiazol-5-yl | CH | CH | CH | CH | H | H | 2,6-dibromo-4-{1,1,2,3,3,3-hexafluoropropoxy)phenyl |
| 2-147 | 3-methyl-isothiazol-5-yl | CH | CH | CH | CH | H | H | 2,6-dibromo-4-{1,1,2,3,3,3-hexafluoropropoxy)phenyl |
| 2-148 | 3,4-dichloro-isothiazol-5-yl | CH | CH | CH | CH | H | H | 2,6-dibromo-4-{1,1,2,3,3,3-hexafluoropropoxy)phenyl |
| 2-149 | 3-chlorobenzothiazol-2-yl | CH | CH | CH | CH | H | H | 2,6-dibromo-4-{1,1,2,3,3,3-hexafluoropropoxy)phenyl |
| 2-150 | 2,2-difluoro-benzo[1.3]dioxol-5-yl | CH | CH | CH | CH | H | H | 2,6-dibromo-4-{1,1,2,3,3,3-hexafluoropropoxy)phenyl |
| 2-151 | 2,2-difluoro-benzo[1.3]dioxol-4-yl | CH | CH | CH | CH | H | H | 2,6-dibromo-4-{1,1,2,3,3,3-hexafluoropropoxy)phenyl |
| 2-152 | phenyl | CF | CH | CH | CH | H | H | 2,6-dibromo-4-{1,1,2,3,3,3-hexafluoropropoxy)phenyl |
| 2-153 | 2-fluorophenyl | CF | CH | CH | CH | H | H | 2,6-dibromo-4-{1,1,2,3,3,3-hexafluoropropoxy)phenyl |
| 2-154 | 4-fluorophenyl | CF | CH | CH | CH | H | H | 2,6-dibromo-4-{1,1,2,3,3,3-hexafluoropropoxy)phenyl |
| 2-155 | 4-chlorophenyl | CF | CH | CH | CH | H | H | 2,6-dibromo-4-{1,1,2,3,3,3-hexafluoropropoxy)phenyl |
| 2-156 | 2-chloropyridin-3-yl | CF | CH | CH | CH | H | H | 2,6-dibromo-4-{1,1,2,3,3,3-hexafluoropropoxy)phenyl |
| 2-157 | 4-nitrophenyl | CF | CH | CH | CH | H | H | 2,6-dibromo-4-{1,1,2,3,3,3-hexafluoropropoxy)phenyl |
| 2-158 | 4-cyanophenyl | CF | CH | CH | CH | H | H | 2,6-dibromo-4-{1,1,2,3,3,3-hexafluoropropoxy)phenyl |
| 2-159 | phenyl | CH | CH | CH | CH | Me | H | 2,6-dibromo-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-160 | 2-fluorophenyl | CH | CH | CH | CH | Me | H | 2,6-dibromo-4-{1,1,2,3,3,3-hexafluoropropoxy)phenyl |
| 2-161 | 4-fluorophenyl | CH | CH | CH | CH | Me | H | 2,6-dibromo-4-{1,1,2,3,3,3-hexafluoropropoxy)phenyl |
| 2-162 | 4-chlorophenyl | CH | CH | CH | CH | Me | H | 2,6-dibromo-4-{1,1,2,3,3,3-hexafluoropropoxy)phenyl |
| 2-163 | 2-chloropyridin-3-yl | CH | CH | CH | CH | Me | H | 2,6-dibromo-4-{1,1,2,3,3,3-hexafluoropropoxy)phenyl |
| 2-164 | 4-nitrophenyl | CH | CH | CH | CH | Me | H | 2,6-dibromo-4-{1,1,2,3,3,3-hexafluoropropoxy)phenyl |
| 2-165 | 4-cyanophenyl | CH | CH | CH | CH | Me | H | 2,6-dibromo-4-{1,1,2,3,3,3-hexafluoropropoxy)phenyl |
| 2-166 | phenyl | CH | CH | CH | CH | H | Me | 2,6-dibromo-4-{1,1,2,3,3,3-hexafluoropropoxy)phenyl |
| 2-167 | 2-fluorophenyl | CH | CH | CH | CH | H | Me | 2,6-dibromo-4-{1,1,2,3,3,3-hexafluoropropoxy)phenyl |
| 2-168 | 4-fluorophenyl | CH | CH | CH | CH | H | Me | 2,6-dibromo-4-{1,1,2,3,3,3-hexafluoropropoxy)phenyl |
| 2-169 | 4-chlorophenyl | CH | CH | CH | CH | H | Me | 2,6-dibromo-4-{1,1,2,3,3,3-hexafluoropropoxy)phenyl |
| 2-170 | 2-chloropyridin-3-yl | CH | CH | CH | CH | H | Me | 2,6-dibromo-4-{1,1,2,3,3,3-hexafluoropropoxy)phenyl |
| 2-171 | 4-nitrophenyl | CH | CH | CH | CH | H | Me | 2,6-dibromo-4-{1,1,2,3,3,3-hexafluoropropoxy)phenyl |
| 2-172 | 4-cyanophenyl | CH | CH | CH | CH | H | Me | 2,6-dibromo-4-{1,1,2,3,3,3-hexafluoropropoxy)phenyl |
| 2-173 | 2-chloro-3-nitrophenyl | CH | CH | CH | CH | H | Me | 2,6-dibromo-4-{1,1,2,3,3,3-hexafluoropropoxy)phenyl |
| 2-174 | phenyl | CH | CH | CH | CH | Me | Me | 2,6-dibromo-4-{1,1,2,3,3,3-hexafluoropropoxy)phenyl |
| 2-175 | 2-fluorophenyl | CH | CH | CH | CH | Me | Me | 2,6-dibromo-4-{1,1,2,3,3,3-hexafluoropropoxy)phenyl |
| 2-176 | 4-fluorophenyl | CH | CH | CH | CH | Me | Me | 2,6-dibromo-4-{1,1,2,3,3,3-hexafluoropropoxy)phenyl |
| 2-177 | 4-chlorophenyl | CH | CH | CH | CH | Me | Me | 2,6-dibromo-4-{1,1,2,3,3,3-hexafluoropropoxy)phenyl |
| 2-178 | 2-chloropyridin-3-yl | CH | CH | CH | CH | Me | Me | 2,6-dibromo-4-{1,1,2,3,3,3-hexafluoropropoxy)phenyl |
| 2-179 | 4-nitrophenyl | CH | CH | CH | CH | Me | Me | 2,6-dibromo-4-{1,1,2,3,3,3-hexafluoropropoxy)phenyl |
| 2-180 | 4-cyanophenyl | CH | CH | CH | CH | Me | Me | 2,6-dibromo-4-{1,1,2,3,3,3-hexafluoropropoxy)phenyl |
| 2-181 | 2-chloropyrazin-3-yl | CH | CH | CH | CH | Me | Me | 2,6-dibromo-4-{1,1,2,3,3,3-hexafluoropropoxy)phenyl |
| 2-182 | pyrimidin-5-yl | CH | CH | CH | CH | Me | Me | 2,6-dibromo-4-{1,1,2,3,3,3-hexafluoropropoxy)phenyl |
| 2-183 | phenyl | CH | CH | CH | CH | H | H | 2-bromo-4-{1,1,2,3,3,3-hexafluoropropoxy)-6-methylphenyl |
| 2-184 | phenyl | CH | CH | CH | CH | Me | H | 2-bromo-4-{1,1,2,3,3,3-hexafluoropropoxy)-6-trifluoromethylphenyl |
| 2-185 | phenyl | CH | CH | CH | CH | H | H | 2-bromo-4-{1,1,2,3,3,3-hexafluoropropoxy)-6-trifluoromethylphenyl |
| 2-186 | 2-chloro-3-pyridyl | CH | CH | CH | CH | H | H | 2-bromo-4-{1,1,2,3,3,3-hexafluoropropoxy)-6-trifluoromethylphenyl |
| 2-187 | phenyl | CH | CH | CH | CH | Me | H | 2-bromo-4-{1,1,2,3,3,3-hexafluoropropoxy)-6-nitrophenyl |
| 2-188 | 2-chloro-3-pyridyl | CH | CH | CH | CH | Me | H | 2-bromo-4-{1,1,2,3,3,3-hexafluoropropoxy)-6-nitrophenyl |
| 2-189 | phenyl | CH | CH | CH | CH | H | H | 2,6-dimethyl-4-{1,1,2,3,3,3-hexafluoropropoxy)phenyl |
| 2-190 | 2-chloro-3-pyridyl | CH | CH | CH | CH | Me | H | 2,6-dimethyl-4-{1,1,2,3,3,3-hexafluoropropoxy)phenyl |
| 2-191 | 2-chloropyridin-3-yl | CH | CH | CH | CH | Me | H | 2,6-dimethyl-4-{1,1,2,3,3,3-hexafluoropropoxy)phenyl |
| 2-192 | phenyl | CF | CH | CH | CH | H | H | 2,6-dimethyl-4-{1,1,2,3,3,3-hexafluoropropoxy)phenyl |
| 2-193 | 2-fluorophenyl | CF | CH | CH | CH | H | H | 2,6-dimethyl-4-{1,1,2,3,3,3-hexafluoropropoxy)phenyl |
| 2-194 | 2-chloro-3-pyridyl | CF | CH | CH | CH | H | H | 2,6-dimethyl-4-{1,1,2,3,3,3-hexafluoropropoxy)phenyl |
| 2-195 | phenyl | CH | CF | CH | CH | H | H | 2,6-dimethyl-4-{1,1,2,3,3,3-hexafluoropropoxy)phenyl |

TABLE 2-continued

| Compound No. | Q₁ | A'₁ | A'₂ | A'₃ | A'₄ | R₁ | R₂ | Q₂ |
|---|---|---|---|---|---|---|---|---|
| 2-196 | 2-chloro-3-pyridyl | CH | CH | CH | CH | H | H | 2,6-dimethyl-4-{1,1,2,3,3,3-hexafluoropropoxy)phenyl |
| 2-197 | phenyl | CH | CH | CH | CH | H | H | 6-bromo-8-{1,1,2,3,3,3-hexafluoropropoxy)quinolin-5-yl |
| 2-198 | 2-fluorophenyl | CH | CH | CH | CH | H | H | 6-bromo-8-{1,1,2,3,3,3-hexafluoropropoxy)quinolin-5-yl |
| 2-199 | 2-chloro-3-pyridyl | CH | CH | CH | CH | H | H | 6-bromo-8-{1,1,2,3,3,3-hexafluoropropoxy)quinolin-5-yl |
| 2-200 | phenyl | CH | CH | CH | CH | Me | H | 6-bromo-8-{1,1,2,3,3,3-hexafluoropropoxy)quinolin-5-yl |
| 2-201 | phenyl | CH | CH | CH | CH | H | H | 2,6-dibromo-4-{1,1,2,2-tetrafluoroethoxy)phenyl |
| 2-202 | 2-fluorophenyl | CH | CH | CH | CH | H | H | 2,6-dibromo-4-{1,1,2,2-tetrafluoroethoxy)phenyl |
| 2-203 | 2-chloro-3-pyridyl | CH | CH | CH | CH | H | H | 2,6-dibromo-4-{1,1,2,2-tetrafluoroethoxy)phenyl |
| 2-204 | phenyl | CH | CH | CH | CH | H | H | 2-bromo-4,6-bis{1,1,2,3,3,3-hexafluoropropoxy)phenyl |
| 2-205 | 2-fluorophenyl | CH | CH | CH | CH | H | H | 2-bromo-4,6-bis{1,1,2,3,3,3-hexafluoropropoxy)phenyl |
| 2-206 | 2-chloro-3-pyridyl | CH | CH | CH | CH | H | H | 2-bromo-4,6-bis{1,1,2,3,3,3-hexafluoropropoxy)phenyl |
| 2-207 | phenyl | CH | CH | CH | CH | H | H | 2,4,6-tri{1,1,2,3,3,3-hexafluoropropoxy)phenyl |
| 2-208 | 2-fluorophenyl | CH | CH | CH | CH | H | H | 2,4,6-tri{1,1,2,3,3,3-hexafluoropropoxy)phenyl |
| 2-209 | 2-chloro-3-pyridyl | CH | CH | CH | CH | H | H | 2,4,6-tri{1,1,2,3,3,3-hexafluoropropoxy)phenyl |
| 2-210 | phenyl | CH | CH | CH | CH | H | H | 2,6-dibromo-4-{1,1,2,3,3,3-hexafluoropropylthio)phenyl |
| 2-211 | 2-fluorophenyl | CH | CH | CH | CH | H | H | 2,6-dibromo-4-{1,1,2,3,3,3-hexafluoropropylthio)phenyl |
| 2-212 | 2-chloro-3-pyridyl | CH | CH | CH | CH | H | H | 2,6-dibromo-4-{1,1,2,3,3,3-hexafluoropropylthio)phenyl |
| 2-213 | phenyl | CH | CH | CH | CH | H | H | 2-bromo-6-chloro-4-{1,1,2,3,3,3-hexafluoropropylthio)phenyl |
| 2-214 | 2-fluorophenyl | CH | CH | CH | CH | H | H | 2-bromo-6-chloro-4-{1,1,2,3,3,3-hexafluoropropylthio)phenyl |
| 2-215 | 2-chloro-3-pyridyl | CH | CH | CH | CH | H | H | 2-bromo-6-chloro-4-{1,1,2,3,3,3-hexafluoropropylthio)phenyl |
| 2-216 | phenyl | CH | CH | CH | CH | Me | H | 2-bromo-6-chloro-4-{1,1,2,3,3,3-hexafluoropropylthio)phenyl |
| 2-217 | 2-fluorophenyl | CH | CH | CH | CH | Me | H | 2-bromo-6-chloro-4-{1,1,2,3,3,3-hexafluoropropylthio)phenyl |
| 2-218 | 2-chloro-3-pyridyl | CH | CH | CH | CH | Me | H | 2-bromo-6-chloro-4-{1,1,2,3,3,3-hexafluoropropylthio)phenyl |
| 2-219 | 2-chloro-3-pyridyl | CH | CH | CH | CH | Me | H | 2,6-dimethyl-4-{1,1,2-trifluoro-2-trifluoromethoxyethoxy)phenyl |
| 2-220 | 2-chloro-3-pyridyl | CH | CH | CH | CH | H | H | 2,6-dimethyl-4-{1,1,2,3,3,3-hexafluoropropoxy)phenyl |

General Formula (B)

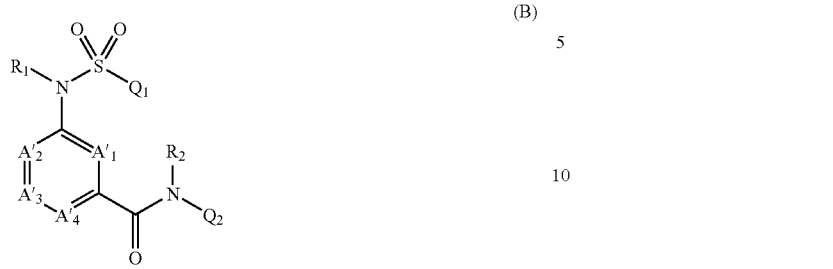

TABLE 3

| Compound No. | $Q_1$ | $A'_1$ | $A'_2$ | $A'_3$ | $A'_4$ | $R_1$ | $R_2$ | $Q_2$ |
|---|---|---|---|---|---|---|---|---|
| 4-1 | phenyl | CH | CH | CH | CH | H | H | 2,6-dimethyl-4-heptafluoroisopropylphenyl |
| 4-2 | 2-methylphenyl | CH | CH | CH | CH | H | H | 2,6-dimethyl-4-heptafluoroisopropylphenyl |
| 4-3 | 2-fluorophenyl | CH | CH | CH | CH | H | H | 2,6-dimethyl-4-heptafluoroisopropylphenyl |
| 4-4 | 3-fluorophenyl | CH | CH | CH | CH | H | H | 2,6-dimethyl-4-heptafluoroisopropylphenyl |
| 4-5 | 4-fluorophenyl | CH | CH | CH | CH | H | H | 2,6-dimethyl-4-heptafluoroisopropylphenyl |
| 4-6 | 4-chlorophenyl | CH | CH | CH | CH | H | H | 2,6-dimethyl-4-heptafluoroisopropylphenyl |
| 4-7 | 2-bromophenyl | CH | CH | CH | CH | H | H | 2,6-dimethyl-4-heptafluoroisopropylphenyl |
| 4-8 | 2-iodophenyl | CH | CH | CH | CH | H | H | 2,6-dimethyl-4-heptafluoroisopropylphenyl |
| 4-9 | 4-cyanophenyl | CH | CH | CH | CH | H | H | 2,6-dimethyl-4-heptafluoroisopropylphenyl |
| 4-10 | 2-nitrophenyl | CH | CH | CH | CH | H | H | 2,6-dimethyl-4-heptafluoroisopropylphenyl |
| 4-11 | 4-nitrophenyl | CH | CH | CH | CH | H | H | 2,6-dimethyl-4-heptafluoroisopropylphenyl |
| 4-12 | 2-trifluoromethylphenyl | CH | CH | CH | CH | H | H | 2,6-dimethyl-4-heptafluoroisopropylphenyl |
| 4-13 | 4-methoxyphenyl | CH | CH | CH | CH | H | H | 2,6-dimethyl-4-heptafluoroisopropylphenyl |
| 4-14 | 2-(acetylamino)phenyl | CH | CH | CH | CH | H | H | 2,6-dimethyl-4-heptafluoroisopropylphenyl |
| 4-15 | 2,4-difluorophenyl | CH | CH | CH | CH | H | H | 2,6-dimethyl-4-heptafluoroisopropylphenyl |
| 4-16 | 2,3,4,5,6-pentafluorophenyl | CH | CH | CH | CH | H | H | 2,6-dimethyl-4-heptafluoroisopropylphenyl |
| 4-17 | pyridin-2-yl | CH | CH | CH | CH | H | H | 2,6-dimethyl-4-heptafluoroisopropylphenyl |
| 4-18 | pyridin-3-yl | CH | CH | CH | CH | H | H | 2,6-dimethyl-4-heptafluoroisopropylphenyl |
| 4-19 | pyridin-4-yl | CH | CH | CH | CH | H | H | 2,6-dimethyl-4-heptafluoroisopropylphenyl |
| 4-20 | 2-fluoropyridin-3-yl | CH | CH | CH | CH | H | H | 2,6-dimethyl-4-heptafluoroisopropylphenyl |
| 4-21 | 2-chloropyridin-3-yl | CH | CH | CH | CH | H | H | 2,6-dimethyl-4-heptafluoroisopropylphenyl |
| 4-22 | pyridin-N-oxid-2-yl | CH | CH | CH | CH | H | H | 2,6-dimethyl-4-heptafluoroisopropylphenyl |
| 4-23 | methyl | CH | CH | CH | CH | H | H | 2,6-dimethyl-4-heptafluoroisopropylphenyl |
| 4-24 | methyl | CH | CH | CH | CH | Me | H | 2,6-dimethyl-4-heptafluoroisopropylphenyl |
| 4-25 | ethyl | CH | CH | CH | CH | H | H | 2,6-dimethyl-4-heptafluoroisopropylphenyl |
| 4-26 | ethyl | CH | CH | CH | CH | Me | H | 2,6-dimethyl-4-heptafluoroisopropylphenyl |
| 4-27 | 2,2,2-trifluoroethyl | CH | CH | CH | CH | H | H | 2,6-dimethyl-4-heptafluoroisopropylphenyl |
| 4-28 | 2,2,2-trifluoroethyl | CH | CH | CH | CH | Me | H | 2,6-dimethyl-4-heptafluoroisopropylphenyl |
| 4-29 | vinyl | CH | CH | CH | CH | H | H | 2,6-dimethyl-4-heptafluoroisopropylphenyl |
| 4-30 | vinyl | CH | CH | CH | CH | Me | H | 2,6-dimethyl-4-heptafluoroisopropylphenyl |
| 4-31 | propyl | CH | CH | CH | CH | H | H | 2,6-dimethyl-4-heptafluoroisopropylphenyl |
| 4-32 | propyl | CH | CH | CH | CH | Me | H | 2,6-dimethyl-4-heptafluoroisopropylphenyl |
| 4-33 | isopropyl | CH | CH | CH | CH | H | H | 2,6-dimethyl-4-heptafluoroisopropylphenyl |
| 4-34 | benzyl | CH | CH | CH | CH | H | H | 2,6-dimethyl-4-heptafluoroisopropylphenyl |
| 4-37 | phenyl | CH | CH | CH | CH | H | H | 2-bromo-4,6-bis-(trifluoromethyl)phenyl |
| 4-38 | phenyl | CH | CH | CH | CH | H | H | 2,4-bis(trifluoromethyl)phenyl |
| 4-39 | phenyl | CH | CH | CH | CH | H | H | 2-bromo-4-(heptafluoroisopropyl)-6-(methylsulfonyl)phenyl |
| 4-40 | phenyl | CH | CH | CH | CH | H | H | 2,6-dibromo-4-(heptafluoro-n-propylthio)phenyl |
| 4-41 | phenyl | CH | CH | CH | CH | H | H | 2,6-dibromo-4-(heptafluoro-n-propylsulfinyl)phenyl |
| 4-42 | phenyl | CH | CH | CH | CH | H | H | 2,6-dimethyl-4-(nonafluoro-2-butyl)phenyl |
| 4-43 | phenyl | CH | CH | CH | CH | H | H | 2,6-dibromo-4-{1,1,2,3,3,3-hexafluoropropyloxy)phenyl |
| 4-44 | phenyl | CH | CH | CH | CH | H | H | 2-bromo-4-{1,1,2,3,3,3-hexafluoropropyloxy)-6-methylphenyl |
| 4-45 | phenyl | CH | CH | CH | CH | H | H | 6-bromo-8-heptafluoroisopropylquinolin-5-yl |

TABLE 3-continued

| Compound No. | Q₁ | A'₁ | A'₂ | A'₃ | A'₄ | R₁ | R₂ | Q₂ |
|---|---|---|---|---|---|---|---|---|
| 4-46 | phenyl | CH | CH | CH | CH | H | H | 2,6-dimethyl-4-(2-bromo-1,2,2-trifluoro-1-trifluoromethylethyl)-phenyl |
| 4-47 | phenyl | CH | CH | CH | CH | H | H | 2,6-dichloro-4-(2,2,2-trifluoro-1-trifluoromethylethoxy)phenyl |
| 4-48 | phenyl | CH | CH | CH | CH | H | H | 2,6-dichloro-4-trifluoromethylphenyl |
| 4-49 | phenyl | CH | CH | CH | CH | H | H | 2,4-dibromo-6-trifluoromethylphenyl |
| 4-50 | phenyl | CH | CH | CH | CH | H | H | 2-bromo-4,6-bis-(trifluoromethyl)phenyl |
| 4-51 | phenyl | CH | CH | CH | CH | H | H | 2,4-bis(trifluoromethyl)phenyl |
| 4-52 | phenyl | CH | CH | CH | CH | H | H | 2-bromo-6-(2,2,2-trifluoro-1-trifluoromethylethoxy)pyridin-3-yl |

General Formula (C)

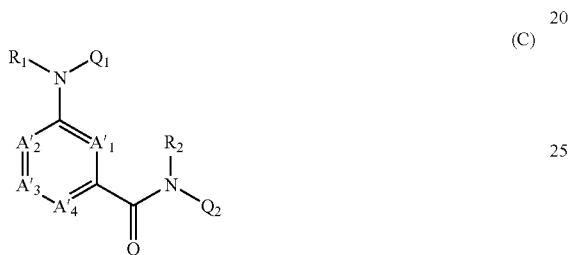

(C)

TABLE 4

| Compound No. | Q₁ | A'₁ | A'₂ | A'₃ | A'₄ | R₁ | R₂ | Q₂ |
|---|---|---|---|---|---|---|---|---|
| 5-1 | phenyl | CH | CH | CH | CH | H | H | 2,6-dimethyl-4-heptafluoroisopropylphenyl |
| 5-2 | 2-methylphenyl | CH | CH | CH | CH | H | H | 2,6-dimethyl-4-heptafluoroisopropylphenyl |
| 5-3 | 2-fluorophenyl | CH | CH | CH | CH | H | H | 2,6-dimethyl-4-heptafluoroisopropylphenyl |
| 5-4 | 3-fluorophenyl | CH | CH | CH | CH | H | H | 2,6-dimethyl-4-heptafluoroisopropylphenyl |
| 5-5 | 4-bromophenyl | CH | CH | CH | CH | H | H | 2,6-dimethyl-4-heptafluoroisopropylphenyl |
| 5-6 | 2-iodophenyl | CH | CH | CH | CH | H | H | 2,6-dimethyl-4-heptafluoroisopropylphenyl |
| 5-7 | 4-cyanophenyl | CH | CH | CH | CH | H | H | 2,6-dimethyl-4-heptafluoroisopropylphenyl |
| 5-8 | 2-nitrophenyl | CH | CH | CH | CH | H | H | 2,6-dimethyl-4-heptafluoroisopropylphenyl |
| 5-9 | 4-nitrophenyl | CH | CH | CH | CH | H | H | 2,6-dimethyl-4-heptafluoroisopropylphenyl |
| 5-10 | 2-aminophenyl | CH | CH | CH | CH | H | H | 2,6-dimethyl-4-heptafluoroisopropylphenyl |
| 5-11 | 4-aminophenyl | CH | CH | CH | CH | H | H | 2,6-dimethyl-4-heptafluoroisopropylphenyl |
| 5-12 | 3-trifluoromethylphenyl | CH | CH | CH | CH | H | H | 2,6-dimethyl-4-heptafluoroisopropylphenyl |
| 5-13 | 2-(acetylamino)phenyl | CH | CH | CH | CH | H | H | 2,6-dimethyl-4-heptafluoroisopropylphenyl |
| 5-14 | 4-(acetylamino)phenyl | CH | CH | CH | CH | H | H | 2,6-dimethyl-4-heptafluoroisopropylphenyl |
| 5-15 | 2,4-difluorophenyl | CH | CH | CH | CH | H | H | 2,6-dimethyl-4-heptafluoroisopropylphenyl |
| 5-16 | pyridin-2-yl | CH | CH | CH | CH | H | H | 2,6-dimethyl-4-heptafluoroisopropylphenyl |
| 5-17 | pyridin-3-yl | CH | CH | CH | CH | H | H | 2,6-dimethyl-4-heptafluoroisopropylphenyl |
| 5-18 | pyridin-4-yl | CH | CH | CH | CH | H | H | 2,6-dimethyl-4-heptafluoroisopropylphenyl |
| 5-19 | 2-fluoropyridin-3-yl | CH | CH | CH | CH | H | H | 2,6-dimethyl-4-heptafluoroisopropylphenyl |
| 5-20 | 2-chloropyridin-3-yl | CH | CH | CH | CH | H | H | 2,6-dimethyl-4-heptafluoroisopropylphenyl |
| 5-21 | 6-bromopyridin-2-yl | CH | CH | CH | CH | H | H | 2,6-dimethyl-4-heptafluoroisopropylphenyl |
| 5-22 | pyridin-N-oxid-2-yl | CH | CH | CH | CH | H | H | 2,6-dimethyl-4-heptafluoroisopropylphenyl |
| 5-23 | 5-amino-[1,2,4]oxadiazol-3-yl | CH | CH | CH | CH | H | H | 2,6-dimethyl-4-heptafluoroisopropylphenyl |
| 5-24 | 3-amino-[1,2,4]oxadiazol-5-yl | CH | CH | CH | CH | H | H | 2,6-dimethyl-4-heptafluoroisopropylphenyl |
| 5-25 | 5-amino-2H-[1,2,4]triazol-3-yl | CH | CH | CH | CH | H | H | 2,6-dimethyl-4-heptafluoroisopropylphenyl |
| 5-26 | Me | CF | CH | CH | CH | Me | H | 2,6-dimethyl-4-heptafluoroisopropylphenyl |
| 5-27 | Me | CH | CH | CH | CH | Me | H | 2,6-dimethyl-4-heptafluoroisopropylphenyl |
| 5-28 | Me | CH | CH | CH | CH | Me | H | 2,6-dimethyl-4-heptafluoroisopropylphenyl |
| 5-29 | Me | CH | CH | CH | CH | Me | H | 2-bromo-4-heptafluoroisopropyl-6-methylsulfonylphenyl |

TABLE 4-continued

| Compound No. | Q₁ | A'₁ | A'₂ | A'₃ | A'₄ | R₁ | R₂ | Q₂ |
|---|---|---|---|---|---|---|---|---|
| 5-30 | Me | CH | CH | CH | CH | Me | H | 2,6-dibromo-4-heptafluoropropylthiophenyl |
| 5-31 | Me | CH | CH | CH | CH | Me | H | 2,6-dibromo-4-{1,1,2,3,3,3-hexafluoropropylthio)phenyl |
| 5-32 | Me | CH | CH | CH | CH | Me | Me | 2,6-dibromo-4-heptafluoropropylsulfonyl)phenyl |
| 5-33 | 1-phenylethyl | CH | CH | CH | CH | Me | H | 2,6-dimethyl-4-heptafluoroisopropylphenyl |
| 5-34 | phenyl | CH | CH | CH | CH | H | Me | 2-bromo-4,6-bis(trifluoromethyl)phenyl |
| 5-35 | phenyl | CH | CH | CH | CH | H | H | 2,4-bis(trifluoromethyl)phenyl |
| 5-36 | phenyl | CH | CH | CH | CH | H | H | 2-bromo-4-(heptafluoroisopropyl)-6-(methylsulfonyl)phenyl |
| 5-37 | phenyl | CH | CH | CH | CH | H | H | 2,6-dibromo-4-(heptafluoro-n-propylthio)phenyl |
| 5-38 | phenyl | CH | CH | CH | CH | H | H | 2,6-dibromo-4-(heptafluoro-n-propylsulfinyl)phenyl |
| 5-39 | phenyl | CH | CH | CH | CH | H | H | 2,6-dimethyl-4-(nonafluoro-2-butyl)phenyl |
| 5-40 | phenyl | CH | CH | CH | CH | H | H | 2,6-dibromo-4-{1,1,2,3,3,3-hexafluoropropyloxy)phenyl |
| 5-41 | phenyl | CH | CH | CH | CH | H | H | 2-dibromo-4-(1,1,2,3,3,3-hexafluoropropyloxy)6-methylphenyl |
| 5-42 | phenyl | CH | CH | CH | CH | H | H | 6-bromo-8-heptafluoroisopropylquinolin-5-yl |
| 5-43 | phenyl | CH | CH | CH | CH | H | H | 2,6-dimethyl-4-(2-bromo-1,2,2-trifluoro-1-trifluoromethylethyl)-phenyl |
| 5-44 | phenyl | CH | CH | CH | CH | H | H | 2,6-dichloro-4-(2,2,2-trifluoro-1-trifluoromethylethoxy)phenyl |
| 5-45 | phenyl | CH | CH | CH | CH | H | H | 2,6-dichloro-4-trifluoromethylphenyl |
| 5-46 | phenyl | CH | CH | CH | CH | H | H | 2,4-dibromo-6-trifluoromethylphenyl |
| 5-47 | phenyl | CH | CH | CH | CH | H | H | 2-bromo-4,6-bis-(trifluoromethyl)phenyl |
| 5-48 | phenyl | CH | CH | CH | CH | H | H | 2,4-bis(trifluoromethyl)phenyl |
| 5-49 | phenyl | CH | CH | CH | CH | H | H | 2-bromo-6-(2,2,2-trifluoro-1-trifluoromethylethoxy)pyridin-3-yl |
| 5-50 | phenyl | CH | CH | CH | CH | H | H | 2-bromo-4,6-bis-(trifluoromethyl)phenyl |
| 5-51 | phenyl | CH | CH | CH | CH | H | H | 2-bromo-4,6-bis-(trifluoromethyl)phenyl |
| 5-52 | phenyl | CH | CH | CH | CH | H | H | 2-bromo-4,6-bis-(trifluoromethyl)phenyl |
| 5-53 | phenyl | CH | CH | CH | CH | H | H | 2,4-bis(trifluoromethyl)phenyl |
| 5-54 | phenyl | CH | CH | CH | CH | H | H | 2-bromo-6-(2,2,2-trifluoro-1-trifluoromethylethoxy)pyridin-3-yl |

The physical properties of the compound of the present invention represented by general formula (1) or (5) are shown in Table 5 below. Tetramethylsilane is used as an internal standard substance to record shift values of 1H-NMR as shown herein, unless otherwise particularly mentioned.

TABLE 5

| Compound No. | Physical Property |
|---|---|
| 1-1 | $^1$H-NMR (DMSO-d$_6$) δ 7.51-7.62 (4H, m), 7.78 (1H, d, J = 7.8 Hz), 7.97-8.00 (2H, m), 8.05-8.08 (2H, m), 8.30 (1H, d, J = 2.4 Hz), 8.37 (1H, d, J = 2.0 Hz), 10.48 (1H, s), 10.65 (1H, s). |
| 1-159 | $^1$H-NMR (CDCl$_3$) δ 3.47 (3H, s), 7.12-7.16 (2H, m), 7.21-7.32 (5H, m), 7.70 (1H, s), 7.72 (1H, t, J = 7.8 Hz), 7.82-7.83 (2H, m), 8.56 (1H, s). |
| 1-163 | $^1$H-NMR (CDCl$_3$) δ 3.57 (3H, s), 7.11-7.14 (1H, m), 7.40-7.41 (2H, m), 7.58 (1H, d, J = 7.8 Hz), 7.69-7.78 (2H, m), 7.91-8.02 (3H, m), 8.24 (1H, d, J = 4.9 Hz). |
| 1-264 | $^1$H-NMR (CDCl$_3$) δ 7.49-7.63 (4H, m), 7.70-7.73 (1H, m), 7.76 (1H, d, J = 2.0 Hz), 7.86-7.93 (3H, m), 7.98-8.02 (3H, m), 8.23 (1H, t, J = 2.0 Hz). |

TABLE 5-continued

| Compound No. | Physical Property |
| --- | --- |
| 1-265 | $^1$H-NMR (DMSO-d$_6$) δ 7.52-7.64 (4H, m), 7.79 (1H, d, J = 7.8 Hz), 7.97-8.02 (3H, m), 8.06-8.09 (1H, m), 8.21 (1H, d, J = 2.0 Hz), 8.38 (1H, t, J = 2.0 Hz), 10.48 (1H, s), 10.60 (1H, broad). |
| 1-266 | $^1$H-NMR (DMSO-d$_6$) δ 7.53-7.64 (4H, m), 7.81 (1H, d, J = 7.8 Hz), 7.99-8.10 (7H, m), 8.18 (1H, s), 8.27 (1H, d, J = 2.0 Hz), 8.41 (1H, s), 10.50 (1H, s), 10.75 (1H, s). |
| 1-267 | $^1$H-NMR (CDCl$_3$) δ 7.35 (1H, d, J = 7.3 Hz), 7.50-7.63 (7H, m), 7.72-7.80 (3H, m), 7.89-7.92 (2H, m), 8.00 (1H, s), 8.05-8.10 (2H, m), 8.22 (1H, t, J = 2.0 Hz). |
| 1-303 | $^1$H-NMR (DMSO-d$_6$) δ 7.48-7.67 (4H, m), 7.78 (1H, dd, J = 4.4, 8.8 Hz), 7.91 (1H, d, J = 7.8 Hz), 8.00-8.03 (2H, m), 8.12-8.17 (1H, m), 8.46-8.50 (3H, m), 9.08 (1H, dd, J = 2.0, 4.4 Hz), 10.54 (1H, s), 10.84 (1H, s). |
| 1-304 | $^1$H-NMR (DMSO-d$_6$) δ 7.33-7.40 (2H, m), 7.57-7.63 (2H, m), 7.68-7.73 (1H, m), 7.77 (1H, dd, J = 3.9, 8.8 Hz), 7.90 (1H, d, J = 7.8 Hz), 8.03 (1H, d, J = 7.8 Hz), 8.41-8.49 (3H, m), 9.08 (1H, dd, J = 1.5, 3.9 Hz), 10.70 (1H, s), 10.84 (1H, s). |
| 1-305 | $^1$H-NMR (DMSO-d$_6$) δ 7.64 (1H, t, J = 7.8 Hz), 7.77 (1H, dd, J = 3.9, 8.8 Hz), 7.95 (1H, d, J = 7.8 Hz), 8.13 (1H, d, J = 7.8 Hz), 8.24 (2H, d, J = 8.3 Hz), 8.39-8.50 (5H, m), 9.08 (1H, dd, J = 1.5, 3.9 Hz), 10.84 (1H, s), 10.85 (1H, s). |
| 1-306 | $^1$H-NMR (DMSO-d$_6$) δ 10.5 (1H, s), 9.95 (1H, s), 8.36 (1H, t, J = 1.5 Hz), 7.98-8.07 (3H, m), 7.75 (1H, d, J = 7.8 Hz), 7.50-7.63 (4H, m), 7.42 (2H, s), 2.30 (6H, s). |
| 1-307 | $^1$H-NMR (CDCl$_3$) δ 4.76-4.82 (1H, m), 7.15 (2H, s), 7.45-8.17 (10H, m), 8.30 (1H, brs). |
| 1-308 | $^1$H-NMR (CDCl$_3$) δ 4.78-4.84 (1H, m), 7.19 (2H, s), 7.33-8.66 (10H, m). |
| 1-309 | $^1$H-NMR (DMSO-d$_6$) δ 7.53-7.63 (4H, m), 7.79 (1H, d, J = 7.8 Hz), 7.99-8.02 (2H, m), 8.08 (1H, dd, J = 1.5, 7.8 Hz), 8.18 (1H, s), 8.39 (1H, t, J = 1.5 Hz), 10.50 (1H, s), 10.56 (1H, s). |
| 1-310 | $^1$H-NMR (CDCl$_3$) δ 7.19-7.25 (1H, m), 7.35 (1H, t, J = 7.8 Hz), 7.51-7.60 (3H, m), 7.76-7.78 (2H, m), 7.92 (1H, d, J = 7.8 Hz), 8.19 (1H, d, J = 7.8 Hz), 8.34 (1H, s), 8.63 (1H, d, J = 16.1 Hz). |
| 1-311 | $^1$H-NMR (DMSO-d$_6$) δ 7.37-7.41 (2H, m), 7.56 (1H, t, J = 7.8 Hz), 7.79 (1H, d, J = 7.8 Hz), 8.06-8.14 (3H, m), 8.18 (1H, s), 8.36 (1H, s), 10.51 (1H, s), 10.56 (1H, s). |
| 1-312 | $^1$H-NMR (DMSO-d$_6$) δ 7.60 (1H, d, J = 6.8 Hz), 7.83 (1H, d, J = 6.8 Hz), 8.09 (1H, d, J = 7.3 Hz), 8.18-8.25 (4H, m), 8.40 (2H, d, J = 8.8 Hz), 10.59 (1H, s), 10.81 (1H, s). |
| 1-313 | $^1$H-NMR (DMSO-d$_6$) δ 7.53-7.64 (4H, m), 7.77 (1H, d, J = 7.8 Hz), 7.97-8.01 (3H, m), 8.07 (1H, dd, J = 1.5, 7.8 Hz), 8.41 (1H, s), 10.49 (1H, s), 10.52 (1H, s). |
| 1-314 | $^1$H-NMR (DMSO-d$_6$) δ 7.33-7.40 (2H, m), 7.54-7.63 (2H, m), 7.68-7.72 (1H, m), 7.78 (1H, d, J = 7.8 Hz), 7.98 (1H, d, J = 8.3 Hz), 8.10 (2H, s), 8.36 (1H, s), 10.62 (1H, s), 10.67 (1H, s). |
| 1-315 | $^1$H-NMR (DMSO-d$_6$) δ 7.25-7.30 (2H, m), 7.56-7.65 (2H, m), 7.80 (1H, d, J = 8.3 Hz), 7.92-7.95 (1H, m), 8.10 (2H, s), 8.32 (1H, s), 10.65 (1H, s), 11.06 (1H, s). |
| 1-316 | $^1$H-NMR (DMSO-d$_6$) δ 7.52-7.63 (4H, m), 7.72 (1H, d, J = 7.8 Hz), 7.98-8.01 (2H, m), 8.05-8.07 (2H, m), 8.34 (1H, t, J = 2.0 Hz), 8.44 (1H, d, J = 2.0 Hz), 10.40 (1H, s), 10.48 (1H, s). |
| 1-317 | MS (APCI) = 604 (M + 1) |
| 1-318 | MS (APCI) = 604 (M + 1) |
| 1-319 | MS (APCI) = 685 (M + 1) |
| 1-320 | MS (APCI) = 586 (M + 1) |
| 1-321 | MS (APCI) = 645 (M + 1) |
| 1-322 | MS (APCI) = 685 (M + 1) |
| 1-323 | MS (APCI) = 599 (M + 1) |
| 1-324 | MS (APCI) = 601 (M + 1) |
| 1-325 | MS (APCI) = 530 (M + 1) |
| 1-326 | MS (APCI) = 631 (M + 1) |
| 1-327 | MS (APCI) = 642 (M + 1) |
| 1-328 | MS (APCI) = 542 (M + 1) |
| 1-329 | MS (APCI) = 610 (M + 1) |
| 1-330 | MS (APCI) = 547 (M + 1) |
| 1-331 | MS (APCI) = 571 (M + 1) |
| 1-332 | MS (APCI) = 633 (M + 1) |
| 1-333 | MS (APCI) = 592 (M + 1) |
| 1-334 | MS (APCI) = 592 (M + 1) |
| 1-335 | MS (APCI) = 668 (M + 1) |
| 1-336 | MS (APCI) = 591 (M + 1) |
| 1-337 | MS (APCI) = 641 (M + 1) |
| 1-338 | MS (APCI) = 642 (M + 1) |
| 1-339 | $^1$H-NMR (DMSO-d$_6$) δ 7.53-7.63 (4H, m), 7.75 (1H, d, J = 7.8 Hz), 7.98-8.09 (3H, m), 8.20 (1H, s), 8.37 (1H, s), 8.61 (1H, s), 10.50 (1H, s), 10.64 (1H, s). |

TABLE 5-continued

| Compound No. | Physical Property |
|---|---|
| 1-340 | $^1$H-NMR (DMSO-d$_6$) δ 7.53-7.64 (4H, m), 7.70-7.73 (1H, m), 7.87 (1H, d, J = 8.3 Hz), 7.98-8.07 (3H, m), 8.13-8.17 (2H, m), 8.38 (1H, t, J = 1.7 Hz), 10.40 (1H, s), 10.50 (1H, s). |
| 1-341 | MS (APCI) = 478 (M + 1) |
| 1-342 | MS (APCI) = 489 (M + 1) |
| 1-343 | MS (APCI) = 489 (M + 1) |
| 1-344 | MS (APCI) = 507 (M + 1) |
| 1-345 | MS (APCI) = 487 (M + 1) |
| 1-346 | MS (APCI) = 521 (M + 1) |
| 1-347 | MS (APCI) = 534 (M + 1) |
| 1-348 | MS (APCI) = 485 (M + 1) |
| 1-349 | MS (APCI) = 467 (M + 1) |
| 1-350 | MS (APCI) = 481 (M + 1) |
| 1-351 | MS (APCI) = 483 (M + 1) |
| 1-352 | MS (APCI) = 483 (M + 1) |
| 1-353 | MS (APCI) = 543 (M + 1) |
| 1-354 | MS (APCI) = 503 (M + 1) |
| 1-355 | MS (APCI) = 503 (M + 1) |
| 1-356 | MS (APCI) = 493 (M + 1) |
| 1-357 | MS (APCI) = 488 (M + 1) |
| 1-358 | MS (APCI) = 468 (M + 1) |
| 1-359 | MS (APCI) = 488 (M + 1) |
| 1-360 | MS (APCI) = 470 (M + 1) |
| 1-361 | MS (APCI) = 469 (M + 1) |
| 1-362 | MS (APCI) = 455 (M + 1) |
| 1-363 | MS (APCI) = 473 (M + 1) |
| 1-364 | MS (APCI) = 473 (M + 1) |
| 1-365 | $^1$H-NMR (DMSO-d$_6$) δ 7.53-7.73 (5H, m), 7.93-8.09 (6H, m), 8.38 (1H, d, J = 2.0 Hz), 10.4 (1H, s), 10.5 (1H, s). |
| 1-366 | $^1$H-NMR (DMSO-d$_6$) δ 7.53-7.63 (4H, m), 7.74 (1H, d, J = 7.8 Hz), 7.98-8.01 (2H, m), 8.07 (1H, dd, J = 1.5, 7.8 Hz), 8.18 (1H, s), 8.37 (1H, t, J = 1.5 Hz), 8.51 (1H, d, J = 1.5 Hz), 10.50 (1H, s), 10.62 (1H, s). |
| 1-367 | $^1$H-NMR (CDCl$_3$) δ 7.00-7.06 (2H, m), 7.43-7.58 (2H, m), 7.73-7.79 (3H, m), 7.91-7.93 (2H, m), 8.00 (1H, s), 8.26 (1H, s). |
| 1-368 | $^1$H-NMR (CDCl$_3$) δ 7.27-7.29 (1H, m), 7.54 (1H, t, J = 8.3 Hz), 7.77 (1H, d, J = 8.3 Hz), 7.91 (1H, s), 8.00 (1H, s), 8.21-8.34 (5H, m), 8.91 (1H, s), 9.95 (1H, s). |
| 1-369 | $^1$H-NMR (DMSO-d$_6$) δ 2.32 (3H, s), 7.52-7.63 (5H, m), 7.76 (1H, d, J = 7.8 Hz), 7.87 (1H, d, J = 2.7 Hz), 8.00 (2H, dd, J = 1.5 Hz, 7.8), 8.06 (1H, d, J = 7.8 Hz), 8.37 (1H, s), 10.18 (1H, s), 10.47 (1H, s). |
| 1-371 | $^1$H-NMR (DMSO-d$_6$) δ 2.32 (3H, s), 7.54-7.61 (5H, m), 7.72-7.77 (2H, m), 7.98-8.08 (3H, m), 8.37 (1H, s), 10.17 (1H, s), 10.46 (1H, s). |
| 1-372 | $^1$H-NMR (CDCl$_3$) δ 2.32 (3H, s), 7.04-8.23 (14H, m). |
| 1-373 | $^1$H-NMR (DMSO-d$_6$) δ 2.46 (3H, s), 7.53-7.71 (6H, m), 7.80 (1H, s), 7.90 (1H, d, J = 7.8 Hz), 8.00-8.02 (2H, m), 8.10-8.17 (2H, m), 8.38 (1H, d, J = 7.8 Hz), 8.45 (1H, s), 10.51 (1H, s), 10.52 (1H, s). |
| 1-374 | $^1$H-NMR (DMSO-d$_6$) δ 2.46 (3H, s), 7.33-7.40 (2H, m), 7.57-7.63 (2H, m), 7.66-7.73 (3H, m), 7.79 (1H, s), 7.88-7.91 (1H, m), 8.02 (1H, d, J = 7.8 Hz), 8.10-8.12 (1H, m), 8.36-8.40 (2H, m), 10.54 (1H, s), 10.68 (1H, s). |
| 1-375 | $^1$H-NMR (DMSO-d$_6$) δ 2.04 (2H, quint, J = 7.3 Hz), 2.91 (2H, t, J = 7.3 Hz), 3.11 (2H, dd, J = 7.3, 12.2 Hz), 7.40 (1H, d, J = 8.8 Hz), 7.51-7.67 (5H, m), 7.71 (1H, d, J = 7.8 Hz), 7.98-8.07 (3H, m), 8.35 (1H, s), 10.10 (1H, s), 10.48 (1H, s). |
| 1-376 | $^1$H-NMR (DMSO-d$_6$) δ 7.53-7.64 (4H, m), 7.78 (1H, d, J = 7.8 Hz), 7.99-8.02 (2H, m), 8.08 (1H, dd, J = 2.0, 7.8 Hz), 8.32 (2H, s), 8.40 (1H, t, J = 2.0 Hz), 10.51 (1H, s), 10.66 (1H, s). |
| 1-377 | $^1$H-NMR (CDCl$_3$) δ 2.33 (6H, s), 7.18-7.38 (5H, m), 7.49-7.60 (5H, m), 7.72 (1H, d, J = 7.8 Hz), 7.87-7.96 (3H, m), 8.10 (1H, s), 8.29 (1H, d, J = 8.0 Hz). |
| 1-378 | $^1$H-NMR (CDCl$_3$) δ 2.33 (3H, s), 2.34 (6H, s), 7.04 (1H, t, J = 8.8 Hz), 7.33-7.57 (8H, m), 7.77 (1H, d, J = 7.9 Hz), 8.00-8.02 (2H, m), 8.14 (1H, dd, J = 1.4, 8.3 Hz), 8.36 (1H, t, J = 2.0 Hz), 8.81 (1H, s), 9.85 (1H, s). |
| 1-379 | $^1$H-NMR (CDCl$_3$) δ 2.29 (6H, s), 6.67 (1H, s), 7.21 (2H, s), 7.47-7.59 (6H, m), 7.70-7.72 (2H, m), 7.87-7.89 (2H, m), 7.95 (1H, d, J = 7.8 Hz), 8.13 (1H, s), 8.25 (1H, s). |
| 1-380 | $^1$H-NMR (CDCl$_3$) δ 2.32 (6H, s), 7.07-7.09 (1H, m), 7.27-7.29 (1H, m), 7.37 (2H), 7.38-7.57 (6H, m), 7.73-7.78 (2H, m), 7.88 (1H, d, J = 8.3 Hz), 8.14 (1H, s), 8.27 (1H, s). |
| 1-381 | $^1$H-NMR (CDCl$_3$) δ 2.34 (6H, s), 7.35-7.55 (10H, m), 7.74-7.80 (2H, m), 7.89 (1H, d, J = 8.3 Hz), 8.11 (1H, s), 8.28 (1H, s). |

TABLE 5-continued

| Compound No. | Physical Property |
|---|---|
| 1-382 | ¹H-NMR (DMSO-d₆) δ 1.23-1.39 (5H, m), 1.57-1.71 (5H, m), 2.45-2.51 (1H, m), 7.40-7.52 (6H, m), 7.66 (1H, d, J = 7.8 Hz), 7.85-7.97 (3H, m), 8.23 (1H, s), 10.17 (1H, s), 10.37 (1H, s). |
| 1-383 | ¹H-NMR (DMSO-d₆) δ 1.20-1.40 (5H, m), 1.67-1.79 (5H, m), 2.45-2.50 (1H, m), 7.19 (2H, d, J = 8.8 Hz), 7.47-7.68 (7H, m), 7.97-8.02 (3H, m), 8.29 (1H, t, J = 2.0 Hz), 10.20 (1H, s), 10.45 (1H, s). |
| 1-384 | ¹H-NMR (CDCl₃) δ 2.19 (6H, s), 7.00-7.09 (2H, m), 7.40-7.45 (3H, m), 7.53 (1H, t, J = 7.8 Hz), 7.63 (1H, d, J = 7.8 Hz), 7.67 (1H, s), 7.84 (2H, d, J = 7.8 Hz), 7.95 (1H, dd, J = 1.5, 7.8 Hz), 8.18 (1H, s), 8.46 (1H, s). |
| 1-385 | ¹H-NMR (CDCl₃) δ 2.35 (6H, s), 7.44-7.53 (3H, m), 7.59 (1H, t, J = 7.8 Hz), 7.72 (1H, d, J = 7.8 Hz), 7.79-7.89 (6H, m), 8.12 (1H, s), 8.36 (1H, s). |
| 1-386 | ¹H-NMR (CDCl₃) δ 2.33 (6H, s), 4.11 (1H, septet, J = 6.9 Hz), 7.17 (2H, s), 7.50-7.61 (5H, m), 7.71 (1H, d, J = 7.8 Hz), 7.87-7.90 (3H, m), 8.03 (1H, s), 8.29 (1H, s). |
| 1-387 | ¹H-NMR (CDCl₃) δ 6.30 (1H, septet, J = 6.8 Hz), 7.01 (1H, d, J = 8.8 Hz), 7.49-7.61 (4H, m), 7.68 (1H, dd, J = 1.0, 7.8 Hz), 7.88-7.91 (2H, m), 7.96-8.01 (2H, m), 8.26 (1H, t, J = 1.9 Hz), 8.33 (1H, s), 8.81 (1H, d, J = 8.8 Hz). |
| 1-389 | ¹H-NMR (CDCl₃) δ 4.13 (2H, dt, J = 6.4, 14.6 Hz), 7.41-7.57 (4H, m), 7.62 (1H, d, J = 7.8 Hz), 7.99-8.01 (2H, m), 8.09 (2H, d, J = 7.3 Hz), 8.22 (1H, t, J = 2.0 Hz), 9.79 (1H, s). |
| 1-390 | ¹H-NMR (CDCl₃) δ 7.50-7.61 (4H, m), 7.75 (1H, d, J = 7.8 Hz), 7.89 (2H, d, J = 7.8 Hz), 7.93 (1H, s), 7.95 (1H, s), 8.07 (1H, s), 8.10 (1H, s), 8.33 (1H, s). |
| 1-391 | ¹H-NMR (CDCl₃) δ 7.44 (1H, dd, J = 4.9, 7.8 Hz), 7.57 (1H, t, J = 7.8 Hz), 7.79 (1H, d, J = 7.8 Hz), 7.87-7.91 (2H, m), 8.13 (1H, s), 8.23 (1H, dd, J = 2.0, 7.8 Hz), 8.31 (1H, s), 8.42 (1H, s), 8.55 (1H, dd, J = 2.0, 4.9 Hz). |
| 1-392 | ¹H-NMR (CDCl₃) δ 7.22 (1H, dd, J = 7.8, 12.2 Hz), 7.35 (1H, t, J = 7.8 Hz), 7.53-7.60 (2H, m), 7.77 (1H, d, J = 7.8 Hz), 7.90-7.92 (2H, m), 8.13 (1H, s), 8.19 (1H, dt, J = 1.4, 7.8 Hz), 8.34 (1H, s), 8.64 (1H, d, J = 16.1 Hz). |
| 1-393 | ¹H-NMR (DMSO-d₆) δ 7.31-7.38 (2H, m), 7.50-7.62 (2H, m), 7.66-7.72 (4H, m), 7.92-7.96 (3H, m), 8.27 (1H, s), 10.61 (1H, s), 10.63 (1H, s). |
| 1-394 | ¹H-NMR (DMSO-d₆) δ 7.32-7.38 (2H, m), 7.52-7.60 (2H, m), 7.65-7.73 (2H, m), 7.94 (1H, d, J = 8.3 Hz), 8.11 (2H, d, J = 8.8 Hz), 8.20-8.23 (2H, m), 8.29 (1H, s), 10.67 (1H, s), 11.01 (1H, s). |
| 1-395 | ¹H-NMR (CDCl₃) δ 7.45-7.62 (6H, m), 7.69 (1H, d, J = 7.8 Hz), 7.93 (2H, d, J = 7.3 Hz), 8.01 (2H, d, J = 7.3 Hz), 8.14 (1H, d, J = 7.8 Hz), 8.28 (1H, t, J = 1.9 Hz), 9.95 (1H, s), 9.99 (1H, s). |
| 1-396 | ¹H-NMR (CDCl₃) δ 7.44-7.61 (5H, m), 7.73 (1H, d, J = 8.3 Hz), 7.93 (2H, d, J = 8.3 Hz), 8.01 (2H, d, J = 6.8 Hz), 8.07-8.13 (2H, m), 8.29 (1H, s), 9.97 (1H, s), 10.10 (1H, s). |
| 1-397 | ¹H-NMR (CDCl₃) δ 2.41 (3H, s), 7.51-7.58 (6H, m), 7.67 (1H, d, J = 6.3 Hz), 7.86-7.91 (4H, m), 7.99 (1H, s), 8.23 (1H, d, J = 8.3 Hz), 8.30 (1H, t, J = 2.0 Hz). |
| 1-398 | ¹H-NMR (CDCl₃) δ 3.32 (3H, s), 3.46 (3H, s), 6.65 (2H, d, J = 8.0 Hz), 6.94 (1H, d, J = 2.8 Hz), 7.07-7.12 (5H, m), 7.25 (2H, d, J = 8.4 Hz), 7.94 (2H, d, J = 8.8 Hz), 9.50 (1H, s, OH). |
| 1-399 | ¹H-NMR (CDCl₃) δ 2.41 (3H, s), 7.21 (1H, dd, J = 1.0, 8.3 Hz), 7.35 (1H, t, J = 7.3 Hz), 7.52-7.59 (4H, m), 7.69 (1H, d, J = 8.3 Hz), 7.86 (1H, d, J = 8.3 Hz), 7.91 (1H, s), 8.19 (1H, dt, J = 1.4, 8.3 Hz), 8.23 (1H, d, J = 8.3 Hz), 8.33 (1H, t, J = 2.0 Hz), 8.63 (1H, d, J = 15.6 Hz). |
| 1-400 | ¹H-NMR (CDCl₃) δ 2.36 (3H, s), 6.63 (1H, septet, J = 6.3 Hz), 6.91 (1H, s), 7.45-7.57 (4H, m), 7.74 (1H, d, J = 7.8 Hz), 8.03 (2H, d, J = 8.8 Hz), 8.11 (1H, d, J = 8.3 Hz), 8.17 (1H, s), 8.39 (1H, t, J = 1.9 Hz), 9.75 (1H, brs), 10.2 (1H, brs). |
| 1-401 | ¹H-NMR (DMSO-d₆) δ 2.28 (3H, s), 7.12-7.19 (2H, m), 7.33-7.40 (2H, m), 7.52-7.63 (2H, m), 7.67-7.75 (2H, m), 7.94 (1H, d, J = 6.8 Hz), 8.17 (1H, s), 8.33 (1H, s), 10.1 (1H, brs), 10.6 (1H, s). |
| 1-402 | ¹H-NMR (CDCl₃) δ 6.31 (1H, septet, J = 5.9 Hz), 7.03 (1H, d, J = 8.8 Hz), 7.20-7.25 (2H, m), 7.34-7.37 (1H, m), 7.54-7.57 (2H, m), 7.69 (1H, d, J = 7.8 Hz), 8.18-8.23 (1H, m), 8.29-8.30 (2H, m), 8.60 (1/2H, brs), 8.64 (1/2H, brs), 8.83 (1H, d, J = 8.8 Hz). |
| 1-403 | ¹H-NMR (CDCl₃) δ 6.58 (1H, septet, J = 6.3 Hz), 6.95 (1H, d, J = 8.8 Hz), 7.45-7.58 (4H, m), 7.70 (1H, d, J = 7.8 Hz), 8.00-8.02 (2H, m), 8.12 (1H, d, J = 7.8 Hz), 8.24-8.28 (2H, m), 8.56 (1H, d, J = 2.5 Hz), 9.72 (1H, brs), 9.86 (1H, s). |
| 1-404 | ¹H-NMR (CDCl₃) δ 6.60 (1H, septet, J = 6.3 Hz), 6.96 (1H, d, J = 9.2 Hz), 7.19-7.23 (1H, m), 7.29-7.33 (1H, m), 7.46-7.54 (2H, m), 7.71 (1H, d, J = 7.8 Hz), 7.87-7.91 (1H, m), 8.06 (1H, d, |

TABLE 5-continued

| Compound No. | Physical Property |
|---|---|
| | J = 9.2 Hz), 8.24-8.28 (2H, m), 8.60 (1H, d, J = 2.5 Hz), 9.72 (1H, d, J = 5.3 Hz), 10.1 (1H, s). |
| 1-405 | $^1$H-NMR (DMSO-$d_6$) δ 7.52-7.65 (4H, m), 7.74 (1H, d, J = 7.8 Hz), 7.85 (1H, d, J = 1.5 Hz), 7.98-8.01 (2H, m), 8.06 (1H, dd, J = 1.5, 8.3 Hz), 8.13 (1H, d, J = 1.5 Hz), 8.35 (1H, t, J = 1.5 Hz), 10.34 (1H, s), 10.47 (1H, s). |
| 1-406 | $^1$H-NMR (DMSO-$d_6$) δ 7.32-7.39 (2H, m), 7.52-7.63 (2H, m), 7.67-7.74 (2H, m), 7.84 (1H, s), 7.96 (1H, d, J = 7.8 Hz), 8.13 (1H, d, J = 2.0 Hz), 8.30 (1H, s), 10.36 (1H, s), 10.64 (1H, s). |
| 1-407 | $^1$H-NMR (DMSO-$d_6$) δ 7.58 (1H, t, J = 7.8 Hz), 7.78 (1H, d, J = 7.8 Hz), 7.85 (1H, d, J = 1.5 Hz), 8.05-8.08 (1H, m), 8.13 (1H, d, J = 1.5 Hz), 8.21-8.24 (2H, m), 8.34 (1H, d, J = 1.5 Hz), 8.37-8.40 (2H, m), 10.37 (1H, s), 10.78 (1H, s). |
| 1-408 | $^1$H-NMR (DMSO-$d_6$) δ 7.50-7.69 (7H, m), 7.72 (1H, s), 7.97-8.04 (3H, m), 8.34 (1H, t, J = 2.0 Hz), 10.27 (1H, s), 10.46 (1H, s). |
| 1-409 | $^1$H-NMR (CDCl$_3$, ppm) δ 6.88-7.95 (11H, m). |
| 1-411 | $^1$H-NMR (CDCl$_3$) δ 7.15-7.20 (1H, m), 7.26-7.32 (1H, m), 7.45-7.56 (2H, m), 7.69 (1H, d, J = 7.8 Hz), 7.89 (1H, d, J = 2.0 Hz), 7.92 (1H, d, J = 2.0 Hz), 7.99 (1H, dd, J = 2.0, 7.8 Hz), 8.10-8.15 (1H, m), 8.19 (1H, s), 8.22 (1H, s), 8.64 (1H, d, J = 15.1 Hz). |
| 1-412 | $^1$H-NMR (DMSO-$d_6$) δ 7.59 (1H, t, J = 7.8 Hz), 7.82 (1H, d, J = 7.8 Hz), 8.07-8.10 (2H, m), 8.23 (2H, d, J = 8.8 Hz), 8.34-8.40 (4H, m), 10.69 (1H, s), 10.78 (1H, s). |
| 1-413 | $^1$H-NMR (CDCl$_3$) δ 7.40-7.45 (3H, m), 7.50-7.54 (1H, m), 7.64 (1H, d, J = 7.8 Hz), 7.75 (1H, d, J = 1.5 Hz), 7.81-7.85 (3H, m), 8.07 (1H, d, J = 7.8 Hz), 8.19 (1H, s), 8.25 (1H, s), 8.54 (1H, s). |
| 1-414 | $^1$H-NMR (DMSO-$d_6$) δ 7.31-7.38 (2H, m), 7.51-7.61 (2H, m), 7.66-7.72 (2H, m), 7.94-7.97 (2H, m), 8.28 (1H, d, J = 2.4 Hz), 8.31 (1H, d, J = 2.4 Hz), 10.42 (1H, s), 10.63 (1H, s). |
| 1-415 | $^1$H-NMR (DMSO-$d_6$) δ 7.51-7.62 (4H, m), 7.72 (1H, d, J = 7.8 Hz), 7.96-8.00 (3H, m), 8.05 (1H, dd, J = 1.5, 7.8 Hz), 8.32 (1H, d, J = 2.0 Hz), 8.33 (1H, d, J = 2.0 Hz), 10.40 (1H, s), 10.46 (1H, s). |
| 1-416 | $^1$H-NMR (DMSO-$d_6$) δ 7.33-7.40 (2H, m), 7.54-7.63 (2H, m), 7.67-7.72 (1H, m), 7.79 (1H, d, J = 7.8 Hz), 7.98 (1H, d, J = 7.8 Hz), 8.13 (1H, d, J = 1.5 Hz), 8.20 (1H, d, J = 1.5 Hz), 8.35 (1H, s), 10.62 (1H, s), 10.67 (1H, s). |
| 1-417 | $^1$H-NMR (DMSO-$d_6$) δ 7.51-7.62 (4H, m), 7.71 (1H, d, J = 7.8 Hz), 7.97-8.06 (4H, m), 8.30-8.34 (2H, m), 10.35 (1H, s), 10.46 (1H, s). |
| 1-418 | $^1$H-NMR (CDCl$_3$, ppm) δ 6.86-6.98 (3H, m), 7.18 (2H, t, J = 7.8 Hz), 7.33-7.45 (2H, m), 7.58 (1H, t, J = 7.8 Hz), 7.85-8.11 (3H, m). |
| 1-419 | $^1$H NMR (DMSO-$d_6$) δ 7.52-7.85 (6H, m), 7.99-8.06 (3H, m), 8.15-8.19 (1H, m), 8.34 (1H, s), 10.4 (1H, s), 10.5 (1H, s). |
| 1-420 | $^1$H-NMR (DMSO-$d_6$, ppm) δ 7.51 8.05 (11H, m), 8.34 (1H, t, J = 1.5), 10.2 (1H, s), 10.5 (1H, s). |
| 1-421 | $^1$H-NMR (CDCl$_3$) δ 2.44 (3H, s), 7.16-7.21 (1H, m), 7.44-7.57 (5H, m), 7.66-7.72 (2H, m), 7.83 (1H, d, J = 8.3 Hz), 7.92-7.95 (2H, m), 8.25 (1H, d, J = 8.8 Hz), 8.31 (1H, s). |
| 1-422 | $^1$H-NMR (DMSO-$d_6$) δ 0.75 (3H, t, J = 7.3 Hz), 1.19 (3H, d, J = 6.8 Hz), 1.51-1.59 (2H, m), 3.02-3.11 (1H, m), 7.50-7.63 (7H, m), 7.73 (1H, d, J = 7.8 Hz), 7.99-8.07 (3H, m), 8.36 (1H, s), 10.17 (1H, s), 10.48 (1H, s). |
| 1-423 | $^1$H-NMR (CDCl$_3$, ppm) σ 7.48-7.69 (7H, m), 7.88-8.00 (4H, m), 8.23 (1H, t, J = 2.0 Hz), 8.61 (1H, br.s), 8.76 (1H, d, J = 8.8 Hz). |
| 1-424 | $^1$H-NMR (DMSO-$d_6$) δ 7.33-7.40 (2H, m), 7.52-7.63 (2H, m), 7.66-7.73 (4H, m), 7.95 (1H, d, J = 7.8 Hz), 8.05 (2H, d, J = 8.8 Hz), 8.30 (1H, s), 10.67 (2H, s). |
| 1-425 | $^1$H-NMR (CDCl$_3$) δ 3.21 (3H, s), 3.41 (3H, s), 7.46-7.75 (6H, m), 7.86-7.93 (4H, m), 8.00 (1H, s), 8.01 (1H, s), 8.40 (1H, s). |
| 1-426 | $^1$H-NMR (CDCl$_3$) δ 3.21 (3H, s), 3.41 (3H, s), 7.51-7.57 (2H, m), 7.64 (1H, d, J = 8.8 Hz), 7.89 (2H, d, J = 7.8 Hz), 7.93 (1H, s), 8.02 (2H, d, J = 7.8 Hz), 8.08 (1H, d, J = 8.3 Hz), 8.33-8.40 (3H, m). |
| 1-427 | $^1$H-NMR (DMSO-$d_6$) δ 7.53-7.63 (4H, m), 7.79 (1H, d, J = 7.8 Hz), 7.98-8.01 (2H, m), 8.06-8.09 (1H, m), 8.23 (2H, s), 8.39 (1H, s), 10.50 (1H, s), 10.62 (1H, s). |
| 1-428 | $^1$H-NMR (DMSO-$d_6$) δ 7.33-7.40 (2H, m), 7.54-7.63 (2H, m), 7.68-7.72 (1H, m), 7.79 (1H, d, J = 7.8 Hz), 7.98 (1H, d, J = 8.3 Hz), 8.23 (2H, s), 8.35 (1H, s), 10.64 (1H, s), 10.67 (1H, s). |
| 1-429 | $^1$H-NMR (DMSO-$d_6$) δ 7.25-7.30 (2H, m), 7.56-7.65 (2H, m), 7.81 (1H, d, J = 7.8 Hz), 7.94 (1H, d, J = 8.3 Hz), 8.23 (2H, s), 8.31 (1H, s), 10.67 (1H, s), 11.06 (1H, s). |
| 1-430 | $^1$H-NMR (CDCl$_3$) δ 4.41 (2H, t, J = 11.7 Hz), 7.02 (2H, s), 7.50-7.64 (5H, m), 7.73-7.74 (1H, m), 7.89-7.90 (2H, m), 7.95-7.97 (1H, m), 8.04 (1H, s), 8.26 (1H, s). |
| 1-431 | $^1$H-NMR (CDCl$_3$) δ 4.43 (2H, t, J = 12.0 Hz), 7.05 (2H, s), 7.20-8.21 (8H, m), 8.30 (1H, s), 8.61-8.65 (1H, m). |

TABLE 5-continued

| Compound No. | Physical Property |
|---|---|
| 1-432 | ¹H-NMR (CDCl₃) δ 2.33 (3H, s), 4.38 (2H, q, J = 8.3 Hz), 6.82 (1H, dd, J = 2.9, 8.8 Hz), 7.44-7.57 (7H, m), 7.70 (1H, d, J = 7.8 Hz), 7.99 (1H, dd, J = 7.8, 1.5 Hz), 8.10 (1H, d, J = 7.8 Hz), 8.34 (1H, s), 8.73 (1H, brs), 9.86 (1H, brs). |
| 1-433 | ¹H-NMR (CDCl₃) δ 4.43 (2H, t, J = 11.7 Hz), 7.04 (2H, s), 7.40-7.44 (1H, m), 7.52-7.56 (1H, m), 7.66 (1H, brs), 7.76-7.78 (1H, m), 7.91-7.93 (1H, m), 8.19-8.24 (2H, m), 8.45 (1H, s), 8.52-8.54 (1H, m). |
| 1-434 | ¹H-NMR (CDCl₃) δ 2.34 (6H, s), 7.47-7.57 (6H, m), 7.68 (1H, s), 7.74 (1H, d, J = 7.8 Hz), 7.98-8.00 (2H, m), 8.12 (1H, d, J = 7.8 Hz), 8.33 (1H, s), 8.64 (1H, s), 9.63 (1H, s). |
| 1-435 | ¹H-NMR (CDCl₃) δ 2.35 (6H, s), 3.51 (3H, s), 7.32 (2H, s), 7.50-7.62 (4H, m), 7.66 (1H, s), 7.72 (1H, d, J = 7.8 Hz), 7.86-7.90 (3H, m), 8.04 (1H, s), 8.31 (1H, d, J = 2.0 Hz). |
| 1-436 | ¹H-NMR (CDCl₃) δ 2.37 (6H, s), 3.52 (3H, s), 7.23 (1H, dd, J = 7.8, 12.2 Hz), 7.33 (2H, s), 7.35 (1H, t, J = 7.8 Hz), 7.52-7.60 (2H, m), 7.63 (1H, s), 7.74 (1H, d, J = 7.8 Hz), 7.87 (1H, d, J = 7.8 Hz), 8.19 (1H, dt, J = 1.4, 7.8 Hz), 8.34 (1H, s), 8.64 (1H, d, J = 16.6 Hz). |
| 1-437 | ¹H-NMR (DMSO-d₆) δ 7.53-7.63 (4H, m), 7.75-7.78 (1H, m), 7.83 (2H, s), 7.99-8.08 (3H, m), 8.37 (1H, m), 10.4 (1H, br.), 10.5 (1H, br.). |
| 1-438 | ¹H-NMR (CDCl₃) δ 2.38 (3H, s), 7.09-7.12 (2H, m), 7.48-7.57 (4H, m), 7.70 (1H, d, J = 8.3 Hz), 7.76 (1H, d, J = 8.3 Hz), 7.99-8.01 (2H, m), 8.10 (1H, d, J = 8.3 Hz), 8.35 (1H, d, J = 2.0 Hz), 8.67 (1H, s), 9.74 (1H, s). |
| 1-439 | ¹H-NMR (CDCl₃) δ 6.49 (1H, d, J = 9.3 Hz), 7.51-7.62 (6H, m), 8.00 (1H, d, J = 7.3 Hz), 8.12 (1H, d, J = 7.3 Hz), 8.45 (1H, d, J = 9.3 Hz), 8.84 (1H, s), 9.24 (1H, s), 10.49 (1H, s), 11.55 (1H, s). |
| 1-440 | MS (APCI) = 352 (M + 1) |
| 1-441 | ¹H-NMR (CDCl₃) δ 2.44 (3H, s), 7.31-7.59 (5H, m), 7.73 (1H, d, J = 7.8 Hz), 7.97 (2H, dd, J = 1.5, 7.8 Hz), 8.06 (1H, d, J = 7.8 Hz), 8.36 (1H, t, J = 1.9 Hz), 8.94 (1H, s), 9.03 (1H, s), 9.32 (1H, s). |
| 1-442 | ¹H-NMR (CDCl₃) δ 7.46-7.68 (4H, m), 7.77 (1H, d, J = 7.9 Hz), 8.00-8.02 (2H, m), 8.09 (1H, d, J = 2.0 Hz), 8.17 (1H, dd, J = 8.3, 1.5 Hz), 8.38 (1H, t, J = 1.5 Hz), 8.67 (1H, d, J = 2.0 Hz), 10.2 (1H, brs), 10.4 (1H, brs). |
| 1-443 | ¹H-NMR (DMSO-d₆) δ 2.23 (3H, d, J = 2.9 Hz), 3.81 (3H, s), 7.53-7.63 (4H, m), 7.75 (1H, d, J = 7.3 Hz), 8.01-8.06 (3H, m), 8.37 (1H, s), 10.29 (1H, s), 10.49 (1H, s). |
| 1-444 | ¹H-NMR (DMSO-d₆) δ 2.23 (3H, d, J = 2.0 Hz), 3.81 (3H, s), 7.33-7.40 (2H, m), 7.53-7.63 (2H, m), 7.67-7.76 (2H, m), 7.95 (1H, d, J = 7.8 Hz), 8.33 (1H, s), 10.30 (1H, s), 10.66 (1H, s). |
| 1-445 | ¹H-NMR (CDCl₃) δ 2.36 (3H, s), 7.25 (1H, s), 7.47-7.57 (4H, m), 7.77 (1H, d, J = 7.8 Hz), 7.99 (2H, dd, J = 1.5, 8.7 Hz), 8.14 (1H, dd, J = 1.5, 7.8 Hz), 8.38 (1H, t, J = 1.5 Hz), 9.28 (1H, brs), 9.82 (1H, brs). |
| 1-446 | ¹H-NMR (DMSO-d₆) δ 2.29 (6H, s), 7.51-7.63 (6H, m), 7.76 (1H, d, J = 7.8 Hz), 7.98-8.01 (2H, m), 8.05 (1H, dd, J = 2.0, 7.8 Hz), 8.37 (1H, t, J = 2.0 Hz), 10.02 (1H, s), 10.47 (1H, s). |
| 1-447 | ¹H-NMR (DMSO-d₆) δ 2.28 (6H, s), 7.33-7.40 (2H, m), 7.53 (2H, s), 7.54-7.77 (4H, m), 7.95 (1H, d, J = 8.3 Hz), 8.33 (1H, s), 10.03 (1H, s), 10.64 (1H, s). |
| 1-448 | ¹H-NMR (CDCl₃) δ 4.67 (2H, d, J = 5.9 Hz), 7.40-7.65 (9H, m), 7.97-8.03 (4H, m), 8.27 (1H, t, J = 2.0 Hz), 9.73 (1H, s). |
| 1-449 | ¹H-NMR (CDCl₃) δ 4.68 (2H, d, J = 5.8 Hz), 7.43-7.65 (9H, m), 7.98-8.00 (3H, m), 8.04 (1H, d, J = 8.2 Hz), 8.24 (1H, d, J = 1.9 Hz), 9.68 (1H, s). |
| 1-450 | ¹H-NMR (CDCl₃) δ 4.83 (2H, d, J = 5.8 Hz), 6.58 (1H, brs), 7.40-7.69 (9H, m), 7.86-7.88 (2H, m), 7.92 (1H, d, J = 8.3 Hz), 7.97 (1H, s), 8.05 (1H, t, J = 2.0 Hz). |
| 1-451 | MS (APCI) = 376 (M + 1) |
| 1-452 | ¹H-NMR (CDCl₃) δ 4.76 (2H, d, J = 5.9 Hz), 6.82 (1H, brs), 7.45-7.63 (5H, m), 7.79 (2H, s), 7.80 (2H, s), 7.87 (2H, d, J = 7.4 Hz), 8.00 (1H, s), 8.21 (1H, t, J = 2.0 Hz). |
| 1-453 | ¹H-NMR (DMSO-d₆) δ 2.19 (6H, s), 7.24 (2H, s), 7.49-7.63 (4H, m), 7.73-7.75 (1H, m), 7.98-8.05 (3H, m), 8.35 (1H, t, J = 1.5 Hz), 9.83 (1H, s), 10.46 (1H, s). |
| 1-454 | ¹H-NMR (DMSO-d₆) δ 2.19 (6H, s), 7.37 (2H, s), 7.49-7.63 (4H, m), 7.74 (1H, d, J = 7.8 Hz), 7.98-8.05 (3H, m), 8.35 (1H, t, J = 2.0 Hz), 9.82 (1H, s), 10.44 (1H, s). |
| 1-455 | ¹H-NMR (CDCl₃) δ 2.24 (6H, s), 7.43-7.57 (6H, m), 7.74 (1H, d, J = 7.3 Hz), 8.01 (2H, d, J = 8.3 Hz), 8.12 (1H, d, J = 8.3 Hz), 8.36 (1H, brs), 9.32 (1H, brs), 10.1 (1H, brs). |
| 1-456 | ¹H-NMR (CDCl₃) δ 2.19 (6H, s), 6.97-7.04 (2H, m), 7.39-7.49 (4H, m), 7.55 (1H, brs), 7.69 (1H, d, J = 8.3 Hz), 7.79 (1H, dd, J = 8.3, 1.5 Hz), 8.04 (1H, brs), 8.24 (1H, t, J = 1.5 Hz). |
| 1-457 | ¹H-NMR (DMSO-d₆) δ 7.50-7.62 (5H, m), 7.67-7.69 (1H, m), 7.83 (1H, dd, J = 2.4, 8.3 Hz), 7.88 (1H, d, J = 2.4 Hz), 7.97-8.04 (3H, m), 8.33 (1H, t, J = 2.0 Hz), 10.20 (1H, s), 10.46 (1H, s). |
| 1-458 | ¹H-NMR (DMSO-d₆) δ 7.51-7.64 (5H, m), 7.72 (1H, d, J = 7.8 Hz), 7.82 (1H, d, J = 6.8 Hz), 7.94-8.00 (3H, m), 8.03-8.06 (1H, m), 8.33 (1H, s), 10.33 (1H, s), 10.46 (1H, s). |

TABLE 5-continued

| Compound No. | Physical Property |
| --- | --- |
| 1-459 | $^1$H-NMR (DMSO-d$_6$) δ 7.45-7.63 (6H, m), 7.91-8.01 (4H, m), 8.16 (1H, d, J = 8.3 Hz), 8.32 (1H, t, J = 1.5 Hz), 8.65 (1H, brs), 10.0 (1H, brs). |
| 1-460 | $^1$H-NMR (DMSO-d$_6$) δ 2.21 (3H, s), 7.51-7.63 (4H, m), 7.72-7.76 (2H, m), 7.80 (1H, d, J = 1.9 Hz), 7.99 (2H, d, J = 8.8 Hz), 8.05 (1H, d, J = 8.8 Hz), 8.36 (1H, brs), 10.0 (1H, brs), 10.5 (1H, brs). |
| 1-461 | $^1$H-NMR (CDCl$_3$) δ 2.27 (6H, s), 7.08-7.15 (3H, m), 7.48-7.60 (5H, m), 7.69 (1H, d, J = 7.8 Hz), 7.86-7.89 (2H, m), 7.95-7.97 (1H, m), 8.11 (1H, brs), 8.22 (1H, s). |
| 1-462 | $^1$H-NMR (CDCl$_3$) δ 3.87 (3H, s), 7.47-7.59 (3H, m), 7.72 (1H, d, J = 2.9 Hz), 7.78 (1H, d, J = 7.8 Hz), 7.99-8.03 (2H, m), 8.12 (1H, d, J = 7.8 Hz), 8.46 (1H, s), 10.3 (1H, brs), 10.4 (1H, brs). |
| 1-463 | $^1$H-NMR (DMSO-d$_6$) δ 7.53-7.64 (4H, m), 7.77 (1H, d, J = 8.3 Hz), 7.98-8.01 (2H, m), 8.07 (1H, dd, J = 1.5, 8.3 Hz), 8.43 (1H, t, J = 1.5 Hz), 10.51 (1H, s), 10.97 (1H, s). |
| 1-464 | $^1$H-NMR (DMSO-d$_6$) δ 7.53-7.64 (4H, m), 7.75 (1H, d, J = 8.3 Hz), 7.99-8.08 (3H, m), 8.41 (1H, s), 10.50 (1H, s), 10.59 (1H, s). |
| 1-465 | $^1$H-NMR (DMSO-d$_6$) δ 7.33-7.44 (4H, m), 7.51-7.63 (2H, m), 7.67-7.74 (2H, m), 7.95 (1H, d, J = 7.8 Hz), 8.32 (1H, s), 10.40 (1H, s), 10.65 (1H, s). |
| 1-466 | $^1$H-NMR (DMSO-d$_6$) δ 7.33-7.40 (2H, m), 7.52-7.63 (2H, m), 7.68-7.71 (2H, m), 7.74 (2H, d, J = 8.8 Hz), 7.96 (1H, d, J = 7.8 Hz), 8.02 (2H, d, J = 8.8 Hz), 8.30 (1H, s), 10.67 (2H, s). |
| 1-467 | 1H-NMR (DMSO-d$_6$) δ 7.33-7.40 (2H, m), 7.53-7.63 (2H, m), 7.68-7.72 (1H, m), 7.77 (1H, d, J = 7.8 Hz), 7.83 (1H, dd, J = 2.0, 8.3 Hz), 7.89 (1H, d, J = 8.3 Hz), 7.97 (1H, d, J = 7.8 Hz), 8.13 (1H, s), 8.36 (1H, s), 10.26 (1H, s), 10.68 (1H, s). |
| 1-468 | $^1$H-NMR (DMSO-d$_6$) δ 7.53-7.63 (4H, m), 7.78 (1H, d, J = 7.8 Hz), 7.98-8.01 (2H, m), 8.06-8.07 (1H, m), 8.13 (1H, d, J = 2.0 Hz), 8.20 (1H, d, J = 2.0 Hz), 8.39 (1H, d, J = 2.0 Hz), 10.50 (1H, s), 10.60 (1H, s). |
| 1-469 | $^1$H-NMR (DMSO-d$_6$) δ 7.27-7.39 (2H, m), 7.51-7.63 (4H, m), 7.68-7.77 (3H, m), 7.81 (1H, d, J = 7.8 Hz), 7.95-7.98 (1H, m), 8.31 (1H, s), 10.19 (1H, s), 10.66 (1H, s). |
| 1-470 | $^1$H-NMR (DMSO-d$_6$) δ 7.51-7.62 (4H, m), 7.71 (1H, d, J = 7.8 Hz), 7.94 (1H, d, J = 2.4 Hz), 7.97-8.06 (3H, m), 8.20 (1H, d, J = 2.4 Hz), 8.33 (1H, t, J = 2.0 Hz), 10.37 (1H, s), 10.46 (1H, s). |
| 1-471 | $^1$H-NMR (DMSO-d$_6$) δ 1.26 (6H, d, J = 6.8 Hz), 3.08 (1H, septet, J = 6.8 Hz), 7.52-7.63 (4H, m), 7.69-7.74 (2H, m), 7.98-8.01 (3H, m), 8.06 (1H, dd, J = 1.5, 7.8 Hz), 8.32 (1H, t, J = 1.5 Hz), 10.28 (1H, s), 10.47 (1H, s). |
| 1-472 | $^1$H-NMR (DMSO-d$_6$) δ 1.26 (6H, d, J = 6.8 Hz), 3.08 (1H, septet, J = 6.8 Hz), 7.32-7.39 (2H, m), 7.51-7.63 (2H, m), 7.67-7.73 (3H, m), 7.96-7.98 (2H, m), 8.27 (1H, s), 10.30 (1H, s), 10.65 (1H, s). |
| 1-473 | $^1$H-NMR (DMSO-d$_6$) δ 7.44-8.06 (13H, m), 10.39 (1H, s), 10.48 (1H, s). |
| 1-474 | $^1$H-NMR (DMSO-d$_6$) δ 2.42 (3H, s), 7.53-7.64 (4H, m), 7.75 (1H, d, J = 7.8 Hz), 7.83 (1H, d, J = 7.8 Hz), 8.00 (2H, d, J = 6.8 Hz), 8.06 (1H, d, J = 8.3 Hz), 8.13 (1H, d, J = 8.3 Hz), 8.21 (1H, s), 8.40 (1H, s), 10.17 (1H, s), 10.50 (1H, s). |
| 1-475 | MS (APCI) = 385 (M + 1) |
| 1-476 | MS (APCI) = 488 (M + 1) |
| 1-477 | $^1$H-NMR (CDCl$_3$) δ 3.35 (6H, s), 7.51-7.61 (5H, m), 7.77 (1H, t, J = 8.8 Hz), 8.00 (2H, d, J = 7.8 Hz), 8.05-8.07 (2H, m), 8.40 (1H, s), 10.14 (1H, s), 10.48 (1H, s). |
| 1-478 | $^1$H-NMR (DMSO-d$_6$) δ 7.48-7.56 (3H, m), 7.63-7.67 (2H, m), 7.94-7.99 (4H, m), 8.22 (1H, s), 9.03 (1H, s), 9.46 (2H, s). |
| 1-479 | $^1$H-NMR (CDCl$_3$) δ 7.53-7.62 (5H, m), 7.76 (1H, d, J = 7.8 Hz), 8.00 (2H, d, J = 7.3 Hz), 8.08 (1H, d, J = 7.8 Hz), 8.42 (1H, s), 8.95 (1H, s), 9.30 (1H, s), 10.50 (1H, s). |
| 1-480 | $^1$H-NMR (CDCl$_3$, ppm) δ 1.36 (9H, s), 2.34 (3H, s), 6.92-6.95 (2H, m), 7.49-8.22 (12H, m). |
| 1-481 | $^1$H-NMR (DMSO-d$_6$) δ 2.50 (3H, s), 7.14 (1H, dd, J = 2.5, 8.8 Hz), 7.21 (1H, d, J = 2.4 Hz), 7.41 (1H, d, J = 8.8 Hz), 7.50-7.75 (8H, m), 7.97-8.14 (5H, m), 8.34 (1H, s), 9.98 (1H, s), 10.47 (1H, s). |
| 1-482 | $^1$H-NMR (DMSO-d$_6$) δ 2.28 (3H, s), 7.31 (1H, s), 7.50-8.16 (14H, m), 8.38 (1H, s), 10.09 (1H, s), 10.48 (1H, s). |
| 1-483 | $^1$H-NMR (DMSO-d$_6$) δ 2.15 (3H, s), 6.69 (1H, d, J = 2.4 Hz), 6.78 (1H, d, J = 2.4 Hz), 7.48-7.63 (4H, m), 7.74 (1H, d, J = 8.8 Hz), 7.98-8.05 (3H, m), 8.32 (1H, t, J = 2.4 Hz), 9.77 (1H, s), 9.82 (1H, s), 10.4 (1H, s). |
| 1-484 | $^1$H-NMR (DMSO-d$_6$) δ 2.16 (3H, s), 6.72 (1H, d, J = 2.4 Hz), 6.94 (1H, d, J = 2.4 Hz), 7.50-7.63 (4H, m), 7.74 (1H, d, J = 8.3 Hz), 7.98-8.05 (3H, m), 8.32 (1H, s), 9.79 (1H, s), 9.81 (1H, s), 10.4 (1H, s). |
| 1-485 | $^1$H-NMR (CDCl$_3$) δ 2.29 (3H, s), 2.48 (3H, s), 6.94 (1H, d, J = 2.9 Hz), 7.14 (1H, d, J = 2.9 Hz), 7.36 (2H, d, J = 8.3 Hz), 7.51-7.61 (5H, m), 7.71-7.77 (3H, m), 7.88-7.92 (3H, m), 7.99 (1H, br.s), 8.28 (1H, s). |
| 1-486 | $^1$H-NMR (CDCl$_3$) δ 1.82-1.89 (4H, m), 3.30-3.60 (7H, m), 7.23-7.30 (5H, m), 7.44 (2H, s), 7.76 (2H, d, J = 4.9 Hz), 7.87 (2H, d, J = 6.4 Hz), 10.4 (1H, s). |

TABLE 5-continued

| Compound No. | Physical Property |
|---|---|
| 1-487 | ¹H-NMR (CDCl₃, ppm) δ 1.41 (3H, t, J = 7.3 Hz), 3.57 (3H, s), 4.41 (2H, q, J = 7.3 Hz), 7.20-7.34 (6H, m), 7.40 (2H, t, J = 7.8 Hz), 7.61 (1H, d, J = 2.0 Hz), 7.71 (1H, d, J = 7.8 Hz), 8.27 (2H, s). |
| 1-488 | ¹H-NMR (DMSO-d₆) δ 7.51-7.59 (3H, m), 7.62 (2H, s), 7.78 (1H, d, J = 7.8 Hz), 7.86 (1H, d, J = 7.8 Hz), 7.89-7.91 (2H, m), 8.05 (2H, d, J = 7.3 Hz), 8.38 (1H, s), 9.47 (1H, s). |
| 1-489 | ¹H-NMR (CDCl₃, ppm) δ 2.92 (4H, s), 7.48 (2H, s), 7.48-7.59 (4H, m), 7.76 (1H, d, J = 7.8 Hz), 7.85 (1H, s), 7.90 (2H, d, J = 7.8 Hz), 7.96 (1H, d, J = 7.8 Hz), 8.03 (1H, s), 8.24 (1H, s). |
| 1-490 | ¹H-NMR (CDCl₃, ppm) δ 7.49-8.02 (15H, m), 8.10 (1H, d, J = 7.3 Hz), 8.22 (1H, s). |
| 1-491 | MS (APCI) = 374 (M + 1) |
| 1-492 | MS (APCI) = 374 (M + 1) |
| 1-493 | MS (APCI) = 408 (M + 1) |
| 1-494 | MS (APCI) = 402 (M + 1) |
| 1-495 | MS (APCI) = 404 (M + 1) |
| 1-496 | MS (APCI) = 392 (M + 1) |
| 1-497 | ¹H-NMR (DMSO-d₆) δ 7.52-7.62 (5H, m), 7.80 (1H, d, J = 6.8 Hz), 7.97-8.00 (2H, m), 8.05 (1H, d, J = 7.8 Hz), 8.32 (1H, d, J = 5.9 Hz), 8.38 (1H, s), 8.92 (1H, t, J = 3.9 Hz), 10.48-10.54 (2H, m). |
| 1-498 | ¹H-NMR (DMSO-d₆) δ 7.51-7.59 (3H, m), 7.80-7.85 (1H, m), 7.92-7.96 (1H, m), 8.09 (1H, dd, J = 7.3, 2.0 Hz), 8.21 (1H, dd, J = 7.3, 2.0 Hz), 8.40 (1H, brs), 8.54 (2H, d, J = 2.0 Hz), 10.38 (1H, s), 10.86 (1H, s). |
| 1-499 | MS (APCI) = 368 (M + 1) |
| 1-500 | MS (APCI) = 368 (M + 1) |
| 1-501 | MS (APCI) = 368 (M + 1) |
| 1-502 | MS (APCI) = 421 (M + 1) |
| 1-503 | MS (APCI) = 400 (M + 1) |
| 1-504 | MS (APCI) = 338 (M + 1) |
| 1-505 | MS (APCI) = 383 (M + 1) |
| 1-506 | MS (APCI) = 405 (M + 1) |
| 1-507 | MS (APCI) = 419 (M + 1) |
| 1-508 | MS (APCI) = 375 (M + 1) |
| 1-509 | MS (APCI) = 375 (M + 1) |
| 1-510 | MS (APCI) = 356 (M + 1) |
| 1-511 | MS (APCI) = 347 (M + 1) |
| 1-512 | MS (APCI) = 367 (M + 1) |
| 1-513 | MS (APCI) = 354 (M + 1) |
| 1-514 | MS (APCI) = 402 (M + 1) |
| 1-515 | MS (APCI) = 338 (M + 1) |
| 1-516 | MS (APCI) = 335 (M + 1) |
| 1-517 | ¹H-NMR (CDCl₃, ppm) d 2.72 (3H, s), 7.48-8.01 (12H, m), 8.41 (1H, d, J = 2.0 Hz). |
| 1-518 | ¹H-NMR (CDCl₃) δ 2.56 (6H, s), 7.13-7.18 (1H, m), 7.24-7.31 (2H, m), 7.50-7.57 (2H, m), 7.94 (2H, d, J = 7.3 Hz), 8.21 (1H, d, J = 7.3 Hz), 8.50 (1H, s), 9.43 (1H, d, J = 8.8 Hz). |
| 1-519 | ¹H-NMR (CDCl₃) δ 3.56 (3H, s), 4.05 (6H, s), 7.09 (1H, s), 7.14 (1H, t, J = 4.9 Hz), 7.35 (1H, d, J = 5.3 Hz), 7.56 (1H, d, J = 1.5 Hz), 7.58 (1H, d, J = 1.5 Hz), 7.65 (1H, d, J = 5.9 Hz), 7.73 (1H, s), 8.27 (1H, t, J = 1.5 Hz). |
| 1-520 | ¹H-NMR (CDCl₃) δ 3.53 (3H, s), 4.03 (6H, s), 7.16-7.27 (5H, m), 7.28-7.35 (4H, m), 7.66 (1H, d, J = 1.46 Hz). |
| 1-521 | ¹H-NMR (CDCl₃-DMSO-d₆) δ 7.43-7.53 (5H, m), 7.70 (1H, d, J = 7.8 Hz), 7.99 (1H, d, J = 6.8 Hz), 8.17 (1H, d, J = 7.8 Hz), 8.28 (1H, s), 9.21 (1H, br.s.), 9.70 (1H, br.s.). |
| 1-522 | ¹H-NMR (CDCl₃-DMSO-d₆) δ 7.13-7.32 (2H, m), 7.45-7.55 (2H, m), 7.75 (1H, t, J = 3.9 Hz), 7.86-7.90 (1H, m), 7.94-8.12 (1H, m), 8.25 (1H, s), 9.73 (1H, d, J = 6.3 Hz), 9.86 (1H, br.s.). |
| 1-523 | ¹H-NMR (CDCl₃) δ 2.56 (6H, s), 7.13-7.18 (1H, m), 7.24-7.31 (2H, m), 7.50-7.57 (2H, m), 7.94 (2H, d, J = 7.3 Hz), 8.21 (1H, d, J = 7.3 Hz), 8.50 (1H, s), 9.43 (1H, d, J = 8.8 Hz). |
| 1-524 | ¹H-NMR (CDCl₃-DMSO-d₆) δ 2.90 (3H, d, J = 4.4 Hz), 3.51 (3H, s), 7.20-7.43 (8H, m), 7.74-7.79 (2H, m), 7.99-8.02 (2H, m), 8.75 (1H, d, J = 4.4 Hz), 11.9 (1H, s). |
| 1-525 | ¹H-NMR (CDCl₃-DMSO-d₆) δ 1.25 (6H, d, J = 6.8 Hz), 3.53 (3H, s), 4.22 (1H, sep., J = 7.8 Hz), 6.19 (1H, d, J = 7.8 Hz), 7.13-7.27 (3H, m), 7.29-7.34 (5H, m), 7.72-7.75 (2H, m), 7.81 (1H, t, J = 2.0 Hz), 8.01 (1H, d.d., J = 1.5, 6.8 Hz), 11.21 (1H, s). |
| 1-526 | ¹H-NMR (CDCl₃-DMSO-d₆) δ 6.82 (1H, q., J = 2.0, 7.2, 6.3, 2.0 Hz), 7.48-7.62 (5H, m), 7.85 (1H, d.d., J = 1.5, 6.8, 1.0 Hz), 8.00 (2H, m), 8.25-8.28 (1H, m), 8.34-8.52 (3H, m), 8.64 (1H, br.s.), 10.28 (1H, br.s.). |
| 1-527 | ¹H-NMR (CDCl₃-DMSO-d₆) δ 3.53 (3H, s), 7.20-7.27 (3H, m), 7.32 (3H, t, J = 7.3 Hz), 7.44 (1H, t, J = 7.8 Hz), 7.54 (1H, t, J = 7.8 Hz), 7.90-7.91 (1H, m), 7.95-7.98 (1H, m), 8.07-8.13 (3H, m). |

TABLE 5-continued

| Compound No. | Physical Property |
|---|---|
| 1-528 | ¹H-NMR (CDCl₃-DMSO-d₆) δ 3.46 (3H, s), 7.22-7.31 (4H, m), 7.32-7.34 (2H, m), 7.47-7.53 (2H, t, J = 7.8 Hz), 8.00-8.03 (2H, m), 8.21 (1H, d, J = 2.0 Hz), 8.43 (1H, t, J = 1.5 Hz). |
| 1-529 | ¹H-NMR (CDCl₃-DMSO-d₆) δ 3.43 (3H, s), 7.21-7.29 (4H, m), 7.30-7.32 (2H, m), 7.44-7.49 (2H, m), 7.98-8.00 (2H, m), 8.05 (1H, d, J = 2.0 Hz), 8.19 (1H, t, J = 2.4, 1.0 Hz). |
| 1-530 | ¹H-NMR (CDCl₃, ppm) δ 3.11 (3H, s), 3.56 (3H, s), 7.21-7.34 (6H, m), 7.42 (1H, t, J = 8.3 Hz), 7.60 (1H, brs), 7.63 (1H, brs), 7.71 (1H, dd, J = 1.5 Hz, J = 8.3 Hz), 7.96 (2H, s). |
| 1-531 | ¹H-NMR (CDCl₃) δ 2.07 (3H, s), 2.18 (3H, s), 3.19-3.50 (3H, m), 6.09-7.84 (8H, m), 8.00 (2H, s). |
| 1-532 | ¹H-NMR (DMSO-d₆) δ 2.50 (3H, s), 3.39 (3H, s), 3.42 (3H, s), 6.30-7.30 (8H, m), 7.72 (2H, s). |
| 1-533 | ¹H-NMR (DMSO-d₆) δ 3.17 (3H, s), 3.22 (3H, s), 3.72 (3H, s), 6.52-7.76 (11H, m). |
| 1-534 | ¹H-NMR (CDCl₃) δ 1.02 (3H, t, J = 7.3 Hz), 1.65 (2H, tq, J = 7.3, 7.3 Hz), 2.87 (2H, t, J = 7.3 Hz), 7.21 (1H, dd, J = 8.3, 11.7 Hz), 7.31-7.34 (3H, m), 7.49 (1H, t, J = 8.3 Hz), 7.53-7.57 (1H, m), 7.69-7.74 (3H, m), 8.04-8.08 (2H, m), 8.14 (1H, s), 9.11 (1H, d, J = 11.7 Hz), 9.27 (1H, s). |
| 1-535 | ¹H-NMR (CDCl₃) δ 1.05 (3H, t, J = 7.3 Hz), 1.66-1.79 (2H, m), 2.72-2.86 (2H, m), 7.22 (1H, d, J = 8.3 Hz), 7.31-7.34 (1H, m), 7.50 (1H, t, J = 8.3 Hz), 7.55-7.56 (1H, m), 7.61 (2H, d, J = 8.8 Hz), 7.75 (1H, d, J = 8.3 Hz), 7.98 (2H, d, J = 8.8 Hz), 8.06-8.08 (2H, m), 8.17 (1H, s), 9.06 (1H, d, J = 11.7 Hz), 9.65 (1H, s). |
| 1-536 | ¹H-NMR (CDCl₃) δ 1.06 (3H, t, J = 7.3 Hz), 1.72 (2H, tq, J = 7.3, 7.3 Hz), 2.93 (2H, t, J = 7.3 Hz), 7.19-7.25 (1H, m), 7.35 (1H, t, J = 7.8 Hz), 7.52 (2H, s), 7.53-7.59 (2H, m), 7.72 (1H, s), 7.76 (1H, d, J = 7.8 Hz), 7.96 (1H, d, J = 8.3 Hz), 8.19 (1H, t, J = 6.3 Hz), 8.27 (1H, s), 8.62 (1H, d, J = 16.1 Hz). |
| 1-537 | ¹H-NMR (CDCl₃) δ 1.07 (3H, t, J = 7.3 Hz), 1.80-1.86 (2H, m), 3.12 (2H, t, J = 7.3 Hz), 7.20-7.23 (1H, m), 7.38 (1H, t, J = 7.3 Hz), 7.54-7.58 (2H, m), 7.79 (1H, d, J = 8.3 Hz), 7.90 (1H, d, J = 7.8 Hz), 7.98 (1H, s), 8.16 (2H, s), 8.18-8.20 (1H, m), 8.38 (1H, s), 8.6 (1H, d). |
| 1-538 | ¹H-NMR (CDCl₃) δ 1.11 (3H, t, J = 7.3 Hz), 1.72-1.91 (2H, m), 2.64-2.86 (2H, m), 7.20-7.23 (1H, m), 7.35 (1H, t, J = 7.3 Hz), 7.53-7.57 (2H, m), 7.79 (1H, d, J = 7.5 Hz), 7.85 (2H, s), 7.95 (1H, d, J = 7.8 Hz), 8.05 (1H, s), 8.20 (1H, t, J = 7.3 Hz), 8.33 (1H, s), 8.64 (1H, d, J = 16.0 Hz). |
| 1-539 | ¹H-NMR (CDCl₃) δ 7.19 (1H, d, J = 8.3 Hz), 7.34 (1H, t, J = 8.3 Hz), 7.41-7.59 (9H, m), 7.65 (1H, s), 7.74 (1H, d, J = 7.3 Hz), 7.96 (1H, d, J = 7.3 Hz), 8.18 (1H, dt, J = 1, 8.3 Hz), 8.60 (1H, s), 8.62 (1H, s). |
| 1-540 | ¹H-NMR (CDCl₃) δ 7.39-7.41 (4H, m), 7.42-7.59 (7H, m), 7.67 (1H, s), 7.72 (1H, d, J = 7.3 Hz), 7.88-7.90 (2H, m), 7.98 (1H, d, J = 8.3 Hz), 8.04 (1H, s), 8.22 (1H, s). |
| 1-541 | ¹H-NMR (CDCl₃) δ 4.18 (2H, s), 7.44 (2H, d, J = 7.8 Hz), 7.50-7.61 (8H, m), 7.74 (1H, d, J = 7.8 Hz), 7.78 (1H, s), 7.88-7.94 (3H, m), 8.03 (1H, s), 8.27 (1H, s). |
| 1-542 | ¹H-NMR (CDCl₃) δ 4.18 (2H, s), 7.19-7.25 (1H, m), 7.35 (1H, t, J = 7.3 Hz), 7.44 (2H, d, J = 7.5 Hz), 7.52 (2H, s), 7.54-7.58 (2H, m), 7.60 (2H, d, J = 7.8 Hz), 7.75-7.77 (2H, m), 7.92 (1H, d, J = 6.8 Hz), 8.19 (1H, t, J = 7.8 Hz), 8.30 (1H, s), 8.65 (1H, s). |
| 1-543 | ¹H-NMR (CDCl₃) δ 4.18 (2H, s), 7.41-7.46 (3H, m), 7.51 (2H, s), 7.55 (1H, t, J = 7.8 Hz), 7.60 (2H, d, J = 7.8 Hz), 7.72 (1H, s), 7.77 (1H, d, J = 7.8 Hz), 7.91 (1H, d, J = 7.8 Hz), 8.21 (1H, d, J = 2.0 Hz), 8.24 (1H, d, J = 8.3 Hz), 8.42 (1H, s), 8.54 (1H, s). |
| 1-544 | ¹H-NMR (CDCl₃) δ 4.19 (2H, s), 7.46-7.54 (5H, m), 7.60 (2H, d, J = 8.3 Hz), 7.79 (1H, d, J = 8.3 Hz), 8.22-8.26 (4H, m), 8.32 (2H, d, J = 9.3 Hz), 8.95 (1H, s), 10.18 (1H, s). |
| 1-545 | ¹H-NMR (CDCl₃) δ 4.16 (2H, s), 7.13-7.20 (2H, m), 7.40-7.46 (4H, m), 7.52 (1H, t, J = 8.3 Hz), 7.60 (2H, d, J = 8.3 Hz), 7.71 (1H, d, J = 7.3 Hz), 7.82 (1H, s), 7.86-7.93 (2H, m), 7.98 (1H, d, J = 7.8 Hz), 8.21 (1H, d, J = 9.3 Hz). |
| 1-546 | ¹H-NMR (CDCl₃) δ 3.48 (2H, q, J = 9.8 Hz), 7.49-7.60 (4H, m), 7.69 (2H, s), 7.73 (1H, d, J = 7.8 Hz), 7.87-7.90 (3H, m), 7.95 (1H, d, J = 7.8 Hz), 8.14 (1H, s), 8.27 (1H, s). |
| 1-547 | ¹H-NMR (CDCl₃) δ 3.49 (2H, q, J = 9.8 Hz), 7.20-7.25 (1H, m), 7.35 (1H, t, J = 7.8 Hz), 7.52-7.58 (2H, m), 7.74 (2H, s), 7.76 (1H, d, J = 7.8 Hz), 7.83 (1H, s), 7.92 (1H, d, J = 7.8 Hz), 8.19 (1H, t, J = 7.8 Hz), 8.31 (1H, s), 8.64 (1H, d, J = 15.6 Hz). |
| 1-548 | ¹H-NMR (CDCl₃) δ 3.49 (2H, q, J = 9.8 Hz), 7.42-7.45 (1H, m), 7.54 (1H, t, J = 7.3 Hz), 7.73 (2H, s), 7.77-7.79 (2H, m), 7.92 (1H, d, J = 7.8 Hz), 8.21-8.23 (1H, m), 8.26 (1H, s), 8.43 (1H, s), 8.53-8.55 (1H, m). |
| 1-549 | ¹H-NMR (CDCl₃) δ 3.54 (2H, q, J = 9.3 Hz), 7.52 (1H, t, J = 7.8 Hz), 7.73 (2H, s), 7.82 (1H, d, J = 7.8 Hz), 8.23-8.27 (4H, m), 8.32 (2H, d, J = 9.3 Hz), 9.33 (1H, s), 10.29 (1H, s). |
| 1-550 | ¹H-NMR (CDCl₃, ppm) δ 3.57 (3H, s), 7.22-7.33 (6H, m), 7.43 (1H, t, J = 7.8 Hz), 7.67 (1H, s), 7.72-7.78 (2H, m), 8.30 (2H, s). |

TABLE 5-continued

| Compound No. | Physical Property |
|---|---|
| 1-551 | $^1$H-NMR (CDCl$_3$, ppm) δ 3.56 (3H, s), 7.21-7.34 (6H, m), 7.41 (1H, t, J = 7.8 Hz), 7.46 (1H, brs), 7.60 (1H, s), 7.69 (1H, d, J = 1.5 Hz), 7.70 (2H, s). |
| 1-552 | $^1$H-NMR (CDCl$_3$, ppm) δ 3.99 (2H, brs), 6.66 (2H, s), 6.95-7.02 (4H, m), 7.72 (1H, d, J = 7.3 Hz), 7.93-7.96 (3H, m), 8.08 (1H, d, J = 8.3 Hz), 8.25 (1H, s), 8.85 (1H, s). |
| 1-553 | $^1$H-NMR (DMSO-d$_6$) δ 3.88 (3H, s), 7.48-7.57 (4H, m), 7.71 (2H, d, J = 8.3 Hz), 7.82 (1H, d, J = 7.8 Hz), 8.02 (2H, d, J = 8.3 Hz), 8.10 (2H, d, J = 8.3 Hz), 8.17 (1H, d, J = 8.3 Hz), 8.41 (1H, s), 10.06 (1H, s), 10.9 (1H, s). |
| 1-554 | $^1$H-NMR (DMSO-d$_6$) δ 2.09 (3H, s), 7.50-7.63 (4H, m), 7.75 (1H, d, J = 7.8 Hz), 7.79 (2H, s), 7.99-8.06 (3H, m), 8.35 (1H, s), 10.2 (1H, s), 10.3 (1H, s), 10.5 (1H, s). |
| 1-555 | $^1$H-NMR (CDCl$_3$) δ 7.40 (2H, t, J = 7.3 Hz), 7.47-7.52 (5H, m), 7.57 (1H, t, J = 7.3 Hz), 7.64 (2H, s), 7.74 (1H, d, J = 8.3 Hz), 7.87-7.97 (6H, m), 8.25 (1H, d, J = 8.3 Hz), 8.86 (1H, brs). |
| 1-556 | $^1$H-NMR (CDCl$_3$, ppm) d 3.01 (3H, d, J = 4.8 Hz), 3.56 (3H, s), 6.27 (1H, d, J = 4.8 Hz), 7.19-7.33 (6H, m), 7.38 (1H, t, J = 7.8 Hz), 7.58 (1H, br), 7.65 (1H, s), 7.72 (1H, d, J = 7.8 Hz), 7.94 (2H, s). |
| 1-558 | $^1$H-NMR (DMSO-d$_6$) δ 3.80 (3H, s), 7.40-7.43 (1H, m), 7.50 (1H, t, J = 7.8 Hz), 7.76 (1H, s), 7.81 (1H, d, J = 7.8 Hz), 7.94 (1H, d, J = 7.8 Hz), 8.11 (1H, dt, J = 8.3, 2.0 Hz), 8.33 (1H, t, J = 2.0 Hz), 8.51 (1H, dd, J = 8.3, 2.0 Hz), 10.48 (1H, s), 10.78 (1H, s). |
| 1-559 | $^1$H-NMR (DMSO-d$_6$) δ 3.80 (3H, s), 7.21 (1H, dd, J = 8.3, 10.2 Hz), 7.30 (1H, dd, J = 6.8, 7.8 Hz), 7.51-7.55 (2H, m), 7.76 (1H, s), 7.81 (1H, dd, J = 1.5, 7.8 Hz), 7.93 (1H, d, J = 1.5 Hz), 8.12 (1H, d, J = 8.3 Hz), 8.33 (1H, s), 9.62 (1H, d, J = 7.8 Hz), 10.78 (1H, s). |
| 1-560 | $^1$H-NMR (CDCl$_3$) δ 1.68 (9H, s), 7.48-7.54 (3H, m), 7.58 (1H, d, J = 7.8 Hz), 7.68 (1H, d, J = 7.8 Hz), 7.78 (1H, s), 7.86-7.92 (3H, m), 7.97 (1H, s), 8.11 (1H, s), 8.25 (1H, s). |
| 1-562 | $^1$H-NMR (CDCl$_3$, ppm) δ 3.44 (3H, s), 7.23-7.30 (5H, m), 7.41-7.45 (2H, m), 7.71 (1H, brs), 7.77 (1H, d, J = 6.3 Hz), 7.80 (1H, s), 8.02 (2H, s), 8.22 (1H, s), 10.4 (1H, s). |
| 1-563 | $^1$H-NMR (CDCl$_3$, ppm) δ 3.57 (3H, s), 7.21-7.44 (8H, m), 7.61 (1H, s), 7.72 (1H, d, J = 7.8 Hz), 8.01 (2H, s), 8.13 (1H, s), 8.58 (1H, s). |
| 1-564 | $^1$H-NMR (CDCl$_3$, ppm) δ 3.57 (3H, s), 7.21-7.30 (7H, m), 7.34 (1H, dt, J = 7.3 Hz, J = 1.5 Hz), 7.41 (1H, t, J = 7.3 Hz), 7.87 (1H, s), 7.96 (1H, dt, J = 1.5 Hz, J = 8.3 Hz), 8.17 (1H, d, J = 1.5 Hz), 8.35 (1H, s), 8.65 (1H, d, J = 7.8 Hz) |
| 1-565 | $^1$H-NMR (CDCl$_3$, ppm) δ 7.53-7.62 (4H, m), 7.81 (1H, d, J = 7.8 Hz), 8.00-8.02 (2H, m), 8.07 (1H, d, J = 7.3 Hz), 8.40 (1H, s), 8.57 (2H, s), 9.90 (1H, s), 10.49 (1H, s), 10.51 (1H, s). |
| 1-566 | $^1$H-NMR (CDCl$_3$) δ 2.48 (3H, s), 7.05 (1H, s), 7.23 (1H, s), 7.50-7.62 (4H, m), 7.69 (1H, d, J = 7.8 Hz), 7.84 (1H, dd, J = 2.0, 7.8 Hz), 7.89 (2H, d, J = 6.8 Hz), 8.13 (1H, s), 8.16 (1H, d, J = 6.8 Hz), 8.39 (1H, t, J = 1.9 Hz), 8.89 (1H, s). |
| 1-567 | $^1$H-NMR (CDCl$_3$) δ 2.33 (3H, s), 3.56 (3H, s), 7.03 (1H, s), 7.22-7.38 (6H, m), 7.45 (1H, t, J = 7.8 Hz), 7.58 (1H, s), 7.62 (1H, s), 7.67 (1H, d, J = 7.8 Hz), 8.63 (1H, s). |
| 1-568 | $^1$H-NMR (CDCl$_3$) δ 2.37 (3H, s), 3.21 (3H, s), 3.56 (3H, s), 7.20-7.29 (4H, m), 7.33-7.41 (4H, m), 7.52 (1H, s), 7.69 (1H, d, J = 7.8 Hz), 7.72 (1H, s), 8.30 (1H, s). |
| 1-569 | $^1$H-NMR (CDCl$_3$) δ 2.38 (3H, s), 3.56 (3H, s), 7.19-7.33 (6H, m), 7.38-7.40 (2H, m), 7.42 (1H, s), 7.57 (1H, s), 7.61 (1H, s), 7.66 (1H, d, J = 7.8 Hz). |
| 1-570 | $^1$H-NMR (CDCl$_3$) δ 2.03 (3H, s), 2.37 (3H, s), 3.55 (3H, s), 6.75 (1H, s), 7.20-7.44 (9H, m), 7.92 (1H, s), 7.99 (1H, d, J = 7.8 Hz). |
| 1-571 | $^1$H-NMR (DMSO-d$_6$) δ 2.30 (3H, s), 4.55 (2H, d, J = 2.9 Hz), 5.48 (1H, broad), 7.51-7.60 (5H, m), 7.69-7.73 (2H, m), 7.98-8.00 (2H, m), 8.06 (1H, dd, J = 1.5, 8.3 Hz), 8.35 (1H, t, J = 1.5 Hz), 9.93 (1H, s), 10.48 (1H, s). |
| 1-572 | $^1$H-NMR (CDCl$_3$) δ 2.31 (3H, s), 3.36 (3H, s), 3.53 (3H, s), 4.44 (2H, s), 7.17-7.40 (8H, m), 7.49 (1H, s), 7.67-7.71 (2H, m), 8.69 (1H s). |
| 1-573 | $^1$H-NMR (DMSO-d$_6$) δ 1.96 (3H, s), 3.84 (2H, broad), 7.53-7.63 (4H, m), 7.73 (1H, d, J = 7.8 Hz), 7.89 (1H, s), 7.99-8.01 (2H, m), 8.07 (1H, dd, J = 1.5, 7.8 Hz), 8.19 (1H, s), 8.33 (1H, t, J = 2.0 Hz), 10.43 (1H, s), 10.49 (1H, s). |
| 1-574 | $^1$H-NMR (CDCl$_3$) δ 7.31 (1H, d, J = 2.9 Hz), 7.41 (1H, d, J = 2.9 Hz), 7.50-7.61 (4H, m), 7.65 (1H, broad-s), 7.74 (1H, d, J = 7.8 Hz), 7.81 (1H, d, J = 2.0 Hz), 7.88-7.91 (2H, m), 8.01-8.05 (3H, m), 8.23 (1H, broad-s). |
| 1-575 | $^1$H-NMR (DMSO-d$_6$) δ 2.30 (3H, s), 3.56 (3H, s), 6.32 (1H, septet, J = 5.9 Hz), 6.85 (1H, s), 7.19-7.43 (8H, m), 7.58 (1H, broad-s), 7.70 (1H, d, J = 7.8 Hz). |
| 1-576 | $^1$H-NMR (DMSO-d$_6$) δ 2.35 (3H, s), 7.05 (1H, d, J = 2.4 Hz), 7.33 (1H, d, J = 2.4 Hz), 7.48-7.59 (4H, m), 7.67 (1H, broad-s), 7.72 (1H, |

TABLE 5-continued

| Compound No. | Physical Property |
|---|---|
| | d, J = 7.8 Hz), 7.88-7.90 (2H, m), 7.99-8.03 (2H, m), 8.17 (1H, broad-s), 8.24 (1H, broad-s), 8.28 (1H, t, J = 1.0 Hz). |
| 1-577 | $^1$H-NMR (DMSO-d$_6$) δ 2.40 (3H, s), 7.11 (1H, d, J = 2.5 Hz), 7.20-7.25 (1H, m), 7.30-7.37 (2H, m), 7.53-7.59 (2H, m), 7.60 (1H, s), 7.76 (1H, d, J = 7.8 Hz), 7.97-8.00 (2H, m), 8.17-8.22 (1H, m), 8.29 (2H, d, J = 8.8 Hz), 8.61, 8.65 (1H, two broad-s). |
| 1-578 | $^1$H-NMR (DMSO-d$_6$) δ 2.37 (3H, s), 7.01 (2H, t, J = 8.3 Hz), 7.09 (1H, d, J = 2.5 Hz), 7.35 (1H, d, J = 2.5 Hz), 7.42-7.46 (1H, m), 7.53 (1H, t, J = 8.3 Hz), 7.65 (1H, s), 7.76 (1H, d, J = 7.8 Hz), 7.92-8.00 (3H, m), 8.23 (1H, s), 8.29 (1H, s). |
| 1-579 | $^1$H-NMR (DMSO-d$_6$) δ 2.39 (3H, s), 7.11 (1H, d, J = 2.4 Hz), 7.36 (1H, d, J = 2.4 Hz), 7.42-7.44 (1H, m), 7.57 (1H, t, J = 7.8 Hz), 7.63 (1H, s), 7.78 (1H, d, J = 7.8 Hz), 7.95 (1H, d, J = 8.3 Hz), 7.99 (1H, d, J = 2.0 Hz), 8.21-8.25 (2H, m), 8.29 (1H, s), 8.41 (1H, s), 8.54-8.55 (1H, m). |
| 1-580 | $^1$H-NMR (CDCl$_3$) δ 3.56 (3H, s), 7.13 (1H, dd, J = 9.3, 2.4 Hz), 7.19-7.23 (2H, m), 7.27-7.34 (5H, m), 7.39 (1H, d, J = 8.3 Hz), 7.61 (1H, t, J = 1.5 Hz), 7.65 (1H, d, J = 8.3 Hz), 7.78 (1H, d, J = 2.4 Hz), 7.98 (1H, d, J = 2.4 Hz), 8.13 (1H, broad-s), 8.55 (1H, d, J = 9.3 Hz). |
| 1-581 | $^1$H-NMR (CDCl$_3$) δ 7.12-7.18 (2H, m), 7.36-7.53 (6H, m), 7.63 (1H, d, J = 2.0 Hz), 7.68 (1H, d, J = 7.8 Hz), 7.75 (1H, s), 7.82 (2H, d, J = 7.8 Hz), 8.02-8.05 (1H, m), 8.21 (1H, s), 8.31 (1H, s), 8.53 (1H, s). |
| 1-582 | $^1$H-NMR (CDCl$_3$) δ 7.13-7.18 (2H, m), 7.31 (1H, dd, J = 4.9, 7.8 Hz), 7.45-7.53 (3H, m), 7.70-7.73 (2H, m), 7.84 (1H, d, J = 1.5 Hz), 7.90 (1H, dd, J = 1.5, 7.8 Hz), 8.04 (1H, dd, J = 2.0, 7.8 Hz), 8.20 (1H, s), 8.33 (1H, s), 8.42 (1H, dd, J = 2.0, 4.9 Hz), 8.83 (1H, s). |
| 1-583 | $^1$H-NMR (CDCl$_3$) δ 7.49-7.60 (4H, m), 7.76 (1H, d, J = 7.8 Hz), 7.83 (1H, d, J = 2.4 Hz), 7.88-8.03 (7H, m), 8.08 (1H, s), 8.18 (1H, s), 8.29 (1H, t, J = 2.0 Hz). |
| 1-584 | $^1$H-NMR (DMSO-d$_6$) δ 3.45 (3H, s), 7.24-7.32 (5H, m), 7.45-7.47 (2H, m), 7.77-7.80 (2H, m), 7.92 (1H, s), 8.22 (2H, s), 10.49 (1H, broad). |
| 1-585 | $^1$H-NMR (CDCl$_3$) δ 3.48 (3H, broad-s), 6.80 (1H, broad), 7.01 (1H, broad), 7.11 (1H, s), 7.14 (1H, broad), 7.21-7.30 (3H, broad-m), 7.78 (4H, broad), 8.38 (1H, |
| 1-586 | $^1$H-NMR (CDCl$_3$) δ 3.52 (3H, s), 7.09 (1H, dd, J = 4.9, 7.3 Hz), 7.13 (1H, s), 7.34-7.36 (2H, m), 7.53 (1H, dd, J = 1.5, 7.8 Hz), 7.77-7.82 (4H, m), 8.21 (1H, dd, J = 2.0, 4.9 Hz), 8.41 (1H, s). |
| 1-587 | $^1$H-NMR (DMSO-d$_6$) δ 7.53-7.64 (4H, m), 7.80 (1H, d, J = 7.8 Hz), 7.92 (1H, s), 7.99-8.02 (2H, m), 8.07-8.09 (1H, m), 8.23 (2H, s), 8.40 (1H, s), 10.50 (1H, s), 10.57 (1H, s). |
| 1-588 | $^1$H-NMR (DMSO-d$_6$) δ 7.33-7.40 (2H, m), 7.54-7.63 (2H, m), 7.68-7.72 (1H, m), 7.80 (1H, d, J = 7.8 Hz), 7.92 (1H, s), 7.99 (1H, d, J = 7.8 Hz), 8.23 (2H, s), 8.35 (1H, s), 10.05 (1H, broad), 10.66 (1H, s). |
| 1-589 | $^1$H-NMR (DMSO-d$_6$) δ 7.56-7.60 (2H, m), 7.82 (1H, d, J = 7.8 Hz), 7.92-7.97 (2H, m), 8.12 (1H, dd, J = 2.0, 7.8 Hz), 8.23 (2H, s), 8.33 (1H, d, J = 2.0 Hz), 8.55 (1H, dd, J = 2.0, 4.9 Hz), 10.55 (1H, broad), 10.90 (1H, s). |
| 1-590 | $^1$H-NMR (DMSO-d$_6$) δ 7.36-7.42 (2H, m), 7.57 (1H, t, J = 7.8 Hz), 7.80 (1H, d, J = 7.8 Hz), 7.92 (1H, s), 8.06-8.11 (3H, m), 8.23 (2H, s), 8.38 (1H, s), 10.50 (1H, s), 10.56 (1H, s). |
| 1-591 | $^1$H-NMR (CDCl$_3$) δ 3.56 (3H, s), 7.12 (1H, s), 7.20-7.33 (6H, m), 7.40 (1H, t, J = 7.8 Hz), 7.55 (1H, s), 7.62 (2H, s), 7.64 (1H, d, J = 1.0 Hz), 7.72 (1H, d, J = 7.8 Hz). |
| 1-592 | $^1$H-NMR (DMSO-d$_6$) δ 2.23 (3H, s), 5.64 (2H, s), 7.15 (1H, s), 7.42 (1H, d, J = 1.5 Hz), 7.50-7.63 (4H, m), 7.68 (1H, s), 7.75 (1H, d, J = 7.8 Hz), 7.98-8.01 (2H, m), 8.03-8.06 (1H, m), 8.35 (1H, s), 10.08 (1H, s), 10.46 (1H, s). |
| 1-593 | $^1$H-NMR (CDCl$_3$) δ 2.30 (3H, s), 5.39 (2H, s), 6.94 (1H, s), 7.12 (1H, s), 7.15-7.21 (1H, m), 7.28-7.33 (1H, m), 7.36 (1H, d, J = 2.0 Hz), 7.44-7.54 (2H, m), 7.72 (1H, d, J = 7.8 Hz), 7.86 (1H, s), 7.90 (1H, dd, J = 1.5, 7.8 Hz), 8.10-8.15 (1H, m), 8.25 (1H, s), 8.64 (1H, d, J = 15.6 Hz). |
| 1-594 | $^1$H-NMR (CDCl$_3$) δ 2.24 (3H, s), 5.39 (2H, s), 6.94 (1H, s), 7.09 (1H, s), 7.28 (1H, dd, J = 4.9, 7.3 Hz), 7.33 (1H, d, J = 1.5 Hz), 7.42 (1H, t, J = 7.8 Hz), 7.67 (1H, d, J = 7.8 Hz), 7.83 (1H, d, J = 7.8 Hz), 7.92 (1H, s), 7.99 (1H, dd, J = 2.0, 7.3 Hz), 8.18 (1H, s), 8.40 (1H, dd, J = 2.0, 4.9 Hz), 8.85 (1H, s). |
| 1-595 | $^1$H-NMR (CDCl$_3$) δ 2.21 (3H, s), 3.50 (3H, s), 5.39 (2H, s), 6.94 (1H, s), 7.10 (1H, s), 7.13-7.19 (2H, m), 7.21-7.27 (4H, m), 7.32 (1H, t, J = 7.8 Hz), 7.35 (1H, d, J = 1.5 Hz), 7.63 (1H, s), 7.70 (1H, d, J = 7.8 Hz), 7.76 (1H, s). |
| 1-596 | $^1$H-NMR (DMSO-d$_6$) δ 2.06 (2H, quint, J = 7.3 Hz), 2.87 (2H, t, J = 7.3 Hz), 3.12-3.14 (2H, m), 7.52-7.63 (5H, m), 7.75 (1H, d, J = 7.8 Hz), 7.99-8.01 (2H, m), 8.07 (1H, d, J = 7.8 Hz), 8.37 (1H, s), 10.33 (1H, s), 10.49 (1H, s). |

TABLE 5-continued

| Compound No. | Physical Property |
| --- | --- |
| 1-597 | $^1$H-NMR (DMSO-d$_6$) δ 2.06 (2H, quint, J = 7.3 Hz), 2.87 (2H, t, J = 7.3 Hz), 3.13 (2H, dd, J = 7.3, 12.2 Hz), 7.33-7.40 (2H, m), 7.52-7.63 (3H, m), 7.67-7.72 (1H, m), 7.75 (1H, d, J = 7.8 Hz), 7.97 (1H, d, J = 7.8 Hz), 8.33 (1H, s), 10.35 (1H, s), 10.66 (1H, s). |
| 1-598 | $^1$H-NMR (DMSO-d$_6$) δ 2.07 (2H, quint, J = 7.3 Hz), 2.87 (2H, t, J = 7.3 Hz), 3.15 (2H, dd, J = 7.3, 12.2 Hz), 7.45 (1H, s), 7.52-7.64 (4H, m), 7.75 (1H, d, J = 8.3 Hz), 7.98-8.01 (2H, m), 8.06 (1H, dd, J = 1.5, 7.8 Hz), 8.37 (1H, t, J = 1.5 Hz), 10.34 (1H, s), 10.49 (1H, s). |
| 1-599 | $^1$H-NMR (DMSO-d$_6$) δ 2.07 (2H, quint, J = 7.3 Hz), 2.87 (2H, t, J = 7.3 Hz), 3.15 (2H, dd, J = 7.3, 12.2 Hz), 7.33-7.40 (2H, m), 7.45 (1H, s), 7.52-7.63 (2H, m), 7.67-7.76 (2H, m), 7.98 (1H, d, J = 7.8 Hz), 8.33 (1H, s), 10.37 (1H, s), 10.66 (1H, s). |
| 1-600 | $^1$H-NMR (CDCl$_3$) δ 2.35 (3H, s), 7.12-7.16 (2H, m), 7.50-7.65 (5H, m), 7.72 (1H, dd, J = 1.5, 7.8 Hz), 8.01 (2H, d, J = 8.3 Hz), 8.24 (1H, s), 10.2 (1H, brs), 10.3 (1H, brs). |
| 1-601 | $^1$H-NMR (DMSO-d$_6$) δ 2.37 (3H, s), 7.29-8.01 (10H, m), 10.3 (1H, s), 10.6 (1H, s). |
| 1-602 | $^1$H-NMR (DMSO-d$_6$) δ 7.47-7.65 (5H, m), 7.75 (1H, dd, J = 1.5, 7.8 Hz), 7.93 (1H, d, J = 7.8 Hz), 8.01-8.04 (2H, m), 8.12 (1H, s), 8.17 (1H, d, J = 8.8 Hz), 10.17 (1H, s), 10.71 (1H, s). |
| 1-603 | $^1$H-NMR (CDCl$_3$) δ 3.22 (3H, s), 3.42 (3H, s), 7.17-7.23 (1H, m), 7.29-7.35 (2H, m), 7.49-7.57 (2H, m), 7.64 (1H, d, J = 8.3 Hz), 7.81-7.83 (1H, m), 8.00-8.10 (2H, m), 8.14-8.18 (1H, m), 8.41 (1H, s), 8.62 (1H, d, J = 15.1 Hz). |
| 1-604 | $^1$H-NMR (CDCl$_3$) δ 1.09 (3H, t, J = 7.3 Hz), 1.51 (9H, s), 1.84-1.93 (2H, m), 4.38 (2H, t, J = 6.8 Hz), 6.34 (1H, d, J = 8.3 Hz), 6.95 (1H, d, J = 8.3 Hz), 7.09 (1H, d, J = 7.8 Hz), 7.18 (1H, d, J = 8.3 Hz), 7.48-7.72 (7H, m), 7.79-7.81 (2H, m). |
| 1-605 | $^1$H-NMR (DMSO-d$_6$) δ 7.51-7.63 (5H, m), 7.79 (1H, d, J = 7.8 Hz), 7.83-7.86 (2H, m), 7.99-8.02 (2H, m), 8.07 (1H, dd, J = 1.0, 8.3 Hz), 8.38 (1H, s), 10.48 (1H, s), 10.63 (1H, s). |
| 1-96 | $^1$H-NMR (DMSO-d$_6$) δ 7.54-7.59 (2H, m), 7.80 (1H, d, J = 7.8 Hz), 7.93 (1H, dd, J = 1.0, 7.8 Hz), 8.06-8.11 (2H, m), 8.29-8.31 (2H, m), 8.54 (1H, dd, J = 2.0, 4.9 Hz), 10.68 (1H, s), 10.88 (1H, s). |
| 2-1 | $^1$H-NMR (DMSO-d$_6$) δ 6.15 (1H, dddd, J = 42.0, 11.6, 11.6, 5.6 Hz), 7.47-7.59 (4H, m), 7.62 (2H, s), 7.78 (1H, d, J = 7.2 Hz), 8.01 (2H, d, J = 7.2 Hz), 8.11 (1H, s), 8.38 (1H, s), 10.35 (1H, s), 10.40 (1H, s). |
| 2-159 | $^1$H-NMR (DMSO-d$_6$) δ 3.53 (3H, s), 5.80 (1H, brdd, J = 42.4, 5.6 Hz), 7.21-7.49 (7H, m), 7.55 (2H, s), 7.84 (2H, brs), 10.18 (1H, s). |
| 2-160 | $^1$H-NMR (CDCl$_3$) δ 3.53 (3H, brs), 5.02 (1H, dddd, J = 44.0, 10.8, 10.8, 5.2 Hz), 6.83 (1H, brs), 7.07 (1H, brs), 7.16-7.38 (5H, m), 7.52 (2H, s), 7.61 (1H, brs), 7.73 (1H, brs). |
| 2-163 | $^1$H-NMR (CDCl$_3$) δ 3.57 (3H, s), 5.02 (1H, brdd, J = 44.0, 5.6 Hz), 7.11-7.14 (1H, m), 7.39 (2H, brs), 7.49-7.59 (4H, m), 7.73 (2H, brs), 8.26 (1H, brs). |
| 2-166 | $^1$H-NMR (CDCl$_3$) δ 3.31 (3H, s), 4.97 (1H, dddd, J = 44.0, 11.2, 11.2, 5.2 Hz), 7.15-7.18 (2H, m), 7.40 (2H, s), 7.45-7.57 (3H, m), 7.70 (1H, s), 7.76 (1H, ddd, J = 7.2, 2.0, 2.0 Hz), 7.82-7.92 (3H, m). |
| 2-167 | $^1$H-NMR (CDCl$_3$) δ 3.33 (3H, s), 4.96 (1H, dddd, J = 44.0, 11.2, 11.2, 6.0 Hz), 7.18-7.21 (3H, m), 7.31-7.33 (1H, m), 7.40 (2H, s), 7.52-7.56 (1H, m), 7.71 (1H, brs), 7.74-7.76 (1H, m), 8.11-8.16 (1H, m), 8.40 (1H, brs). |
| 2-170 | $^1$H-NMR (CDCl$_3$) δ 3.31 (3H, s), 4.96 (1H, dddd, J = 44.0, 11.2, 11.2, 6.0 Hz), 7.21-7.28 (2H, m), 7.38-7.41 (3H, m), 7.69 (2H, brs), 8.14 (1H, dd, J = 8.0, 2.0 Hz), 8.26 (1H, s), 8.52 (1H, t, J = 2.0 Hz). |
| 2-173 | $^1$H-NMR (CDCl$_3$) δ 3.19 (3H, s), 4.97 (1H, dddd, J = 43.9, 10.7, 10.7, 5.7 Hz), 7.16-7.20 (2H, m), 7.39 (2H, s), 7.47-7.51 (1H, m), 7.67 (1H, s), 7.72-7.75 (2H, m), 7.85 (1H, dd, J = 7.8, 1.5 Hz), 8.49 (1H, s). |
| 2-174 | $^1$H-NMR (CDCl$_3$) δ 3.30 (3H, s), 3.35 (3H, s), 5.00 (1H, brdd, J = 44.0, 5.2 Hz), 6.81 (1H, d, J = 7.2 Hz), 6.97 (1H, t, J = 8.0 Hz), 7.09-7.24 (6H, m), 7.36-7.39 (3H, m). |
| 2-175 | $^1$H-NMR (CDCl$_3$) δ 3.30 (3H, s), 3.34 (3H, s), 5.00 (1H, dddd, J = 44.0, 10.8, 10.8, 5.2 Hz), 6.73-7.00 (4H, m), 7.15-7.26 (3H, m), 7.34 (1H, s), 7.38 (2H, s). |
| 2-178 | $^1$H-NMR (CDCl$_3$) δ 3.29 (3H, s), 3.37 (3H, s), 5.00 (1H, dddd, J = 44.0, 10.8, 10.8, 5.2 Hz), 7.02 (3H, brd, J = 4.8 Hz), 7.22 (1H, brd, J = 4.8 Hz), 7.33-7.40 (4H, m), 8.22 (1H, brs). |
| 2-181 | $^1$H-NMR (CDCl$_3$) δ 3.29 (3H, s), 3.37 (3H, s), 4.99 (1H, brdd, J = 43.9, 5.4 Hz), 6.99-7.07 (2H, m), 7.23-7.26 (1H, m), 7.37-7.41 (1H, m), 7.38 (2H, s), 8.18 (1H, d, J = 2.4 Hz), 8.26 (1H, d, J = 2.4 Hz). |
| 2-182 | $^1$H-NMR (CDCl$_3$) δ 3.30 (3H, s), 3.41 (3H, s), 5.00 (1H, brdd, J = 43.9, 17.9 Hz), 6.89-6.91 (1H, m), 7.08 (1H, t, J = 7.8 Hz), 7.26-7.29 (1H, m), 7.43 (2H, s), 7.44 (1H, t, J = 2.0 Hz), 8.48 (2H, s), 9.02 (1H, s). |
| 2-183 | $^1$H-NMR (DMSO-d$_6$) δ 2.30 (3H, s), 6.47 (1H, brdd, J = 41.0, 5.9 Hz), 7.34 (1H, d, J = 2.4 Hz), 7.50-7.63 (5H, m), 7.77 (1H, d, |

TABLE 5-continued

| Compound No. | Physical Property |
|---|---|
| | J = 7.8 Hz), 7.94-8.01 (2H, m), 8.06 (1H, dd, J = 8.3, 1.5 Hz), 8.37 (1H, t, J = 1.5 Hz), 10.14 (1H, s), 10.48 (1H, s). |
| 2-184 | $^1$H-NMR (CDCl$_3$) δ 3.55 (3H, s), 5.43 (1H, brdd, J = 43.2, 5.6 Hz), 7.18-7.37 (6H, m), 7.54-7.55 (2H, m), 7.78-7.82 (3H, m), 9.91 (1H, s). |
| 2-185 | $^1$H-NMR (DMSO-d$_6$:CDCl$_3$ = 1:1) δ 5.51 (1H, brdd, J = 43.0, 5.4 Hz), 7.44-7.57 (5H, m), 7.76 (1H, d, J = 7.8 Hz), 7.80 (1H, d, J = 2.4 Hz), 8.01-8.03 (2H, m), 8.20 (1H, d, J = 8.3 Hz), 8.30 (1H, s), 9.97 (1H, s), 10.15 (1H, s). |
| 2-186 | $^1$H-NMR (CDCl$_3$) δ 5.06 (1H, brdd, J = 44.0, 5.9 Hz), 7.44 (1H, dd, J = 7.3, 4.9 Hz), 7.55-7.59 (2H, m), 7.74-7.80 (3H, m), 7.94 (1H, d, J = 7.8 Hz), 8.22-8.24 (2H, m), 8.40 (1H, s), 8.54-8.57 (1H, m). |
| 2-187 | $^1$H-NMR (CDCl$_3$) δ 3.54 (3H, s), 5.47 (1H, brdddd, J = 5.9, 11.7, 42.9 Hz), 7.19-7.30 (4H, m), 7.31-7.36 (3H, m), 7.82-7.84 (4H, m), 10.15 (1H, s). |
| 2-188 | $^1$H-NMR (CDCl$_3$) δ 3.56 (3H, s), 5.01 (1H, brdddd, J = 5.4, 11.2, 49.3 Hz), 7.13 (1H, d.d., J = 4.9, 7.3 Hz), 7.41 (2H, s), 7.58 (1H, m), 7.72 (2H, s), 7.80 (1H, d, J = 2.5 Hz), 7.86 (1H, d, J = 2.5 Hz), 8.25 (1H, d, J = 2.9 Hz), 8.34 (1H, s). |
| 2-189 | $^1$H-NMR (CDCl$_3$) δ 2.29 (6H, s), 4.95 (1H, brd, J = 44.0 Hz), 6.86 (1H, d, J = 6.3 Hz), 6.96 (1H, s), 7.44-7.53 (3H, m), 7.57-7.61 (1H, m), 7.63 (1H, brs), 7.71 (1H, d, J = 8.3 Hz), 7.86-7.90 (2H, m), 8.06 (1H, dd, J = 8.3, 1.5 Hz), 8.12 (1H, brs), 8.32 (1H, t, J = 1.5 Hz) |
| 2-190 | $^1$H-NMR (CDCl$_3$) δ 2.20 (6H, s), 3.55 (3H, s), 5.00 (1H, brdd, J = 43.9, 5.9 Hz), 6.95 (2H, s), 7.10 (1H, dd, J = 7.8, 4.9 Hz), 7.35 (2H, brd, J = 4.4 Hz), 7.44 (1H, s), 7.55 (1H, dd, J = 7.8, 1.5 Hz), 7.68 (1H, brd, J = 3.4 Hz), 7.73 (1H, s), 8.23 (1H, dd, J = 4.9, 2.0 Hz). |
| 2-192 | $^1$H-NMR (CDCl$_3$) δ 2.31 (6H, s), 5.00 (1H, brdd, J = 43.9, 5.9 Hz), 6.99 (2H, s), 7.35 (1H, t, J = 8.3 Hz), 7.47-7.63 (3H, m), 7.71 (1H, d, J = 11.2 Hz), 7.82 (1H, t, J = 2.0 Hz), 7.92 (2H, d, J = 7.3 Hz), 8.08-8.14 (1H, m), 8.58-8.63 (1H, m). |
| 2-193 | $^1$H-NMR (CDCl$_3$) δ 2.32 (6H, s), 4.98-5.02 (1H, m), 7.00 (2H, brs), 7.23-7.24 (1H, m), 7.34-7.39 (2H, m), 7.56-7.60 (1H, m), 7.74 (1H, d, J = 11.7 Hz), 7.85 (1H, ddd, J = 9.3, 1.5, 1.5 Hz), 8.22 (1H, ddd, J = 7.8, 7.8, 2.0 Hz), 8.67 (1H, ddd, J = 8.3, 8.3, 2.0 Hz), 8.80-8.90 (1H, m). |
| 2-194 | $^1$H-NMR (CDCl$_3$) δ 2.31 (6H, s), 4.99 (1H, brdd, J = 44.4, 5.9 Hz), 6.99 (2H, brs), 7.38 (1H, t, J = 8.3 Hz), 7.46 (1H, dd, J = 7.8, 4.9 Hz), 7.71 (1H, d, J = 11.2 Hz), 7.88 (1H, ddd, J = 7.3, 7.3, 1.5 Hz), 8.32 (1H, dd, J = 7.8, 2.0 Hz), 8.57 (1H, dd, J = 4.9, 2.0 Hz), 8.61 (1H, ddd, J = 8.3, 8.3, 1.5 Hz), 8.74 (1H, brs). |
| 2-195 | $^1$H-NMR (DMSO-d$_6$) δ 2.30 (6H, s), 4.92-5.07 (1H, m), 6.98 (2H, s), 7.29-7.32 (1H, m), 7.53-7.57 (3H, m), 7.60-7.64 (1H, m), 7.80-7.84 (1H, m), 7.89-7.91 (2H, m), 8.20 (1H, broad-s), 9.10-9.13 (1H, m). |
| 2-196 | $^1$H-NMR (DMSO-d$_6$) δ 2.31 (6H, s), 5.80-6.10 (1H, m), 6.99 (2H, s), 7.29-7.34 (1H, m), 7.44-7.50 (2H, m), 7.82-7.86 (1H, m), 8.27 (1H, dd, J = 7.3, 1.5 Hz), 8.57 (1H, dd, J = 4.9, 2.0 Hz), 8.75 (1H, broad-s), 9.68 (1H, dd, J = 6.8, 2.0 Hz). |
| 2-197 | $^1$H-NMR (DMSO-d$_6$) δ 6.59 (1H, brd, J = 41.5 Hz), 7.53-7.63 (4H, m), 7.72-7.76 (1H, m), 7.90 (1H, d, J = 7.8 Hz), 8.01-8.05 (3H, m), 8.10-8.13 (1H, m), 8.38 (1H, d, J = 8.8 Hz), 8.45 (1H, s), 9.08 (1H, t, J = 2.0 Hz), 10.50 (1H, s), 10.66 (1H, s). |
| 2-198 | $^1$H-NMR (DMSO-d$_6$) δ 6.63 (1H, brdd, J = 41.0, 6.3 Hz), 7.34-7.40 (2H, m), 7.58-7.62 (2H, m), 7.70-7.76 (2H, m), 7.90 (1H, d, J = 7.8 Hz), 8.01 (1H, d, J = 7.8 Hz), 8.08 (1H, s), 8.37-8.40 (2H, m), 9.09 (1H, dd, J = 4.4, 1.5 Hz), 10.69 (2H, s). |
| 2-199 | $^1$H-NMR (DMSO-d$_6$) δ 6.63 (1H, brdd, J = 41.0, 5.9 Hz), 7.57-7.64 (2H, m), 7.75 (1H, dd, J = 8.8, 3.9 Hz), 7.93 (1H, d, J = 7.8 Hz), 7.98 (1H, dd, J = 7.8, 1.5 Hz), 8.08-8.13 (2H, m), 8.38-8.40 (2H, m), 8.56 (1H, dd, J = 4.9, 2.0 Hz), 9.08 (1H, dd, J = 3.9, 1.5 Hz), 10.71 (1H, s), 10.91 (1H, s). |
| 2-200 | $^1$H-NMR (DMSO-d$_6$) δ 3.46 (3H, s), 6.61 (1H, brdd, J = 41.0, 2.1 Hz), 7.25-7.48 (7H, m), 7.73 (1H, brdd, J = 8.8, 3.9 Hz), 7.83-7.88 (2H, m), 8.05 (1H, brs), 8.25 (1H, dd, J = 8.8, 1.5 Hz), 9.06 (1H, dd, J = 3.9, 1.5 Hz), 10.58 (1H, s). |
| 2-201 | $^1$H-NMR (CDCl$_3$) δ 6.07 (1H, dddd, J = 53.2, 53.2, 2.9, 2.9 Hz), 7.43-7.58 (6H, m), 7.79 (1H, d, J = 7.8 Hz), 8.00-8.02 (2H, m), 8.18 (1H, d, J = 8.3 Hz), 8.34 (1H, s), 9.61 (1H, s), 9.95 (1H, s). |
| 2-202 | $^1$H-NMR (CDCl$_3$) δ 5.93 (1H, dddd, J = 53.2, 53.2, 2.9, 2.9 Hz), 7.18-7.36 (3H, m), 7.50-7.57 (3H, m), 7.77 (1H, d, J = 7.3 Hz), 7.82 (1H, s), 7.92-7.94 (1H, m), 8.17 (1H, brd, J = 1.5 Hz), 8.31 (1H, s), 8.65 (1H, brd, J = 1.5 Hz). |
| 2-203 | $^1$H-NMR (CDCl$_3$) δ 5.93 (1H, dddd, J = 53.2, 53.2, 2.9, 2.9 Hz), 7.38 (1H, dd, J = 7.8, 4.9 Hz), 7.49-7.53 (3H, m), 7.76 (1H, brd, J = 7.8 Hz), 7.89 (1H, s), 7.91 (1H, d, J = 1.5 Hz), 8.14 (1H, dd, J = 7.8, 2.0 Hz), 8.24 (1H, s), 8.50 (1H, dd, J = 4.9, 2.0 Hz), 8.61 (1H, s). |

TABLE 5-continued

| Compound No. | Physical Property |
| --- | --- |
| 2-204 | ¹H-NMR (CDCl₃) δ 5.06-5.20 (2H, m), 7.25 (1H, d, J = 2.0 Hz), 7.46-7.57 (5H, m), 7.71 (1H, d, J = 7.8 Hz), 7.96 (2H, dd, J = 7.3, 1.5 Hz), 8.15 (1H, dd, J = 7.8, 1.0 Hz), 8.29 (1H, t, J = 2.0 Hz), 8.72 (1H, s), 9.51 (1H, s). |
| 2-205 | ¹H-NMR (CDCl₃) δ 5.12-5.25 (2H, m), 7.21 (1H, ddd, J = 11.7, 8.3, 1.0 Hz), 7.27 (1H, s), 7.32 (1H, ddd, J = 7.3, 7.3, 1.0 Hz), 7.48-7.55 (3H, m), 7.76 (1H, d, J = 7.8 Hz), 8.03 (1H, ddd, J = 7.8, 7.8, 2.0 Hz), 8.11 (1H, d, J = 8.3 Hz), 8.20 (1H, brs), 9.07 (1H, s), 9.19 (1H, d, J = 10.7 Hz). |
| 2-206 | ¹H-NMR (CDCl₃) δ 4.97-5.12 (2H, m), 7.40 (1H, dd, J = 7.8, 4.9 Hz), 7.50-7.54 (2H, m), 7.67-7.70 (2H, m), 7.91 (1H, dd, J = 8.3, 1.5 Hz), 8.15-8.20 (2H, m), 8.50-8.52 (2H, m). |
| 2-207 | ¹H-NMR (CDCl₃:DMSO-d₆ 1:1) δ 5.51-5.67 (3H, m), 7.24 (2H, s), 7.42-7.57 (3H, m), 7.66-7.69 (2H, m), 8.00-8.02 (2H, m), 8.08 (1H, dd, J = 8.3, 1.5 Hz), 8.36 (1H, s), 8.61 (1H, brd, J = 11.2 Hz), 10.19 (1H, brs). |
| 2-208 | ¹H-NMR (CDCl₃:DMSO-d₆ 1:1) δ 5.99-6.25 (3H, m), 7.23-7.33 (4H, m), 7.46 (1H, t, J = 7.8 Hz), 7.54-7.56 (1H, m), 7.68-7.72 (2H, m), 7.98-8.00 (1H, m), 8.29 (1H, s), 10.00 (1H, s), 10.46 (1H, s). |
| 2-209 | ¹H-NMR (CDCl₃:DMSO-d₆ 1:1) δ 6.00-6.25 (3H, m), 7.29 (2H, s), 7.45-7.52 (2H, m), 7.72 (1H, d, J = 7.8 Hz), 7.96-8.02 (2H, m), 8.24 (1H, d, J = 2.0 Hz), 8.50 (1H, dd, J = 4.9, 2.0 Hz), 10.03 (1H, s), 10.75 (1H, s). |
| 2-210 | ¹H-NMR (CDCl₃) δ 5.15-5.31 (1H, m), 7.41-7.57 (4H, m), 7.79 (1H, d, J = 7.8 Hz), 7.92 (2H, s), 8.01-8.04 (2H, brd, J = 7.3 Hz), 8.18 (1H, d, J = 8.3 Hz), 8.35 (1H, s), 9.85 (1H, s), 10.04 (1H, s). |
| 2-211 | ¹H-NMR (CDCl₃) δ 4.89-4.97 (1H, m), 7.18-7.26 (1H, m), 7.32-7.36 (1H, m), 7.50-7.57 (2H, m), 7.76 (1H, d, J = 7.8 Hz), 7.89 (1H, d, J = 1.5 Hz), 7.91 (2H, s), 8.02 (1H, s), 8.16 (1H, ddd, J = 7.8, 7.8, 2.0 Hz), 8.32 (1H, t, J = 1.5 Hz), 8.65 (1H, brd, J = 16.1 Hz). |
| 2-212 | ¹H-NMR (CDCl₃) δ 4.96 (1H, brd, J = 44.0 Hz), 7.37 (1H, dd, J = 7.8, 4.9 Hz), 7.52 (1H, brd, J = 7.8 Hz), 7.75 (1H, d, J = 7.8 Hz), 7.89 (1H, d, J = 8.3 Hz), 7.90 (2H, s), 8.02 (1H, s), 8.12 (1H, dd, J = 7.8, 2.0 Hz), 8.25 (1H, s), 8.48 (1H, dd, J = 4.9, 2.0 Hz), 8.64 (1H, s). |
| 2-213 | ¹H-NMR (CDCl₃: DMSO-d₆ (5:1)) δ 5.79 (1H, brd, J = 44.0 Hz), 7.46-7.59 (5H, m), 7.79 (1H, t, J = 2.0 Hz), 7.90 (1H, t, J = 2.0 Hz), 8.00 (1H, d, J = 1.5 Hz), 8.03 (1H, s), 8.12 (1H, dd, J = 7.8, 1.5 Hz), 8.39 (1H, t, J = 2.0 Hz), 10.29 (1H, s), 10.32 (1H, s). |
| 2-214 | ¹H-NMR (CDCl₃) δ 5.30-5.95 (1H, m), 7.19-7.24 (1H, m), 7.32-7.36 (1H, m), 7.51-7.59 (2H, m), 7.76 (2H, d, J = 2.0 Hz), 7.88 (1H, d, J = 2.0 Hz), 7.90-7.92 (2H, m), 8.18 (1H, ddd, J = 7.8, 7.8, 2.0 Hz), 8.34 (1H, t, J = 2.0 Hz), 8.64 (1H, d, J = 16.1 Hz). |
| 2-215 | ¹H-NMR (CDCl₃) δ 5.80-5.10 (1H, m), 7.40 (1H, dd, J = 7.8, 4.9 Hz), 7.53 (1H, t, J = 7.8 Hz), 7.75-7.78 (2H, m), 7.87 (1H, d, J = 2.0 Hz), 7.88-7.91 (1H, m), 7.97 (1H, s), 8.16 (1H, dd, J = 7.8, 2.0 Hz), 8.26 (1H, d, J = 2.0 Hz), 8.51 (1H, dd, J = 4.4, 2.0 Hz), 8.56 (1H, s). |
| 2-216 | ¹H-NMR (CDCl₃) δ 3.55 (3H, s), 4.81-4.97 (1H, m), 7.19-7.33 (6H, m), 7.39 (1H, t, J = 7.8 Hz), 7.50 (1H, s), 7.58-7.61 (1H, m), 7.70-7.74 (1H, m), 7.74 (1H, d, J = 1.5 Hz), 7.85 (1H, d, J = 1.5 Hz). |
| 2-217 | ¹H-NMR (CDCl₃) δ 3.53 (3H, brs), 4.74-4.98 (2H, m), 6.84 (1H, brs), 7.08 (1H, brs), 7.17 (1H, dd, J = 10.7, 8.3 Hz), 7.39-7.47 (3H, m), 7.55-7.60 (2H, m), 7.74 (1H, d, J = 2.0 Hz), 7.86 (1H, d, J = 2.0 Hz). |
| 2-218 | ¹H-NMR (CDCl₃) δ 3.57 (3H, s), 4.91 (1H, brd, J = 43.9 Hz), 7.13 (1H, dd, J = 7.8, 4.9 Hz), 7.39 (2H, d, J = 4.4 Hz), 7.58 (2H, brs), 7.71-7.75 (3H, m), 7.88 (1H, brs), 8.25 (1H, d, J = 3.4 Hz). |
| 2-219 | ¹H-NMR (CDCl₃) δ 2.20 (6H, s), 3.55 (3H, s), 5.93 (1H, ddd, J = 54.2, 2.9, 2.9 Hz), 6.96 (2H, s), 7.10 (1H, dd, J = 7.3, 4.9 Hz), 7.35 (2H, d, J = 4.4 Hz), 7.46 (1H, s), 7.54 (1H, dd, J = 7.8, 2.0 Hz), 7.68 (1H, brd, J = 3.9 Hz), 7.73 (1H, s), 8.23 (1H, dd, J = 4.4, 1.5 Hz). |
| 2-220 | ¹H-NMR (CDCl₃) δ 2.28 (6H, s), 5.00 (1H, brdd, J = 43.9, 5.4 Hz), 6.87 (1H, d, J = 6.8 Hz), 6.97 (1H, s), 7.41 (1H, dd, J = 7.8, 4.9 Hz), 7.52 (1H, t, J = 8.3 Hz), 7.58 (1H, brs), 7.72-7.74 (1H, m), 7.83-7.86 (1H, m), 8.17 (1H, dd, J = 7.8, 2.0 Hz), 8.27 (1H, brs), 8.52 (2H, brs). |
| 2-8 | ¹H-NMR (DMSO-d₆) δ 6.18 (1H, brdd, J = 42.0, 5.2 Hz), 7.23-7.32 (2H, m), 7.47-7.55 (2H, m), 7.62 (2H, s), 7.70 (1H, t, J = 6.4 Hz), 7.78 (1H, d, J = 6.8 Hz), 8.03 (1H, d, J = 7.6 Hz), 8.34 (1H, s), 10.38 (1H, s), 10.50 (1H, s). |
| 4-1 | ¹H-NMR (CDCl₃) δ 2.28 (6H, s), 7.30-7.44 (5H, m), 7.34 (2H, s), 7.51-7.64 (4H, m), 7.75-7.78 (2H, m). |
| 4-2 | ¹H-NMR (CDCl₃) δ 2.29 (6H, s), 2.64 (3H, s), 7.22-7.36 (4H, m), 7.34 (2H, s), 7.43-7.47 (2H, m), 7.57-7.68 (3H, m), 7.99 (1H, d, J = 7.3 Hz). |
| 4-6 | ¹H-NMR (CDCl₃) δ 2.29 (6H, s), 7.32-7.39 (6H, m), 7.58-7.66 (6H, m). |
| 4-10 | ¹H-NMR (CDCl₃) δ 2.31 (6H, s), 7.35 (2H, s), 7.43-7.47 (2H, m), 7.49 (1H, s), 7.53 (1H, s), 7.61-7.65 (1H, m), 7.71-7.77 (3H, m), 7.87-7.91 (2H, m). |
| 4-16 | ¹H-NMR (CDCl₃) δ 2.33 (6H, s), 7.36 (2H, s), 7.42-7.49 (3H, m), 7.71 (1H, d, J = 6.8 Hz), 7.81 (1H, s), 7.89 (1H, s). |

TABLE 5-continued

| Compound No. | Physical Property |
|---|---|
| 4-24 | $^1$H-NMR (CDCl$_3$) δ 2.29 (6H, s), 2.85 (3H, s), 3.35 (3H, s), 7.34 (2H, s), 7.49 (1H, t, J = 7.8 Hz), 7.58 (1H, dd, J = 1.0, 7.8 Hz), 7.80-7.83 (2H, m), 7.96 (1H, s). |
| 4-25 | $^1$H-NMR (CDCl$_3$) δ 1.35 (3H, t, J = 7.3 Hz), 2.32 (6H, s), 3.14 (2H, q, J = 7.3 Hz), 7.29 (1H, s), 7.35 (2H, s), 7.42-7.48 (2H, m), 7.66-7.71 (2H, m), 7.80 (1H, s). |
| 4-26 | $^1$H-NMR (CDCl$_3$) δ 1.33 (3H, t, J = 7.3 Hz), 2.27 (6H, s), 3.03 (2H, q, J = 7.3 Hz), 3.35 (3H, s), 7.33 (2H, s), 7.44 (1H, t, J = 7.8 Hz), 7.57 (1H, d, J = 7.8 Hz), 7.79 (1H, d, J = 7.8 Hz), 7.97 (1H, s), 8.05 (1H, s). |
| 4-27 | $^1$H-NMR (CDCl$_3$) δ 2.27 (6H, s), 3.73 (2H, q, J = 8.8 Hz), 7.33 (2H, s), 7.39-7.45 (2H, m), 7.68-7.71 (1H, m), 7.83-7.85 (2H, m), 8.09 (1H, s). |
| 4-28 | $^1$H-NMR (CDCl$_3$) δ 2.27 (6H, s), 3.40 (3H, s), 3.75 (2H, q, J = 8.8 Hz), 7.34 (2H, s), 7.51 (1H, t, J = 7.8 Hz), 7.58 (1H, d, J = 7.8 Hz), 7.86 (1H, d, J = 7.8 Hz), 7.90 (1H, s), 7.97 (1H, s). |
| 4-29 | $^1$H-NMR (CDCl$_3$) δ 2.25 (6H, s), 5.87 (1H, d, J = 9.8 Hz), 6.19 (1H, d, J = 16.1 Hz), 6.46 (1H, dd, J = 9.8, 16.1 Hz), 7.23-7.35 (5H, m), 7.61 (1H, s), 7.75 (1H, s), 7.94 (1H, s). |
| 4-30 | $^1$H-NMR (CDCl$_3$) δ 2.28 (6H, s), 3.25 (3H, s), 6.03 (1H, d, J = 9.8 Hz), 6.18 (1H, d, J = 16.6 Hz), 6.42 (1H, dd, J = 9.8, 16.6 Hz), 7.33 (2H, s), 7.44 (1H, t, J = 7.8 Hz), 7.51 (1H, d, J = 7.8 Hz), 7.80 (1H, d, J = 7.8 Hz), 7.91 (1H, s), 7.94 (1H, s). |
| 4-31 | $^1$H-NMR (DMSO-d$_6$) δ 1.02 (3H, t, J = 7.3 Hz), 1.80-1.90 (2H, m), 2.35 (6H, s), 3.05-3.09 (2H, m), 7.32 (2H, s), 7.42 (1H, t, J = 7.8 Hz), 7.50-7.53 (1H, m), 7.71 (1H, d, J = 7.8 Hz), 7.86 (1H, d, J = 2.0 Hz), 8.54 (1H, s), 9.24 (1H, s). |
| 4-32 | $^1$H-NMR (CDCl$_3$) δ 1.01 (3H, t, J = 7.8 Hz), 1.77-1.87 (2H, m), 2.28 (6H, s), 2.97 (2H, t, J = 7.8 Hz), 3.35 (3H, s), 7.34 (2H, s), 7.45 (1H, t, J = 7.8 Hz), 7.57 (1H, d, J = 7.8 Hz), 7.80 (1H, d, J = 7.8 Hz), 7.97 (2H, s). |
| 4-33 | $^1$H-NMR (CDCl$_3$) δ 1.37 (6H, d, J = 6.8 Hz), 2.32 (6H, s), 3.31 (1H, septet, J = 6.8 Hz), 7.24 (1H, s), 7.35 (2H, s), 7.41-7.49 (2H, m), 7.66 (1H, d, J = 7.3 Hz), 7.71 (1H, s), 7.81 (1H, s). |
| 4-34 | $^1$H-NMR (CDCl$_3$) δ 2.35 (6H, s), 4.37 (2H, s), 6.72 (1H, s), 7.27-7.37 (8H, m), 7.43-7.47 (2H, m), 7.62 (1H, d, J = 2.0 Hz), 7.68 (1H, d, J = 7.8 Hz). |
| 5-1 | $^1$H NMR (CDCl$_3$) δ 2.35 (6H, s), 5.89 (1H, brs), 7.01 (1H, t, J = 7.3 Hz), 7.14 (2H, d, J = 7.3 Hz), 7.28-7.40 (8H, m), 7.60 (1H, brs). |
| 5-2 | $^1$H NMR (CDCl$_3$) δ 2.28 (3H, s), 2.35 (6H, s), 5.58 (1H, brs), 7.00 (1H, t, J = 7.3 Hz), 7.09 (1H, d, J = 7.3 Hz), 7.18 (1H, t, J = 7.3 Hz), 7.24-7.35 (7H, m), 7.53 (1H, brs). |
| 5-4 | $^1$H NMR (CDCl$_3$) δ 2.35 (6H, s), 5.98 (1H, brs), 6.64-6.69 (1H, m), 6.80-6.85 (2H, m), 7.20-7.24 (1H, m), 7.31-7.43 (6H, m), 7.63 (1H, brs). |
| 5-5 | $^1$H-NMR (CDCl$_3$) δ 2.34 (6H, s), 5.88 (1H, brs), 7.00 (2H, d, J = 8.8 Hz), 7.36 (2H, s), 7.38-7.41 (6H, m), 7.59 (1H, brs). |
| 5-8 | $^1$H-NMR (CDCl$_3$) δ 2.37 (6H, s), 6.85-6.89 (1H, m), 7.32 (1H, d, J = 8.8 Hz), 7.37-7.46 (4H, m), 7.51-7.59 (2H, m), 7.71 (1H, d, J = 7.3 Hz), 7.87 (1H, brs), 8.23 (1H, dd, J = 8.8, 1.5 Hz), 9.54 (1H, brs). |
| 5-9 | $^1$H-NMR (CDCl$_3$) δ 2.36 (6H, s), 6.50 (1H, brs), 7.02 (2H, d, J = 8.7 Hz), 7.38 (2H, s), 7.42 (1H, s), 7.46 (1H, d, J = 7.8 Hz), 7.53 (1H, t, J = 7.8 Hz), 7.60 (1H, d, J = 7.8 Hz), 7.91 (1H, brs), 8.19 (2H, d, J = 8.7 Hz). |
| 5-10 | $^1$H-NMR (CDCl$_3$) δ 2.32 (6H, s), 3.81 (2H, brs), 5.42 (1H, brs), 6.76-6.83 (2H, m), 6.87-6.89 (1H, m), 7.05-7.09 (1H, m), 7.12 (1H, d, J = 7.8 Hz), 7.27-7.37 (6H, m). |
| 5-11 | $^1$H-NMR (CDCl$_3$) δ 2.33 (6H, s), 5.60 (1H, brs), 6.64 (2H, brs), 6.69 (2H, d, J = 8.8 Hz), 7.00-7.02 (3H, m), 7.23-7.37 (6H, m). |
| 5-12 | $^1$H-NMR (CDCl$_3$) δ 2.34 (6H, s), 6.04 (1H, brs), 7.20-7.52 (10H, m), 7.64 (1H, brs). |
| 5-13 | $^1$H-NMR (CDCl$_3$) δ 2.08 (3H, s), 2.32 (6H, s), 5.98 (1H, brs), 6.98 (1H, d, J = 7.3 Hz), 7.16-7.22 (2H, m), 7.29-7.40 (7H, m), 7.59 (1H, brs), 7.68 (1H, d, J = 7.3 Hz). |
| 5-14 | $^1$H-NMR (CDCl$_3$) δ 2.13 (3H, s), 2.33 (6H, s), 5.87 (1H, brs), 7.06 (2H, d, J = 8.8 Hz), 7.19 (1H, brs), 7.30-7.41 (7H, m), 7.50 (1H, brs), 7.53 (1H, brs). |
| 5-15 | $^1$H-NMR (CDCl$_3$) δ 2.34 (6H, s), 5.74 (1H, broad-s), 6.83-6.95 (2H, m), 7.15-7.18 (1H, m), 7.18-7.39 (6H, m), 7.54 (1H, broad-s). |
| 5-21 | $^1$H-NMR (CDCl$_3$) δ 2.36 (6H, s), 6.73-6.77 (2H, m), 6.96 (1H, d, J = 7.3 Hz), 7.33-7.38 (3H, m), 7.43-7.49 (2H, m), 7.56-7.58 (2H, m), 8.12 (1H, s). |
| 5-23 | $^1$H-NMR (CDCl$_3$) δ 2.31 (6H, s), 6.08 (2H, brs), 7.35 (2H, s), 7.43-7.59 (2H, m), 7.70-7.82 (3H, m), 8.29 (1H, brs). |
| 5-24 | $^1$H-NMR (CDCl$_3$) δ 2.33 (6H, s), 5.93 (2H, brs), 7.36 (2H, s), 7.45-7.49 (2H, m), 7.63 (1H, s), 7.85 (1H, d, J = 7.3 Hz), 7.92 (1H, s), 8.04 (1H, s). |
| 5-25 | $^1$H-NMR (DMSO-d$_6$) δ 2.29 (6H, s), 5.90 (2H, brs), 7.30-7.36 (2H, m), 7.43 (2H, s), 7.75 (1H, d, J = 7.8 Hz), 8.04 (1H, brs), 8.85 (1H, brs), 9.80 (1H, brs), 11.2 (1H, brs). |

TABLE 5-continued

| Compound No. | Physical Property |
|---|---|
| 5-26 | $^1$H-NMR (DMSO-$d_6$) δ 2.33 (6H, s), 2.83 (6H, s), 7.10-7.21 (3H, m), 7.43 (2H, s), 9.96 (1H, s). |
| 5-27 | $^1$H-NMR (CDCl$_3$) δ 0.92 (3H, t, J = 7.3 Hz), 1.59-1.69 (2H, m), 2.72 (2H, t, J = 7.8 Hz), 3.03 (6H, s), 6.93 (1H, dd, J = 2.4, 8.3 Hz), 7.23 (1H, d, J = 8.3 Hz), 7.32-7.39 (2H, m), 7.50 (1H, s), 7.55 (1H, s), 7.95 (1H, d, J = 1.5 Hz). |
| 5-28 | $^1$H-NMR (CDCl$_3$) δ 1.23 (6H, d, J = 6.8 Hz), 3.04 (6H, s), 3.25 (1H, septet, J = 6.8 Hz), 6.93 (1H, dd, J = 2.0, 7.8 Hz), 7.23 (1H, t, J = 7.8 Hz), 7.33-7.39 (2H, m), 7.51 (1H, s), 7.57 (1H, s), 7.95 (1H, d, J = 2.0 Hz). |
| 5-29 | $^1$H-NMR (CDCl$_3$) δ 3.05 (6H, s), 3.07 (3H, s), 6.97 (1H, dd, J = 2.0, 7.8 Hz), 7.25-7.27 (1H, m), 7.32-7.33 (1H, m), 7.39 (1H, t, J = 7.8 Hz), 8.20 (1H, d, J = 2.0 Hz), 8.26 (1H, d, J = 2.0 Hz), 8.89 (1H, s). |
| 5-30 | $^1$H-NMR (CDCl$_3$) δ 3.04 (6H, s), 6.95 (1H, d, J = 7.8 Hz), 7.21-7.23 (1H, m), 7.33-7.39 (2H, m), 7.66 (1H, s), 7.93 (2H, s). |
| 5-31 | $^1$H-NMR (DMSO-$d_6$) δ 2.97 (6H, s), 6.38-6.52 (1H, m), 6.96 (1H, brdd, J = 8.8, 2.0 Hz), 7.28-7.36 (3H, m), 8.06 (2H, s), 10.34 (1H, s). |
| 5-32 | $^1$H NMR (CDCl$_3$) δ 2.84 (6H, s), 3.35 (3H, s), 6.63-6.65 (1H, m), 6.73 (1H, d, J = 3.9 Hz), 6.75 (1H, s), 7.03 (1H, t, J = 8.3 Hz), 8.09 (2H, s). |
| 5-33 | $^1$H-NMR (CDCl$_3$) δ 1.57 (3H, d, J = 6.8 Hz), 2.28 (6H, s), 2.74 (3H, s), 5.18 (1H, q, J = 6.8 Hz), 6.99 (1H, dd, J = 2.4, 8.3 Hz), 7.15 (1H, d, J = 7.3 Hz), 7.22-7.35 (8H, m), 7.41 (1H, s), 7.55 (1H, s). |

Harmful organisms in the present invention refer to insect pests in the fields of agriculture and horticulture, stockbreeding, and hygiene and sanitation. An insecticide comprising the compound represented by the general formula (1) or (5) of the present invention as an active ingredient is suitable for preventing insect pests such as various agricultural, forest insect pests and horticultural insect pests, stored grain insect pests, hygienic insect pests, nematodes or the like which are injurious to paddy rice, fruit trees, vegetables, other crops, flowers and the like, and has a strong insecticidal effect, for example, on LEPIDOPTERA such as cucumber moth (*Diaphania indica*), oriental tea tortrix moth (*Homona magnanima*), cabbage webworm (*Hellulla undalis*), summer fruit tortrix (*Adoxophyes orana fasciata*), smaller tea tortrix (*Adoxophyes* sp.), apple tortrix (*Archips fuscocupreanus*), peach fruit moth (*Carposina niponensis*), Manchurian apple moth (*Grapholita inopinata*), oriental fruit moth (*Grapholita molesta*), soybean pod borer (*Leguminivora glycinivorella*), mulberry leafroller (*Olethreutes mori*), citrus leafminer (*Phyllocnistis citrella*), persimmon fruit moth (*Stathmopoda masinissa*), tea leafroller (*Caloptilia thevivora*), azalea leafminer (*Caloptilia zachrysa*), apple leafminer (*Phyllonorycter ringoniella*), pear barkminer (*Spulerrina astaurota*), swallowtail butterfly (*Papilio xuthus*), common white (*Piers rapae crucivora*), tobacco budworm (*Heliothis armigera*), codling moth (*Lapsey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), cabbage moth (*Mamestra brassicae*), common cutworm (*Spodoptera litura*), beet armyworm (*Spodoptera exigua*), black cutworm (*Agrotis ipsilon*), turnip moth (*Agrotis segetum*), semilooper (*Autographa nigrisigna*), cabbage looper (*Trichoplusia ni*) and the like; HEMIPTERA such as aster leafhopper (*Macrosteles fascifrons*), green rice leafhopper (*Nephotettix cincticeps*), brown rice planthopper (*Nilaparvata lugens*), small brown planthopper (*Laodelphax striatellus*), whitebacked rice planthopper (*Sogatella furcifera*), citrus psylla (*Diaphorina citri*), grape whitefly (*Aleurolobus taonabae*), silverleaf whitefly (*Bermisia argentifolii*), sweetpotato whitefly (*Bemisia tabaci*), greenhouse whitefly (*Trialeurodes vaporariorum*), turnip aphid (*Lipaphis erysimi*), cotton melon aphid (*Aphis gossypii*), spirea aphid (*Aphis citricola*), green peach aphid (*Myzus persicae*), Indian wax scale (*Ceroplastes ceriferus*), comstock mealybug (*Pseudococcus comstocki*), Japanese mealybug (*Planococcus kraunhiae*), cottony citrus scale (*Pulvinaria aurantii*), camphor scale (*Pseudaonidia duplex*), San Jose scale (*Comstockaspis perniciosa*), arrowhead scale (*Unaspis yanonensis*), brownwinged green bug (*Plautia stali*), brown marmorated stink bug (*Halyomorpha mista*) and the like; COLEOPTERA such as soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintioctopunctata*), adzuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican beetle (*Epilachna varivestis*), corn rootworm (*Diabrotica* sp.), yellow-spotted longicorn beetle (*Psacothea hilaris*), white-spotted longicorn beetle (*Anoplophora malasiaca*) and the like; DIPTERA such as oriental fruit fly (*Dacus* (*Bactrocera*) *dorsalis*), rice leafminer (*Agromyza oryzae*), onion maggot (*Delia antiqua*), seedcorn maggot (*Delia platura*), soybean pod gall midge (*Asphondylia* sp.), muscid fly (*Musca domestica*), leafminer (*Chromatomyia horticola*), serpentine leafminer (*Liriomyza trifolii*), tomato leafminer (*Liriomyza bryoniae*), house mosquito (*Culex pipiens pipiens*) and the like; TYLENCHIDA such as coffee root-lesion nematode (*Pratylenchus coffeae*), lesion nematode (*Pratylenchus* sp.), potato cyst nematode (*Globodera rostochiensis*), root-knot nematode (*Meloidogyne* sp.), citrus nematode (*Tylenchulus semipenetrans*), phagous nematode (*Aphelenchus avenae*), chrysanthemum foliar nematode (*Aphelenchoides ritzemabosi*) and the like; THYSANOPTERA such as melon thrip (*Thrips palmi*), western flower thrip (*Frankliniella occidentalis*), yellow tea thrip (*Scirtothrips dorsalis*), yellow flower thrip (*Thrips flavus*), onion thrip (*Thrips tabaci*) and the like; and ORTHOPTERA such as German cockroach (*Blattella germanica*), American cockroach (*Periplaneta americana*), rice grasshopper (*Oxya yezoensis*) and the like.

The insecticide comprising the compound represented by the general formula (1) or (5) of the present invention as an active ingredient has a remarkable control effect on the above-exemplified insect pests which are injurious to paddy field crops, upland crops, fruit trees, vegetables, other crops, flowers and the like. Therefore, the desired effect as an insecticide of the present invention can be obtained by applying the insecticide to the paddy field, upland, paddy field water, stalks and leaves of fruit trees, vegetables, other crops, flowers and the like, or soil at a season at which the insect pests are expected to appear, before their appearance or at the time when their appearance is confirmed.

The insecticide of the present invention is generally prepared into conveniently usable forms according to an ordinary manner for preparation of agricultural and horticultural chemicals. That is, the compound represented by the general formula (1) or (5) and, optionally, an adjuvant may be blended with a suitable inert carrier in a proper proportion and prepared into a suitable preparation form such as a suspension, emulsifiable concentrate, soluble concentrate, wettable powder, granules, dust, tablets or the like through dissolution, separation, suspension, mixing, impregnation, adsorption or adhering.

The inert carrier which can be used in the present invention may be either solid or liquid. Such a material which can be an inert solid carrier includes, for example, soybean flour, cereal flour, wood flour, bark flour, saw dust, powered tobacco stalks, powered walnut shells, bran, powered cellulose, extraction residue of vegetables, synthetic polymers such as powdered synthetic resins, inorganic mineral powder such as clays (for example, kaolin, bentonite, acid clay and the like), talcs (for example, talc, pyrophyllite and the like), silica powders or flakes (for example, diatomaceous earth, silica sand, mica, white carbon [synthetic, high-dispersion silicic acid, also called finely divided hydrated silicon, hydrated silicic acid, some of commercially available products contain calcium silicate as the major component]), activated carbon, powdered sulfur, pumice stone, calcined diatomite, brick groats, fly ash, sand, calcium carbonate powder, calcium phosphate powder and other inorganic mineral powders, chemical fertilizers (for example, ammonium sulfate, ammonium phosphate, ammonium nitrate, urea, ammonium chloride and the like), compost and the like. These carriers can be used singly or in combination of two or more kinds.

A material which can be the inert liquid carrier is selected from such a material which itself has solvency or which does not have such solvency but is capable of dispersing an effective ingredient compound with the aid of an adjuvant. The following are typical examples of the carrier and can be used singly or in combination of two or more kinds. Examples thereof include water, alcohols (for example, methanol, ethanol, isopropanol, butanol, ethylene glycol and the like), ketones (for example, acetone, methylethyl ketone, methylisobutyl ketone, diisobutyl ketone, cyclohexanone and the like), ethers (for example, diethyl ether, dioxane, cellosolve, diisopropyl ether, tetrahydrofuran and the like), aliphatic hydrocarbons (for example, kerosene, mineral oil and the like), aromatic hydrocarbons (for example, benzene, toluene, xylene, solvent naphtha, alkyl naphthalene and the like), halogenated hydrocarbons (for example, dichloromethane, chloroform, carbon tetrachloride, chlorobenzene and the like), esters (for example, ethyl acetate, butyl acetate, ethyl propionate, diisobutyl phthalate, dibutyl phthalate, dioctyl phthalate and the like), amides (for example, dimethylformamide, diethylformamide, dimethylacetamide and the like), nitriles (for example, acetonitrile and the like).

The following typical adjuvants can be exemplified. These adjuvants can be used depending on purposes and used singly or in combination of two or more kinds or need not to be used at all in some cases.

To emulsify, disperse, dissolve and/or wet a compound as an active ingredient, a surfactant is used. Examples thereof include sufactants such as polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonates, lignin sulfonates, higher alcohol sulfate esters and the like.

Furthermore, to stabilize the dispersion of a compound as an active ingredient, adhere it and/or bind it, the following adjuvants can be used. Examples thereof include casein, gelatin, starch, methyl cellulose, carboxymethyl cellulose, gum Arabic, polyvinyl alcohols, pine oil, bran oil, bentonite, Xanthan gum, lignin sulfonates and the like.

In order to improve fluidity of a solid product, the following adjuvants can be used. Examples thereof include waxes, stearates, alkyl phosphates and the like. Adjuvants such as naphthalenesulfonic acid condensation products, polycondensates of phosphates and the like can be used as a peptizer for suspendible products. As a defoaming agent, adjuvants such as silicon oils and the like can also be used.

Incidentally, the compound represented by the general formula (1) or (5) of the present invention is stable to light, heat, oxidation and the like. However, an anti-oxidant or an ultraviolet absorber including a phenol derivative, for example, BHT (2,6-di-t-butyl-4-methylphenol) and BHA (butylated hydroxyanisole), a bisphenol derivative or arylamines such as phenyl-α-naphthylamine, phenyl-β-naphthylamine, condensates of phenetidine and acetone and the like, or a benzophenone-based compound is added as a stabilizer in a proper amount when necessary, whereby a composition with much stabilized effect can be obtained.

The amount of the active ingredient of the compound represented by the general formula (1) or (5) of the present invention is usually from 0.5 weight % to 20 weight % for dust formulation, from 5 weight % to 50 weight % for emulsifiable concentrate, from 10 weight % to 90 weight % for wettable powder, from 0.1 weight % to 20 weight % for granule, and from 10 weight % to 90 weight % for flowable formulation. On the other hand, the amount of the carrier in each formulation is usually from 60 weight % to 99 weight % for dust formulation, from 40 weight % to 95 weight % for emulsifiable concentrate, from 10 weight % to 90 weight % for wettable powder, from 80 weight % to 99 weight % for granule, and from 10 weight % to 90 weight % for flowable formulation. Meanwhile, the amount of the adjuvant is usually from 0.1 weight % to 20 weight % for dust formulation, from 1 weight % to 20 weight % for emulsifiable concentrate, from 0.1 weight % to 20 weight % for wettable powder, from 0.1 weight % to 20 weight % for granule, and from 0.1 weight % to 20 weight % for flowable formulation.

In order to control various kinds of insect pests, the compound of the present invention may be suitably applied to crops which are expected to create insect pests or places where such creation is not desired in an amount effective in controlling insect pests as intact, as appropriately diluted with water or the like, or as suspended, and used accordingly. The amount thereof is varied according to various factors such as purpose, target insect pests, reared status of crops, occurrence trend of insect pests, weather, environmental conditions, the type of formulation, method of application, place of application, time of application and the like. However, usually, the amount is preferably at a concentration of 0.0001 ppm to 5000 ppm and preferably at a concentration of 0.01 ppm to 1000 ppm as an active ingredient. Furthermore, the application amount is generally from 1 to 300 g per 10 are as an active ingredient.

The insecticide comprising the compound represented by the general formula (1) or (5) of the present invention as an active ingredient may be used singly for preventing insect pests such as various agricultural, forest and horticultural insect pests, stored grain insect pests, hygienic insect pests, nematodes or the like which are injurious to paddy rice, fruit trees, vegetables, other crops, flowers and the like. Also, it may be used in combination of one or more kinds of other insecticides and/or fungicides in order to obtain a much higher control effect on controlling various diseases and insect pests occurring at the same time.

EXAMPLES

The representative examples of the present invention are now more specifically illustrated below with reference to the following Examples. However, the present invention is not restricted to these Examples.

Example 1-1

Preparation of
5-amino-6-bromo-8-heptafluoroisopropylquinoline

A solution containing 1.21 g of 5-amino-8-heptafluoroisopropylquinoline in 5 ml of N,N-dimethylformamide was stirred under an ice-water bath, and 0.69 g of N-bromosuccinic acid imide dissolved in 10 ml of N,N-dimethylformamide was subsequently introduced dropwise thereto. The reaction solution was stirred under an ice-water bath for 1 hour and at room temperature for 4 hours, and then ethyl acetate and water were added thereto for separating the organic phase. The organic phase was washed with water two times and dried over anhydrous magnesium sulfate, and a solvent was removed under a reduced pressure. The resulting residue was purified by silica gel column chromatography (n-hexane:EtOAc=8:1→4:1) to obtain 1.09 g of the desired product (Yield: 72%) as a light brown solid.

1H-NMR (CDCl$_3$) δ 4.98 (2H, broad-s), 7.43 (1H, dd, J=3.9, 8.3 Hz), 8.08 (1H, d, J=1.0 Hz), 8.13 (1H, dd, J=1.5, 8.3 Hz), 8.91 (1H, dd, J=1.5, 3.9 Hz).

Example 1-2

Preparation of
N-(6-bromo-8-heptafluoroisopropylquinolin-5-yl)
3-nitrobenzamide 0.47 g of 3-nitrobenzoyl chloride and 1.5 g of 5-amino-6-bromo-8-heptafluoroisopropylquinoline were added to 5 ml of pyridine, and the resulting mixture was stirred at room temperature. After 5 hours, to the reaction solution were added ethyl acetate and 1N hydrochloric acid for separating the organic phase. The organic phase was washed with water two times and with saturated sodium hydrogen carbonate solution three times. The solvent was removed under a reduced pressure to obtain a residue. The resulting residue was dissolved in a mixed solvent of 8 ml of THF and 2 ml of MeOH, and stirred under an ice-water bath. As that time, 0.10 g of NaOH was added thereto and stirred for 1 hour and further stirred at room temperature for 4 hours. To the reaction solution were added ethyl acetate and water for taking the organic phase and the organic phase was dried over anhydrous magnesium sulfate. The solvent was removed under a reduced pressure to obtain a residue. The resulting residue was purified by silica gel column chromatography (n-hexane:EtOAc=4:1) to obtain 0.72 g of the desired product (Yield: 52%) as a white amorphous substance.

1H-NMR (CDCl$_3$) δ 7.41 (1H, dd, J=3.9, 8.3 Hz), 7.61 (1H, t, J=7.8 Hz), 8.15 (1H, dd, J=1.5, 8.3 Hz), 8.25 (1H, s), 8.28 (1H, d, J=7.8 Hz), 8.39 (1H, d, J=7.8 Hz), 8.84 (1H, s), 8.87 (1H, s), 8.92 (1H, dd, J=1.5, 3.9 Hz).

Example 1-3

Preparation of
N-(6-bromo-8-heptafluoroisopropylquinolin-5-yl)
3-aminobenzamide

To a solution of 0.70 g of N-(6-bromo-8-heptafluoroisopropylquinolin-5-yl) 3-nitrobenzamide and 0.98 g of tin(II) chloride (anhydrous) in 10 ml of EtOH was added 1 ml of concentrated hydrochloric acid and the resulting mixture was stirred at 60° C. for 1 hour. The reaction solution was poured into ice water, neutralized with potassium carbonate, and then filtered off to remove the precipitated insoluble substance with celite. The insoluble substance was washed with ethyl acetate and combined with the filtrate for separating the organic phase, and then the organic phase was dried over anhydrous magnesium sulfate. The solvent was removed under a reduced pressure to precipitate a solid. The precipitated solid was washed with hexane to obtain 0.56 g of the desired product (Yield: 85%) as a pale orange solid.

1H-NMR (DMSO-d6) δ 5.41 (2H, broad-s), 6.83 (1H, dd, J=1.5, 9.3 Hz), 7.20-7.27 (3H, m), 7.76 (1H, dd, J=4.4, 8.8 Hz), 8.40-8.43 (2H, m), 9.06 (1H, dd, J=1.5, 4.4 Hz), 10.58 (1H, s).

Example 1-4

Preparation of N-(6-bromo-8-heptafluoroisopropylquinolin-5-yl) 3-[(2-fluorobenzoyl)amino]benzamide (Compound No. 1-304)

To a solution with 0.15 g of N-(6-bromo-8-heptafluoroisopropylquinolin-5-yl) 3-aminobenzamide and 0.03 g of pyridine added to 5 ml of tetrahydrofuran and stirred at room temperature was introduced dropwise 0.05 g of 2-fluorobenzoyl chloride with 1 ml of tetrahydrofuran dissolved therein. The reaction solution was stirred at room temperature for 1 hour, and then ethyl acetate and 1N hydrochloric acid were added thereto for separating the organic phase. The organic phase was washed with saturated sodium hydrogen carbonate solution one time and then dried over anhydrous magnesium sulfate. The solution was filtered off, the filtrate was collected and the solvent was removed under a reduced pressure to precipitate a solid. The precipitated solid was washed with diisopropyl ether to obtain 0.17 g of the desired product (Yield: 88%) as a white solid.

1H-NMR (DMSO-d6) δ 7.33-7.40 (2H, m), 7.57-7.63 (2H, m), 7.68-7.73 (1H, m), 7.77 (1H, dd, J=3.9, 8.8 Hz), 7.90 (1H, d, J=7.8 Hz), 8.03 (1H, d, J=7.8 Hz), 8.41-8.49 (3H, m), 9.08 (1H, dd, J=1.5, 3.9 Hz), 10.70 (1H, s), 10.84 (1H, s).

Example 2-1

Preparation of N-(4-heptafluoroisopropyl-2-methylsulfonylphenyl)-N-methyl 3-nitrobenzamide To a solution of 0.15 g of 60% sodium hydride suspended in 5 ml of tetrahydrofuran was introduced dropwise 1.5 g of N-(4-heptafluoroisopropyl-2-methylsulfonylphenyl) 3-nitrobenzamide dissolved in 5 ml of tetrahydrofuran at room temperature. The resulting mixture was stirred at room temperature for 30 minutes, and then 0.94 g of methyl iodide dissolved in 5 ml of tetrahydrofuran was introduced dropwise thereto. Subsequently, the reaction solution was elevated to 70° C. to stir for 12 hours and then returned to room temperature, and ethyl acetate and water were added thereto. The organic phase was separated and washed with water one time, and then dried over anhydrous magnesium sulfate. The solvent was removed under a reduced pressure. The resulting residue was purified by silica gel column chromatography (n-hexane:ethyl acetate=6:1) to obtain 0.98 g of the desired product (Yield: 64%) as a light yellow solid.

1H-NMR (CDCl$_3$) δ 3.21 (3H, s), 3.39 (3H, s), 7.64 (1H, d, J=8.3 Hz), 7.73 (1H, t, J=7.8 Hz), 8.03 (1H, d, J=8.3 Hz), 8.07 (1H, d, J=7.8 Hz), 8.38-8.41 (2H, m), 8.55 (1H, s).

Example 2-2

Preparation of N-(4-heptafluoroisopropyl-2-methylsulfonylphenyl)-N-methyl 3-aminobenzamide 0.93 g of N-(4-heptafluoroisopropyl-2-methylsulfonylphenyl)-N-methyl 3-nitrobenzamide and 1.40 g of tin(II) chloride (anhydrous) were added to 20 ml of EtOH, and 2 ml of concentrated hydrochloric acid was then introduced dropwise thereto. After the introduction, the reaction solution was elevated to 60° C. to stir for 1.5 hour, and poured into ice water. The reaction solution was neutralized with potassium carbonate and ethyl acetate was added thereto, and then filtered off to remove the precipitated insoluble substance with celite. The filtered product on celite was well washed with ethyl acetate. The organic phase of the filtrate was separated and dried over anhydrous magnesium sulfate, and the solvent was removed under a reduced pressure to obtain a residue. The resulting residue was purified by silica gel column chromatography (n-hexane:EtOAc=1:1) to obtain 0.82 g of the desired product (Yield: 94%) as colorless oil.

1H-NMR (CDCl$_3$) δ 3.19 (3H, s), 3.39 (3H, s), 3.88 (2H, broad-s), 6.80 (1H, d, J=7.8 Hz), 6.96 (1H, s), 7.04 (1H, d, J=7.8 Hz), 7.26 (1H, t, J=7.8 Hz), 7.60 (1H, d, J=7.8 Hz), 7.99 (1H, d, J=7.8 Hz), 8.40 (1H, s).

Example 2-3

Preparation of N-(4-heptafluoroisopropyl-2-methylsulfonylphenyl)-N-methyl 3-(2-fluorobenzoylamino)benzamide (Compound No. 1-603)

The desired title product was prepared according to the conditions as described in Example 1-4. White solid.

1H-NMR (CDCl$_3$) δ 3.22 (3H, s), 3.42 (3H, s), 7.17-7.23 (1H, m), 7.29-7.35 (2H, m), 7.49-7.57 (2H, m), 7.64 (1H, d, J=8.3 Hz), 7.81-7.83 (1H, m), 8.00-8.10 (2H, m), 8.14-8.18 (1H, m), 8.41 (1H, s), 8.62 (1H, d, J=15.1 Hz).

Example 3-1

Preparation of 3-(benzoylamino)benzoic acid

To a solution of 1.37 g of 3-aminobenzoic acid and 0.4 g of sodium hydroxide added to 50 ml of water was added dropwise 1.41 g of benzoyl chloride and a solution of 0.4 g of sodium hydroxide dissolved in 5 ml of water under an ice bath at the same time, and the resulting mixture was stirred at room temperature for 6 hours. The reaction solution with 1N hydrochloric acid added thereto was adjusted to pH 1, and then the precipitated solid was filtered off and collected to obtain 1.92 g of the desired product (Yield: 80%) as a white solid.

1H-NMR (CDCl$_3$, ppm) δ 7.40-7.56 (5H, m), 7.78 (1H, d, J=7.8 Hz), 8.00 (2H, d, J=8.3 Hz), 8.15 (1H, d, J=7.8 Hz), 8.35 (1H, t, J=2.0 Hz), 9.89 (1H, s).

Example 3-2

Preparation of 3-(benzoylamino)benzoyl chloride

To a solution of 1.5 g of 3-(benzoylamino) benzoic acid suspended in 10 ml of toluene was added 2 ml of thionyl chloride, and the resulting mixture was stirred under a reflux condition for 2 hours. The reaction solution was returned to room temperature, and then the solvent was removed under a reduced pressure to obtain 1.53 g of the desired product (Yield: 95%) as a white solid.

1H-NMR (CDCl$_3$, ppm) δ 7.51-7.62 (4H, m), 7.90 (2H, d, J=7.3 Hz), 7.93 (1H, s), 7.97 (1H, s), 8.15 (1H, dt, J=1.0, 5.9 Hz), 8.28 (1H, t, J=2.0 Hz).

Example 3-3

Preparation of N-benzothiazol-6-yl 3-(benzoylamino)benzamide (Compound No. 1-492)

To a solution of 0.1 g of 6-aminobenzothiazole and 0.1 g of pyridine added to 5 ml of tetrahydrofuran and stirred at room temperature was introduced dropwise 0.2 g of 3-(benzoylamino)benzoyl chloride dissolved in 1 ml of tetrahydrofuran. The resulting solution was stirred at room temperature for 1 hour, and then ethyl acetate and 1N hydrochloric acid were added thereto for separating the organic phase. The organic phase was washed with saturated sodium hydrogen carbonate solution one time, and then dried over anhydrous magnesium sulfate. The solution was filtered off, the filtrate was collected, and the solvent was removed under a reduced pressure to obtain a residue. The resulting residue was purified by silica gel column chromatography (n-hexane:ethyl acetate=3:1) to obtain 0.15 g of the desired product (Yield: 52%) as a white solid.

MS (APCI)=374 (M+1).

Example 4-1

Preparation of 2,6-difluoro-3-nitrobenzoic acid 0.73 g of 2,6-difluoro-3-nitrobenzonitrile was added to 5 ml of 90% aqueous sulfuric acid solution and the resulting mixture was stirred at 120° C. for 2 hours. The solution was cooled to room temperature and 5 ml of an aqueous solution with 21.9 g of sodium nitrite dissolved therein was added thereto, and then the resulting mixture was stirred at 80° C. for 1 hour. The solution was cooled to room temperature, poured into ice and extracted with ethyl acetate. The organic phase was dried over anhydrous magnesium sulfate and the solvent was removed under a reduced pressure. The resulting residue was purified by silica gel column chromatography (ethyl acetate) to obtain 1.80 g of the desired product (Yield: 96%) as a white solid.

IR(KBr,cm$^{-1}$); 3098, 1720, 1625, 1545, 1477, 1353.

Example 4-2

Preparation of 3-amino-2,6-difluorobenzoic acid

A solution of 2,6-difluoro-3-nitrobenzoic acid and 10% palladium carbon added to 10 ml of methanol was stirred in a hydrogen atmosphere at room temperature for 2 hours. The catalyst was filtered off and then the solvent was removed under a reduced pressure to obtain the desired product (Yield: 93%) as a white solid.

Example 4-3

Preparation of N-(4-heptafluoroisopropyl-2-methylphenyl) 3-(benzoylamino)-2,6-difluorobenzamide (Compound No. 1-601)

Using 3-amino-2,6-difluorobenzoic acid, 3-(benzoylamino)-2,6-difluorobenzoic acid was prepared according to the conditions as described in Examples 3-1, and then 3-(benzoylamino)-2,6-difluorobenzoyl chloride was prepared according to the conditions as described in Examples 3-2. Then, using heptafluoroisopropyl-2-methylaniline, the desired product was prepared according to the conditions as described in Examples 3-3.

1H NMR (DMSO-d6) δ 2.37 (3H, s), 7.29-8.01 (10H, m), 10.3 (1H, s), 10.6 (1H, s).

Example 5-1

Preparation of 3-(heptafluoro-n-propylthio)aniline

To a solution 1.25 g of 3-aminothiophenol and 1.11 g of triethylamine in 20 ml of acetonitrile was added 5.91 g of 1-iodineheptafluoro-n-propane, and the resulting mixture was stirred at room temperature for 3 hours. The resultant was diluted with ether, and then washed with aqueous 1N sodium hydroxide solution, purified by silica gel column chromatography (hexane:ethyl acetate=4:1) to obtain 0.38 g of the desired product (Yield: 14%).

Example 5-2

Preparation of 2,4,6-tribromo-3-(heptafluoro-n-propylthio)aniline

To a solution of 0.38 g of 3-(heptafluoro-n-propylthio) aniline added to 10 ml of N,N-dimethylformamide was introduced 0.72 g of N-bromosuccinic acid imide. The resulting solution was stirred at 60° C. for 2 hours, and then ether and water were added thereto for separating the organic phase. The organic phase was washed with water two times, and then dried over anhydrous magnesium sulfate, and the solvent was removed under a reduced pressure to obtain a residue. The resulting residue was purified by silica gel column chromatography (n-hexane:ethyl acetate=8:1) to obtain 0.61 g of the desired product (Yield: 89%) as red oil.

1H NMR (CDCl$_3$) δ 4.87 (2H, s), 7.83 (1H, s).

Example 5-3

Preparation of N-{2,4,6-tribromo-3-(heptafluoro-n-propylthio)}phenyl 3-nitrobenzamide 0.61 g of 2,4,6-tribromo-3-(heptafluoro-n-propylthio) aniline and 0.43 g of 3-nitrobenzoyl chloride were added to 20 ml of pyridine, and the resulting mixture was stirred at 70° C. for 2 hours. Then, ethyl acetate and water were added to the reaction solution. The organic phase was separated and dried over anhydrous magnesium sulfate. The solution was filtered off, the filtrate was collected, and the solvent was removed under a reduced pressure to obtain a residue. The resulting residue was purified by silica gel column chromatography (hexane:ethyl acetate=4:1) to obtain 0.69 g of the desired product (Yield: 89%) as a white solid.

1H NMR (CDCl$_3$) δ 7.76 (1H, t, J=7.8 Hz), 7.78 (1H, s), 8.15 (1H, s), 8.32 (1H, d, J=7.8 Hz), 8.47-8.50 (1H, m), 8.79 (1H, s).

Example 5-4

Preparation of N-{2,4,6-tribromo-3-(heptafluoro-n-propylthio)}phenyl 3-aminobenzamide To a solution of 0.69 g of N-{2,4,6-tribromo-3-(heptafluoro-n-propylthio)}phenyl 3-nitrobenzamide and 0.60 g of anhydrous tin(II)chloride added to 20 ml of ethanol and stirred at room temperature was added 1 ml of concentrated hydrochloric acid, and the resulting mixture was heated and stirred at 60° C. for 2 hours. The reaction solution was returned to room temperature, poured into water, and then neutralized with potassium carbonate. Ethyl acetate was added thereto and the insoluble substance was filtered off, and then the organic phase was separated and dried over anhydrous magnesium sulfate. The solution was filtered off, the filtrate was collected, and the solvent was removed under a reduced pressure to obtain a residue. The resulting residue was washed with hexane to obtain 0.62 g of the desired product (Yield: 94%) as a white solid.

1H NMR (CDCl$_3$) δ 3.89 (2H, s), 6.89 (1H, dt, J=6.4, 2.4 Hz), 7.27-7.31 (3H, m), 7.64 (1H, s), 8.11 (1H, s).

Example 5-5

Preparation of N-(2,4,6-tribromo-3-heptafluoro-n-propylthio)phenyl 3-(2-chloropyridine-3-carbonylamino)benzamide (Compound No. 1-391)

To a solution of 0.15 g of N-(2,4,6-tribromo-3-(heptafluoro-n-propylthio)phenyl 3-aminobenzamide and 0.04 g of pyridine added to 5 ml of tetrahydrofuran and stirred at room temperature was introduced dropwise 0.05 g of 2-chloronicotinoyl chloride dissolved in 1 ml of tetrahydrofuran. The resulting solution was stirred at room temperature for 1 hour, and then ethyl acetate and 1N hydrochloric acid were added thereto for separating the organic phase. The organic phase was washed with saturated sodium hydrogen carbonate solution one time, and then dried over anhydrous magnesium sulfate. The solution was filtered off, the filtrate was collected, and the solvent was removed under a reduced pressure to obtain a residue. The resulting residue was purified by silica gel column chromatography (n-hexane:ethyl acetate=3:1) to obtain 0.17 g of the desired product (Yield: 94%) as oil.

1H NMR (CDCl$_3$) δ 7.44 (1H, dd, J=4.9, 7.8 Hz), 7.57 (1H, t, J=7.8 Hz), 7.79 (1H, d, J=7.8 Hz), 7.87-7.91 (2H, m), 8.13 (1H, s), 8.23 (1H, dd, J=2.0, 7.8 Hz), 8.31 (1H, s), 8.42 (1H, s), 8.55 (1H, dd, J=2.0, 4.9 Hz).

Example 6-1

Preparation of 5-nitro-2-(2,2,2-trifluoro-1-trifluoromethylethoxy)pyridine 2.45 g (61.2 mmol) of sodium hydride was introduced to 15 ml of THF and cooled to 5° C., and then 10.6 g of 1,1,1,3,3,3-hexafluoro-2-propanol was added dropwise thereto. The resulting solution was stirred at 5° C. for 30 minutes, and then 5.0 g of 2-chloro-5-nitropyridine dissolved in 10 ml of THF was added dropwise thereto and stirred at room temperature for 3 hours. The reaction solution was allowed to stand at room temperature for 3 days, the water was added thereto, and the mixture was extracted with ethyl acetate and then washed with saturated salt water. The resultant was dried over anhydrous magnesium sulfate, and then the solvent was removed under a reduced pressure to obtain a residue. The resulting residue was purified by silica gel column chromatography (n-hexane AcOEt=10:1) to obtain 8.4 g of the desired product (Yield: 92%) as yellow oil.

1H NMR (CDCl$_3$) δ 6.57 (1H, septet), 7.13 (1H, d, J=8.8 Hz), 8.54 (1H, dd, J=8.8, 2.9 Hz), 9.09 (1H, d, J=2.9 Hz).

Example 6-2

Preparation of 5-amino-2-(2,2,2-trifluoro-1-trifluoromethylethoxy)pyridine

Using 5-nitro-2-(2,2,2-trifluoro-1-trifluoromethylethoxy)pyridine, the desired title product was prepared according to the conditions as described in Example 2-2 (Yield: 97%).

1H NMR (CDCl$_3$) δ 3.53 (2H, brs), 6.40 (1H, septet, J=6.4 Hz), 6.77 (1H, d, J=8.8 Hz), 7.09 (1H, dd, J=2.9, 8.8 Hz), 7.60 (1H, d, J=2.9 Hz).

Example 6-3

Preparation of 6-bromo-5-amino-2-(2,2,2-trifluoro-1-trifluoromethylethoxy)pyridine 2.0 g of 5-amino-2-(2,2,2-trifluoro-1-trifluoromethylethoxy)pyridine was introduced to 15 ml of N,N-dimethylformamide and 1.36 g of N-bromosuccinic acid was added thereto at room temperature. The resulting mixture was stirred at room temperature for 2 hours, and then ethyl acetate was added thereto and washed with water. The resultant was dried over anhydrous magnesium sulfate, and then purified by silica gel column chromatography (n-hexane:AcOEt=10:1) to obtain 2.35 g of the desired product as oil (Yield: 90%).

1H NMR (CDCl$_3$) δ 3.92 (2H, brs), 6.23 (1H, septet, J=7.4 Hz), 6.77 (1H, d, J=8.3 Hz), 7.12 (1H, d, J=8.3 Hz).

Example 6-4

Preparation of N-[2-bromo-4-(2,2,2-trifluoro-1-trifluoromethylethoxy)-pyridin-3-yl]3-nitrobenzamide Using 6-bromo-5-amino-2-(2,2,2-trifluoro-1-trifluoromethylethoxy)pyridine, the desired title product was prepared according to the conditions as described in Example 1-2 (Yield: 92%).

1H NMR (CDCl$_3$) δ 6.31 (1H, septet, J=5.8 Hz), 7.06 (1H, d, J=8.8 Hz), 7.77 (1H, t, J=8.3 Hz), 8.25-8.29 (2H, m), 8.47-8.50 (1H, m), 8.77-8.82 (2H, m).

Example 6-5

Preparation of N-[2-bromo-4-(2,2,2-trifluoro-1-trifluoromethylethoxy)-pyridin-3-yl]3-aminobenzamide Using N-[2-bromo-4-(2,2,2-trifluoro-1-trifluoromethylethoxy)-pyridin-3-yl]3-nitrobenzamide, the desired title product was prepared according to the conditions as described in Example 1-3 (Yield: 81%).

1H NMR (CDCl$_3$) δ 3.90 (2H, brs), 6.29 (1H, septet, J=5.9 Hz), 6.88-6.91 (1H, m), 7.00 (1H, d, J=8.8 Hz), 7.21-7.32 (3H, m), 8.23 (1H, brs), 8.85 (1H, d, J=8.8 Hz).

Example 6-6

Preparation of N-[2-bromo-6-(2,2,2-trifluoro-1-trifluoromethylethoxy)-pyridin-3-yl]3-(benzoylamino)benzamide (Compound No. 1-387)

Using N-[2 bromo-6-(2,2,2-trifluoro-1-trifluoromethylethoxy)-pyridin-3-yl]3-aminobenzamide and benzoyl chloride, the desired title product was prepared according to the conditions as described in Example 1-4 (Yield: 76%).

$^1$H NMR (CDCl$_3$) δ 6.30 (1H, septet, J=6.8 Hz), 7.01 (1H, d, J=8.8 Hz), 7.49-7.61 (4H, m), 7.68 (1H, dd, J=1.0, 7.8 Hz), 7.88-7.91 (2H, m), 7.96-8.01 (2H, m), 8.26 (1H, t, J=1.9 Hz), 8.33 (1H, s), 8.81 (1H, d, J=8.8 Hz).

Example 7-1

Preparation of N-(2-bromo-6-methyl-4-pivaloyloxyphenyl) 3-nitrobenzamide

Using 2-methyl-4-(pivaloyloxy)aniline which was synthesized according to a method as described in Tetrahedron p. 12263 to 12276 (1995), 2-bromo-6-methyl-4-(pivaloyloxy) aniline was prepared according to the conditions as described in Examples 1-1. Then, the desired title product was prepared according to the conditions as described in Examples 1-2 (Yield 52%).

$^1$H NMR (CDCl$_3$, ppm) σ 1.36 (9H, s), 2.36 (3H, s), 7.00 (1H, d, J=2.0 Hz), 7.27 (1H, d, J=2.0 Hz), 7.65 (1H, br.), 7.74 (1H, t, J=8.3 Hz), 8.31 (1H, dd, J=1.5, 6.3 Hz), 8.44-8.47 (1H, m), 8.79 (1H, t, J=2.0 Hz).

Example 7-2

Preparation of N-(2-bromo-6-methyl-4-hydroxyphenyl) 3-aminobenzamide

N-(2-bromo-6-methyl-4-pivaloyloxyphenyl) 3-nitrobenzamide and an aqueous solution of sodium hydroxide were added to methanol, and the resulting mixture was stirred at 70° C. for 3 hours. The solvent was removed under a reduced pressure to obtain a residue. The resulting residue was dissolved in ethyl acetate, washed with aqueous 2N hydrochloric acid solution, and then dried over anhydrous magnesium sulfate. The solvent was removed under a reduced pressure. The resulting residue was purified by silica gel column chromatography (n-hexane:EtOAc=1:1) to obtain N-(2-bromo-6-methyl-4-hydroxyphenyl) 3-nitrobenzamide. Then, the desired title product was prepared according to the conditions as described in Example 1-3 (Yield: 97%).

Example 7-3

Preparation of N-(2-bromo-6-methyl-4-hydroxyphenyl) 3-(benzoylamino)benzamide (Compound No. 1-484)

Using N-(2-bromo-6-methyl-4-hydroxyphenyl) 3-aminobenzamide, the desired title product was prepared according to the conditions as described in Example 1-4 (Yield: 95%).

1H NMR (DMSO, ppm) σ 2.16 (3H, s), 6.72 (1H, d, J=2.4 Hz), 6.94 (1H, d, J=2.4 Hz), 7.50-7.63 (4H, m), 7.74 (1H, d, J=8.3 Hz), 7.98-8.05 (3H, m), 8.32 (1H, s), 9.79 (1H, s), 9.81 (1H, s), 10.4 (1H, s).

Example 7-4

Preparation of N-(2-bromo-6-methyl-4-trifluoromethanesulfonyloxyphenyl) 3-(benzoylamino)benzamide (Compound No. 1-369)

0.2 g of N-(2-bromo-6-methyl-4-hydroxyphenyl) 3-(benzoylamino)benzamide and 0.14 g of trifluoromethanesulfonyl anhydride were added to pyridine, and the resulting mixture was stirred at 80° C. for 7 hours. The solvent was removed under a reduced pressure to obtain a residue. The resulting residue was purified by silica gel column chromatography (n-hexane:EtOAc=1:1) to obtain 0.08 g of the desired product (Yield: 31%).
1H NMR (DMSO, ppm) δ 2.32 (3H, s), 7.52-7.63 (5H, m), 7.76 (1H, d, J=7.8 Hz), 7.87 (1H, d, J=2.7 Hz), 8.00 (2H, dd, J=1.5, 7.8 Hz), 8.06 (1H, d, J=7.8 Hz), 8.37 (1H, s), 10.18 (1H, s), 10.47 (1H, s).

Example 7-5

Preparation of N-[2-bromo-6-methyl-4-(p-toluenesulfonyloxy)phenyl]3-(benzoylamino)benzamide (Compound No. 1-485)

0.30 g of N-(2-bromo-6-methyl-4-hydroxyphenyl) 3-(benzoylamino)benzamide, 0.23 g of 1,1,1,3,3,3-hexafluoroisopropyl p-toluenesulfonate, 0.19 g of potassium carbonate and 0.03 g of 18-crown-6 ether were added to 5 ml of N,N-dimethylformamide, and the resulting mixture was stirred at 70° C. for 6 hours. 100 ml of ethyl acetate was added thereto and washed with water (50 ml×2). The organic phase was dried over anhydrous magnesium sulfate and the solvent was removed under a reduced pressure to obtain a residue. The resulting residue was purified by silica gel column chromatography (n-hexane EtOAc=3:1) to obtain 0.05 g of the desired product (Yield: 13%).
1H NMR (CDCl$_3$, ppm) δ 2.29 (3H, s), 2.48 (3H, s), 6.94 (1H, d, J=2.9 Hz), 7.14 (1H, d, J=2.9 Hz), 7.36 (2H, d, J=8.3 Hz), 7.51-7.61 (5H, m), 7.71-7.77 (3H, m), 7.88-7.92 (3H, m), 7.99 (1H, br.s), 8.28 (1H, s).

Example 8-1

Preparation of N-(2,6-dimethyl-4-heptafluoroisopropyl)phenyl 3-nitrobenzamide

To a solution of 20.0 g of 2,6-dimethyl-4-heptafluoroisopropylaniline and 11.0 g of pyridine added to 100 ml of tetrahydrofuran and stirred at room temperature was introduced dropwise 13.0 g of 3-nitrobenzoyl chloride dissolved in 20 ml of tetrahydrofuran little by little. The reaction solution was stirred at room temperature for 10 hours, and then ethyl acetate and water were added thereto. Solution separation was performed for taking out the organic phase. The organic phase was dried over anhydrous magnesium sulfate. The solution was filtered off, the filtrate was collected, and the solvent was removed under a reduced pressure to obtain a residue. The resulting residue was washed with a mixed solvent of hexane and diisopropyl ether to obtain 26.0 g of the desired product (Yield: 85%) as a white solid.

1H-NMR (CDCl$_3$, ppm) δ 2.33 (6H, s), 7.37 (2H, s), 7.68 (1H, s), 7.72 (1H, t, J=8.1 Hz), 8.28 (1H, d, J=8.1 Hz), 8.44 (1H, dd, J=1.2, 8.1 Hz), 8.75 (1H, t, J=1.2 Hz).

Example 8-2

Preparation of N-(2,6-dimethyl-4-heptafluoroisopropyl)phenyl 3-aminobenzamide

To a solution of 0.90 g of N-(2,6-dimethyl-4-heptafluoroisopropyl)phenyl 3-nitrobenzamide and 1.56 g of anhydrous tin(II)chloride added to 25 ml of ethanol and stirred at room temperature was added 2 ml of concentrated hydrochloric acid, and the resulting mixture was stirred at 60° C. for 1 hour. The reaction solution was returned to room temperature, poured into water, and then neutralized with potassium carbonate. Ethyl acetate was added thereto, the insoluble substance was filtered off, and then the organic phase was separated and dried over anhydrous magnesium sulfate. The solution was filtered off, the filtrate was collected, and the solvent was removed under a reduced pressure to obtain a residue. The resulting residue was washed with hexane to obtain 0.44 g of the desired product (Yield: 53%) as a white solid.
1H-NMR (CDCl$_3$, ppm) 52.34 (6H, s), 3.87 (2H, broad), 6.86-6.89 (1H, m), 7.20-7.35 (6H, m).

Example 8-3

Preparation of N-[2,6-dimethyl-4-(heptafluoroisopropyl)phenyl]-3-(4-nitrophenylamino)-benzamide (Compound No. 5-9)

0.3 g of N-(2,6-dimethyl-4-heptafluoroisopropyl)phenyl 3-aminobenzamide, 0.18 g of 4-bromo-nitrobenzene, 21 mg of 9,9-dimethyl-4,5-bis(diphenylphosphino)xanthene and 0.29 g of cesium carbonate were introduced into a reaction vessel, and the resultant was stirred under nitrogen flow for 15 minutes at room temperature. 6 mg of palladium acetate was introduced thereinto, and then reacted at 90° C. for 6 hours in a nitrogen atmosphere. The reaction solution was cooled to room temperature, and then ethyl acetate was introduced thereinto and washed with water. The resultant was dried over anhydrous magnesium sulfate and then the solvent was removed under a reduced pressure to obtain a residue. The resulting residue was purified by silica gel column chromatography (n-hexane:AcOEt=10:1→8:2→2:1) to obtain 0.16 g of the desired product (Yield: 74%) as a yellow crystal.
1H NMR (CDCl$_3$) δ 2.36 (6H, s), 6.50 (1H, brs), 7.02 (2H, d, J=8.7 Hz), 7.38 (2H, s), 7.42 (1H, s), 7.46 (1H, d, J=7.8 Hz), 7.53 (1H, t, J=7.8 Hz), 7.60 (1H, d, J=7.8 Hz), 7.91 (1H, brs), 8.19 (2H, d, J=8.7 Hz).

Example 9-1

Preparation of N-[3-[(2,6-dimethyl-4-heptafluoroisopropylphenyl)aminocarbonyl]phenyl]-4-chlorobenzenesulfonamide (Compound No. 4-6)

To a solution of 0.30 g of N-(2,6-dimethyl-4-heptafluoroisopropyl)phenyl 3-aminobenzamide prepared in Example 8-2 added to 5 ml of pyridine was introduced to 0.16 g of 4-chlorobenzenesulfonyl chloride, and the resulting mixture was stirred at room temperature for 2 hours. Subsequently, ethyl acetate was added thereto, and then poured into ice water. The aqueous layer became acid using concentrated hydrochloric acid for separating the organic phase. The organic phase was washed with an aqueous solution of saturated sodium hydrogen carbonate two times, and then dried over anhydrous magnesium sulfate. The solvent was removed under a reduced pressure to obtain a residue. The resulting residue was purified by silica gel column chromatography (n-hexane:EtOAc=2:1) to obtain 0.30 g of the desired product (Yield: 70%) as a white amorphous substance.

1H-NMR (CDCl$_3$) δ 2.29 (6H, s), 7.32-7.39 (6H, m), 7.58-7.66 (6H, m).

Example 10-1

Preparation of 4-(1,1,2,3,3,3-hexafluoropropoxy)-nitrobenzene

To a solution of 4.63 g of p-nitrophenol and 0.56 g of potassium hydrate added to 100 ml of N,N-dimethylformamide blowed hexafluoropropene at room temperature, and then the solution was stirred at 50° C. for 1 hour. Next, ethyl acetate and water were introduced in the reaction solution for separating the organic phase. The organic phase was dried over anhydrous sodium sulfate and the solvent was removed under a reduced pressure. The resulting residue was purified by silica gel column chromatography (n-hexane:EtOAc=20:1) to obtain 3.81 g of the desired product (Yield: 42%) as a yellow oil.

1H NMR (CDCl$_3$) δ 5.06 (1H, ddt, J=44.0, 11.2, 5.2 Hz), 7.39 (2H, d, J=8.8 Hz), 8.30 (2H, d, J=8.8 Hz).

Example 10-2

Preparation of 4-(1,1,2,3,3,3-hexafluoropropoxy)-aniline

Using 4-(1,1,2,3,3,3-hexafluoropropoxy)-nitrobenzene, the desired title product was prepared according to the conditions as described in Example 1-3 as oil.

1H NMR (CDCl$_3$) δ 3.69 (2H, brs), 4.96 (1H, dddd, J=44.0, 11.2, 11.2, 5.6 Hz), 6.64 (2H, d, J=8.8 Hz), 6.98 (2H, d, J=8.8 Hz).

Example 10-3

Preparation of 2,6-dibromo-4-(1,1,2,3,3,3-hexafluoropropoxy)-aniline

Using two equivalent of N-bromosuccinimide, the desired title product was prepared according to the conditions as described in Example 1-1 as an oil.

1H NMR (CDCl$_3$) δ4.51 (2H, brs), 4.96 (1H, dddd, J=44.0, 11.2, 11.2, 6.0 Hz), 7.30 (2H, s).

Example 10-4

Preparation of N-(2,6-dibromo-4-(1,1,2,3,3,3-hexafluoropropoxy)phenyl) 3-nitrobenzamide The desired title product was prepared according to the conditions as described in Example 1-2 as a solid.

1H NMR (CDCl$_3$) δ 5.01 (1H, brd, J=44.0 Hz), 7.52 (1H, s), 7.57-7.78 (2H, m), 8.13 (1H, d, J=7.6 Hz), 8.32-8.38 (2H, m), 8.65 (1H, s).

Example 10-5

Preparation of N-(2,6-dibromo-4-(1,1,2,3,3,3-hexafluoropropoxy)phenyl) 3-aminobenzamide The desired title product was prepared according to the conditions as described in Example 1-3 as a solid.

1H NMR (DMSO-d6) δ 5.18 (2H, brs), 6.26 (1H, brd, J=44.0 Hz), 6.80 (1H, d, J=6.4 Hz), 7.14 (2H, t, J=7.6 Hz), 7.20 (1H, s), 7.63 (2H, s), 10.14 (1H, s).

Example 10-6

Preparation of N-(2,6-dibromo-4-(1,1,2,3,3,3-hexafluoropropoxy)phenyl) 3-[(2-fluorobenzoyl)amino]benzamide (Compound No. 2-8)

The desired title product was prepared according to the conditions as described in Example 1-4 as an amorphous substance.

1H NMR (CDCl$_3$) δ 5.01 (1H, brd, J=44.0 Hz), 7.23 (2H, d, J=8.0 Hz), 7.42 (4H, t, J=7.2 Hz), 7.52-7.55 (6H, m), 7.65 (2H, d, J=7.6 Hz), 7.82 (4H, d, J=8.0 Hz), 8.02 (2H, s), 8.25 (2H, s).

Next, formulation examples including the compound represented by the general formula (1) or (5) of the present invention as an active ingredient will be illustrated. However, the present invention is not restricted to these formulation examples. Incidentally, in the formulation examples, the term "part(s)" means "part(s) by weight"

Formulation Example 1

20 parts of the compound represented by the general formula (1) or (5) of the present invention, 10 parts of Sorpol 355S (a surface active agent, a product of Toho Chemical Industry, Co., Ltd.) and 70 parts of xylene were uniformly stirred and mixed to obtain emulsifiable formulation.

Formulation Example 2

10 parts of the compound represented by the general formula (1) or (5) of the present invention, 2 parts of sodium alkylnaphthalene sulfonate, 1 part of sodium lignin sulfonate, 5 parts of white carbon and 82 parts of diatomaceous earth were uniformly stirred and mixed to obtain a wettable powder.

Formulation Example 3

0.3 part of the compound represented by the general formula (1) or (5) of the present invention and 0.3 part of white carbon were uniformly mixed, and 99.2 parts of clay and 0.2 part of Driless A (a product of Sankyo Co., Ltd.) were added thereto. The resultant was uniformly pulverized and mixed to obtain a dust formulation.

Formulation Example 4

2 parts of the compound represented by the general formula (1) or (5) of the present invention, 2 parts of white carbon, 2 parts of sodium lignin sulfonate and 94 parts of bentonite were uniformly pulverized and mixed, and then water was added thereto. The resulting mixture was kneaded, granulated and dried to obtain a granule.

Formulation Example 5

20 parts of the compound represented by the general formula (1) or (5) of the present invention and 5 parts of 20% aqueous polyvinyl alcohol solution were fully stirred and mixed, and then 75 parts of 0.8% aqueous Xanthan gum solution was added thereto. The resulting mixture was stirred and mixed again to obtain a flowable formulation.

Furthermore, to make sure that the compound represented by the general formula (1) or (5) of the present invention has an excellent insecticidal activity, the following test examples are illustrated. However, the present invention is not restricted to these test examples.

Test Example 1

Insecticidal Test on Common Cutworm (*Spodoptera litura*)

A piece of cabbage leaf was immersed for 30 seconds in a liquid chemical prepared by diluting a test compound to a prescribed concentration. After air-drying, the piece was put into a 7-cm polyethylene cup and second-instar larvae of common cutworms were released thereinto. The polyethylene cups were set in an isothermal chamber thermostated at 25° C. From the release 6 days later, the dead and alive were counted. The test was carried out with two replications of 5 insects per a plot.

As a result of the above test, at 100 ppm, the following compounds showed 70% mortality or more: compound Nos. 1-1, 1-96, 1-159, 1-163, 1-264, 1-265, 1-266, 1-303, 1-304, 1-305, 1-306, 1-307, 1-308, 1-309, 1-311, 1-312, 1-315, 1-316, 1-331, 1-332, 1-333, 1-337, 1-339, 1-345, 1-346, 1-367, 1-368, 1-369, 1-371, 1-373, 1-374, 1-376, 1-377, 1-384, 1-385, 1-386, 1-387, 1-391, 1-406, 1-409, 1-412, 1-414, 1-418, 1-421, 1-426, 1-492, 1-517, 1-518, 1-539, 1-553, 1-567, 1-568, 1-569, 1-572, 1-573, 1-574, 1-575, 1-576, 1-577, 1-578, 1-579, 1-581, 1-582, 1-584, 1-585, 1-586, 1-587, 1-589, 1-591, 1-592, 1-593, 1-595, 1-596, 1-597, 1-598, 1-599, 1-600, 1-605, 2-1, 2-8, 2-159, 2-160, 2-163, 2-166, 2-167, 2-170, 2-173, 2-174, 2-175, 2-178, 2-183, 2-184, 2-185, 2-186, 2-187, 2-189, 2-190, 2-192, 2-194, 2-195, 2-196, 2-198, 2-199, 2-200, 2-201, 2-202, 2-203, 2-204, 2-210, 2-211, 2-212, 2-213, 2-214, 2-215, 2-216, 2-217, 2-218, 2-219, 2-220, 4-1, 4-6, 4-10, 4-23, 4-24, 4-25, 4-26, 4-31, 4-32, 4-33, 4-34, 5-5, 5-9, 5-12, 5-13, 5-21, 5-23, 5-24, 5-27, 5-28, 5-29 and 5-33.

Test Example 2

Insecticidal Test on Diamondback Moth (*Plutella xylostella*)

A piece of cabbage leaf was immersed for 30 seconds in a liquid chemical prepared by diluting a test compound to a prescribed concentration. After air-drying, the piece was put into a 7-cm polyethylene cup and second-instar larvae of diamondback moths were released thereinto. The polyethylene cups were set in an isothermal chamber thermostated at 25° C. From the release 6 days later, the dead and alive were counted. The test was carried out with two replications of 5 insects per a plot.

As a result of the above test, at 100 ppm, the following compounds showed 70% mortality or more: compound Nos. 1-159, 1-303, 1-304, 1-305, 1-306, 1-307, 1-308, 1-309, 1-310, 1-315, 1-316, 1-339, 1-340, 1-366, 1-367, 1-368, 1-369, 1-371, 1-372, 1-373, 1-374, 1-376, 1-380, 1-384, 1-386, 1-387, 1-409, 1-414, 1-415, 1-416, 1-417, 1-421, 1-423, 1-425, 1-426, 1-428, 1-429, 1-430, 1-433, 1-434, 1-435, 1-436, 1-437, 1-439, 1-441, 1-456, 1-462, 1-487, 1-489, 1-490, 1-517, 1-539, 1-550, 1-562, 1-566, 1-567, 1-568, 1-569, 1-571, 1-572, 1-573, 1-596, 1-597, 1-598, 1-599, 2-1, 2-8, 2-159, 2-160, 2-163, 2-166, 2-167, 2-170, 2-174, 2-175, 2-178, 2-183, 2-184, 2-185, 2-186, 2-187, 2-188, 2-189, 2-197, 2-198, 2-199, 2-200, 2-204, 2-207, 2-210, 2-211, 2-212, 2-213, 2-214, 2-215, 2-216, 2-217, 2-218, 2-220, 4-1, 4-2, 4-6, 4-10, 4-23, 4-24, 4-25, 4-26, 4-27, 4-28, 4-29, 4-32, 4-34, 5-9, 5-12, 5-21, 5-23, 5-24, 5-25, 5-26 and 5-27.

Test Example 3

Insecticidal Test on Small Brown Planthopper (*Laodelphax striatellus*)

An acetone solution prepared by diluting a test compound to a prescribed concentration was dispersed on rice seedlings. After air-drying, 10 insects of small brown planthoppers were provided thereto. All Chemicals used were ingredients. The seedlings were set in an isothermal chamber thermostated at 25° C. From the treatment 6 days later, the dead and alive were counted. The test was carried out with one plot of 10 insects per a plot.

As a result of the above test, at 1000 ppm, the following compounds showed 70% mortality or more: compound Nos. 1-367, 1-572, 2-183, 2-200, 1-304, 1-303, 1-305, 1-496, 1-499, 1-558, 1-559, 1-592, 2-194, 4-32 and 5-29.

The invention claimed is:
1. A compound represented by the general formula (1),

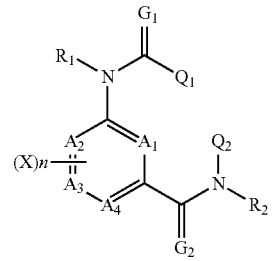

(1)

wherein, in the formula,
$A_1$, $A_2$, $A_3$ and $A_4$ represent a carbon atom;
$R_1$ and $R_2$ mutually independently represent a hydrogen atom or a methyl group;
$G_1$ and $G_2$ represent an oxygen atom;
Xs may be the same or different and are a hydrogen atom, a fluorine atom or a chlorine atom;
n represents an integer of 0 to 4;
$Q_1$ represents a phenyl group,
a substituted phenyl group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group, or a substituted heterocyclic group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group; and $Q_2$ is represented by the general formula (2),

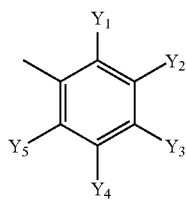

(2)

wherein, in the formula, $Y_1$ and $Y_5$ may be the same or different and represent a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a pentafluorosulfanyl group, a substituted C1-C6 haloalkoxy group having one or more substituents which may be the same or different wherein the substituents are selected from the group consisting of a hydroxy group, a chlorine atom, a bromine atom, an iodine atom, a C1-C6 alkoxy group and a C1-C6 haloalkoxy group, a substituted C1-C6 haloalkylthio group having one or more substituents which may be the same or different wherein the substituents are selected from the group consisting of a hydroxy group, a chlorine atom, a bromine atom, an iodine atom, a C1-C6 alkoxy group and a C1-C6 haloalkoxy group, a substituted C1-C6 haloalkylsulfinyl group having one or more substituents which may be the same or different wherein the substituents are selected from the group consisting of a hydroxy group, a chlorine atom, a bromine atom, an iodine atom, a C1-C6 alkoxy group and a C1-C6 haloalkoxy group, or a substituted C1-C6 haloalkylsulfonyl group having one or more substituents which may be the same or different wherein the substituents are selected from the group consisting of a hydroxy group, a chlorine atom, a bromine atom, an iodine atom, a C1-C6 alkoxy group and a C1-C6 haloalkoxy group.

2. A compound represented by the general formula (1),

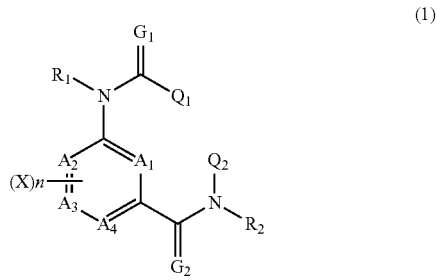

(1)

wherein, in the formula,

A1, A2, A3 and A4 represent a carbon atom;

R1 and R2 mutually independently represent a hydrogen atom or a methyl group;

G1 and G2 represent an oxygen atom;

Xs may be the same or different and are a hydrogen atom, a fluorine atom or a chlorine atom;

n represents an integer of 0 to 4;

$Q_1$ represents a phenyl group, a substituted phenyl group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group, or a substituted heterocyclic group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group; and Q2 is represented by the general formula (2),

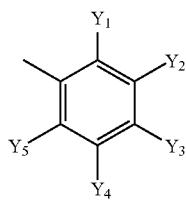

(2)

wherein, in the formula, $Y_1$ represents a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, or a C1-C4 alkyl group having one or more substituents which may be the same or different wherein the substituents are selected from the group consisting of a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and an alkylsilyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a C1-C4 haloalkoxy group, a C2-C6 perfluoroalkyl group, a C1-C6 perfluoroalkylthio group, a C1-C6 perfluoroalkylsulfinyl group, a C1-C6 perfluoroalkylsulfonyl group, a trifluoromethyl group, a C1-C6 perfluoroalkoxy group, a pentafluorosulfanyl group, a substituted C1-C6 haloalkoxy group having at least one or more substituents which may be the same or different wherein the substituents are selected from the group consisting of a hydrogen atom, a hydroxy group, a chlorine atom, a bromine atom, an iodine atom, a C1-C6 alkoxy group and a C1-C6 haloalkoxy group, a substituted C1-C6 haloalkylthio group having at least one or more substituents which may be the same or different wherein the substituents are selected from the group consisting of a hydrogen atom, a hydroxy group, a chlorine atom, a bromine atom, an iodine atom, a C1-C6 alkoxy group and a C1-C6 haloalkoxy group, a substituted C1-C6 haloalkylsulfinyl group having at least one or more substituents which may be the same or different wherein the substituents are selected from the group consisting of a hydrogen atom, a hydroxy group, a chlorine atom, a bromine atom, an iodine atom, a C1-C6 alkoxy group and a C1-C6 haloalkoxy group, or a substituted C1-C6 haloalkylsulfonyl group having at least one or more substituents which may be the same or different wherein the substituents are selected from the group consisting of a hydrogen atom, a hydroxy group, a chlorine atom, a bromine atom, an iodine atom, a C1-C6 alkoxy group and a C1-C6 haloalkoxy group.

3. A compound represented by the general formula (1), $$\text{(1)}$$

wherein, in the formula, $A_1$, $A_2$, $A_3$ and $A_4$ represent a carbon atom;

$R_1$ and $R_2$ mutually independently represent a hydrogen atom or a methyl group;

$G_1$ and $G_2$ represent an oxygen atom;

Xs may be the same or different and are a hydrogen atom, a fluorine atom or a chlorine atom;

n represents an integer of 0 to 4;

$Q_1$ represents a phenyl group, a substituted phenyl group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group, a heterocyclic group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group, or a substituted heterocyclic group having one or more substituents which may be the same or different wherein the substituents are selected from the group consisting of a halogen atom, a C1-C4 alkyl group, a C1-C4 haloalkyl group, a substituted C1-C4 alkyl group, a C2-C4 alkenyl group, a C2-C4 haloalkenyl group, a C2-C4 alkynyl group, a C2-C4 haloalkynyl group, a C3-C8 cycloalkyl group, a C3-C8 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 haloalkylcarbonyl group, a C1-C4 alkylcarbonyloxy group, a C1-C4 haloalkylcarbonyloxy group, a C1-C4 alkoxycarbonyl group, a C1-C4 haloalkoxycarbonyl group, a C1-C4 alkylcarbonylamino group, a C1-C4 haloalkylcarbonylamino group, a C1-C4 alkylsulfonyloxy group, a C1-C4 haloalkylsulfonyloxy group, an arylsulfonyloxy group, a pentafluorosulfanyl group and a phenyl group wherein the heterocyclic group is selected from the group consisting of a pyrazinyl group, a pyridyl group, a pyridine N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a pyrrole group, an imidazolyl group, a triazolyl group, a pyrazolyl group, a tetrazolyl group, a 2,3-dihydro-benzo[1,4]dioxinyl group, a benzo[1,3]dioxolyl group, a tetrahydropyranyl group and a dihydropyranyl group; and $Q_2$ is represented by the general formula (2), $$\text{(2)}$$

wherein, in the formula, $Y_1$ represents a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group or a C1-C6 haloalkylsulfonyl group;

$Y_5$ represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group or a nitro group;

$Y_2$ and $Y_4$ may be the same or different and represent a hydrogen atom, a halogen atom or a C1-C6 alkyl group; and $Y_3$ represents a halogen atom.

4. The compound according to claim 1, wherein, in the general formula (1), at least one of $R_1$ and $R_2$ is a C1-C4 alkyl group.

5. The compound according to claim 2, wherein, in the general formula (1), at least one of $R_1$ and $R_2$ is a C1-C4 alkyl group.

6. The compound according to claim 3, wherein, in the general formula (1), at least one of $R_1$ and $R_2$ is a C1-C4 alkyl group.

7. An insecticide comprising the compound according to claim 1 and an active ingredient.

8. An insecticide comprising the compound according to claim 2 and an active ingredient.

9. An insecticide comprising the compound according to claim 3 and an active ingredient.

* * * * *